US009714215B2

(12) United States Patent
Shinohata et al.

(10) Patent No.: US 9,714,215 B2
(45) Date of Patent: Jul. 25, 2017

(54) METHOD FOR PRODUCING ISOCYANATE

(71) Applicant: Asahi Kasei Chemicals Corporation, Tokyo (JP)

(72) Inventors: Masaaki Shinohata, Tokyo (JP); Kouji Takeuchi, Tokyo (JP); Naoki Fujimoto, Tokyo (JP); Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 14/781,192

(22) PCT Filed: Mar. 28, 2014

(86) PCT No.: PCT/JP2014/059187
§ 371 (c)(1),
(2) Date: Sep. 29, 2015

(87) PCT Pub. No.: WO2014/157636
PCT Pub. Date: Oct. 2, 2014

(65) Prior Publication Data
US 2016/0052874 A1 Feb. 25, 2016

(30) Foreign Application Priority Data

Mar. 29, 2013 (JP) ................. 2013-072440
Mar. 29, 2013 (JP) ................. 2013-072441

(51) Int. Cl.
C07C 229/00 (2006.01)
C07C 263/04 (2006.01)
C07C 269/04 (2006.01)

(52) U.S. Cl.
CPC .......... *C07C 263/04* (2013.01); *C07C 269/04* (2013.01)

(58) Field of Classification Search
None
See application file for complete search history.

(56) References Cited

U.S. PATENT DOCUMENTS

| | | | | |
|---|---|---|---|---|
| 2,677,698 | A * | 5/1954 | Deutschman, Jr. ... | C07C 271/06 549/496 |
| 5,427,759 | A | 6/1995 | Heitmann | |
| 7,416,644 | B2 * | 8/2008 | Bonde ................. | B01D 3/346 202/155 |
| 8,053,595 | B2 * | 11/2011 | Shinohata .......... | C07C 263/04 560/345 |
| 8,097,065 | B2 | 1/2012 | Bleifuss et al. | |
| 8,884,047 | B2 | 11/2014 | Miyake et al. | |
| 2005/0043561 | A1 | 2/2005 | Kohlstruk et al. | |
| 2005/0043563 | A1 | 2/2005 | Kohlstruk et al. | |
| 2008/0262263 | A1 | 10/2008 | Wolfert et al. | |
| 2010/0036154 | A1 | 2/2010 | Michalczak et al. | |
| 2011/0133121 | A1 | 6/2011 | Shinohata et al. | |
| 2011/0160476 | A1 | 6/2011 | Miyake et al. | |
| 2013/0079546 | A1 | 3/2013 | Takamatsu et al. | |

FOREIGN PATENT DOCUMENTS

| | | |
|---|---|---|
| CN | 1365969 A | 8/2002 |
| CN | 101451711 A | 6/2009 |
| CN | 102105439 A | 6/2011 |
| CN | 102107887 A | 6/2011 |
| EP | 2322504 A1 | 5/2011 |
| JP | S47-006608 B | 2/1972 |
| JP | S49-025560 B1 | 7/1974 |
| JP | S52-065219 A | 5/1977 |
| JP | H05-310677 A | 11/1993 |
| JP | H06-115928 A | 4/1994 |
| JP | 2007-307477 A | 11/2007 |
| JP | 2009-510015 A | 3/2009 |
| JP | 2012-153708 A | 8/2012 |
| JP | 2012-179881 A | 9/2012 |
| TW | 201107278 A | 3/2011 |
| WO | 2007/036479 A1 | 4/2007 |

(Continued)

OTHER PUBLICATIONS

Supp, Dipl-Ing Emil. "How to Process By-Products and Wastes." How to Produce Methanol from Coal. Springer Berlin Heidelberg, 1990. 146-169.*
Partial Supplementary European Search Report issued in counterpart European Patent Application No. 14774772.9 dated Apr. 19, 2016.
Fields, "Recovering Ammonia from Ammonia-Water Vapors," Industrial and Engineering Chemistry, 53: 131-136 (1961).
International Preliminary Report on Patentability and Written Opinion issued in corresponding International Patent Application No. PCT/JP2014/059187 dated Sep. 29, 2015.

(Continued)

*Primary Examiner* — Patrick Lewis
(74) *Attorney, Agent, or Firm* — Morgan, Lewis & Bockius LLP

(57) ABSTRACT

A method for producing an isocyanate, comprising: a carbamation step of generating an N-substituted carbamate from an organic primary amine, urea and an organic hydroxy compound according to a carbamation reaction, and then recovering a first gaseous phase component containing the urea and/or a compound having a carbonyl group derived from the urea, the organic hydroxy compound, and ammonia; a condensation step of condensing the first gaseous phase component with a condenser; an isocyanate production step of producing an isocyanate by subjecting the N-substituted carbamate to pyrolysis; an ammonia absorption step of allowing a second gaseous phase component containing ammonia recovered as a gaseous phase component from the condenser as a main component, to be absorbed by absorption water, and generating gas-absorbed water; and an ammonia stripping step of heating the gas-absorbed water to separate ammonia from the gas-absorbed water.

9 Claims, 22 Drawing Sheets

(56) References Cited

FOREIGN PATENT DOCUMENTS

| WO | 2011/021258 A1 | 2/2011 |
| WO | 2011/078000 A1 | 6/2011 |
| WO | 2011/158598 A1 | 12/2011 |
| WO | 2012/115110 A1 | 8/2012 |

OTHER PUBLICATIONS

International Search Report issued in corresponding International Patent Application No. PCT/JP2014/059187 dated Jun. 24, 2014.
"Wet Scrubbers-Ammonia Scrubbers," Pollution Systems (https://web.archive.org/web/20120512160437/http:www.pollutionsystems.com/ammonia-scrubbers.htm), (2012).
Supplementary European Search Report issued in counterpart European Patent Application No. 14774772.9 dated Oct. 24, 2016.

* cited by examiner

METHOD FOR PRODUCING ISOCYANATE

TECHNICAL FIELD

The present invention relates to a method for producing isocyanates.

BACKGROUND ART

Isocyanates have been industrially widely used as raw materials for, for example, polyurethane or polyurea. Conventionally, isocyanates have been industrially produced by a reaction of an amine with phosgene (phosgene method). However, phosgene has various problems such as high toxicity, complicated handling, and further, the necessity of special consideration for corrosion of apparatuses caused by a large amount of hydrochloric acid generated as a by-product from phosgene. Accordingly, it has been desired to develop a method for industrially producing an isocyanate, which will replace the aforementioned phosgene method.

As a method for producing an isocyanate without using phosgene, a method for producing an isocyanate by performing pyrolysis on a carbamate obtained by reacting an amine, urea and/or an N-unsubstituted carbamic acid ester, and alcohol (carbamation reaction) has been known (urea method), for example. With regard to the production of an isocyanate according to this method, it has been known that gaseous ammonia is generated as a by-product, and that high-boiling components are generated after the recovery of an isocyanate. Thus, a method for recovering and treating such components has been studied.

In the case of the carbamation reaction performed in the urea method, ammonia is generated as a by-product. Since ammonia is used as a raw material for basic chemicals such as nitric acid and nitrogen fertilizers such as ammonia sulfate, it is an industrially extremely important substance. Ammonia is used in the form of liquid ammonia or ammonia water.

As a method for recovering ammonia generated as a by-product in the production of a carbamate, there has been proposed, for example, a method which comprises washing exhaust gas containing an organic matter, carbon dioxide and ammonia with an alkaline solution (e.g. caustic soda solution) to remove the organic matter and the like, and at the same time, distilling the ammonia as a top product (see, for example, Patent Literature 1 below). In addition, Patent Literature 2 discloses a method which comprises washing alcohol contained in ammonia generated as a by-product with a small amount of water and recycling it.

On the other hand, with regard to high-boiling components obtained after the recovery of the isocyanate, for example, Patent Literature 3 discloses a method which comprises separating isocyanates from an organic residual matter containing diisocyanates at a specific temperature and under a specific pressure, and carrying the residual matter out of the reaction system according to forced transfer.

CITATION LIST

Patent Literature

Patent Literature 1: JP 6-115928 A
Patent Literature 2: WO2011/158598 A1
Patent Literature 3: WO2007/036479 A1

SUMMARY OF INVENTION

Technical Problem

In the method for recovering ammonia generated as a by-product, which is disclosed in the above-mentioned Patent Literature 1, while ammonia can be recovered, an alkaline solution (e.g. caustic soda solution) needs to be continuously supplied, and thus, this method is problematic in terms of cost disadvantage. Moreover, the use of a highly corrosive alkaline solution would cause a high load on apparatuses, and thus, this method is disadvantageous in terms of equipment maintenance.

In this respect, it can be said that the method disclosed in Patent Literature 2 is advantageous in terms of the use of a small amount of water. However, if components that are hardly dissolved in such a small amount of water were contained in ammonia generated as a by-product, it could not be said that the effect of increasing the purity of the ammonia is sufficient. Furthermore, there may be a case in which some compounds contained in ammonia are not only dissolved in water, but they are also be cooled and solidified as a result of contact with water, so that they would adhere to the inside of the system or would cause the clogging of the system. Further, when the carbamation reaction is carried out under a reduced pressure, because of the need to maintain pressure in the carbamation reaction, it is necessary to supply ammonia generated as a by-product that has swollen under a low pressure to a step of contacting it with water, by using a pump or the like, or to eliminate ammonia after contact with water by using a pump or the like. Accordingly, this method is also problematic in that it requires large equipment including a pump and the like.

It is a first object of the present invention to provide a method for producing an isocyanate, which comprises a step of recovering ammonia that can efficiently recover ammonia generated in a carbamation reaction at a high purity.

On the other hand, with regard to the recovery of high-boiling components after the recovery of isocyanates, in the method of Patent Literature 3, there are many cases in which a diisocyanate-containing organic residue is highly viscous when it is transferred to an apparatus for separating diisocyanates, and thus, the transfer itself is difficult.

It is a second object of the present invention to provide a method for facilitating the transfer of a mixture after the recovery of isocyanates in the recovery of high-boiling components after the recovery of the isocyanates, and the recovery of an active component.

Solution to Problem

As a result of intensive studies directed towards achieving the aforementioned objects, at first, regarding the first object, the present inventors have conceived of a method which comprises supplying a gaseous phase component containing ammonia obtained in a carbamation step to a condenser comprised in a reaction vessel in which the aforementioned step is carried out, allowing the thus recovered gaseous phase component to be absorbed by absorption water to generate gas-absorbed water, and heating the gas-absorbed water to obtain ammonia. In addition, regarding the second object, the inventors have conceived of a method which comprises subjecting a carbamate to a pyrolytic reaction, heating a residual liquid containing non-regenerable by-products obtained by separating the generated isocyanate, and recovering an organic hydroxy compound contained in the residual liquid and/or an organic hydroxy compound derived from an organic hydroxy compound precursor. The present inventors have found that the aforementioned objects can be achieved by these methods, thereby completing the present invention.

Specifically, the present invention is as follows.

First, as a first aspect of the present invention, the following [1] to [9] are provided.

[1] A method for producing an isocyanate, from using an organic primary amine, urea and an organic hydroxy compound as raw materials, comprising:

a carbamation step (step (1)) of generating an N-substituted carbamate from the organic primary amine, the urea and the organic hydroxy compound according to a carbamation reaction, and then recovering a first gaseous phase component containing the urea and/or a compound having a carbonyl group derived from the urea, the organic hydroxy compound, and ammonia;

a condensation step (step (2)) of condensing the first gaseous phase component with a condenser;

an isocyanate production step (step (3)) of producing an isocyanate by subjecting the N-substituted carbamate to pyrolysis;

an ammonia absorption step (step (4)) of allowing a second gaseous phase component containing ammonia recovered as a gaseous phase component from the condenser as a main component, to be absorbed by absorption water, and generating gas-absorbed water; and an ammonia stripping step (step (5)) of heating the gas-absorbed water to separate the ammonia from the gas-absorbed water.

[2] The method according to [1], wherein a liquid phase component obtained after the separation of the ammonia in the ammonia stripping step is used as the absorption water in the ammonia absorption step.

[3] The method according to [1] or [2], wherein
the second gaseous phase component contains urea and/or isocyanic acid, and an organic hydroxy compound, and
the gas-absorbed water contains ammonia, urea and/or isocyanic acid, and an organic hydroxy compound.

[4] The method according to [3], wherein a liquid phase component obtained after the separation of the ammonia in the ammonia stripping step contains an organic hydroxy compound and a water phase, and the organic hydroxy compound is separated from the water phase according to phase separation.

[5] The method according to [3] or [4], further comprising:

an organic hydroxy compound separation step of separating an organic hydroxy compound and a water phase, both contained in a liquid phase component obtained after the separation of the ammonia in the ammonia stripping step.

[6] The method according to [5], further comprising:

a liquid phase blow-down step of substituting a portion of an aqueous solution obtained in the organic hydroxy compound separation step with water.

[7] The method according to any one of [1] to [6], wherein ammonia obtained in the ammonia stripping step is further burned to recover heat, and the thus recovered heat is used as a heat source in the carbamation step and/or the isocyanate production step.

[8] The method according to any one of [1] to [6], wherein ammonia obtained in the ammonia stripping step is recovered as liquid ammonia.

[9] A method for producing an isocyanate, from using an organic primary amine, urea and an organic hydroxy compound as raw materials, comprising:

a carbamation step (step (1)) of generating an N-substituted carbamate from the organic primary amine, the urea and the organic hydroxy compound according to a carbamation reaction, and then recovering a first gaseous phase component containing the urea and/or a compound having a carbonyl group derived from the urea, the organic hydroxy compound, and ammonia;

a condensation step (step (2)) of condensing the first gaseous phase component with a condenser;

an isocyanate production step (step (3)) of producing an isocyanate by subjecting the N-substituted carbamate to pyrolysis; and an ammonia absorption step (step (4)) of allowing a second gaseous phase component containing ammonia discharged from the condenser as a main component, to be absorbed by sulfuric acid water, and generating ammonium sulfate.

Moreover, as a second aspect of the present invention, the following [10] to [13] are provided.

[10] A method for producing an isocyanate, from using an organic primary amine, urea and an organic hydroxy compound as raw materials, comprising:

a carbamation step (step (1)) of generating an N-substituted carbamate from the organic primary amine, the urea and the organic hydroxy compound according to a carbamation reaction, and then recovering a first gaseous phase component containing the urea and/or a compound having a carbonyl group derived from the urea, the organic hydroxy compound, and ammonia;

a condensation step (step (2)) of condensing the first gaseous phase component with a condenser;

an isocyanate production step (step (3)) of producing an isocyanate by subjecting the N-substituted carbamate to pyrolysis;

a regeneration step (step (6)) of allowing a part or the whole of a first residual liquid, from which low-boiling components containing the isocyanate and the organic hydroxy compound obtained in the isocyanate production step have been separated, to react with urea and an organic hydroxy compound;

a separation step (step (7)) of subjecting a reaction solution in the regeneration step to a pyrolytic reaction, so as to separate the generated isocyanate from a second residual liquid containing a non-regeneratable by-product; and a blow-down step (step (8)) of heating the first residual liquid and/or the second residual liquid to recover low-boiling components containing an organic hydroxy compound, recycling the low-boiling components to at least one of the steps (1), (3), and (6), and removing high-boiling components containing non-regeneratable by-products from the system.

[11] The method according to [10], wherein, in the blow-down step, the first residual liquid and/or the second residual liquid are heated by using at least one device selected from the group consisting of:

(a) a paddle type dryer comprising a forced transfer device;

(b) an extruder comprising a degassing function; and (c) a vertical thin film evaporator comprising a forced transfer device.

[12] The method according to [11], wherein, in the blow-down step, the first residual liquid and/or the second residual liquid are heated by using either one of:

(a) a paddle type dryer comprising a forced transfer device; and (c) a vertical thin film evaporator comprising a forced transfer device.

[13] The method according to [10], wherein a viscosity of the first residual liquid and/or the second residual liquid is 1000 mPa·s or less.

Advantageous Effects of Invention

According to the present invention, upon the production of isocyanates, it is possible to efficiently recover ammonia generated as a by-product in a carbamation step at a high purity. Moreover, upon the recovery of high-boiling components after the recovery of isocyanates, it becomes easy to transfer a mixture after the recovery of the isocyanates and to recover an active component.

DESCRIPTION OF EMBODIMENTS

Figure 1:
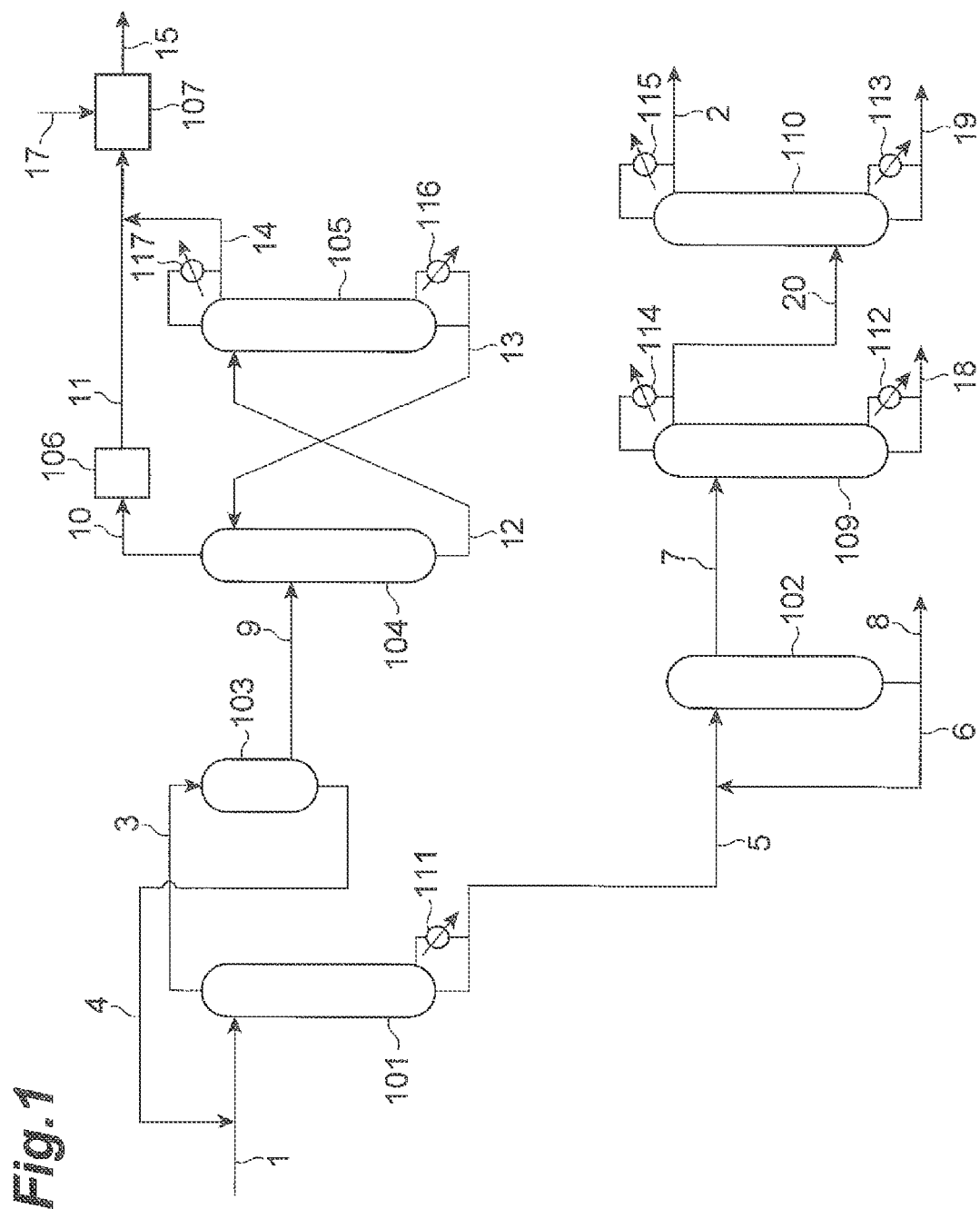
FIG. 1 is a schematic view of an apparatus according to the method for producing an isocyanate of the present embodiment.

Hereinafter, an embodiment for carrying out the present invention (hereinafter referred to as "the present embodiment") will be described in detail. It is to be noted that the present invention is not limited to the following embodiment, and that it can be carried out by being modified in various ways in the range of the gist thereof.

<<Compound Used in the Present Embodiment>>

First, a compound used in the present embodiment will be described.

<Organic Primary Amine>

The organic primary amine used in the present embodiment indicates "the primary amine" (a mono primary amine and a poly primary amine) stipulated by the Regulation C-8 described in Nomenclature (IUPAC Nomenclature of Organic Chemistry) defined by IUPAC (The International Union of Pure and Applied Chemistry). Such an organic amine is represented by the following formula (1). This regulation is based on Recommendations on Organic & Biochemical Nomenclature. Hereinafter, when the IUPAC regulations, and the Nomenclature regulations defined by IUPAC (except for the case of particularly citing IUPAC recommendation in other business years, etc.) are applied in the present application, there is cited "*Yuki Kagaku/Seikagaku Meimeihou* (Nomenclature of Organic Chemistry/Biochemistry)" (Nankodo Co., Ltd., Japan, Revised $2^{nd}$ edition, 1992), which is based on "Edition 1980" that is on the basis of Recommendations 1979 and includes all of the regulations for organic chemistry and biochemistry and the regulations regarding translation into Japanese, published as a supplementary volume of "Kagaku no Ryoiki (Field of Chemistry)," and which includes all of the subsequent revisions and recommendations. The term "organic" is used herein to mean a general group of compounds that are considered as targets of the nomenclature disclosed in the aforementioned publication. The targets may be the same as those described in the recommendations published in 1993. However, the "organic" compound as a target of the above described Nomenclature also includes organic metal compounds and metal complexes. In the present embodiment, "organic" and/or "organic groups" and/or "substituents," as well as the compounds used in the present embodiment will be described below. Such compounds are constituted with atoms excluding metal atoms and/or semi-metal atoms, unless otherwise specified. More preferably, "organic compounds," "organic groups," and "substituents" that are constituted with atoms selected from H (hydrogen atom), C (carbon atom), N (nitrogen atom), O (oxygen atom), S (sulfur atom), Cl (chlorine atom), Br (bromine atom), and I (iodine atom), are used in the present embodiment.

Moreover, in the subsequent descriptions, the terms "aliphatic" and "aromatic" will be frequently used. In accordance with the above-mentioned IUPAC Regulations, organic compounds are classified into aliphatic compounds and aromatic compounds. The aliphatic compounds are defined based on the IUPAC Recommendations in 1995. In the Recommendations, the aliphatic compounds are defined as "Acyclic or cyclic, saturated or unsaturated carbon compounds, excluding aromatic compounds". Furthermore, the aliphatic compounds used in the descriptions of the present embodiment include all of saturated and unsaturated, acyclic and cyclic compounds, and indicate the above described "organic compounds," "organic groups," and "substituents" that are constituted with atoms selected from H (hydrogen atom); C (carbon atom); N (nitrogen atom); O (oxygen atom); S (sulfur atom); Si (silicon atom); a halogen atom selected from Cl (chlorine atom), Br (bromine atom), and I (iodine atom).

When an aromatic group binds to an aliphatic group as in the case of an aralkyl group, such a group is often referred to as an "aliphatic group substituted with an aromatic group" or a "group consisting of an aromatic group-binding aliphatic group". This is based on the reactivity in the present embodiment, and this is because the properties of a group such as an aralkyl group regarding reactivity are extremely similar, not to the reactivity of aromatic compounds, but to that of aliphatic compounds. Further, there may be cases in which a non-aromatic reactive group including an aralkyl group and an alkyl group is often referred to as an "aliphatic group optionally substituted with an aromatic group," "an aliphatic group substituted with an aromatic group," "an aromatic group-binding aliphatic group," etc.

It is to be noted that when the general formulae of the compounds used in the present specification will be described, they are defined using the Nomenclature Regulations defined by the above described IUPAC. However, as names of specific groups and names of exemplified compounds, trivial names are often used. In addition, the number of atoms, the number of substituents, and other numbers are all indicated as integers in the present specification.

[Chemical Formula 1]

wherein $R^1$ represents an organic group containing 1 to 85 carbon atoms, which is substituted with an a number of amino groups, and a represents an integer from 1 to 10.

In the above formula (1), $R^1$ represents an aliphatic group, an aromatic group, and a group formed by binding an aliphatic group to an aromatic group, and thus, $R^1$ represents a group consisting of an acyclic hydrocarbon group, a cyclic hydrocarbon group (for example, a monocyclic hydrocarbon group, a condensed polycyclic hydrocarbon group, a cross-linked cyclic hydrocarbon group, a spiro hydrocarbon group, a multi-ring hydrocarbon group, a cyclic hydrocarbon group having a side chain, a heterocyclic group, a heterocyclic spiro group, a hetero crosslinked cyclic group, and a heterocyclic group), a group to which at least one selected from the acyclic hydrocarbon group and the cyclic hydrocarbon group binds, and a group to which the above described group binds via a covalent bond with specific non-metal atoms (carbon, oxygen, nitrogen, sulfur, and silicon). In addition, the above described covalent bond with specific non-metal atoms (carbon, oxygen, nitrogen, sulfur, and silicon) indicates a condition, in which a group represented by, for example, each of the following formulae (2) to (10) binds to the above described group via a covalent bond.

[Chemical Formula 2]

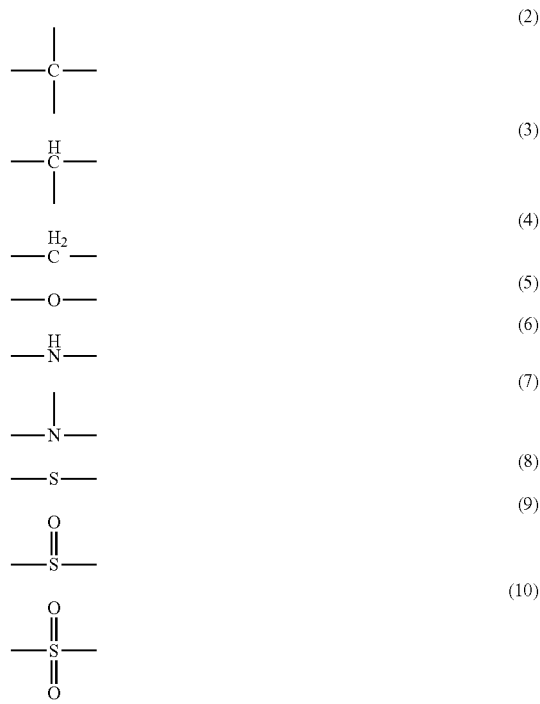

Among these $R^1$ groups, if taking into consideration the unlikeliness of side reactions, the $R^1$ group that can be preferably used in the present embodiment is a group selected from the group consisting of an acyclic hydrocarbon group and a cyclic hydrocarbon group (a monocyclic hydrocarbon group, a condensed polycyclic hydrocarbon group, a crosslinked cyclic hydrocarbon group, a spiro hydrocarbon group, a multi-ring hydrocarbon group, and a cyclic hydrocarbon group having a side chain) which are selected from an aliphatic group, an aromatic group, and a group formed by binding an aliphatic group to an aromatic group, and a group to which at least one group selected from the aforementioned group binds (wherein the two groups are substituted with each other), wherein the above-mentioned group contains 1 to 85 carbon atoms. If taking into consideration flowability and the like, the $R^1$ group is preferably a group containing 1 to 70 carbon atoms, and more preferably a group containing 1 to 13 carbon atoms.

Preferred examples of the organic primary amine constituted with the $R^1$ group include:

1) an aromatic organic mono primary amine, in which the $R^1$ group represents a group containing 6 to 85 carbon atoms, which contains one or more aromatic rings optionally substituted with aliphatic and/or aromatic groups, the aromatic groups in the $R^1$ group are substituted with $NH_2$ groups, and a is 1, 2) an aromatic organic poly primary amine, in which the $R^1$ group represents a group containing 6 to 85 carbon atoms, which contains one or more aromatic rings optionally substituted with aliphatic and/or aromatic groups, the aromatic groups in the $R^1$ group are substituted with $NH_2$ groups, and a is 2 or greater, and 3) an aliphatic organic poly primary amine, in which the $R^1$ group represents an aliphatic group containing 1 to 85 carbon atoms, which is optionally substituted with an aromatic group, and a is 2 or 3.

With regard to the above-mentioned organic amines, an organic amine, in which an atom (preferably, a carbon atom) to which an $NH_2$ group binds is contained in the aromatic ring, is referred to as an aromatic organic amine, whereas an organic amine, in which such an atom binds to an atom (mainly, a carbon atom) that is not in the aromatic ring, is referred to as an aliphatic organic amine. Examples of the further preferred aliphatic group include an acyclic hydrocarbon group, a cyclic hydrocarbon group, and a group to which at least one group selected from the acyclic hydrocarbon group and the cyclic hydrocarbon group binds (for example, a cyclic hydrocarbon group substituted with an acyclic hydrocarbon group, an acyclic hydrocarbon group substituted with a cyclic hydrocarbon group, etc.), each of which contains 6 to 70 carbon atoms.

Specific examples of preferred organic primary amines will be given below.

1) Aromatic Organic Mono Primary Amine

A preferred example of the aromatic organic mono primary amine is an aromatic organic mono primary amine, wherein the $R^1$ group is a group containing 6 to 85 carbon atoms, which contains one or more aromatic rings optionally substituted with aliphatic and/or aromatic groups, the aromatic groups in the $R^1$ group are substituted with $NH_2$ groups, and a is an integer of 1. A more preferred example of the aromatic organic mono primary amine is an aromatic organic mono primary amine, wherein the $R^1$ group is a group containing 6 to 70 carbon atoms and a is 1. If taking into consideration flowability and the like, a further preferred example is an aromatic organic mono primary amine, wherein the $R^1$ group is a group containing 6 to 13 carbon atoms, which contains one or more aromatic rings "substituted with $NH_2$ groups," and a is 1, and it is an aromatic organic mono primary amine represented by the following formula (11):

[Chemical Formula 3]

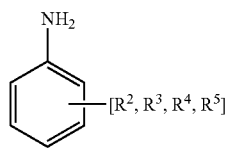

(11)

At least one of the ortho-position and/or para-position of the $NH_2$ group of the aromatic organic mono primary amine represented by the above formula (11) is unsubstituted, and each of the $R^2$ to $R^5$ groups represents a group substituted in any given position at which the aromaticity of the ring is maintained, and the $R^2$ to $R^5$ groups may independently substitute an aromatic ring, or the $R^2$ to $R^5$ groups may bind to one another to form a ring together with an aromatic ring, and further, each of the $R^2$ to $R^5$ groups represents a hydrogen atom, or a group selected from the group consisting of an alkyl group, a cycloalkyl group and an aryl group, and a group to which a group selected from the above described groups binds via a saturated aliphatic bond and/or an ether bond, wherein the number of carbon atoms contained in each of the $R^2$ to $R^5$ groups is an integer from 0 to 7, and the total number of carbon atoms constituting the aromatic organic mono primary amine represented by the above formula (11) is from 6 to 13.

A more preferred example of the aromatic organic mono primary amine represented by the formula (11) is an aromatic organic mono primary amine, wherein the $R^2$ to $R^5$ groups each represent a hydrogen atom, or a group selected from alkyl groups such as a methyl group and an ethyl group, and examples of such an aromatic organic mono primary amine include aniline, aminotoluene (each isomer), dimethylaniline (each isomer), diethylaniline (each isomer), dipropylaniline (each isomer), aminonaphthalene (each isomer), aminomethylnaphthalene (each isomer), dimethylnaphthylamine (each isomer), and trimethylnaphthylamine (each isomer). Of these, aniline is more preferably used.

2) Aromatic Organic Poly Primary Amine

A preferred example of the aromatic organic poly primary amine is an aromatic organic poly primary amine, wherein the $R^1$ group is a group containing 6 to 85 carbon atoms, which contains one or more aromatic rings optionally substituted with aliphatic and/or aromatic groups, the aromatic groups in the $R^1$ group are substituted with $NH_2$ groups, and a is 2 or greater. A more preferred example of the aromatic organic poly primary amine is an aromatic organic poly primary amine, wherein the $R^1$ group is a group containing 6 to 70 carbon atoms and a is 2 or greater. If taking into consideration flowability and the like, a further preferred example is an aromatic organic poly primary amine, wherein the $R^1$ group is a group containing 6 to 13 carbon atoms, which contains one or more aromatic rings "substituted with $NH_2$ groups," wherein the aromatic rings are further optionally substituted with alkyl groups, aryl groups or aralkyl groups, and a is 2 or greater. Examples of such an aromatic organic poly primary amine include diaminobenzene (each isomer), diaminotoluene (each isomer), methylenedianiline (each isomer), diaminomesitylene (each isomer), diaminobiphenyl (each isomer), diaminodibenzyl (each isomer), bis(aminophenyl)propane (each isomer), bis(aminophenyl) ether (each isomer), bis(aminophenoxyethane) (each isomer), diaminoxylene (each isomer), diaminoanisole (each isomer), diaminophenetole (each isomer), diaminonaphthalene (each isomer), diamino-methylbenzene (each isomer), diamino-methylpyridine (each isomer), diamino-methylnaphthalene (each isomer), and polymethylenepolyphenylpolyamine represented by the following formula (12):

[Chemical Formula 4]

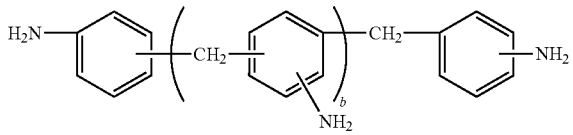

(12)

wherein b represents an integer from 0 to 6.

3) Aliphatic Organic Poly Primary Amine

A preferred example of the aliphatic organic poly primary amine is an aliphatic organic poly primary amine, wherein the $R^1$ group of the organic amine represented by the above formula (1) is an aliphatic group containing an integer from 1 to 85 carbon atoms, which is optionally substituted with an aromatic group, and a is 2 or 3. A more preferred example of the aliphatic organic poly primary amine is an aliphatic organic poly primary amine, wherein the aliphatic group represents an acyclic hydrocarbon group, a cyclic hydrocarbon group, and a group to which at least one group selected from the acyclic hydrocarbon group and the cyclic hydrocarbon group binds (for example, a cyclic hydrocarbon group substituted with an acyclic hydrocarbon group, an acyclic hydrocarbon group substituted with a cyclic hydrocarbon group, etc.). A further preferred example of the aliphatic organic poly primary amine is an aliphatic organic poly primary amine, wherein the $R^1$ group is an aliphatic group, and the aliphatic group represents an acyclic hydrocarbon group, a cyclic hydrocarbon group, and a group to which at least one group selected from the acyclic hydrocarbon group and the cyclic hydrocarbon group binds (for example, a cyclic hydrocarbon group substituted with an acyclic hydrocarbon group, an acyclic hydrocarbon group substituted with a cyclic hydrocarbon group, etc.), each of which contains 1 to 70 carbon atoms, and a is 2 or 3. Taking into consideration flowability necessary for industrial mass production, a most preferred example of the aliphatic organic poly primary amine is an aliphatic organic poly primary amine, wherein the $R^1$ group represents an acyclic hydrocarbon group, a cyclic hydrocarbon group, and a group to which at least one group selected from the acyclic hydrocarbon group and the cyclic hydrocarbon group binds (e.g. a cyclic hydrocarbon group substituted with an acyclic hydrocarbon, an acyclic hydrocarbon group substituted with a cyclic hydrocarbon group, etc.), each of which is constituted with carbon atoms and hydrogen atoms, and each of which contains 6 to 13 carbon atoms. That is to say, the case is an aliphatic organic poly primary amine, wherein the $R^1$ group is a straight chain and/or branched chain alkyl group, a cycloalkyl group, and a group constituted with the alkyl group and the cycloalkyl group. Examples of such groups include: aliphatic di-primary amines such as ethylenediamine, diaminopropane (each isomer), diaminobutane (each isomer), diaminopentane (each isomer), diaminohexane (each isomer), and diaminodecane (each isomer); aliphatic triamines such as triaminohexane (each isomer), triaminononane (each isomer), and triaminodecane (each isomer); and substituted cyclic aliphatic polyamines such as diaminocyclobutane (each isomer), diaminocyclohexane (each isomer), 3-aminomethyl-3,5,5-trimethylcyclohexylamine (cis and/or trans forms), and methylenebis(cyclohexylamine) (each isomer).

<Carbonic Acid Derivative>

The carbonic acid derivative used in the present embodiment indicates a compound represented by the following formula (13). The carbonic acid derivative is a compound that may be used in the production of carbamates. Among others, urea and an N-unsubstituted carbamate are components, which are used as raw materials for the production of carbamates, together with an organic primary amine and an organic hydroxy compound.

[Chemical Formula 5]

(13)

wherein X and Y independently represent an organic group containing 1 to 20 carbon atoms, or a group containing 0 to 20 carbon atoms and having an amino group.

Examples of the compound represented by the above formula (13) include a urea compound, an N-unsubstituted carbamate, and a carbonic acid ester.

(Urea Compound)

The urea compound is a compound having at least one urea bond in a molecule thereof. Preferably, the urea compound is a compound having one urea bond, which is represented by the following formula (14):

[Chemical Formula 6]

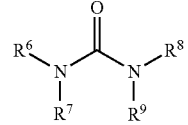

(14)

wherein $R^6$, $R^7$, $R^8$ and $R^9$ independently represent an aliphatic group containing 1 to 20 carbon atoms, an aliphatic group containing 7 to 20 carbon atoms, which is substituted with an aromatic compound, an aromatic group containing 6 to 20 carbon atoms, or a hydrogen atom, wherein the total number of carbon atoms constituting $R^6$ and $R^7$ is an integer from 0 to 20, and the total number of carbon atoms constituting $R^8$ and $R^9$ is an integer from 0 to 20.

Examples of $R^6$, $R^7$, $R^8$ and $R^9$ include:

alkyl groups such as a hydrogen atom, a methyl group, an ethyl group, a propyl group (each isomer), a butyl group (each isomer), a pentyl group (each isomer), a hexyl group (each isomer), a heptyl group (each isomer), an octyl group (each isomer), a nonyl group (each isomer), a decyl group (each isomer), an undecyl group (each isomer), a dodecyl group (each isomer), a tridecyl group (each isomer), a tetradecyl group (each isomer), a pentadecyl group (each isomer), a hexadecyl group (each isomer), a heptadecyl group (each isomer), an octadecyl group (each isomer), and a nonadecyl (each isomer);

aryl groups containing 6 to 20 carbon atoms which constitute the below-mentioned groups, such as a phenyl group, a methylphenyl group (each isomer), an ethylphenyl group (each isomer), a propylphenyl group (each isomer), a butylphenyl group (each isomer), a pentylphenyl group (each isomer), a hexylphenyl group (each isomer), a heptylphenyl group (each isomer), an octylphenyl group (each isomer), a nonylphenyl group (each isomer), a decylphenyl group (each isomer), a biphenyl group (each isomer), a dimethylphenyl group (each isomer), a diethylphenyl group (each isomer), a dipropylphenyl group (each isomer), a dibutylphenyl group (each isomer), a dipentylphenyl group (each isomer), a dihexylphenyl group (each isomer), a diheptylphenyl group (each isomer), a terphenyl group (each isomer), a trimethylphenyl group (each isomer), a triethylphenyl group (each isomer), a tripropylphenyl group (each isomer), and a tributylphenyl group (each isomer); and aralkyl groups containing 7 to 20 carbon atoms which constitute the below-mentioned groups, such as a phenylmethyl group, a phenylethyl group (each isomer), a phenylpropyl group (each isomer), a phenylbutyl group (each isomer), a phenylpentyl group (each isomer), a phenylhexyl group (each isomer), a phenylheptyl group (each isomer), a phenyloctyl group (each isomer), and a phenylnonyl group (each isomer).

Specific examples include urea, methyl urea, ethyl urea, propyl urea (each isomer), butyl urea (each isomer), pentyl urea (each isomer), hexyl urea (each isomer), heptyl urea (each isomer), octyl urea (each isomer), nonyl urea (each isomer), decyl urea (each isomer), undecyl urea (each isomer), dodecyl urea (each isomer), tridecyl urea (each isomer), tetradecyl urea (each isomer), pentadecyl urea (each isomer), hexadecyl urea (each isomer), heptadecyl urea (each isomer), octadecyl urea (each isomer), nonadecyl urea (each isomer), phenyl urea, N-(methylphenyl)urea (each isomer), N-(ethylphenyl)urea (each isomer), N-(propylphenyl)urea (each isomer), N-(butylphenyl)urea (each isomer), N-(pentylphenyl)urea (each isomer), N-(hexylphenyl)urea (each isomer), N-(heptylphenyl)urea (each isomer), N-(octylphenyl)urea (each isomer), N-(nonylphenyl)urea (each isomer), N-(decylphenyl)urea (each isomer), N-biphenyl urea (each isomer), N-(dimethylphenyl)urea (each isomer), N-(diethylphenyl)urea (each isomer), N-(dipropylphenyl) urea (each isomer), N-(dibutylphenyl)urea (each isomer), N-(dipentylphenyl)urea (each isomer), N-(dihexylphenyl) urea (each isomer), N-(diheptylphenyl)urea (each isomer), N-terphenyl urea (each isomer), N-(trimethylphenyl)urea (each isomer), N-(triethylphenyl)urea (each isomer), N-(tripropylphenyl)urea (each isomer), N-(tributylphenyl) urea (each isomer), N-(phenylmethyl)urea, N-(phenylethyl) urea (each isomer), N-(phenylpropyl)urea (each isomer), N-(phenylbutyl)urea (each isomer), N-(phenylpentyl)urea (each isomer), N-(phenylhexyl)urea (each isomer), N-(phenylheptyl)urea (each isomer), N-(phenyloctyl)urea (each isomer), N-(phenylnonyl)urea (each isomer), dimethyl urea (each isomer), diethyl urea (each isomer), dipropyl urea (each isomer), dibutyl urea (each isomer), dipentyl urea (each isomer), dihexyl urea (each isomer), diheptyl urea (each isomer), dioctyl urea (each isomer), dinonyl urea (each isomer), didecyl urea (each isomer), diundecyl urea (each isomer), didodecyl urea (each isomer), ditridecyl urea (each isomer), ditetradecyl urea (each isomer), dipentadecyl urea (each isomer), dihexadecyl urea (each isomer), diheptadecyl urea (each isomer), dioctadecyl urea (each isomer), dinonadecyl (each isomer), diphenyl urea, di(methylphenyl)urea (each isomer), di(ethylphenyl)urea (each isomer), di(propylphenyl)urea (each isomer), di(butylphenyl)urea (each isomer), di(pentylphenyl)urea (each isomer), di(hexylphenyl) urea (each isomer), di(heptylphenyl)urea (each isomer), di(octylphenyl)urea (each isomer), di(nonylphenyl)urea (each isomer), di(decylphenyl)urea (each isomer), di(biphenyl)urea (each isomer), di(dimethylphenyl)urea (each isomer), di(diethylphenyl)urea (each isomer), di(dipropylphenyl)urea (each isomer), di(dibutylphenyl)urea (each isomer), di(dipentylphenyl)urea (each isomer), di(dihexylphenyl)urea (each isomer), di(diheptylphenyl)urea (each isomer), di(terphenyl)urea (each isomer), di(trimethylphenyl)urea (each isomer), di(triethylphenyl)urea (each isomer), di(tripropylphenyl)urea (each isomer), di(tributylphenyl)urea (each isomer), di(phenylmethyl)urea, di(phenylethyl) urea (each isomer), di(phenylpropyl)urea (each isomer), di(phenylbutyl)urea (each isomer), di(phenylpentyl)urea (each isomer), di(phenylhexyl)urea (each isomer), di(phenylheptyl)urea (each isomer), di(phenyloctyl)urea (each isomer), and di(phenylnonyl)urea (each isomer). Among these compounds, urea, wherein, in the above formula (14), $R^6$, $R^7$, $R^8$ and $R^9$ each represent a hydrogen atom, is preferably used. The urea may comprise biuret, triuret and cyanuric acid. However, in general, the solubility of biuret, triuret and cyanuric acid in a solvent is low. Since a homogeneous solution is preferably used upon the transfer of raw materials or a reaction solution, the content of such a substance is preferably as small as possible. Moreover, the melting point of urea is 135° C., and thus, the urea is a solid when it is treated at ordinary temperature, but the form of the urea is not particularly limited, and it can be used, for example, in a powdery form or a granular form.

(N-Unsubstituted Carbamate)

A compound represented by the following formula (15) is preferably used as an N-unsubstituted carbamate.

[Chemical Formula 7]

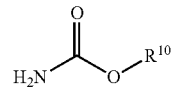

(15)

wherein $R^{10}$ represents an aliphatic group containing 1 to 20 carbon atoms, an aralkyl group containing 7 to 20 carbon atoms, or an aromatic group containing 6 to 20 carbon atoms.

Examples of such $R^{10}$ include:

alkyl groups containing 1 to 20 carbon atoms which constitute the below-mentioned groups, such as a methyl group, an ethyl group, a propyl group (each isomer), a butyl group (each isomer), a pentyl group (each isomer), a hexyl group (each isomer), a heptyl group (each isomer), an octyl group (each isomer), a nonyl group (each isomer), a decyl group (each isomer), an undecyl group (each isomer), a dodecyl group (each isomer), a tridecyl group (each isomer), a tetradecyl group (each isomer), a pentadecyl group (each isomer), a hexadecyl group (each isomer), a heptadecyl group (each isomer), an octadecyl group (each isomer), a nonadecyl (each isomer), and an eicosyl group (each isomer);

aryl groups containing 6 to 20 carbon atoms which constitute the below-mentioned groups, such as a phenyl group, a methylphenyl group (each isomer), an ethylphenyl group (each isomer), a propylphenyl group (each isomer), a butylphenyl group (each isomer), a pentylphenyl group (each isomer), a hexylphenyl group (each isomer), a heptylphenyl group (each isomer), an octylphenyl group (each isomer), a nonylphenyl group (each isomer), a decylphenyl group (each isomer), a biphenyl group (each isomer), a dimethylphenyl group (each isomer), a diethylphenyl group (each isomer), a dipropylphenyl group (each isomer), a dibutylphenyl group (each isomer), a dipentylphenyl group (each isomer), a dihexylphenyl group (each isomer), a diheptylphenyl group (each isomer), a terphenyl group (each isomer), a trimethylphenyl group (each isomer), a triethylphenyl group (each isomer), a tripropylphenyl group (each isomer), and a tributylphenyl group (each isomer); and aralkyl groups containing 7 to 20 carbon atoms which constitute the below-mentioned groups, such as a phenylmethyl group, a phenylethyl group (each isomer), phenylpropyl group (each isomer), a phenylbutyl group (each isomer), a phenylpentyl group (each isomer), a phenylhexyl group (each isomer), a phenylheptyl group (each isomer), a phenyloctyl group (each isomer), and a phenylnonyl group (each isomer).

Specific examples include methyl carbamate, ethyl carbamate, propyl carbamate (each isomer), butyl carbamate (each isomer), pentyl carbamate (each isomer), hexyl carbamate (each isomer), heptyl carbamate (each isomer), octyl carbamate (each isomer), nonyl carbamate (each isomer), decyl carbamate (each isomer), undecyl carbamate (each isomer), dodecyl carbamate (each isomer), tridecyl carbamate (each isomer), tetradecyl carbamate (each isomer), pentadecyl carbamate (each isomer), hexadecyl carbamate (each isomer), heptadecyl carbamate (each isomer), octadecyl carbamate (each isomer), nonadecyl carbamate (each isomer), phenyl carbamate, methylphenyl carbamate (each isomer), ethylphenyl carbamate (each isomer), propylphenyl carbamate (each isomer), butylphenyl carbamate (each isomer), pentylphenyl carbamate (each isomer), hexylphenyl carbamate (each isomer), heptylphenyl carbamate (each isomer), octylphenyl carbamate (each isomer), nonylphenyl carbamate (each isomer), decylphenyl carbamate (each isomer), biphenyl carbamate (each isomer), dimethylphenyl carbamate (each isomer), diethylphenyl carbamate (each isomer), dipropylphenyl carbamate (each isomer), dibutylphenyl carbamate (each isomer), dipentylphenyl carbamate (each isomer), dihexylphenyl carbamate (each isomer), diheptylphenyl carbamate (each isomer), terphenyl carbamate (each isomer), trimethylphenyl carbamate (each isomer), triethylphenyl carbamate (each isomer), tripropylphenyl carbamate (each isomer), tributylphenyl carbamate (each isomer), phenylmethyl carbamate, phenylethyl carbamate (each isomer), phenylpropyl carbamate (each isomer), phenylbutyl carbamate (each isomer), phenylpentyl carbamate (each isomer), phenylhexyl carbamate (each isomer), phenylheptyl carbamate (each isomer), phenyloctyl carbamate (each isomer), and phenylnonyl carbamate (each isomer).

(Carbonic Acid Ester)

The carbonic acid ester indicates a compound in which one or two hydrogen atoms of carbonic acid, $CO(OH)_2$, are substituted with an aliphatic group or an aromatic group. In the present embodiment, a compound represented by the following formula (16) is preferably used as a carbonic acid ester:

[Chemical Formula 8]

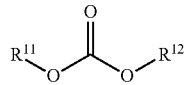

(16)

wherein $R^{11}$ and $R^{12}$ independently represent an aliphatic group containing 1 to 20 carbon atoms, an aralkyl group containing 7 to 20 carbon atoms, or an aromatic group containing 6 to 20 carbon atoms.

Examples of the $R^{11}$ and the $R^{12}$ include:

alkyl groups, such as a methyl group, an ethyl group, a propyl group (each isomer), a butyl group (each isomer), a pentyl group (each isomer), a hexyl group (each isomer), a heptyl group (each isomer), an octyl group (each isomer), a nonyl group (each isomer), a decyl group (each isomer), an undecyl group (each isomer), a dodecyl group (each isomer), a tridecyl group (each isomer), a tetradecyl group (each isomer), a pentadecyl group (each isomer), a hexadecyl group (each isomer), a heptadecyl group (each isomer), an octadecyl group (each isomer), a nonadecyl (each isomer), and an eicosyl group (each isomer);

aryl groups, such as a phenyl group, a methylphenyl group (each isomer), an ethylphenyl group (each isomer), a propylphenyl group (each isomer), a butylphenyl group (each isomer), a pentylphenyl group (each isomer), a hexylphenyl group (each isomer), a heptylphenyl group (each isomer), an octylphenyl group (each isomer), a nonylphenyl group (each isomer), a decylphenyl group (each isomer), a biphenyl group (each isomer), a dimethylphenyl group (each isomer), a diethylphenyl group (each isomer), a dipropylphenyl group (each isomer), a dibutylphenyl group (each isomer), a dipentylphenyl group (each isomer), a dihexylphenyl group (each isomer), a diheptylphenyl group (each isomer), a terphenyl group (each isomer), a trimethylphenyl group (each isomer), a triethylphenyl group (each isomer), a tripropylphenyl group (each isomer), and a tributylphenyl group (each isomer); and aralkyl groups, such as a phenylmethyl group, a phenylethyl group (each isomer), a phenylpropyl group (each isomer), a phenylbutyl group (each isomer), a phenylpentyl group (each isomer), a phenylhexyl group (each isomer), a phenylheptyl group (each isomer), a phenyloctyl group (each isomer), and a phenylnonyl group (each isomer).

Specific examples include dimethyl carbonate, diethyl carbonate, dipropyl carbonate (each isomer), dibutyl carbonate (each isomer), dipentyl carbonate (each isomer), dihexyl carbonate (each isomer), diheptyl carbonate (each isomer), dioctyl carbonate (each isomer), dinonyl carbonate (each isomer), didecyl carbonate (each isomer), diundecyl carbonate (each isomer), didodecyl carbonate (each isomer), ditridecyl carbonate (each isomer), ditetradecyl carbonate (each isomer), dipentadecyl carbonate (each isomer), dihexadecyl carbonate (each isomer), diheptadecyl carbonate (each isomer), dioctadecyl carbonate (each isomer), dinonadecyl carbonate (each isomer), diphenyl carbonate, di(methylphenyl) carbonate (each isomer), di(ethylphenyl) carbonate (each isomer), di(propylphenyl) carbonate (each isomer), di(butylphenyl) carbonate (each isomer), di(pentylphenyl) carbonate (each isomer), di(hexylphenyl) carbonate (each isomer), di(heptylphenyl) carbonate (each isomer), di(octylphenyl) carbonate (each isomer), di(nonylphenyl) carbonate (each isomer), di(decylphenyl) carbonate (each isomer), di(biphenyl) carbonate (each isomer), di(dimethylphenyl) carbonate (each isomer), di(diethylphenyl) carbonate (each isomer), di(dipropylphenyl) carbonate (each isomer), di(dibutylphenyl) carbonate (each isomer), di(dipentylphenyl) carbonate (each isomer), di(dihexylphenyl) carbonate (each isomer), di(diheptylphenyl) carbonate (each isomer), di(phenylphenyl) carbonate (each isomer), di(trimethylphenyl) carbonate (each isomer), di(triethylphenyl) carbonate (each isomer), di(tripropylphenyl) carbonate (each isomer), di(tributylphenyl) carbonate (each isomer), di(phenylmethyl) carbonate, di(phenylethyl) carbonate (each isomer), di(phenylpropyl) carbonate (each isomer), di(phenylbutyl) carbonate (each isomer), di(phenylpentyl) carbonate (each isomer), di(phenylhexyl) carbonate (each isomer), di(phenylheptyl) carbonate (each isomer), di(phenyloctyl) carbonate (each isomer), di(phenylnonyl) carbonate (each isomer), methyl ethyl carbonate, methyl propyl carbonate (each isomer), methyl butyl carbonate (each isomer), methyl pentyl carbonate (each isomer), methyl hexyl carbonate (each isomer), methyl heptyl carbonate (each isomer), methyl octyl carbonate (each isomer), methyl nonyl carbonate (each isomer), methyl decyl carbonate (each isomer), methyl undecyl carbonate (each isomer), methyl dodecyl carbonate (each isomer), methyl tridecyl carbonate (each isomer), methyl tetradecyl carbonate (each isomer), methyl pentadecyl carbonate (each isomer), methyl hexadecyl carbonate (each isomer), methyl heptadecyl carbonate (each isomer), methyl octadecyl carbonate (each isomer), methyl nonadecyl carbonate (each isomer), methyl phenyl carbonate, methyl methylphenyl carbonate (each isomer), methyl ethylphenyl carbonate (each isomer), methyl propylphenyl carbonate (each isomer), methyl butylphenyl carbonate (each isomer), methyl pentylphenyl carbonate (each isomer), methyl hexylphenyl carbonate (each isomer), methyl heptylphenyl carbonate (each isomer), methyl octylphenyl carbonate (each isomer), methyl nonylphenyl carbonate (each isomer), methyl decylphenyl carbonate (each isomer), methyl biphenyl carbonate (each isomer), methyl dimethylphenyl carbonate (each isomer), methyl diethylphenyl carbonate (each isomer), methyl dipropylphenyl carbonate (each isomer), methyl dibutylphenyl carbonate (each isomer), methyl dipentylphenyl carbonate (each isomer), methyl dihexylphenyl carbonate (each isomer), methyl diheptylphenyl carbonate (each isomer), methyl phenylphenyl carbonate (each isomer), methyl trimethylphenyl carbonate (each isomer), methyl triethylphenyl carbonate (each isomer), methyl tripropylphenyl carbonate (each isomer), methyl tributylphenyl carbonate (each isomer), methyl phenylmethyl carbonate, methyl phenylethyl carbonate (each isomer), methyl phenylpropyl carbonate (each isomer), methyl phenylbutyl carbonate (each isomer), methyl phenylpentyl carbonate (each isomer), methyl phenylhexyl carbonate (each isomer), methyl phenylheptyl carbonate (each isomer), methyl phenyloctyl carbonate (each isomer), methyl phenylnonyl carbonate (each isomer), ethyl propyl carbonate (each isomer), ethyl butyl carbonate (each isomer), ethyl pentyl carbonate (each isomer), ethyl hexyl carbonate (each isomer), ethyl heptyl carbonate (each isomer), ethyl octyl carbonate (each isomer), ethyl nonyl carbonate (each isomer), ethyl decyl carbonate (each isomer), ethyl undecyl carbonate (each isomer), ethyl dodecyl carbonate (each isomer), ethyl tridecyl carbonate (each isomer), ethyl tetradecyl carbonate (each isomer), ethyl pentadecyl carbonate (each isomer), ethyl hexadecyl carbonate (each isomer), ethyl heptadecyl carbonate (each isomer), ethyl octadecyl carbonate (each isomer), ethyl nonadecyl carbonate (each isomer), ethyl phenyl carbonate, ethyl methylphenyl carbonate (each isomer), ethyl ethylphenyl carbonate (each isomer), ethyl propylphenyl carbonate (each isomer), ethyl butylphenyl carbonate (each isomer), ethyl pentylphenyl carbonate (each isomer), ethyl hexylphenyl carbonate (each isomer), ethyl heptylphenyl carbonate (each isomer), ethyl octylphenyl carbonate (each isomer), ethyl nonylphenyl carbonate (each isomer), ethyl decylphenyl carbonate (each isomer), ethyl biphenyl carbonate (each isomer), ethyl dimethylphenyl carbonate (each isomer), ethyl diethylphenyl carbonate (each isomer), ethyl dipropylphenyl carbonate (each isomer), ethyl dibutylphenyl carbonate (each isomer), ethyl dipentylphenyl carbonate (each isomer), ethyl dihexylphenyl carbonate (each isomer), ethyl diheptylphenyl carbonate (each isomer), ethyl phenylphenyl carbonate (each isomer), ethyl trimethylphenyl carbonate (each isomer), ethyl triethylphenyl carbonate (each isomer), ethyl tripropylphenyl carbonate (each isomer), ethyl tributylphenyl carbonate (each isomer), ethyl phenylmethyl carbonate, ethyl phenylethyl carbonate (each isomer), ethyl phenylpropyl carbonate (each isomer), ethyl phenylbutyl carbonate (each isomer), ethyl phenylpentyl carbonate (each isomer), ethyl phenylhexyl carbonate (each isomer), ethyl phenylheptyl carbonate (each isomer), ethyl phenyloctyl carbonate (each isomer), ethyl phenylnonyl carbonate (each isomer), propyl butyl carbonate (each isomer), propyl pentyl carbonate (each isomer), propyl hexyl carbonate (each isomer), propyl heptyl carbonate (each isomer), propyl octyl carbonate (each isomer), propyl nonyl carbonate (each isomer), propyl decyl carbonate (each isomer), propyl undecyl carbonate (each isomer), propyl dodecyl carbonate (each isomer), propyl tridecyl carbonate (each isomer), propyl tetradecyl carbonate (each isomer), propyl pentadecyl carbonate (each isomer), propyl hexadecyl carbonate (each isomer), propyl heptadecyl carbonate (each isomer), propyl octadecyl carbonate (each isomer), propyl nonadecyl carbonate (each isomer), propyl phenyl carbonate (each isomer), propyl methylphenyl carbonate (each isomer), propyl ethylphenyl carbonate (each isomer), propyl propylphenyl carbonate (each isomer), propyl butylphenyl carbonate (each isomer), propyl pentylphenyl carbonate (each isomer), propyl hexylphenyl carbonate (each isomer), propyl heptylphenyl carbonate (each isomer), propyl octylphenyl carbonate (each isomer), propyl nonylphenyl carbonate (each isomer), propyl decylphenyl carbonate (each isomer), propyl biphenyl carbonate (each isomer), propyl dimethylphenyl carbonate (each isomer), propyl diethylphenyl carbonate (each isomer), propyl dipropylphenyl carbonate (each isomer), propyl dibutylphenyl carbonate (each isomer), propyl dipentylphenyl carbonate (each isomer), propyl dihexylphenyl carbonate (each isomer), propyl diheptylphenyl carbonate (each isomer), propyl phenylphenyl carbonate (each isomer), propyl trimethylphenyl carbonate (each isomer), propyl triethylphenyl carbonate (each isomer), propyl tripropylphenyl carbonate (each isomer), propyl tributylphenyl carbonate (each isomer), propyl phenylmethyl carbonate, propyl phenylethyl carbonate (each isomer), propyl phenylpropyl carbonate (each isomer), propyl phenylbutyl carbonate (each isomer), propyl phenylpentyl carbonate (each isomer), propyl phenylhexyl carbonate (each isomer), propyl phenylheptyl carbonate (each isomer), propyl phenyloctyl carbonate (each isomer), propyl phenylnonyl carbonate (each isomer), butyl pentyl carbonate (each isomer), butyl hexyl carbonate (each isomer), butyl heptyl carbonate (each isomer), butyl octyl carbonate (each isomer), butyl nonyl carbonate (each isomer), butyl decyl carbonate (each isomer), butyl undecyl carbonate (each isomer), butyl dodecyl carbonate (each isomer), butyl tridecyl carbonate (each isomer), butyl tetradecyl carbonate (each isomer), butyl pentadecyl carbonate (each isomer), butyl hexadecyl carbonate (each isomer), butyl heptadecyl carbonate (each isomer), butyl octadecyl carbonate (each isomer), butyl nonadecyl carbonate (each isomer), butyl phenyl carbonate (each isomer), butyl methylphenyl carbonate (each isomer), butyl ethylphenyl carbonate (each isomer), butyl propylphenyl carbonate (each isomer), butyl butylphenyl carbonate (each isomer), butyl pentylphenyl carbonate (each isomer), butyl hexylphenyl carbonate (each isomer), butyl heptylphenyl carbonate (each isomer), butyl octylphenyl carbonate (each isomer), butyl nonylphenyl carbonate (each isomer), butyl decylphenyl carbonate (each isomer), butyl biphenyl carbonate (each isomer), butyl dimethylphenyl carbonate (each isomer), butyl diethylphenyl carbonate (each isomer), butyl dipropylphenyl carbonate (each isomer), butyl dibutylphenyl carbonate (each isomer), butyl dipentylphenyl carbonate (each isomer), butyl dihexylphenyl carbonate (each isomer), butyl diheptylphenyl carbonate (each isomer), butyl phenylphenyl carbonate (each isomer), butyl trimethylphenyl carbonate (each isomer), butyl triethylphenyl carbonate (each isomer), butyl tripropylphenyl carbonate (each isomer), butyl tributylphenyl carbonate (each isomer), butyl phenylmethyl carbonate, butyl phenylethyl carbonate (each isomer), butyl phenylpropyl carbonate (each isomer), butyl phenylbutyl carbonate (each isomer), butyl phenylpentyl carbonate (each isomer), butyl phenylhexyl carbonate (each isomer), butyl phenylheptyl carbonate (each isomer), butyl phenyloctyl carbonate (each isomer), butyl phenylnonyl carbonate (each isomer), pentyl hexyl carbonate (each isomer), pentyl heptyl carbonate (each isomer), pentyl octyl carbonate (each isomer), pentyl nonyl carbonate (each isomer), pentyl decyl carbonate (each isomer), pentyl undecyl carbonate (each isomer), pentyl dodecyl carbonate (each isomer), pentyl tridecyl carbonate (each isomer), pentyl tetradecyl carbonate (each isomer), pentyl pentadecyl carbonate (each isomer), pentyl hexadecyl carbonate (each isomer), pentyl heptadecyl carbonate (each isomer), pentyl octadecyl carbonate (each isomer), pentyl nonadecyl carbonate (each isomer), pentyl phenyl carbonate (each isomer), pentyl methylphenyl carbonate (each isomer), pentyl ethylphenyl carbonate (each isomer), pentyl propylphenyl carbonate (each isomer), pentyl butylphenyl carbonate (each isomer), pentyl pentylphenyl carbonate (each isomer), pentyl hexylphenyl carbonate (each isomer), pentyl heptylphenyl carbonate (each isomer), pentyl octylphenyl carbonate (each isomer), pentyl nonylphenyl carbonate (each isomer), pentyl decylphenyl carbonate (each isomer), pentyl biphenyl carbonate (each isomer), pentyl dimethylphenyl carbonate (each isomer), pentyl diethylphenyl carbonate (each isomer), pentyl dipropylphenyl carbonate (each isomer), pentyl dibutylphenyl carbonate (each isomer), pentyl dipentylphenyl carbonate (each isomer), pentyl dihexylphenyl carbonate (each isomer), pentyl diheptylphenyl carbonate (each isomer), pentyl phenylphenyl carbonate (each isomer), pentyl trimethylphenyl carbonate (each isomer), pentyl triethylphenyl carbonate (each isomer), pentyl tripropylphenyl carbonate (each isomer), pentyl tributylphenyl carbonate (each isomer), pentyl phenylmethyl carbonate, pentyl phenylethyl carbonate (each isomer), pentyl phenylpropyl carbonate (each isomer), pentyl phenylbutyl carbonate (each isomer), pentyl phenylpentyl carbonate (each isomer), pentyl phenylhexyl carbonate (each isomer), pentyl phenylheptyl carbonate (each isomer), pentyl phenyloctyl carbonate (each isomer), pentyl phenylnonyl carbonate (each isomer), hexyl heptyl carbonate (each isomer), hexyl octyl carbonate (each isomer), hexyl nonyl carbonate (each isomer), hexyl decyl carbonate (each isomer), hexyl undecyl carbonate (each isomer), hexyl dodecyl carbonate (each isomer), hexyl tridecyl carbonate (each isomer), hexyl tetradecyl carbonate (each isomer), hexyl pentadecyl carbonate (each isomer), hexyl hexadecyl carbonate (each isomer), hexyl heptadecyl carbonate (each isomer), hexyl octadecyl carbonate (each isomer), hexyl nonadecyl carbonate (each isomer), hexyl phenyl carbonate (each isomer), hexyl methylphenyl carbonate (each isomer), hexyl ethylphenyl carbonate (each isomer), hexyl propylphenyl carbonate (each isomer), hexyl butylphenyl carbonate (each isomer), hexyl pentylphenyl carbonate (each isomer), hexyl hexylphenyl carbonate (each isomer), hexyl heptylphenyl carbonate (each isomer), hexyl octylphenyl carbonate (each isomer), hexyl nonylphenyl carbonate (each isomer), hexyl decylphenyl carbonate (each isomer), hexyl biphenyl carbonate (each isomer), hexyl dimethylphenyl carbonate (each isomer), hexyl diethylphenyl carbonate (each isomer), hexyl dipropylphenyl carbonate (each isomer), hexyl dibutylphenyl carbonate (each isomer), hexyl dipentylphenyl carbonate (each isomer), hexyl dihexylphenyl carbonate (each isomer), hexyl diheptylphenyl carbonate (each isomer), hexyl phenylphenyl carbonate (each isomer), hexyl trimethylphenyl carbonate (each isomer), hexyl triethylphenyl carbonate (each isomer), hexyl tripropylphenyl carbonate (each isomer), hexyl tributylphenyl carbonate (each isomer), hexyl phenylmethyl carbonate, hexyl phenylethyl carbonate (each isomer), hexyl phenylpropyl carbonate (each isomer), hexyl phenylbutyl carbonate (each isomer), hexyl phenylpentyl carbonate (each isomer), hexyl phenylhexyl carbonate (each isomer), hexyl phenylheptyl carbonate (each isomer), hexyl phenyloctyl carbonate (each isomer), hexyl phenylnonyl carbonate (each isomer), heptyl octyl carbonate (each isomer), heptyl nonyl carbonate (each isomer), heptyl decyl carbonate (each isomer), heptyl undecyl carbonate (each isomer), heptyl dodecyl carbonate (each isomer), heptyl tridecyl carbonate (each isomer), heptyl tetradecyl carbonate (each isomer), heptyl pentadecyl carbonate (each isomer), heptyl hexadecyl carbonate (each isomer), heptyl heptadecyl carbonate (each isomer), heptyl octadecyl carbonate (each isomer), heptyl nonadecyl carbonate (each isomer), heptyl phenyl carbonate (each isomer), heptyl methylphenyl carbonate (each isomer), heptyl ethylphenyl carbonate (each isomer), heptyl propylphenyl carbonate (each isomer), heptyl butylphenyl carbonate (each isomer), heptyl pentylphenyl carbonate (each isomer), heptyl hexylphenyl carbonate (each isomer), heptyl heptylphenyl carbonate (each isomer), heptyl octylphenyl carbonate (each isomer), heptyl nonylphenyl carbonate (each isomer), heptyl decylphenyl carbonate (each isomer), heptyl biphenyl carbonate (each isomer), heptyl dimethylphenyl carbonate (each isomer), heptyl diethylphenyl carbonate (each isomer), heptyl dipropylphenyl carbonate (each isomer), heptyl dibutylphenyl carbonate (each isomer), heptyl dipentylphenyl carbonate (each isomer), heptyl dihexylphenyl carbonate (each isomer), heptyl diheptylphenyl carbonate (each isomer), heptyl phenylphenyl carbonate (each isomer), heptyl trimethylphenyl carbonate (each isomer), heptyl triethylphenyl carbonate (each isomer), heptyl tripropylphenyl carbonate (each isomer), heptyl tributylphenyl carbonate (each isomer), heptyl phenylmethyl carbonate, heptyl phenylethyl carbonate (each isomer), heptyl phenylpropyl carbonate (each isomer), heptyl phenylbutyl carbonate (each isomer), heptyl phenylpentyl carbonate (each isomer), heptyl phenylhexyl carbonate (each isomer), heptyl phenylheptyl carbonate (each isomer), heptyl phenyloctyl carbonate (each isomer), heptyl phenylnonyl carbonate (each isomer), octyl nonyl carbonate (each isomer), octyl decyl carbonate (each isomer), octyl undecyl carbonate (each isomer), octyl dodecyl carbonate (each isomer), octyl tridecyl carbonate (each isomer), octyl tetradecyl carbonate (each isomer), octyl pentadecyl carbonate (each isomer), octyl hexadecyl carbonate (each isomer), octyl heptadecyl carbonate (each isomer), octyl octadecyl carbonate (each isomer), octyl nonadecyl carbonate (each isomer), octyl phenyl carbonate (each isomer), octyl methylphenyl carbonate (each isomer), octyl ethylphenyl carbonate (each isomer), octyl propylphenyl carbonate (each isomer), octyl butylphenyl carbonate (each isomer), octyl pentylphenyl carbonate (each isomer), octyl hexylphenyl carbonate (each isomer), octyl heptylphenyl carbonate (each isomer), octyl octylphenyl carbonate (each isomer), octyl nonylphenyl carbonate (each isomer), octyl decylphenyl carbonate (each isomer), octyl biphenyl carbonate (each isomer), octyl dimethylphenyl carbonate (each isomer), octyl diethylphenyl carbonate (each isomer), octyl dipropylphenyl carbonate (each isomer), octyl dibutylphenyl carbonate (each isomer), octyl dipentylphenyl carbonate (each isomer), octyl dihexylphenyl carbonate (each isomer), octyl diheptylphenyl carbonate (each isomer), octyl phenylphenyl carbonate (each isomer), octyl trimethylphenyl carbonate (each isomer), octyl triethylphenyl carbonate (each isomer), octyl tripropylphenyl carbonate (each isomer), octyl tributylphenyl carbonate (each isomer), octyl phenylmethyl carbonate, octyl phenylethyl carbonate (each isomer), octyl phenylpropyl carbonate (each isomer), octyl phenylbutyl carbonate (each isomer), octyl phenylpentyl carbonate (each isomer), octyl phenylhexyl carbonate (each isomer), octyl phenylheptyl carbonate (each isomer), octyl phenyloctyl carbonate (each isomer), octyl phenylnonyl carbonate (each isomer), methylphenyl ethylphenyl carbonate (each isomer), methylphenyl propylphenyl carbonate (each isomer), methylphenyl butylphenyl carbonate (each isomer), methylphenyl pentylphenyl carbonate (each isomer), methylphenyl hexylphenyl carbonate (each isomer), methylphenyl heptylphenyl carbonate (each isomer), methylphenyl octylphenyl carbonate (each isomer), methylphenyl nonylphenyl carbonate (each isomer), methylphenyl decylphenyl carbonate (each isomer), methylphenyl biphenyl carbonate (each isomer), methylphenyl dimethylphenyl carbonate (each isomer), methylphenyl diethylphenyl carbonate (each isomer), methylphenyl dipropylphenyl carbonate (each isomer), methylphenyl dibutylphenyl carbonate (each isomer), methylphenyl dipentylphenyl carbonate (each isomer), methylphenyl dihexylphenyl carbonate (each isomer), methylphenyl diheptylphenyl carbonate (each isomer), methylphenyl phenylphenyl carbonate (each isomer), methylphenyl trimethylphenyl carbonate (each isomer), methylphenyl triethylphenyl carbonate (each isomer), methylphenyl tripropylphenyl carbonate (each isomer), methylphenyl tributylphenyl carbonate (each isomer), methylphenyl phenylmethyl carbonate, methylphenyl phenylethyl carbonate (each isomer), methylphenyl phenylpropyl carbonate (each isomer), methylphenyl phenylbutyl carbonate (each isomer), methylphenyl phenylpentyl carbonate (each isomer), methylphenyl phenylhexyl carbonate (each isomer), methylphenyl phenylheptyl carbonate (each isomer), methylphenyl phenyloctyl carbonate (each isomer), methylphenyl phenylnonyl carbonate (each isomer), ethylphenyl propylphenyl carbonate (each isomer), ethylphenyl butylphenyl carbonate (each isomer), ethylphenyl pentylphenyl carbonate (each isomer), ethylphenyl hexylphenyl carbonate (each isomer), ethylphenyl heptylphenyl carbonate (each isomer), ethylphenyl octylphenyl carbonate (each isomer), ethylphenyl nonylphenyl carbonate (each isomer), ethylphenyl decylphenyl carbonate (each isomer), ethylphenyl biphenyl carbonate (each isomer), ethylphenyl dimethylphenyl carbonate (each isomer), ethylphenyl diethylphenyl carbonate (each isomer), ethylphenyl dipropylphenyl carbonate (each isomer), ethylphenyl dibutylphenyl carbonate (each isomer), ethylphenyl dipentylphenyl carbonate (each isomer), ethylphenyl dihexylphenyl carbonate (each isomer), ethylphenyl diheptylphenyl carbonate (each isomer), ethylphenyl phenylphenyl carbonate (each isomer), ethylphenyl trimethylphenyl carbonate (each isomer), ethylphenyl triethylphenyl carbonate (each isomer), ethylphenyl tripropylphenyl carbonate (each isomer), ethylphenyl tributylphenyl carbonate (each isomer), ethylphenyl phenylmethyl carbonate, ethylphenyl phenylethyl carbonate (each isomer), ethylphenyl phenylpropyl carbonate (each isomer), ethylphenyl phenylbutyl carbonate (each isomer), ethylphenyl phenylpentyl carbonate (each isomer), ethylphenyl phenylhexyl carbonate (each isomer), ethylphenyl phenylheptyl carbonate (each isomer), ethylphenyl phenyloctyl carbonate (each isomer), ethylphenyl phenylnonyl carbonate (each isomer), propylphenyl propylphenyl carbonate (each isomer), propylphenyl butylphenyl carbonate (each isomer), propylphenyl pentylphenyl carbonate (each isomer), propylphenyl hexylphenyl carbonate (each isomer), propylphenyl heptylphenyl carbonate (each isomer), propylphenyl octylphenyl carbonate (each isomer), propylphenyl nonylphenyl carbonate (each isomer), propylphenyl decylphenyl carbonate (each isomer), propylphenyl biphenyl carbonate (each isomer), propylphenyl dimethylphenyl carbonate (each isomer), propylphenyl diethylphenyl carbonate (each isomer), propylphenyl dipropylphenyl carbonate (each isomer), propylphenyl dibutylphenyl carbonate (each isomer), propylphenyl dipentylphenyl carbonate (each isomer), propylphenyl dihexylphenyl carbonate (each isomer), propylphenyl diheptylphenyl carbonate (each isomer), propylphenyl phenylphenyl carbonate (each isomer), propylphenyl trimethylphenyl carbonate (each isomer), propylphenyl triethylphenyl carbonate (each isomer), propylphenyl tripropylphenyl carbonate (each isomer), propylphenyl tributylphenyl carbonate (each isomer), propylphenyl phenylmethyl carbonate, propylphenyl phenylethyl carbonate (each isomer), propylphenyl phenylpropyl carbonate (each isomer), propylphenyl phenylbutyl carbonate (each isomer), propylphenyl phenylpentyl carbonate (each isomer), propylphenyl phenylhexyl carbonate (each isomer), propylphenyl phenylheptyl carbonate (each isomer), propylphenyl phenyloctyl carbonate (each isomer), propylphenyl phenylnonyl carbonate (each isomer), butylphenyl pentylphenyl carbonate (each isomer), butylphenyl hexylphenyl carbonate (each isomer), butylphenyl heptylphenyl carbonate (each isomer), butylphenyl octylphenyl carbonate (each isomer), butylphenyl nonylphenyl carbonate (each isomer), butylphenyl decylphenyl carbonate (each isomer), butylphenyl biphenyl carbonate (each isomer), butylphenyl dimethylphenyl carbonate (each isomer), butylphenyl diethylphenyl carbonate (each isomer), butylphenyl dipropylphenyl carbonate (each isomer), butylphenyl dibutylphenyl carbonate (each isomer), butylphenyl dipentylphenyl carbonate (each isomer), butylphenyl dihexylphenyl carbonate (each isomer), butylphenyl diheptylphenyl carbonate (each isomer), butylphenyl phenylphenyl carbonate (each isomer), butylphenyl trimethylphenyl carbonate (each isomer), butylphenyl triethylphenyl carbonate (each isomer), butylphenyl tripropylphenyl carbonate (each isomer), butylphenyl tributylphenyl carbonate (each isomer), butylphenyl phenylmethyl carbonate, butylphenyl phenylethyl carbonate (each isomer), butylphenyl phenylpropyl carbonate (each isomer), butylphenyl phenylbutyl carbonate (each isomer), butylphenyl phenylpentyl carbonate (each isomer), butylphenyl phenylhexyl carbonate (each isomer), butylphenyl phenylheptyl carbonate (each isomer), butylphenyl phenyloctyl carbonate (each isomer), butylphenyl phenylnonyl carbonate (each isomer) pentylphenyl hexylphenyl carbonate (each isomer), pentylphenyl heptylphenyl carbonate (each isomer), pentylphenyl octylphenyl carbonate (each isomer), pentylphenyl nonylphenyl carbonate (each isomer), pentylphenyl decylphenyl carbonate (each isomer), pentylphenyl biphenyl carbonate (each isomer), pentylphenyl dimethylphenyl carbonate (each isomer), pentylphenyl diethylphenyl carbonate (each isomer), pentylphenyl dipropylphenyl carbonate (each isomer), pentylphenyl dibutylphenyl carbonate (each isomer), pentylphenyl dipentylphenyl carbonate (each isomer), pentylphenyl dihexylphenyl carbonate (each isomer), pentylphenyl diheptylphenyl carbonate (each isomer), pentylphenyl phenylphenyl carbonate (each isomer), pentylphenyl trimethylphenyl carbonate (each isomer), pentylphenyl triethylphenyl carbonate (each isomer), pentylphenyl tripropylphenyl carbonate (each isomer), pentylphenyl tributylphenyl carbonate (each isomer), pentylphenyl phenylmethyl carbonate, pentylphenyl phenylethyl carbonate (each isomer), pentylphenyl phenylpropyl carbonate (each isomer), pentylphenyl phenylbutyl carbonate (each isomer), pentylphenyl phenylpentyl carbonate (each isomer), pentylphenyl phenylhexyl carbonate (each isomer), pentylphenyl phenylheptyl carbonate (each isomer), pentylphenyl phenyloctyl carbonate (each isomer), pentylphenyl phenylnonyl carbonate (each isomer), hexylphenyl heptylphenyl carbonate (each isomer), hexylphenyl octylphenyl carbonate (each isomer), hexylphenyl nonylphenyl carbonate (each isomer), hexylphenyl decylphenyl carbonate (each isomer), hexylphenyl biphenyl carbonate (each isomer), hexylphenyl dimethylphenyl carbonate (each isomer), hexylphenyl diethylphenyl carbonate (each isomer), hexylphenyl dipropylphenyl carbonate (each isomer), hexylphenyl dibutylphenyl carbonate (each isomer), hexylphenyl dipentylphenyl carbonate (each isomer), hexylphenyl dihexylphenyl carbonate (each isomer), hexylphenyl diheptylphenyl carbonate (each isomer), hexylphenyl phenylphenyl carbonate (each isomer), hexylphenyl trimethylphenyl carbonate (each isomer), hexylphenyl triethylphenyl carbonate (each isomer), hexylphenyl tripropylphenyl carbonate (each isomer), hexylphenyl tributylphenyl carbonate (each isomer), hexylphenyl phenylmethyl carbonate, hexylphenyl phenylethyl carbonate (each isomer), hexylphenyl phenylpropyl carbonate (each isomer), hexylphenyl phenylbutyl carbonate (each isomer), hexylphenyl phenylpentyl carbonate (each isomer), hexylphenyl phenylhexyl carbonate (each isomer), hexylphenyl phenylheptyl carbonate (each isomer), hexylphenyl phenyloctyl carbonate (each isomer), hexylphenyl phenylnonyl carbonate (each isomer), dimethylphenyl diethylphenyl carbonate (each isomer), dimethylphenyl dipropylphenyl carbonate (each isomer), dimethylphenyl dibutylphenyl carbonate (each isomer), dimethylphenyl dipentylphenyl carbonate (each isomer), dimethylphenyl dihexylphenyl carbonate (each isomer), dimethylphenyl diheptylphenyl carbonate (each isomer), dimethylphenyl phenylphenyl carbonate (each isomer), dimethylphenyl trimethylphenyl carbonate (each isomer), dimethylphenyl triethylphenyl carbonate (each isomer), dimethylphenyl tripropylphenyl carbonate (each isomer), dimethylphenyl tributylphenyl carbonate (each isomer), dimethylphenyl phenylmethyl carbonate, dimethylphenyl phenylethyl carbonate (each isomer), dimethylphenyl phenylpropyl carbonate (each isomer), dimethylphenyl phenylbutyl carbonate (each isomer), dimethylphenyl phenylpentyl carbonate (each isomer), dimethylphenyl phenylhexyl carbonate (each isomer), dimethylphenyl phenylheptyl carbonate (each isomer), dimethylphenyl phenyloctyl carbonate (each isomer), dimethylphenyl phenylnonyl carbonate (each isomer), diethylphenyl dipropylphenyl carbonate (each isomer), diethylphenyl dibutylphenyl carbonate (each isomer), diethylphenyl dipentylphenyl carbonate (each isomer), diethylphenyl dihexylphenyl carbonate (each isomer), diethylphenyl diheptylphenyl carbonate (each isomer), diethylphenyl phenylphenyl carbonate (each isomer), diethylphenyl trimethylphenyl carbonate (each isomer), diethylphenyl triethylphenyl carbonate (each isomer), diethylphenyl tripropylphenyl carbonate (each isomer), diethylphenyl tributylphenyl carbonate (each isomer), diethylphenyl phenylmethyl carbonate, diethylphenyl phenylethyl carbonate (each isomer), diethylphenyl phenylpropyl carbonate (each isomer), diethylphenyl phenylbutyl carbonate (each isomer), diethylphenyl phenylpentyl carbonate (each isomer), diethylphenyl phenylhexyl carbonate (each isomer), diethylphenyl phenylheptyl carbonate (each isomer), diethylphenyl phenyloctyl carbonate (each isomer), diethylphenyl phenylnonyl carbonate (each isomer), dipropylphenyl dibutylphenyl carbonate (each isomer), dipropylphenyl dipentylphenyl carbonate (each isomer), dipropylphenyl dihexylphenyl carbonate (each isomer), dipropylphenyl diheptylphenyl carbonate (each isomer), dipropylphenyl phenylphenyl carbonate (each isomer), dipropylphenyl trimethylphenyl carbonate (each isomer), dipropylphenyl triethylphenyl carbonate (each isomer), dipropylphenyl tripropylphenyl carbonate (each isomer), dipropylphenyl tributylphenyl carbonate (each isomer), dipropylphenyl phenylmethyl carbonate, dipropylphenyl phenylethyl carbonate (each isomer), dipropylphenyl phenylpropyl carbonate (each isomer), dipropylphenyl phenylbutyl carbonate (each isomer), dipropylphenyl phenylpentyl carbonate (each isomer), dipropylphenyl phenylhexyl carbonate (each isomer), dipropylphenyl phenylheptyl carbonate (each isomer), dipropylphenyl phenyloctyl carbonate (each isomer), dipropylphenyl phenylnonyl carbonate (each isomer), dibutylphenyl dipentylphenyl carbonate (each isomer), dibutylphenyl dihexylphenyl carbonate (each isomer), dibutylphenyl diheptylphenyl carbonate (each isomer), dibutylphenyl phenylphenyl carbonate (each isomer), dibutylphenyl trimethylphenyl carbonate (each isomer), dibutylphenyl triethylphenyl carbonate (each isomer), dibutylphenyl tripropylphenyl carbonate (each isomer), dibutylphenyl tributylphenyl carbonate (each isomer), dibutylphenyl phenylmethyl carbonate, dibutylphenyl phenylethyl carbonate (each isomer), dibutylphenyl phenylpropyl carbonate (each isomer), dibutylphenyl phenylbutyl carbonate (each isomer), dibutylphenyl phenylpentyl carbonate (each isomer), dibutylphenyl phenylhexyl carbonate (each isomer), dibutylphenyl phenylheptyl carbonate (each isomer), dibutylphenyl phenyloctyl carbonate (each isomer), dibutylphenyl phenylnonyl carbonate (each isomer), dipentylphenyl dihexylphenyl carbonate (each isomer), dipentylphenyl diheptylphenyl carbonate (each isomer), dipentylphenyl phenylphenyl carbonate (each isomer), dipentylphenyl trimethylphenyl carbonate (each isomer), dipentylphenyl triethylphenyl carbonate (each isomer), dipentylphenyl tripropylphenyl carbonate (each isomer), dipentylphenyl tributylphenyl carbonate (each isomer), dipentylphenyl phenylmethyl carbonate, dipentylphenyl phenylethyl carbonate (each isomer), dipentylphenyl phenylpropyl carbonate (each isomer), dipentylphenyl phenylbutyl carbonate (each isomer), dipentylphenyl phenylpentyl carbonate (each isomer), dipentylphenyl phenylhexyl carbonate (each isomer), dipentylphenyl phenylheptyl carbonate (each isomer), dipentylphenyl phenyloctyl carbonate (each isomer), dipentylphenyl phenylnonyl carbonate (each isomer), trimethylphenyl triethylphenyl carbonate (each isomer), trimethylphenyl tripropylphenyl carbonate (each isomer), trimethylphenyl tributylphenyl carbonate (each isomer), trimethylphenyl phenylmethyl carbonate, trimethylphenyl phenylethyl carbonate (each isomer), trimethylphenyl phenylpropyl carbonate (each isomer), trimethylphenyl phenylbutyl carbonate (each isomer), trimethylphenyl phenylpentyl carbonate (each isomer), trimethylphenyl phenylhexyl carbonate (each isomer), trimethylphenyl phenylheptyl carbonate (each isomer), trimethylphenyl phenyloctyl carbonate (each isomer), and trimethylphenyl phenylnonyl carbonate (each isomer).

<Organic Hydroxy Compound>

The organic hydroxy compound indicates a compound having a hydroxy group (—OH group). As such a hydroxy compound, alcohol and/or an aromatic hydroxy compound, in which a hydroxy group (—OH group) binds to a carbon atom, are preferably used.

(Alcohol)

In accordance with the definition of IUPAC (Rule C-201), alcohol is "a compound in which a hydroxy group binds to a saturated carbon atom (Compounds in which a hydroxy group, —OH, is attached to a saturated carbon atom: $R_3COH$)", and it is a hydroxy compound represented by the following formula (17):

[Chemical Formula 9]

$$R^{13}\text{--}(OH)_c \quad (17)$$

wherein $R^{13}$ represents a group consisting of an aliphatic group containing 1 to 50 carbon atoms or an aliphatic group containing 7 to 50 carbon atoms to which an aromatic group binds, substituted with a c number of hydroxy groups;

the OH group of the alcohol represented by the formula (17) is an OH group that does not bind to an aromatic group; and c represents an integer from 1 to 5.

However, $R^{13}$ is a group having no active hydrogen other than hydroxy groups.

In the above explanation, the term "active hydrogen" is used. The term "active hydrogen" is used to mean a hydrogen atom (excluding an aromatic hydroxy group) that binds to an oxygen atom, a sulfur atom, a nitrogen atom, a silicon atom, etc., and a hydrogen atom of a terminal methine group. For example, it is hydrogen contained in an atomic group such as a —OH group, a —C(=O)OH group, a —C(=O)H group, a —SH group, a —SO$_3$H group, a —SO$_2$H group, a —SOH group, a —NH$_2$ group, a —NH— group, a —SiH group, and a —C≡CH group. The hydroxy group (—OH group) is also active hydrogen, but the hydroxy group is also contained in compositions or reaction raw materials used in the present embodiment, and it is not a group affecting such compositions or raw materials. Thus, unless otherwise specified, the hydroxy group is excluded from groups containing active hydrogen. The term "active hydrogen" is often used in other sites in the present embodiment, and in such cases, the above described definition is applied.

The aliphatic hydrocarbon group of $R^{13}$ is an aliphatic hydrocarbon group in which atoms constituting the group, other than a hydrogen atom, are specific non-metal atoms (carbon, oxygen, nitrogen, sulfur, silicon, and halogen atoms). Preferred examples of the aliphatic group include an acyclic hydrocarbon group, a cyclic hydrocarbon group, and a group to which at least one group selected from the acyclic hydrocarbon group and the cyclic hydrocarbon group binds (for example, a cyclic hydrocarbon group substituted with an acyclic hydrocarbon group, an acyclic hydrocarbon group substituted with a cyclic hydrocarbon group, etc.). In addition, examples of the aliphatic group to which an aromatic group binds include: a group in which a straight chain and/or branched chain alkyl group, or a cycloalkyl group is substituted with an aromatic group; and a group in which the alkyl group containing 1 to 44 carbon atoms is substituted with the aromatic group containing 6 to 49 carbon atoms. As described above, the aromatic group is preferably an aromatic group in which atoms constituting the aromatic group, other than a hydrogen atom, are specific non-metal atoms (carbon, oxygen, nitrogen, sulfur, silicon, and halogen atoms); and examples of the aromatic group include a monocyclic aromatic group, a condensed polycyclic aromatic group, a crosslinked cyclic aromatic group, a multi-ring aromatic group, and a heterocyclic aromatic group; and more preferred examples include a substituted and/or unsubstituted phenyl group, a substituted and/or unsubstituted naphthyl group, and a substituted and/or unsubstituted anthryl group.

Examples of such $R^{13}$ include:

alkyl groups, and/or cycloalkyl groups, and/or cycloalkyl groups substituted with alkyl groups, and/or alkyl groups substituted with cycloalkyl groups, such as a methyl group, an ethyl group, a propyl group (each isomer), a butyl group (each isomer), a pentyl group (each isomer), a hexyl group (each isomer), a heptyl group (each isomer), an octyl group (each isomer), a nonyl group (each isomer), a decyl group (each isomer), a dodecyl group (each isomer), an octadecyl group (each isomer), cyclopentane, cyclohexane, cycloheptane, cyclooctane, methylcyclopentane (each isomer), ethylcyclopentane (each isomer), methylcyclohexane (each isomer), ethylcyclohexane (each isomer), propylcyclohexane (each isomer), butylcyclohexane (each isomer), pentylcyclohexane (each isomer), hexylcyclohexane (each isomer), dimethylcyclohexane (each isomer), diethylcyclohexane (each isomer), and dibutylcyclohexane (each isomer); and aralkyl group, such as a phenylmethyl group, a phenylethyl group (each isomer), a phenylpropyl group (each isomer), a phenylbutyl group (each isomer), a phenylpentyl group (each isomer), a phenylhexyl group (each isomer), a phenylheptyl group (each isomer), a phenyloctyl group (each isomer), and a phenylnonyl group (each isomer).

If considering industrial use, among these alcohols, alcohol having one or two alcoholic hydroxy groups (hydroxy groups directly added to carbon atoms other than an aromatic ring, which constitute a hydroxy compound) is preferable because it has low viscosity. Monoalcohol having one alcoholic hydroxy group is more preferable.

Specific examples include:

alkyl alcohols, and/or cycloalkyl alcohols, and/or cycloalkyl alcohols substituted with alkyl groups, and/or alkyl alcohols substituted with cycloalkyl groups, such as methanol, ethanol, propanol (each isomer), butanol (each isomer), pentanol (each isomer), hexanol (each isomer), heptanol (each isomer), octanol (each isomer), nonanol (each isomer), decanol (each isomer), dodecanol (each isomer), octadecanol (each isomer), cyclopentanol, cyclohexanol, cycloheptanol, cyclooctanol, methylcyclopentanol (each isomer), ethylcyclopentanol (each isomer), methylcyclohexanol (each isomer), ethylcyclohexanol (each isomer), propylcyclohexanol (each isomer), butylcyclohexanol (each isomer), pentylcyclohexanol (each isomer), hexylcyclohexanol (each isomer), dimethylcyclohexanol (each isomer), diethylcyclohexanol (each isomer), and dibutylcyclohexanol (each isomer); and alkyl alcohols substituted with aryl groups, such as phenyl methanol, phenyl ethanol (each isomer), phenyl propanol (each isomer), phenyl butanol (each isomer), phenyl pentanol (each isomer), phenyl hexanol (each isomer), phenyl heptanol (each isomer), phenyl octanol (each isomer), and phenyl nonanol (each isomer).

From the viewpoint of easy availability and the solubility of a raw material and a product therein, among these alcohols, alkyl alcohol containing 1 to 20 carbon atoms is preferably used.

(Aromatic Hydroxy Compound)

A case in which the organic hydroxy compound is an aromatic hydroxy compound will be described below. In accordance with the definition of IUPAC (Rule C-202), the term "aromatic hydroxy compound" is used herein to mean phenols "(compounds having one or more hydroxy groups attached to a benzene or other arene ring.)".

The aromatic hydroxy compound is preferably a compound represented by the following formula (18):

[Chemical Formula 10]

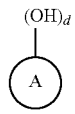

(18)

wherein ring A represents an organic group containing 6 to 50 carbon atoms, which contains an aromatic group substituted with a d number of hydroxy groups in any position at which aromaticity is maintained, and it may be a single ring, multiple rings, or a heterocyclic ring, or it may also be substituted with another substituent, and d represents an integer from 1 to 6.

A substituent substituted with the aromatic group of the aromatic hydroxy compound represented by the above formula (18) is selected from a hydrogen atom, a halogen atom, an aliphatic group, an aromatic group, and a group to which the aforementioned group binds, and thus, it represents a group consisting of an acyclic hydrocarbon group, a cyclic hydrocarbon group (for example, a monocyclic hydrocarbon group, a condensed polycyclic hydrocarbon group, a cross-linked cyclic hydrocarbon group, a spiro hydrocarbon group, a multi-ring hydrocarbon group, a cyclic hydrocarbon group having a side chain, a heterocyclic group, a heterocyclic spiro group, a hetero crosslinked cyclic group, and a heterocyclic group), a group to which at least one selected from the acyclic hydrocarbon group and the cyclic hydrocarbon group binds, and a group to which the above described group binds via a covalent bond with specific non-metal atoms (carbon, oxygen, nitrogen, sulfur, and silicon).

The number of hydroxy groups attached to the aromatic group of the ring A is an integer from 1 to 6, preferably from 1 to 3, more preferably from 1 or 2, and further preferably 1 (that is, d=1).

If the aforementioned substituent is described more in detail, the aromatic hydroxy compound represented by the formula (18) is an aromatic hydroxy compound having at least one substituent selected from the following substituent group, in addition to the aromatic group and hydroxy groups attached to the aromatic group:

(i) hydrogen atom, (ii) a group constituted with a carbon atom and a hydrogen atom (which may further bind to the ring A, so as to form a ring structure), (iii) a group constituted with a carbon atom, a hydrogen atom and an oxygen atom (which indicates, for example, an ether group constituted with an aliphatic group, an ether group constituted with an aromatic group, and an ether group consisting of groups constituted with an aliphatic group and an aromatic group (however, except for a carbonyl group, an ester group, a terminal methine group, and groups containing active hydrogen, such as an alcoholic OH group, a carboxyl group, an $NH_2$ group, an NH group, an NOH group, an SH group, an $SO_3H$ group and an SOH group)), (iv) a halogen atom, and (v) a group constituted with an atom selected from a carbon atom, a hydrogen atom, an oxygen atom, a nitrogen atom, a sulfur atom, and a halogen atom (however, except for a carbonyl group, an ester group, a terminal methine group, and groups containing active hydrogen, such as an alcoholic OH group, a carboxyl group, an $NH_2$ group, an NH group, an NOH group, an SH group, an $SO_3H$ group and an SOH group).

The active hydrogen means a hydrogen atom that binds to oxygen, nitrogen, sulfur and nitrogen (excluding an aromatic hydroxy group). Although the aromatic hydroxy group (a —OH group directly attached to an aromatic group) is a group that is also included in the aforementioned definition of active hydrogen, the aromatic hydroxy group is also contained in compositions or reaction raw materials used in the present embodiment, and it is not a group affecting such compositions or raw materials. Thus, the aromatic hydroxy group is excluded from groups containing active hydrogen, unless otherwise specified. The term "groups containing active hydrogen" is often used in other sites in the present invention, and in such cases, the above described definition is applied.

The aromatic hydroxy compound is preferably a compound represented by the following formula (19):

[Chemical Formula 11]

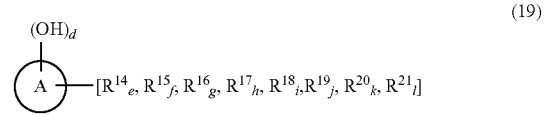

wherein the ring A represents a group defined by the above formula (18), and the OH group and the $R^{14}$ to $R^{21}$ groups each represent a group substituted in any given position at which the aromaticity of the ring A is maintained, wherein the $R^{14}$ to $R^{21}$ groups may independently substitute the ring A, or the $R^{14}$ to $R^{21}$ groups may bind to one another to form a ring that is adjacent to the ring A, or the $R^{14}$ to $R^{21}$ groups independently represent a group selected from groups constituted with a hydrogen atom, a halogen atom, a group selected from the group consisting of an alkyl group, a cycloalkyl group, an aryl group, an aryl group having a hydroxy group, an aralkyl group and an ether group (substituted and/or unsubstituted alkyl ether and/or aryl ether and/or aralkyl ether), and/or a group to which one or more groups selected from the above described group bind, and/or a group to which one or more groups selected from the above described group bind via a saturated aliphatic bond and/or an ether bond, and the ring A and the $R^{14}$ to the $R^{21}$ are constituted with carbon atoms, the total number of which is an integer from 6 to 50.

d represents an integer from 1 to 6; e, f, g, h, i, j, k and l each represent an integer from 0 to 5; and the value of e+f+g+h+i+j+k+l is an integer of 6−d, when the ring A is a benzene ring, and is an integer of 8−d, when the ring A is a naphthalene ring, and is an integer of 10−d, when the ring A is an anthracene ring. As described above, a group selected from the $R^{14}$ to the $R^{21}$ may cyclically bind to the ring A via a carbon-carbon bond and/or an ether bond.

If considering industrial use, among the aromatic hydroxy compounds represented by the above formula (19), an aromatic hydroxy group having one or two aromatic hydroxy groups attached to the ring A (namely, d=1 or 2) is preferable because of its low viscosity, and an aromatic monohydroxy compound having one aromatic hydroxy group is more preferable.

The ring A is configured to contain at least one structure selected from the group consisting of a benzene ring, a naphthalene ring, and an anthracene ring, and the ring A is preferably one structure selected from the group consisting of a benzene ring, a naphthalene ring, and an anthracene ring, and further, if considering industrial use, the ring A is preferably an aromatic hydroxy compound having, as a skeleton, an easily obtainable benzene ring. As such an aromatic hydroxy compound, an aromatic hydroxy compound represented by the following formula (20) is preferable:

[Chemical Formula 12]

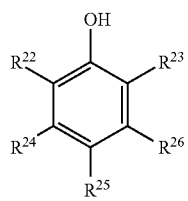

(20)

wherein $R^{22}$, $R^{23}$, $R^{24}$, $R^{25}$ and $R^{26}$ independently represent: a group selected from the group consisting of an alkyl group, a cycloalkyl group, an aryl group, an aralkyl group, an ether group (substituted and/or unsubstituted alkyl ether and/or aryl ether and/or aralkyl ether); a group to which one or more groups selected from the above described group bind; a group selected from groups, to which one or more groups selected from the above described group bind via a saturated aliphatic bond and/or an ether bond; a halogen atom; or a hydrogen atom, and in which the total number of carbon atoms constituting the $R^{22}$, $R^{23}$, $R^{24}$, $R^{25}$ and $R^{26}$ is an integer from 0 to 44.

In the above formula (20), preferred $R^{22}$, $R^{23}$, $R^{24}$, $R^{25}$ and $R^{26}$ are groups independently selected from the groups described in the following (i) to (v):

(i) a hydrogen atom, (ii) a halogen atom, (iii) a group containing 1 to 44 carbon atoms, in which the atom at position α is a carbon atom, wherein three groups attached to the carbon atom at the position α are independently selected from an alkyl group containing 1 to 43 carbon atoms, a cycloalkyl group containing 1 to 43 carbon atoms, an alkoxy group containing 1 to 43 carbon atoms, a polyoxyalkylene alkyl ether group containing 2 to 43 carbon atoms and having no OH groups at the terminus thereof, an aryl group containing 6 to 43 carbon atoms, an aralkyl group containing 7 to 43 carbon atoms, an aralkyloxy group containing 7 to 43 carbon atoms, a group to which one or more of the above described groups bind, and a hydrogen atom, (iv) an aryl group containing 1 to 44 carbon atoms, which is substituted with a substituent, wherein the substituent is an aryl group optionally substituted with the following integer from 1 to 5 substituents, wherein the substituents are selected from a hydrogen atom, an alkyl group containing 1 to 38 carbon atoms, a cycloalkyl group containing 4 to 38 carbon atoms, an alkoxy group containing 1 to 38 carbon atoms, a polyoxyalkylene alkyl ether group containing 2 to 38 carbon atoms and having no OH groups at the terminus thereof, an aryl group containing 6 to 38 carbon atoms, an aralkyl group containing 7 to 38 carbon atoms, an aralkyloxy group containing 7 to 38 carbon atoms, and a group to which one or more of the above described groups bind, and (v) a group containing 1 to 44 carbon atoms, in which the atom at position α is an oxygen atom, wherein the group attached to the oxygen atom at the position α is selected from an alkyl group containing 1 to 44 carbon atoms, a cycloalkyl group containing 1 to 44 carbon atoms, an alkoxy group containing 1 to 44 carbon atoms, a polyoxyalkylene alkyl ether group containing 2 to 44 carbon atoms and having no OH groups at the terminus thereof, an aryl group containing 6 to 44 carbon atoms, an aralkyl group containing 7 to 44 carbon atoms, an aralkyloxy group containing 7 to 44 carbon atoms, and a group to which one or more of the above described groups bind.

In the above formula (20), the term "the atom at position α" is used. This term "the atom at position α" means an atom adjacent to a carbon atom on the aromatic hydrocarbon ring to which the $R^{22}$, $R^{23}$, $R^{24}$, $R^{25}$ and $R^{26}$ groups bind, among atoms constituting the $R^{22}$, $R^{23}$, $R^{24}$, $R^{25}$ and $R^{26}$.

In addition, in the above explanation, the term "aralkyloxy group" is used. The "aralkyloxy group" means a group in which an oxygen atom binds to the above-defined aralkyl group.

Examples of such $R^{22}$, $R^{23}$, $R^{24}$, $R^{25}$ and $R^{26}$ include:

alkyl groups, and/or cycloalkyl groups, and/or cycloalkyl groups substituted with alkyl groups, and/or alkyl groups substituted with cycloalkyl groups, such as a methyl group, an ethyl group, a propyl group (each isomer), a butyl group (each isomer), a pentyl group (each isomer), a hexyl group (each isomer), a heptyl group (each isomer), an octyl group (each isomer), a nonyl group (each isomer), a decyl group (each isomer), a dodecyl group (each isomer), an octadecyl group (each isomer), cyclopentane, cyclohexane, cycloheptane, cyclooctane, methylcyclopentane (each isomer), ethylcyclopentane (each isomer), methylcyclohexane (each isomer), ethylcyclohexane (each isomer), propylcyclohexane (each isomer), butylcyclohexane (each isomer), pentylcyclohexane (each isomer), hexylcyclohexane (each isomer), dimethylcyclohexane (each isomer), diethylcyclohexane (each isomer), and dibutylcyclohexane (each isomer);

alkoxy groups, and/or cycloalkoxy groups, and/or cycloalkoxy groups substituted with alkyl groups, and/or alkoxy groups substituted with cycloalkyl groups, such as a methoxy group, an ethoxy group, propoxy group (each isomer), a butyloxy group (each isomer), a pentyloxy group (each isomer), a hexyloxy group (each isomer), a heptyloxy group (each isomer), an octyloxy group (each isomer), a nonyloxy group (each isomer), a decyloxy group (each isomer), a dodecyloxy group (each isomer), an octadecyloxy group (each isomer), cyclopentyloxy group, a cyclohexyloxy group, a cycloheptyloxy group, a cyclooctyloxy group, a methylcyclopentyloxy group (each isomer), an ethylcyclopentyloxy group (each isomer), a methylcyclohexyloxy group (each isomer), an ethylcyclohexyloxy group (each isomer), a propylcyclohexyloxy group (each isomer), a butylcyclohexyloxy group (each isomer), a pentylcyclohexyloxy group (each isomer), a hexylcyclohexyloxy group (each isomer), a dimethylcyclohexyloxy group (each isomer), a diethylcyclohexyloxy group (each isomer), and a dibutylcyclohexyloxy group (each isomer);

substituted or unsubstituted aryl groups, such as a phenyl group, a methylphenyl group (each isomer), an ethylphenyl group (each isomer), a propylphenyl group (each isomer), a butylphenyl group (each isomer), a pentylphenyl group (each isomer), a hexylphenyl group (each isomer), a heptylphenyl group (each isomer), an octylphenyl group (each isomer), a nonylphenyl group (each isomer), a decylphenyl group (each isomer), a biphenyl group (each isomer), a dimethylphenyl group (each isomer), a diethylphenyl group (each isomer), a dipropylphenyl group (each isomer), a dibutylphenyl group (each isomer), a dipentylphenyl group (each isomer), a dihexylphenyl group (each isomer), a diheptylphenyl group (each isomer), a terphenyl group (each isomer), a trimethylphenyl group (each isomer), a triethylphenyl group (each isomer), a tripropylphenyl group (each isomer), and a tributylphenyl group (each isomer);

substituted or unsubstituted aryloxy groups, such as a phenoxy group, a methylphenoxy group (each isomer), an ethylphenoxy group (each isomer), a propylphenoxy group (each isomer), a butylphenoxy group (each isomer), a pentylphenoxy group (each isomer), a hexylphenoxy group (each isomer), a heptylphenoxy group (each isomer), an octylphenoxy group (each isomer), a nonylphenoxy group (each isomer), a decylphenoxy group (each isomer), a phenylphenoxy group (each isomer), a dimethylphenoxy group (each isomer), a diethylphenoxy group (each isomer), a dipropylphenoxy group (each isomer), a dibutylphenoxy group (each isomer), a dipentylphenoxy group (each isomer), a dihexylphenoxy group (each isomer), a diheptylphenoxy group (each isomer), a diphenylphenoxy group (each isomer), a trimethylphenoxy group (each isomer), a triethylphenoxy group (each isomer), a tripropylphenoxy group (each isomer), and a tributylphenoxy group (each isomer); and aralkyl groups such as a phenylmethyl group, a phenylethyl group (each isomer), a phenylpropyl group (each isomer), a phenylbutyl group (each isomer), a phenylpentyl group (each isomer), a phenylhexyl group (each isomer), a phenylheptyl group (each isomer), a phenyloctyl group (each isomer) and a phenylnonyl group (each isomer), and aralkyloxy groups such as a phenylmethoxy group, a phenylethoxy group (each isomer), a phenylpropyloxy group (each isomer), a phenylbutyloxy group (each isomer), a phenylpentyloxy group (each isomer), a phenylhexyloxy group (each isomer), a phenylheptyloxy group (each isomer), a phenyloctyloxy group (each isomer) and a phenylnonyloxy group (each isomer).

Among such aromatic hydroxy compounds, an aromatic hydroxy compound, in which the $R^{24}$ and the $R^{26}$ are hydrogen atoms, is preferably used.

Preferred examples of the aromatic hydroxy compound represented by the above formula (19) include the following compounds, and also, specific examples of the aromatic hydroxy compound represented by the above formula (20) include the following compounds.

Specific examples include chlorophenol (each isomer), bromophenol (each isomer), dichlorophenol (each isomer), dibromophenol (each isomer), trichlorophenol (each isomer), tribromophenol (each isomer), phenol, methylphenol (each isomer), ethylphenol (each isomer), propylphenol (each isomer), butylphenol (each isomer) pentylphenol (each isomer), hexylphenol (each isomer), heptylphenol (each isomer), octylphenol (each isomer), nonylphenol (each isomer), decylphenol (each isomer), dodecylphenol (each isomer), octadecylphenol (each isomer), dimethylphenol (each isomer), diethylphenol (each isomer), dipropylphenol (each isomer), dibutylphenol (each isomer), dipentylphenol (each isomer), dihexylphenol (each isomer), diheptylphenol (each isomer), dioctylphenol (each isomer), dinonylphenol (each isomer), didecylphenol (each isomer), didodecylphenol (each isomer), dioctadecylphenol (each isomer), trimethylphenol (each isomer), triethylphenol (each isomer), tripropylphenol (each isomer), tributylphenol (each isomer), tripentylphenol (each isomer), trihexylphenol (each isomer), triheptylphenol (each isomer), trioctylphenol (each isomer), trinonylphenol (each isomer), tridecylphenol (each isomer), tridodecylphenol (each isomer), trioctadecylphenol (each isomer), (methoxymethyl)phenol (each isomer), (ethoxymethyl)phenol (each isomer), (propoxymethyl)phenol (each isomer), (butyloxymethyl)phenol (each isomer), (pentyloxymethyl)phenol (each isomer), (hexyloxymethyl)phenol (each isomer), (heptyloxymethyl)phenol (each isomer), (octyloxymethyl)phenol (each isomer), (nonyloxymethyl)phenol (each isomer), (decyloxymethyl)phenol (each isomer), (dodecyloxymethyl)phenol (each isomer), (octadecyloxymethyl)phenol (each isomer), (cyclopentyloxymethyl)phenol (each isomer), (cyclohexyloxymethyl)phenol (each isomer), (cycloheptyloxymethyl)phenol (each isomer), (cyclooctyloxymethyl)phenol (each isomer), (methylcyclopentyloxymethyl)phenol (each isomer), (ethylcyclopentyloxymethyl)phenol (each isomer), (methylcyclohexyloxymethyl)phenol (each isomer), (ethylcyclohexyloxymethyl)phenol (each isomer), (propylcyclohexyloxymethyl)phenol (each isomer), (butylcyclohexyloxymethyl)phenol (each isomer), (pentylcyclohexyloxymethyl)phenol (each isomer), (hexylcyclohexyloxymethyl)phenol (each isomer), (dimethylcyclohexyloxymethyl)phenol (each isomer), (diethylcyclohexyloxymethyl)phenol (each isomer), (dibutylcyclohexyloxymethyl)phenol (each isomer), (phenoxymethyl)phenol, (methylphenoxymethyl)phenol (each isomer), (ethylphenoxymethyl)phenol (each isomer), (propylphenoxymethyl)phenol (each isomer), (butylphenoxymethyl)phenol (each isomer), (pentylphenoxymethyl)phenol (each isomer), (hexylphenoxymethyl)phenol (each isomer), (heptylphenoxymethyl)phenol (each isomer), (octylphenoxymethyl)phenol (each isomer), (nonylphenoxymethyl)phenol (each isomer), (decylphenoxymethyl)phenol (each isomer), (phenylphenoxymethyl)phenol (each isomer), (dimethylphenoxymethyl)phenol (each isomer), (diethylphenoxymethyl)phenol (each isomer), (dipropylphenoxymethyl)phenol (each isomer), (dibutylphenoxymethyl)phenol (each isomer), (dipentylphenoxymethyl)phenol (each isomer), (dihexylphenoxymethyl)phenol (each isomer), (diheptylphenoxymethyl)phenol (each isomer), (diphenylphenoxymethyl)phenol (each isomer), (trimethylphenoxymethyl)phenol (each isomer), (triethylphenoxymethyl)phenol (each isomer), (tripropylphenoxymethyl)phenol (each isomer), (tributylphenoxymethyl)phenol (each isomer), (phenylmethoxymethyl)phenol, (phenylethoxymethyl)phenol (each isomer), (phenylpropyloxymethyl)phenol (each isomer), (phenylbutyloxymethyl)phenol (each isomer), (phenylpentyloxymethyl)phenol (each isomer), (phenylhexyloxymethyl)phenol (each isomer), (phenylheptyloxymethyl)phenol (each isomer), (phenyloctyloxymethyl)phenol (each isomer), (phenylnonyloxymethyl)phenol (each isomer), di(methoxymethyl)phenol, di(ethoxymethyl)phenol, di(propoxymethyl)phenol (each isomer), di(butyloxymethyl)phenol (each isomer), di(pentyloxymethyl)phenol (each isomer), di(hexyloxymethyl)phenol (each isomer), di(heptyloxymethyl)phenol (each isomer), di(octyloxymethyl)phenol (each isomer), di(nonyloxymethyl)phenol (each isomer), di(decyloxymethyl)phenol (each isomer), di(dodecyloxymethyl)phenol (each isomer), di(octadecyloxymethyl)phenol (each isomer), di(cyclopentyloxymethyl)phenol, di(cyclohexyloxymethyl)phenol, di(cycloheptyloxymethyl)phenol, di(cyclooctyloxymethyl)phenol, di(methylcyclopentyloxymethyl)phenol (each isomer), di(ethylcyclopentyloxymethyl)phenol (each isomer), di(methylcyclohexyloxymethyl)phenol (each isomer), di(ethylcyclohexyloxymethyl)phenol (each isomer), di(propylcyclohexyloxymethyl)phenol (each isomer), di(butylcyclohexyloxymethyl)phenol (each isomer), di(pentylcyclohexyloxymethyl)phenol (each isomer), di(hexylcyclohexyloxymethyl)phenol (each isomer), bis(dimethylcyclohexyloxymethyl)phenol (each isomer), bis(diethylcyclohexyloxymethyl)phenol (each isomer), bis(dibutylcyclohexyloxymethyl)phenol (each isomer), di(phenoxymethyl)phenol, di(methylphenoxymethyl)phenol (each isomer), di(ethylphenoxymethyl)phenol (each isomer), di(propylphenoxymethyl)phenol (each isomer), di(butylphenoxymethyl)phenol (each isomer), di(pentylphenoxymethyl)phenol (each isomer), di(hexylphenoxymethyl)phenol (each isomer), di(heptylphenoxymethyl)phenol (each isomer), di(octylphenoxymethyl)phenol (each isomer), di(nonylphenoxymethyl)phenol (each isomer), di(decylphenoxymethyl)phenol (each isomer), di(phenylphenoxymethyl)phenol (each isomer), bis(dimethylphenoxymethyl)phenol (each isomer), bis(diethylphenoxymethyl)phenol (each isomer), bis(dipropylphenoxymethyl)phenol (each isomer), bis(dibutylphenoxymethyl)phenol (each isomer), bis(dipentylphenoxymethyl)phenol (each isomer), bis(dihexylphenoxymethyl)phenol (each isomer), bis(diheptylphenoxymethyl)phenol (each isomer), bis(diphenylphenoxymethyl)phenol (each isomer), di(trimethylphenoxymethyl)phenol (each isomer), di(triethylphenoxymethyl)phenol (each isomer), di(tripropylphenoxymethyl)phenol (each isomer), di(tributylphenoxymethyl)phenol (each isomer), (phenylmethoxymethyl)phenol, di(phenylethoxymethyl)phenol (each isomer), di(phenylpropyloxymethyl)phenol (each isomer), di(phenylbutyloxymethyl)phenol (each isomer), di(phenylpentyloxymethyl)phenol (each isomer), di(phenylhexyloxymethyl)phenol (each isomer), di(phenylheptyloxymethyl)phenol (each isomer), di(phenyloctyloxymethyl)phenol (each isomer), di(phenylnonyloxymethyl)phenol (each isomer), tri(methoxymethyl)phenol, tri(ethoxymethyl)phenol, tri(propoxymethyl)phenol (each isomer), tri(butyloxymethyl)phenol (each isomer), tri(pentyloxymethyl)phenol (each isomer), tri(hexyloxymethyl)phenol (each isomer), tri(heptyloxymethyl)phenol (each isomer), tri(octyloxymethyl)phenol (each isomer), tri(nonyloxymethyl)phenol (each isomer), tri(decyloxymethyl)phenol (each isomer), tri(dodecyloxymethyl)phenol (each isomer), tri(octadecyloxymethyl)phenol (each isomer), tri(cyclopentyloxymethyl)phenol, tri(cyclohexyloxymethyl)phenol, tri(cycloheptyloxymethyl)phenol, tri(cyclooctyloxymethyl)phenol, tri(methylcyclopentyloxymethyl)phenol (each isomer), tri(ethylcyclopentyloxymethyl)phenol (each isomer), tri(methylcyclohexyloxymethyl)phenol (each isomer), tri(ethylcyclohexyloxymethyl)phenol (each isomer), tri(propylcyclohexyloxymethyl)phenol (each isomer), tri(butylcyclohexyloxymethyl)phenol (each isomer), tri(pentylcyclohexyloxymethyl)phenol (each isomer), tri(hexylcyclohexyloxymethyl)phenol (each isomer), bis(dimethylcyclohexyloxymethyl)phenol (each isomer), bis(diethylcyclohexyloxymethyl)phenol (each isomer), bis(dibutylcyclohexyloxymethyl)phenol (each isomer), tri(phenoxymethyl)phenol, tri(methylphenoxymethyl)phenol (each isomer), tri(ethylphenoxymethyl)phenol (each isomer), tri(propylphenoxymethyl)phenol (each isomer), tri(butylphenoxymethyl)phenol (each isomer), tri(pentylphenoxymethyl)phenol (each isomer), tri(hexylphenoxymethyl)phenol (each isomer), tri(heptylphenoxymethyl)phenol (each isomer), tri(octylphenoxymethyl)phenol (each isomer), tri(nonylphenoxymethyl)phenol (each isomer), tri(decylphenoxymethyl)phenol (each isomer), tri(phenylphenoxymethyl)phenol (each isomer), bis(dimethylphenoxymethyl)phenol (each isomer), bis(diethylphenoxymethyl)phenol (each isomer), bis(dipropylphenoxymethyl)phenol (each isomer), bis(dibutylphenoxymethyl)phenol (each isomer), bis(dipentylphenoxymethyl)phenol (each isomer), bis(dihexylphenoxymethyl)phenol (each isomer), bis(diheptylphenoxymethyl)phenol (each isomer), bis(diphenylphenoxymethyl)phenol (each isomer), tri(trimethylphenoxymethyl)phenol (each isomer), tri(triethylphenoxymethyl)phenol (each isomer), tri(tripropylphenoxymethyl)phenol (each isomer), tri(tributylphenoxymethyl)phenol (each isomer), (phenylmethoxymethyl)phenol, tri(phenylethoxymethyl)phenol (each isomer), tri(phenylpropyloxymethyl)phenol (each isomer), tri(phenylbutyloxymethyl)phenol (each isomer), tri(phenylpentyloxymethyl)phenol (each isomer), tri(phenylhexyloxymethyl)phenol (each isomer), tri(phenylheptyloxymethyl)phenol (each isomer), tri(phenyloctyloxymethyl)phenol (each isomer), tri(phenylnonyloxymethyl)phenol (each isomer), (phenylmethyl)phenol (each isomer), ((methylphenyl)methyl)phenol (each isomer), ((ethylphenyl)methyl)phenol (each isomer), ((propylphenyl)methyl)phenol (each isomer), ((butylphenyl)methyl)phenol (each isomer), ((pentylphenyl)methyl)phenol (each isomer), ((hexylphenyl)methyl)phenol (each isomer), ((heptylphenyl)methyl)phenol (each isomer), ((octylphenyl)methyl)phenol (each isomer), ((nonylphenyl)methyl)phenol (each isomer), ((decylphenyl)methyl)phenol (each isomer), ((biphenyl)methyl)phenol (each isomer), ((dimethylphenyl)methyl)phenol (each isomer), ((diethylphenyl)methyl)phenol (each isomer), ((dipropylphenyl)methyl)phenol (each isomer), ((dibutylphenyl)methyl)phenol (each isomer), ((dipentylphenyl)methyl)phenol (each isomer), ((dihexylphenyl)methyl)phenol (each isomer), ((diheptylphenyl)methyl)phenol (each isomer), ((terphenyl)methyl)phenol (each isomer), ((trimethylphenyl)methyl)phenol (each isomer), ((triethylphenyl)methyl)phenol (each isomer), ((tripropylphenyl)methyl)phenol (each isomer), ((tributylphenyl)methyl)phenol (each isomer), di(phenylmethyl)phenol (each isomer), di((methylphenyl)methyl)phenol (each isomer), di((ethylphenyl)methyl)phenol (each isomer), di((propylphenyl)methyl)phenol (each isomer), di((butylphenyl)methyl)phenol (each isomer), di((pentylphenyl)methyl)phenol (each isomer), di((hexylphenyl)methyl)phenol (each isomer), di((heptylphenyl)methyl)phenol (each isomer), di((octylphenyl)methyl)phenol (each isomer), di((nonylphenyl)methyl)phenol (each isomer), di((decylphenyl)methyl)phenol (each isomer), di((biphenyl)methyl)phenol (each isomer), di((dimethylphenyl)methyl)phenol (each isomer), di((diethylphenyl)methyl)phenol (each isomer), di((dipropylphenyl)methyl)phenol (each isomer), di((dibutylphenyl)methyl)phenol (each isomer), di((dipentylphenyl)methyl)phenol (each isomer), di((dihexylphenyl)methyl)phenol (each isomer), di((diheptylphenyl)methyl)phenol (each isomer), di((terphenyl)methyl)phenol (each isomer), di((trimethylphenyl)methyl)phenol (each isomer), di((triethylphenyl)methyl)phenol (each isomer), di((tripropylphenyl)methyl)phenol (each isomer), di((tributylphenyl)methyl)phenol (each isomer), tri(phenylmethyl)phenol (each isomer), tri((methylphenyl)methyl)phenol (each isomer), tri((ethylphenyl)methyl)phenol (each isomer), tri((propylphenyl)methyl)phenol (each isomer), tri((butylphenyl)methyl)phenol (each isomer), tri((pentylphenyl)methyl)phenol (each isomer), tri((hexylphenyl)methyl)phenol (each isomer), tri((heptylphenyl)methyl)phenol (each isomer), tri((octylphenyl)methyl)phenol (each isomer), tri((nonylphenyl)methyl)phenol (each isomer), tri((decylphenyl)methyl)phenol (each isomer), tri((biphenyl)methyl)phenol (each isomer), tri((dimethylphenyl)methyl)phenol (each isomer), tri((diethylphenyl)methyl)phenol (each isomer), tri((dipropylphenyl)methyl)phenol (each isomer), tri((dibutylphenyl)methyl)phenol (each isomer), tri((dipentylphenyl)methyl)phenol (each isomer), tri((dihexylphenyl)methyl)phenol (each isomer), tri((diheptylphenyl)methyl)phenol (each isomer), tri((terphenyl)methyl)phenol (each isomer), tri((trimethylphenyl)methyl)phenol (each isomer), tri((triethylphenyl)methyl)phenol (each isomer), tri((tripropylphenyl)methyl)phenol (each isomer), tri((tributylphenyl)methyl)phenol (each isomer), phenylethylphenol (each isomer), phenyl-n-propylphenol (each isomer), phenyl-n- butylphenol (each isomer), phenyl-n-pentylphenol (each isomer), phenyl-n-hexylphenol (each isomer), phenyl-n-heptylphenol (each isomer), phenyl-n-octylphenol (each isomer), phenyl-n-nonylphenol (each isomer), (methylamino) phenol, (ethylamino)phenol, (propylamino)phenol (each isomer), (butylamino)phenol (each isomer), (pentylamino) phenol (each isomer), (hexylamino)phenol (each isomer), (heptylamino)phenol (each isomer), (octylamino)phenol (each isomer), (nonylamino)phenol (each isomer), (decylamino)phenol (each isomer), (dodecylamino)phenol (each isomer), (octadecylamino)phenol (each isomer), di(methylamino)phenol, di(ethylamino)phenol, di(propylamino)phenol (each isomer), di(butylamino)phenol (each isomer), di(pentylamino)phenol (each isomer), di(hexylamino)phenol (each isomer), di(heptylamino)phenol (each isomer), di(octylamino)phenol (each isomer), di(nonylamino)phenol (each isomer), di(decylamino)phenol (each isomer), di(dodecylamino)phenol (each isomer), di(octadecylamino)phenol (each isomer), tri(methylamino)phenol, tri(ethylamino) phenol, tri(propylamino)phenol (each isomer), tri(butylamino)phenol (each isomer), tri(pentylamino)phenol (each isomer), tri(hexylamino)phenol (each isomer), tri(heptylamino)phenol (each isomer), tri(octylamino)phenol (each isomer), tri(nonylamino)phenol (each isomer), tri(decylamino)phenol (each isomer), tri(dodecylamino)phenol (each isomer), tri(octadecylamino)phenol (each isomer), methoxyphenol (each isomer), ethoxyphenol (each isomer), propyloxyphenol (each isomer), butyloxyphenol (each isomer), pentyloxyphenol (each isomer), hexyloxyphenol (each isomer), heptyloxyphenol (each isomer), octyloxyphenol (each isomer), nonyloxyphenol (each isomer), decyloxyphenol (each isomer), dodecyloxyphenol (each isomer), octadecyloxyphenol (each isomer), cyclopentyloxyphenol (each isomer), cyclohexyloxyphenol (each isomer), cycloheptyloxyphenol (each isomer), cyclooctyloxyphenol (each isomer), (methylcyclopentyloxy)phenol (each isomer), (ethylcyclopentyloxy)phenol (each isomer), (methylcyclohexyloxy)phenol (each isomer), (ethylcyclohexyloxy)phenol (each isomer), (propylcyclohexyloxy)phenol (each isomer), (butylcyclohexyloxy)phenol (each isomer), (pentylcyclohexyloxy)phenol (each isomer), (hexylcyclohexyloxy)phenol (each isomer), (dimethylcyclohexyloxy)phenol (each isomer), (diethylcyclohexyloxy)phenol (each isomer), (dibutylcyclohexyloxy)phenol (each isomer), phenoxyphenol, (methylphenyloxy)phenol (each isomer), (ethylphenyloxy)phenol (each isomer), (propylphenyloxy)phenol (each isomer), (butylphenyloxy)phenol (each isomer), (pentylphenyloxy)phenol (each isomer), (hexylphenyloxy)phenol (each isomer), (heptylphenyloxy)phenol (each isomer), (octylphenyloxy)phenol (each isomer), (nonylphenyloxy)phenol (each isomer), (decylphenyloxy)phenol (each isomer), biphenyloxyphenol (each isomer), (dimethylphenyloxy)phenol (each isomer), (diethylphenyloxy)phenol (each isomer), (dipropylphenyloxy)phenol (each isomer), (dibutylphenyloxy)phenol (each isomer), (dipentylphenyloxy)phenol (each isomer), (dihexylphenyloxy)phenol (each isomer), (diheptylphenyloxy)phenol (each isomer), terphenyloxyphenol (each isomer), (trimethylphenyloxy)phenol (each isomer), (triethylphenyloxy)phenol (each isomer), (tripropylphenyloxy)phenol (each isomer), (tributylphenyloxy)phenol (each isomer), (phenylmethyloxy)phenol, (phenylethyloxy)phenol (each isomer), (phenylpropyloxy)phenol (each isomer), (phenylbutyloxy)phenol (each isomer), (phenylpentyloxy)phenol (each isomer), (phenylhexyloxy)phenol (each isomer), (phenylheptyloxy)phenol (each isomer), (phenyloctyloxy)phenol (each isomer), (phenylnonyloxy)phenol (each isomer), dimethoxyphenol (each isomer), diethoxyphenol (each isomer), dipropyloxyphenol (each isomer), dibutyloxyphenol (each isomer), dipentyloxyphenol (each isomer), dihexyloxyphenol (each isomer), diheptyloxyphenol (each isomer), dioctyloxyphenol (each isomer), dinonyloxyphenol (each isomer), didecyloxyphenol (each isomer), didodecyloxyphenol (each isomer), dioctadecyloxyphenol (each isomer), dicyclopentyloxyphenol (each isomer), dicyclohexyloxyphenol (each isomer), dicycloheptyloxyphenol (each isomer), dicyclooctyloxyphenol (each isomer), di(methylcyclopentyloxy)phenol (each isomer), di(ethylcyclopentyloxy)phenol (each isomer), di(methylcyclohexyloxy)phenol (each isomer), di(ethylcyclohexyloxy)phenol (each isomer), di(propylcyclohexyloxy)phenol (each isomer), di(butylcyclohexyloxy)phenol (each isomer), di(pentylcyclohexyloxy)phenol (each isomer), di(hexylcyclohexyloxy)phenol (each isomer), bis(dimethylcyclohexyloxy)phenol (each isomer), bis(diethylcyclohexyloxy)phenol (each isomer), bis(dibutylcyclohexyloxy)phenol (each isomer), phenyloxyphenol, di(methylphenyloxy)phenol (each isomer), di(ethylphenyloxy)phenol (each isomer), di(propylphenyloxy)phenol (each isomer), di(butylphenyloxy)phenol (each isomer), di(pentylphenyloxy)phenol (each isomer), di(hexylphenyloxy)phenol (each isomer), di(heptylphenyloxy)phenol (each isomer), di(octylphenyloxy)phenol (each isomer), di(nonylphenyloxy)phenol (each isomer), di(decylphenyloxy)phenol (each isomer), dibiphenyloxyphenol (each isomer), bis(dimethylphenyloxy)phenol (each isomer), bis(diethylphenyloxy)phenol (each isomer), bis(dipropylphenyloxy)phenol (each isomer), bis(dibutylphenyloxy)phenol (each isomer), bis(dipentylphenyloxy)phenol (each isomer), bis(dihexylphenyloxy)phenol (each isomer), bis(diheptylphenyloxy)phenol (each isomer), diterphenyloxyphenol (each isomer), di(trimethylphenyloxy)phenol (each isomer), di(triethylphenyloxy)phenol (each isomer), di(tripropylphenyloxy)phenol (each isomer), di(tributylphenyloxy)phenol (each isomer), (phenylmethyloxy)phenol, di(phenylethyloxy)phenol (each isomer), di(phenylpropyloxy)phenol (each isomer), di(phenylbutyloxy)phenol (each isomer), di(phenylpentyloxy)phenol (each isomer), di(phenylhexyloxy)phenol (each isomer), di(phenylheptyloxy)phenol (each isomer), di(phenyloctyloxy)phenol (each isomer), di(phenylnonyloxy)phenol (each isomer), trimethoxyphenol (each isomer), triethoxyphenol (each isomer), tripropyloxyphenol (each isomer), tributyloxyphenol (each isomer), tripentyloxyphenol (each isomer), trihexyloxyphenol (each isomer), triheptyloxyphenol (each isomer), trioctyloxyphenol (each isomer), trinonyloxyphenol (each isomer), tridecyloxyphenol (each isomer), tridodecyloxyphenol (each isomer), trioctadecyloxyphenol (each isomer), tricyclopentyloxyphenol (each isomer), tricyclohexyloxyphenol (each isomer), tricycloheptyloxyphenol (each isomer), tricyclooctyloxyphenol (each isomer), tri(methylcyclopentyloxy)phenol (each isomer), tri(ethylcyclopentyloxy)phenol (each isomer), tri(methylcyclohexyloxy)phenol (each isomer), tri(ethylcyclohexyloxy)phenol (each isomer), tri(propylcyclohexyloxy)phenol (each isomer), tri(butylcyclohexyloxy)phenol (each isomer), tri(pentylcyclohexyloxy)phenol (each isomer), tri(hexylcyclohexyloxy)phenol (each isomer), tri(dimethylcyclohexyloxy)phenol (each isomer), tri(diethylcyclohexyloxy)phenol (each isomer), tri(dibutylcyclohexyloxy)phenol (each isomer), phenyloxyphenol, tri(methylphenyloxy)phenol (each isomer), tri(ethylphenyloxy)phenol (each isomer), tri(propylphenyloxy)phenol (each isomer), tri(butylphenyloxy)phenol (each isomer), tri(pentylphenyloxy)phenol (each isomer), tri(hexylphenyloxy)phenol (each isomer), tri(heptylphenyloxy)phenol (each isomer), tri(octylphenyloxy)phenol (each isomer), tri(nonylphenyloxy)phenol (each isomer), tri(decylphenyloxy)phenol (each isomer), tribiphenyloxyphenol (each isomer), tri(dimethylphenyloxy)phenol (each isomer), tri(diethylphenyloxy)phenol (each isomer), tri(dipropylphenyloxy)phenol (each isomer), tri(dibutylphenyloxy)phenol (each isomer), tri(dipentylphenyloxy)phenol (each isomer), tri(dihexylphenyloxy)phenol (each isomer), tri(diheptylphenyloxy)phenol (each isomer), triterphenyloxyphenol (each isomer), tri(trimethylphenyloxy)phenol (each isomer), tri(triethylphenyloxy)phenol (each isomer), tri(tripropylphenyloxy)phenol (each isomer), tri(tributylphenyloxy)phenol (each isomer), (phenylmethyloxy)phenol, tri(phenylethyloxy)phenol (each isomer), tri(phenylpropyloxy)phenol (each isomer), tri(phenylbutyloxy)phenol (each isomer), tri(phenylpentyloxy)phenol (each isomer), tri(phenylhexyloxy)phenol (each isomer), tri(phenylheptyloxy)phenol (each isomer), tri(phenyloctyloxy)phenol (each isomer), tri(phenylnonyloxy)phenol (each isomer), phenylphenol (each isomer), hydroxyphenylphenol (each isomer), hydroxyphenoxyphenol (each isomer), hydroxyphenyl-propylphenol (each isomer), and naphthol (each isomer).

Among the above described aromatic hydroxy compounds, more preferred examples include aromatic hydroxy compounds in which the number of carbon atoms constituting the $R^{22}$, $R^{23}$, $R^{24}$, $R^{25}$ and $R^{26}$ is from 0 to 13, because it facilitates transfer. Further preferred examples include aromatic hydroxy compounds in which the $R^{22}$, $R^{23}$, $R^{24}$, $R^{25}$ and $R^{26}$ each represent a group containing 0 to 9 carbon atoms, which is selected from a hydrogen atom, a straight chain and/or branched chain alkyl group, a cycloalkyl group, a substituted or unsubstituted aryl group, a straight chain and/or branched chain alkoxy group, a substituted or unsubstituted aryloxy group, and a substituted or unsubstituted aralkyl group.

In addition, as described later, the aromatic hydroxy compound forms a carbamate, and it generates an isocyanate when it is subjected to a pyrolytic reaction. If referring to the reaction formula of the aromatic hydroxy compound generated in the above described operation, it is an aromatic hydroxy compound used in the production of the carbamate. After completion of the pyrolytic step, in one of the present embodiments, the aromatic hydroxy compound may be separated from the isocyanate by distillation, and the thus separated aromatic hydroxy compound may be then recycled as an aromatic hydroxy compound in the reaction of an organic primary amine, urea and an aromatic hydroxy compound, although it depends on situation. Accordingly, if taking into consideration the production step of the isocyanate, it is necessary to consider the separating property between the aromatic hydroxy compound used as a raw material for the carbamate and the isocyanate generated from the carbamate. It is difficult to generally define such a separating property. On the basis of the findings that, in general, if the standard boiling points of two components to be separated are 10° C. or more apart from each other, they can be industrially sufficiently separated by distillation, the separating property will be defined as follows. Thus, this definition is a value that is limited to conventionally known separation means, and it is not a definition that constitutes the essence of the present embodiment.

Next, an active aromatic hydroxy compound will be described. The aromatic hydroxy compound represented by the above formula (20) can be preferably used as an aromatic hydroxy compound, when a carbamate is produced by a reaction of an organic primary amine, a carbonic acid derivative and an aromatic hydroxy compound, or by a reaction of a compound having a ureido group and an aromatic hydroxy compound. In both of the carbamate generation reactions, from the viewpoint of high reactivity, an aromatic hydroxy compound represented by the following formula (21) is preferably used. (In order to express such high reactivity, an aromatic hydroxy compound represented by the following formula (21) is often referred to as an "active aromatic hydroxy compound" in the present specification).

As a result of studies conducted by the present inventors, it was found that the rate of generating carbamates may significantly differ, depending on the type of an aromatic hydroxy compound used in the production of carbamates from an organic amine, a carbonic acid derivative and an aromatic hydroxy compound. Then, as a result of further intensive studies, the present inventors have found that the rate of generating carbamates depends on the type of a substituent in ortho position to the hydroxy group of the used aromatic hydroxy compound, and that, if an aromatic hydroxy compound having a specific substituent in ortho position is used, the rate of generating carbamates becomes much higher than in the case of using other aromatic hydroxy compounds. The fact that specific aromatic hydroxy compounds provide such effects has not been known from prior art, and thus, it is a surprising finding. Although the mechanism of providing such effects has not yet been elucidated, the present inventors have assumed that this is because when the size of a group attached to the atom at the position α is greater than a predetermined size, the group would sterically inhibit the hydroxy group as a reaction point.

The active aromatic hydroxy compound is an aromatic hydroxy compound represented by the following formula (21):

[Chemical Formula 13]

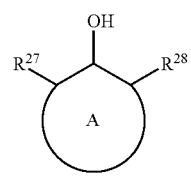

(21)

wherein ring A represents an aromatic hydrocarbon ring optionally having a substituent, and it may be either a single ring or multiple rings, $R^{27}$ and $R^{28}$ independently represent any one group defined in the following (i) to (v), the number of carbon atoms constituting the aromatic hydroxy compound is an integer from 6 to 50, and further, with regard to the $R^{27}$ and $R^{28}$, another portion in the group may bind to the ring A, so as to form a ring structure that is adjacent to A.

(i) a hydrogen atom, (ii) a halogen atom, (iii) a group containing 1 to 44 carbon atoms, in which the atom at position α is a nitrogen atom, wherein the nitrogen atom is a secondary nitrogen atom (which represents a nitrogen atom forming a —NH— bond), and which does not contain active hydrogen (excluding hydrogen binding to the nitrogen atom at the position α), (iv) a group containing 1 to 44 carbon atoms, in which the atom at position α is a carbon atom, wherein the carbon atom is a primary or secondary carbon atom (which represents carbon of a methyl group, and carbon forming a —CH$_2$— bond), and which does not contain active hydrogen; however, when the R$^{27}$ and/or the R$^{28}$ form a saturated and/or unsaturated condensed ring structure with the aromatic ring A, and the condensed ring is a 6- or less-membered ring, the carbon atom at the position α may be a tertiary or quaternary carbon atom; examples of such a case are shown in the following formula (22) and formula (23); and in addition, when the carbon atom at the position α forms a double bond or triple bond with a position β (which represents, among atoms forming the R$^{27}$ and the R$^{28}$, an atom adjacent to the atom binding to the aromatic ring of the ring A), the carbon atom at the position α may be a tertiary or quaternary carbon atom,

[Chemical Formula 14]

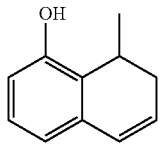

(22)

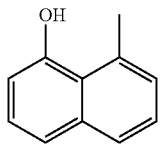

(23)

(v) a group containing 1 to 44 carbon atoms, in which the atom at position α is an oxygen atom, and which does not contain active hydrogen.

In the above formula (21), the term "the atom at position α" is used. This term "the atom at position α" means an atom adjacent to a carbon atom on the aromatic hydrocarbon ring to which the R$^{27}$ and R$^{28}$ groups bind, among atoms constituting the R$^{27}$ and R$^{28}$.

A substituent substituted with the aromatic group of the aromatic hydroxy compound represented by the above formula (21) (excluding R$^{27}$ and R$^{28}$) is selected from a hydrogen atom, a halogen atom, an aliphatic group, and an aromatic group. Examples of such a substituent include a group consisting of an acyclic hydrocarbon group, a cyclic hydrocarbon group (e.g. a monocyclic hydrocarbon group, a condensed polycyclic hydrocarbon group, a crosslinked cyclic hydrocarbon group, a spiro hydrocarbon group, a multi-ring hydrocarbon group, a cyclic hydrocarbon group having a side chain, a heterocyclic group, a heterocyclic spiro group, a hetero crosslinked cyclic group, and a heterocyclic group), a group to which one or more groups selected from the above described acyclic hydrocarbon group and the above described cyclic hydrocarbon group bind, and a group to which the above described group binds via a covalent bond with a specific non-metal atom (carbon, oxygen, nitrogen, sulfur, or silicon).

If taking into consideration the unlikeliness of side reactions, among the aforementioned substituents, examples of a substituent that can be preferably used in the present embodiment include: a group selected from the group consisting of an acyclic hydrocarbon group and a cyclic hydrocarbon group (a monocyclic hydrocarbon group, a condensed polycyclic hydrocarbon group, a crosslinked cyclic hydrocarbon group, a spiro hydrocarbon group, a multi-ring hydrocarbon group, and a cyclic hydrocarbon group having a side chain); and a group to which at least one group selected from the above described group binds (wherein the two groups are substituted with each other).

On the other hand, when an organic primary amine, urea and an aromatic hydroxy compound are reacted at a high temperature, so as to obtain a carbamate, it is preferable to use an aromatic hydroxy compound, in which the substituent substituted with the ring A thereof (excluding R$^{27}$ and R$^{28}$) is an inactive substituent. The term "inactive substituent" is used herein to mean a group that does not contain the above described active hydrogen (provided that it may have an aromatic hydroxy group).

Examples of such a substituent substituted with the ring A (excluding R$^{27}$ and R$^{28}$) include: a group selected from the group consisting of an alkyl group, a cycloalkyl group, an aryl group, an aralkyl group, and an ether group (substituted and/or unsubstituted alkyl ether and/or aryl ether and/or aralkyl ether); a group, to which one or more groups selected from the above described group bind; a group selected from groups composed of groups, to which one or more groups selected from the above described group bind via a saturated aliphatic bond and/or an ether bond; and a group which is a halogen atom and in which a total of the number of carbon atoms constituting the ring A and the number of carbon atoms constituting all of the substituents substituted with the ring A can be an integer from 6 to 50.

In the above definition (iii), it is described that the nitrogen atom at position α of R$^{27}$ and R$^{28}$ may be a nitrogen atom that forms a —NH— bond. According to the definition of the above described "active hydrogen," the hydrogen atom of the —NH— bond is also active hydrogen. However, as a result of the present inventors' studies, it was found that the hydrogen atom attached to the nitrogen atom at the position α has low reactivity and thus it hardly affects the invention of the present embodiment. The present inventors have assumed that it may be due to steric hindrance around the hydroxy group.

In the above formula (21), examples of the ring A include a benzene ring, a naphthalene ring, an anthracene ring, a phenanthrene ring, a naphthacene ring, a chrysene ring, a pyrene ring, a triphenylene ring, a pentalene ring, an azulene ring, a heptalene ring, an indacene ring, a biphenylene ring, an acenaphthylene ring, an aceanthrylene ring, and an acephenanthrylene ring. More preferably, it is a structure containing at least one structure selected from a benzene ring and a naphthalene ring.

If considering industrial use, an aromatic hydroxy compound having an easily available benzene ring as a skeleton is preferable. Such an aromatic hydroxy compound is preferably an aromatic hydroxy compound represented by the following formula (24):

[Chemical Formula 15]

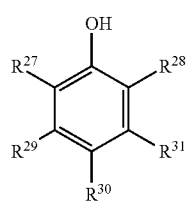

(24)

wherein

R$^{27}$ and R$^{28}$ each represent the above-defined group, and

R$^{29}$, R$^{30}$ and R$^{31}$ independently represent a group selected from the group consisting of an alkyl group, a cycloalkyl group, an aryl group, an aralkyl group, and an ether group (substituted and/or unsubstituted alkyl ether and/or aryl ether and/or aralkyl ether); a group, to which one or more groups selected from the above described groups bind; a group selected from groups composed of groups, to which one or more groups selected from the above described group bind via a saturated aliphatic bond and/or an ether bond; a halogen atom; or a hydrogen atom, and in which the total number of carbon atoms constituting the R$^{27}$, R$^{28}$, R$^{29}$, R$^{30}$ and R$^{31}$ is an integer from 0 to 44.

Preferred R$^{29}$, R$^{30}$ and R$^{31}$ are groups independently selected from the groups described in the following (vi) to (x):

(vi) a hydrogen atom, (vii) a halogen atom, (viii) a group containing 1 to 44 carbon atoms, in which the atom at position α is a carbon atom, wherein three groups attached to the carbon atom at the position α are independently selected from an alkyl group containing 1 to 43 carbon atoms, a cycloalkyl group containing 1 to 43 carbon atoms, an alkoxy group containing 1 to 43 carbon atoms, a polyoxyalkylene alkyl ether group containing 2 to 43 carbon atoms and having no OH groups at the terminus thereof, an aryl group containing 6 to 43 carbon atoms, an aralkyl group containing 7 to 43 carbon atoms, an aralkyloxy group containing 7 to 43 carbon atoms, a group to which one or more of the above described groups bind, and a hydrogen atom, (ix) an aryl group containing 1 to 44 carbon atoms, which is substituted with a substituent, wherein the substituent is an aryl group optionally substituted with the following integer from 1 to 5 substituents, wherein the substituents are selected from a hydrogen atom, an alkyl group containing 1 to 38 carbon atoms, a cycloalkyl group containing 4 to 38 carbon atoms, an alkoxy group containing 1 to 38 carbon atoms, a polyoxyalkylene alkyl ether group containing 2 to 38 carbon atoms and having no OH groups at the terminus thereof, an aryl group containing 6 to 38 carbon atoms, an aralkyl group containing 7 to 38 carbon atoms, an aralkyloxy group containing 7 to 38 carbon atoms, and a group to which one or more of the above described groups bind, and (x) a group containing 1 to 44 carbon atoms, in which the atom at position α is an oxygen atom, wherein the group attached to the oxygen atom at the position α is selected from an alkyl group containing 1 to 44 carbon atoms, a cycloalkyl group containing 1 to 44 carbon atoms, an alkoxy group containing 1 to 44 carbon atoms, a polyoxyalkylene alkyl ether group containing 2 to 44 carbon atoms and having no OH groups at the terminus thereof, an aryl group containing 6 to 44 carbon atoms, an aralkyl group containing 7 to 44 carbon atoms, an aralkyloxy group containing 7 to 44 carbon atoms, and a group to which one or more of the above described groups bind.

In the above formula (24), the term "the atom at position α" is used. This term "the atom at position α" means an atom adjacent to a carbon atom on the aromatic hydrocarbon ring to which the R$^{27}$, R$^{28}$, R$^{29}$, R$^{30}$ and R$^{31}$ groups bind, among atoms constituting the R$^{27}$, R$^{28}$, R$^{29}$, R$^{30}$ and R$^{31}$.

Examples of such R$^{29}$, R$^{30}$ and R$^{31}$ include:

alkyl groups, and/or cycloalkyl groups, and/or cycloalkyl groups substituted with alkyl groups, and/or alkyl groups substituted with cycloalkyl groups, such as a methyl group, an ethyl group, a propyl group (each isomer), a butyl group (each isomer), a pentyl group (each isomer), a hexyl group (each isomer), a heptyl group (each isomer), an octyl group (each isomer), a nonyl group (each isomer), a decyl group (each isomer), a dodecyl group (each isomer), an octadecyl group (each isomer), cyclopentane, cyclohexane, cycloheptane, cyclooctane, methylcyclopentane (each isomer), ethylcyclopentane (each isomer), methylcyclohexane (each isomer), ethylcyclohexane (each isomer), propylcyclohexane (each isomer), butylcyclohexane (each isomer), pentylcyclohexane (each isomer), hexylcyclohexane (each isomer), dimethylcyclohexane (each isomer), diethylcyclohexane (each isomer), and dibutylcyclohexane (each isomer);

alkoxy groups, and/or cycloalkoxy groups, and/or cycloalkoxy groups substituted with alkyl groups, and/or alkoxy groups substituted with cycloalkyl groups, such as a methoxy group, an ethoxy group, a propoxy group (each isomer), a butyloxy group (each isomer), a pentyloxy group (each isomer), a hexyloxy group (each isomer), a heptyloxy group (each isomer), an octyloxy group (each isomer), a nonyloxy group (each isomer), a decyloxy group (each isomer), a dodecyloxy group (each isomer), an octadecyloxy group (each isomer), a cyclopentyloxy group, a cyclohexyloxy group, a cycloheptyloxy group, a cyclooctyloxy group, a methylcyclopentyloxy group (each isomer), an ethylcyclopentyloxy group (each isomer), a methylcyclohexyloxy group (each isomer), an ethylcyclohexyloxy group (each isomer), a propylcyclohexyloxy group (each isomer), a butylcyclohexyloxy group (each isomer), a pentylcyclohexyloxy group (each isomer), a hexylcyclohexyloxy group (each isomer), a dimethylcyclohexyloxy group (each isomer), a diethylcyclohexyloxy group (each isomer), and a dibutylcyclohexyloxy group (each isomer);

substituted or unsubstituted aryl groups, such as a phenyl group, a methylphenyl group (each isomer), an ethylphenyl group (each isomer), a propylphenyl group (each isomer), a butylphenyl group (each isomer), a pentylphenyl group (each isomer), a hexylphenyl group (each isomer), a heptylphenyl group (each isomer), an octylphenyl group (each isomer), a nonylphenyl group (each isomer), a decylphenyl group (each isomer), a biphenyl group (each isomer), a dimethylphenyl group (each isomer), a diethylphenyl group (each isomer), a dipropylphenyl group (each isomer), a dibutylphenyl group (each isomer), a dipentylphenyl group (each isomer), a dihexylphenyl group (each isomer), a diheptylphenyl group (each isomer), a terphenyl group (each isomer), a trimethylphenyl group (each isomer), a triethylphenyl group (each isomer), a tripropylphenyl group (each isomer), and a tributylphenyl group (each isomer);

substituted or unsubstituted aryloxy groups, such as a phenoxy group, a methylphenoxy group (each isomer), an ethylphenoxy group (each isomer), a propylphenoxy group (each isomer), a butylphenoxy group (each isomer), a pentylphenoxy group (each isomer), a hexylphenoxy group (each isomer), a heptylphenoxy group (each isomer), an octylphenoxy group (each isomer), a nonylphenoxy group (each isomer), a decylphenoxy group (each isomer), a phenylphenoxy group (each isomer), a dimethylphenoxy group (each isomer), a diethylphenoxy group (each isomer), a dipropylphenoxy group (each isomer), a dibutylphenoxy group (each isomer), a dipentylphenoxy group (each isomer), a dihexylphenoxy group (each isomer), a diheptylphenoxy group (each isomer), a diphenylphenoxy group (each isomer), a trimethylphenoxy group (each isomer), a triethylphenoxy group (each isomer), a tripropylphenoxy group (each isomer), and a tributylphenoxy group (each isomer); and aralkyl groups such as a phenylmethyl group, a phenylethyl group (each isomer), a phenylpropyl group (each isomer), a phenylbutyl group (each isomer), a phenylpentyl group (each isomer), a phenylhexyl group (each isomer), a phenylheptyl group (each isomer), a phenyloctyl group (each isomer) and a phenylnonyl group (each isomer), and aralkyloxy groups such as a phenylmethoxy group, a phenylethoxy group (each isomer), a phenylpropyloxy group (each isomer), a phenylbutyloxy group (each isomer), a phenylpentyloxy group (each isomer), a phenylhexyloxy group (each isomer), a phenylheptyloxy group (each isomer), a phenyloctyloxy group (each isomer) and a phenylnonyloxy group (each isomer).

Preferred examples of the aromatic hydroxy compound represented by the above formula (21) include the following compounds, and also, specific examples of the aromatic hydroxy compound represented by the above formula (24) include the following compounds.

Specific examples include chlorophenol (each isomer), bromophenol (each isomer), dichlorophenol (each isomer), dibromophenol (each isomer), trichlorophenol (each isomer), tribromophenol (each isomer), phenol, methylphenol (each isomer), ethylphenol (each isomer), 2-n-propylphenol (each isomer), 2-n-butylphenol (each isomer), 2-n-pentylphenol (each isomer), 2-n-hexylphenol (each isomer), 2-n-heptylphenol (each isomer), 2-n-octylphenol (each isomer), 2-n-nonylphenol (each isomer), 2-n-decylphenol (each isomer), 2-n-dodecylphenol (each isomer), 2-n-octadecylphenol (each isomer), 3-propylphenol (each isomer), 3-butylphenol (each isomer), 3-pentylphenol (each isomer), 3-hexylphenol (each isomer), 3-heptylphenol (each isomer), 3-octylphenol (each isomer), 3-nonylphenol (each isomer), 3-decylphenol (each isomer), 3-dodecylphenol (each isomer), 3-octadecylphenol (each isomer), 4-propylphenol (each isomer), 4-butylphenol (each isomer), 4-pentylphenol (each isomer), 4-hexylphenol (each isomer), 4-heptylphenol (each isomer), 4-octylphenol (each isomer), 4-nonylphenol (each isomer), 4-decylphenol (each isomer), 4-dodecylphenol (each isomer), 4-octadecylphenol (each isomer), 4-phenylphenol, dimethylphenol (each isomer), diethylphenol (each isomer), di(n-propyl)phenol (each isomer), di(n-butyl)phenol (each isomer), di(n-pentyl)phenol (each isomer), di(n-hexyl)phenol (each isomer), di(n-heptyl)phenol (each isomer), di(n-octyl)phenol (each isomer), di(n-nonyl)phenol (each isomer), di(n-decyl)phenol (each isomer), di(n-dodecyl)phenol (each isomer), di(n-octadecyl)phenol (each isomer), trimethylphenol (each isomer), triethylphenol (each isomer), tri(n-propyl)phenol (each isomer), tri(n-butyl)phenol (each isomer), tri(n-pentyl)phenol (each isomer), tri(n-hexyl)phenol (each isomer), tri(n-heptyl)phenol (each isomer), tri(n-octyl)phenol (each isomer), tri(n-nonyl)phenol (each isomer), tri(n-decyl)phenol (each isomer), tri(n-dodecyl)phenol (each isomer), tri(n-octadecyl)phenol (each isomer), (methoxymethyl)phenol, (ethoxymethyl)phenol, (propoxymethyl)phenol (each isomer), (butyloxymethyl)phenol (each isomer), (pentyloxymethyl)phenol (each isomer), (hexyloxymethyl)phenol (each isomer), (heptyloxymethyl)phenol (each isomer), (octyloxymethyl)phenol (each isomer), (nonyloxymethyl)phenol (each isomer), (decyloxymethyl)phenol (each isomer), (dodecyloxymethyl)phenol (each isomer), (octadecyloxymethyl)phenol (each isomer), (cyclopentyloxymethyl)phenol, (cyclohexyloxymethyl)phenol, (cycloheptyloxymethyl)phenol, (cyclooctyloxymethyl)phenol, (methylcyclopentyloxymethyl)phenol (each isomer), (ethylcyclopentyloxymethyl)phenol (each isomer), (methylcyclohexyloxymethyl) phenol (each isomer), (ethylcyclohexyloxymethyl)phenol (each isomer), (propylcyclohexyloxymethyl)phenol (each isomer), (butylcyclohexyloxymethyl)phenol (each isomer), (pentylcyclohexyloxymethyl)phenol (each isomer), (hexylcyclohexyloxymethyl)phenol (each isomer), (dimethylcyclohexyloxymethyl)phenol (each isomer), (diethylcyclohexyloxymethyl)phenol (each isomer), (dibutylcyclohexyloxymethyl)phenol (each isomer), (phenoxymethyl)phenol, (methylphenoxymethyl)phenol (each isomer), (ethylphenoxymethyl)phenol (each isomer), (propylphenoxymethyl)phenol (each isomer), (butylphenoxymethyl)phenol (each isomer), (pentylphenoxymethyl)phenol (each isomer), (hexylphenoxymethyl)phenol (each isomer), (heptylphenoxymethyl)phenol (each isomer), (octylphenoxymethyl)phenol (each isomer), (nonylphenoxymethyl)phenol (each isomer), (decylphenoxymethyl)phenol (each isomer), (phenylphenoxymethyl)phenol (each isomer), (dimethylphenoxymethyl)phenol (each isomer), (diethylphenoxymethyl)phenol (each isomer), (dipropylphenoxymethyl)phenol (each isomer), (dibutylphenoxymethyl)phenol (each isomer), (dipentylphenoxymethyl)phenol (each isomer), (dihexylphenoxymethyl)phenol (each isomer), (diheptylphenoxymethyl)phenol (each isomer), (diphenylphenoxymethyl)phenol (each isomer), (trimethylphenoxymethyl)phenol (each isomer), (triethylphenoxymethyl)phenol (each isomer), (tripropylphenoxymethyl)phenol (each isomer), (tributylphenoxymethyl)phenol (each isomer), (phenylmethoxymethyl)phenol, (phenylethoxymethyl)phenol (each isomer), (phenylpropyloxymethyl)phenol (each isomer), (phenylbutyloxymethyl)phenol (each isomer), (phenylpentyloxymethyl)phenol (each isomer), (phenylhexyloxymethyl)phenol (each isomer), (phenylheptyloxymethyl)phenol (each isomer), (phenyloctyloxymethyl)phenol (each isomer), (phenylnonyloxymethyl)phenol (each isomer), di(methoxymethyl)phenol, di(ethoxymethyl)phenol, di(propoxymethyl)phenol (each isomer), di(butyloxymethyl)phenol (each isomer), di(pentyloxymethyl)phenol (each isomer), di(hexyloxymethyl)phenol (each isomer), di(heptyloxymethyl)phenol (each isomer), di(octyloxymethyl)phenol (each isomer), di(nonyloxymethyl)phenol (each isomer), di(decyloxymethyl)phenol (each isomer), di(dodecyloxymethyl)phenol (each isomer), di(octadecyloxymethyl)phenol (each isomer), di(cyclopentyloxymethyl)phenol, di(cyclohexyloxymethyl)phenol, di(cycloheptyloxymethyl)phenol, di(cyclooctyloxymethyl)phenol, di(methylcyclopentyloxymethyl)phenol (each isomer), di(ethylcyclopentyloxymethyl)phenol (each isomer), di(methylcyclohexyloxymethyl)phenol (each isomer), di(ethylcyclohexyloxymethyl)phenol (each isomer), di(propylcyclohexyloxymethyl)phenol (each isomer), di(butylcyclohexyloxymethyl)phenol (each isomer), di(pentylcyclohexyloxymethyl)phenol (each isomer), di(hexylcyclohexyloxymethyl)phenol (each isomer), bis (dimethylcyclohexyloxymethyl)phenol (each isomer), bis (diethylcyclohexyloxymethyl)phenol (each isomer), bis (dibutylcyclohexyloxymethyl)phenol (each isomer), di(phenoxymethyl)phenol, di(methylphenoxymethyl)phenol (each isomer), di(ethylphenoxymethyl)phenol (each isomer), di(propylphenoxymethyl)phenol (each isomer), di(butylphenoxymethyl)phenol (each isomer), di(pentylphenoxymethyl)phenol (each isomer), di(hexylphenoxymethyl) phenol (each isomer), di(heptylphenoxymethyl)phenol (each isomer), di(octylphenoxymethyl)phenol (each isomer), di(nonylphenoxymethyl)phenol (each isomer), di(decylphenoxymethyl)phenol (each isomer), di(phenylphenoxymethyl)phenol (each isomer), bis (dimethylphenoxymethyl)phenol (each isomer), bis (diethylphenoxymethyl)phenol (each isomer), bis (dipropylphenoxymethyl)phenol (each isomer), bis(dibutylphenoxymethyl)phenol (each isomer), bis(dipentylphenoxymethyl)phenol (each isomer), bis(dihexylphenoxymethyl)phenol (each isomer), bis(diheptylphenoxymethyl)phenol (each isomer), bis(diphenylphenoxymethyl)phenol (each isomer), di(trimethylphenoxymethyl)phenol (each isomer), di(triethylphenoxymethyl)phenol (each isomer), di(tripropylphenoxymethyl)phenol (each isomer), di(tributylphenoxymethyl)phenol (each isomer), (phenylmethoxymethyl)phenol, di(phenylethoxymethyl)phenol (each isomer), di(phenylpropyloxymethyl)phenol (each isomer), di(phenylbutyloxymethyl)phenol (each isomer), di(phenylpentyloxymethyl)phenol (each isomer), di(phenylhexyloxymethyl)phenol (each isomer), di(phenylheptyloxymethyl)phenol (each isomer), di(phenyloctyloxymethyl)phenol (each isomer), di(phenylnonyloxymethyl)phenol (each isomer), tri(methoxymethyl)phenol, tri(ethoxymethyl)phenol, tri(propoxymethyl)phenol (each isomer), tri(butyloxymethyl)phenol (each isomer), tri(pentyloxymethyl)phenol (each isomer), tri(hexyloxymethyl)phenol (each isomer), tri(heptyloxymethyl)phenol (each isomer), tri(octyloxymethyl)phenol (each isomer), tri(nonyloxymethyl)phenol (each isomer), tri(decyloxymethyl)phenol (each isomer), tri(dodecyloxymethyl)phenol (each isomer), tri(octadecyloxymethyl)phenol (each isomer), tri(cyclopentyloxymethyl)phenol, tri(cyclohexyloxymethyl)phenol, tri(cycloheptyloxymethyl)phenol, tri(cyclooctyloxymethyl)phenol, tri(methylcyclopentyloxymethyl)phenol (each isomer), tri(ethylcyclopentyloxymethyl)phenol (each isomer), tri(methylcyclohexyloxymethyl)phenol (each isomer), tri(ethylcyclohexyloxymethyl)phenol (each isomer), tri(propylcyclohexyloxymethyl)phenol (each isomer), tri(butylcyclohexyloxymethyl)phenol (each isomer), tri(pentylcyclohexyloxymethyl)phenol (each isomer), tri(hexylcyclohexyloxymethyl)phenol (each isomer), bis(dimethylcyclohexyloxymethyl)phenol (each isomer), bis(diethylcyclohexyloxymethyl)phenol (each isomer), bis(dibutylcyclohexyloxymethyl)phenol (each isomer), tri(phenoxymethyl)phenol, tri(methylphenoxymethyl)phenol (each isomer), tri(ethylphenoxymethyl)phenol (each isomer), tri(propylphenoxymethyl)phenol (each isomer), tri(butylphenoxymethyl)phenol (each isomer), tri(pentylphenoxymethyl)phenol (each isomer), tri(hexylphenoxymethyl)phenol (each isomer), tri(heptylphenoxymethyl)phenol (each isomer), tri(octylphenoxymethyl)phenol (each isomer), tri(nonylphenoxymethyl)phenol (each isomer), tri(decylphenoxymethyl)phenol (each isomer), tri(phenylphenoxymethyl)phenol (each isomer), bis(dimethylphenoxymethyl)phenol (each isomer), bis(diethylphenoxymethyl)phenol (each isomer), bis(dipropylphenoxymethyl)phenol (each isomer), bis(dibutylphenoxymethyl)phenol (each isomer), bis(dipentylphenoxymethyl)phenol (each isomer), bis(dihexylphenoxymethyl)phenol (each isomer), bis(diheptylphenoxymethyl)phenol (each isomer), bis(diphenylphenoxymethyl)phenol (each isomer), tri(trimethylphenoxymethyl)phenol (each isomer), tri(triethylphenoxymethyl)phenol (each isomer), tri(tripropylphenoxymethyl)phenol (each isomer), tri(tributylphenoxymethyl)phenol (each isomer), tri(phenylmethoxymethyl)phenol, tri(phenylethoxymethyl)phenol (each isomer), tri(phenylpropyloxymethyl)phenol (each isomer), tri(phenylbutyloxymethyl)phenol (each isomer), tri(phenylpentyloxymethyl)phenol (each isomer), tri(phenylhexyloxymethyl)phenol (each isomer), tri(phenylheptyloxymethyl)phenol (each isomer), tri(phenyloctyloxymethyl)phenol (each isomer), tri(phenylnonyloxymethyl)phenol (each isomer), (phenylmethyl)phenol (each isomer), ((methylphenyl)methyl)phenol (each isomer), ((ethylphenyl)methyl)phenol (each isomer), ((propylphenyl)methyl)phenol (each isomer), ((butylphenyl)methyl)phenol (each isomer), ((pentylphenyl)methyl)phenol (each isomer), ((hexylphenyl)methyl)phenol (each isomer), ((heptylphenyl)methyl)phenol (each isomer), ((octylphenyl)methyl)phenol (each isomer), ((nonylphenyl)methyl)phenol (each isomer), ((decylphenyl)methyl)phenol (each isomer), ((biphenyl)methyl)phenol (each isomer), ((dimethylphenyl)methyl)phenol (each isomer), ((diethylphenyl)methyl)phenol (each isomer), ((dipropylphenyl)methyl)phenol (each isomer), ((dibutylphenyl)methyl)phenol (each isomer), ((dipentylphenyl)methyl)phenol (each isomer), ((dihexylphenyl)methyl)phenol (each isomer), ((diheptylphenyl)methyl)phenol (each isomer), ((terphenyl)methyl)phenol (each isomer), ((trimethylphenyl)methyl)phenol (each isomer), ((triethylphenyl)methyl)phenol (each isomer), ((tripropylphenyl)methyl)phenol (each isomer), ((tributylphenyl)methyl)phenol (each isomer), di(phenylmethyl)phenol (each isomer), di((methylphenyl)methyl)phenol (each isomer), di((ethylphenyl)methyl)phenol (each isomer), di((propylphenyl)methyl)phenol (each isomer), di((butylphenyl)methyl)phenol (each isomer), di((pentylphenyl)methyl)phenol (each isomer), di((hexylphenyl)methyl)phenol (each isomer), di((heptylphenyl)methyl)phenol (each isomer), di((octylphenyl)methyl)phenol (each isomer), di((nonylphenyl)methyl)phenol (each isomer), di((decylphenyl)methyl)phenol (each isomer), di((biphenyl)methyl)phenol (each isomer), di((dimethylphenyl)methyl)phenol (each isomer), di((diethylphenyl)methyl)phenol (each isomer), di((dipropylphenyl)methyl)phenol (each isomer), di((dibutylphenyl)methyl)phenol (each isomer), di((dipentylphenyl)methyl)phenol (each isomer), di((dihexylphenyl)methyl)phenol (each isomer), di((diheptylphenyl)methyl)phenol (each isomer), di((terphenyl)methyl)phenol (each isomer), di((trimethylphenyl)methyl)phenol (each isomer), di((triethylphenyl)methyl)phenol (each isomer), di((tripropylphenyl)methyl)phenol (each isomer), di((tributylphenyl)methyl)phenol (each isomer), tri(phenylmethyl)phenol (each isomer), tri((methylphenyl)methyl)phenol (each isomer), tri((ethylphenyl)methyl)phenol (each isomer), tri((propylphenyl)methyl)phenol (each isomer), tri((butylphenyl)methyl)phenol (each isomer), tri((pentylphenyl)methyl)phenol (each isomer), tri((hexylphenyl)methyl)phenol (each isomer), tri((heptylphenyl)methyl)phenol (each isomer), tri((octylphenyl)methyl)phenol (each isomer), tri((nonylphenyl)methyl)phenol (each isomer), tri((decylphenyl)methyl)phenol (each isomer), tri((biphenyl)methyl)phenol (each isomer), tri((dimethylphenyl)methyl)phenol (each isomer), tri((diethylphenyl)methyl)phenol (each isomer), tri((dipropylphenyl)methyl)phenol (each isomer), tri((dibutylphenyl)methyl)phenol (each isomer), tri((dipentylphenyl)methyl)phenol (each isomer), tri((dihexylphenyl)methyl)phenol (each isomer), tri((diheptylphenyl)methyl)phenol (each isomer), tri((terphenyl)methyl)phenol (each isomer), tri((trimethylphenyl)methyl)phenol (each isomer), tri((triethylphenyl)methyl)phenol (each isomer), tri((tripropylphenyl)methyl)phenol (each isomer), tri((tributylphenyl)methyl)phenol (each isomer), phenylethylphenol (each isomer), phenyl-n-propylphenol (each isomer), phenyl-n-butylphenol (each isomer), phenyl-n-pentylphenol (each isomer), phenyl-n-hexylphenol (each isomer), phenyl-n-heptylphenol (each isomer), phenyl-n-octylphenol (each isomer), phenyl-n-nonylphenol (each isomer), (methylamino)phenol, (ethylamino)phenol, (propylamino)phenol (each isomer), (butylamino)phenol (each isomer), (pentylamino)phenol (each isomer), (hexylamino)phenol (each isomer), (heptylamino)phenol (each isomer), (octylamino)phenol (each isomer), (nonylamino)phenol (each isomer), (decylamino)phenol (each isomer), (dodecylamino)phenol (each isomer), (octadecylamino)phenol (each isomer), di(methylamino)phenol, di(ethylamino)phenol, di(propylamino)phenol (each isomer), di(butylamino)phenol (each isomer), di(pentylamino)phenol (each isomer), di(hexylamino)phenol (each isomer), di(heptylamino)phenol (each isomer), di(octylamino)phenol (each isomer), di(nonylamino)phenol (each isomer), di(decylamino)phenol (each isomer), di(dodecylamino)phenol (each isomer), di(octadecylamino)phenol (each isomer), tri(methylamino)phenol, tri(ethylamino)phenol, tri(propylamino)phenol (each isomer), tri(butylamino)phenol (each isomer), tri(pentylamino)phenol (each isomer), tri(hexylamino)phenol (each isomer), tri(heptylamino)phenol (each isomer), tri(octylamino)phenol (each isomer), tri(nonylamino)phenol (each isomer), tri(decylamino)phenol (each isomer), tri(dodecylamino)phenol (each isomer), tri(octadecylamino)phenol (each isomer), methoxyphenol (each isomer), ethoxyphenol (each isomer), propyloxyphenol (each isomer), butyloxyphenol (each isomer), pentyloxyphenol (each isomer), hexyloxyphenol (each isomer), heptyloxyphenol (each isomer), octyloxyphenol (each isomer), nonyloxyphenol (each isomer), decyloxyphenol (each isomer), dodecyloxyphenol (each isomer), octadecyloxyphenol (each isomer), cyclopentyloxyphenol (each isomer), cyclohexyloxyphenol (each isomer), cycloheptyloxyphenol (each isomer), cyclooctyloxyphenol (each isomer), (methylcyclopentyloxy)phenol (each isomer), (ethylcyclopentyloxy)phenol (each isomer), (methylcyclohexyloxy)phenol (each isomer), (ethylcyclohexyloxy)phenol (each isomer), (propylcyclohexyloxy)phenol (each isomer), (butylcyclohexyloxy)phenol (each isomer), (pentylcyclohexyloxy)phenol (each isomer), (hexylcyclohexyloxy)phenol (each isomer), (dimethylcyclohexyloxy)phenol (each isomer), (diethylcyclohexyloxy)phenol (each isomer), (dibutylcyclohexyloxy)phenol (each isomer), phenoxyphenol, (methylphenyloxy)phenol (each isomer), (ethylphenyloxy)phenol (each isomer), (propylphenyloxy)phenol (each isomer), (butylphenyloxy)phenol (each isomer), (pentylphenyloxy)phenol (each isomer), (hexylphenyloxy)phenol (each isomer), (heptylphenyloxy)phenol (each isomer), (octylphenyloxy)phenol (each isomer), (nonylphenyloxy)phenol (each isomer), (decylphenyloxy)phenol (each isomer), biphenyloxyphenol (each isomer), (dimethylphenyloxy)phenol (each isomer), (diethylphenyloxy)phenol (each isomer), (dipropylphenyloxy)phenol (each isomer), (dibutylphenyloxy)phenol (each isomer), (dipentylphenyloxy)phenol (each isomer), (dihexylphenyloxy)phenol (each isomer), (diheptylphenyloxy)phenol (each isomer), terphenyloxyphenol (each isomer), (trimethylphenyloxy)phenol (each isomer), (triethylphenyloxy)phenol (each isomer), (tripropylphenyloxy)phenol (each isomer), (tributylphenyloxy)phenol (each isomer), (phenylmethyloxy)phenol, (phenylethyloxy)phenol (each isomer), (phenylpropyloxy)phenol (each isomer), (phenylbutyloxy)phenol (each isomer), (phenylpentyloxy)phenol (each isomer), (phenylhexyloxy)phenol (each isomer), (phenylheptyloxy)phenol (each isomer), (phenyloctyloxy)phenol (each isomer), (phenylnonyloxy)phenol (each isomer), dimethoxyphenol (each isomer), diethoxyphenol (each isomer), dipropyloxyphenol (each isomer), dibutyloxyphenol (each isomer), dipentyloxyphenol (each isomer), dihexyloxyphenol (each isomer), diheptyloxyphenol (each isomer), dioctyloxyphenol (each isomer), dinonyloxyphenol (each isomer), didecyloxyphenol (each isomer), didodecyloxyphenol (each isomer), dioctadecyloxyphenol (each isomer), dicyclopentyloxyphenol (each isomer), dicyclohexyloxyphenol (each isomer), dicycloheptyloxyphenol (each isomer), dicyclooctyloxyphenol (each isomer), di(methylcyclopentyloxy)phenol (each isomer), di(ethylcyclopentyloxy)phenol (each isomer), di(methylcyclohexyloxy)phenol (each isomer), di(ethylcyclohexyloxy)phenol (each isomer), di(propylcyclohexyloxy)phenol (each isomer), di(butylcyclohexyloxy)phenol (each isomer), di(pentylcyclohexyloxy)phenol (each isomer), di(hexylcyclohexyloxy)phenol (each isomer), bis(dimethylcyclohexyloxy)phenol (each isomer), bis(diethylcyclohexyloxy)phenol (each isomer), bis(dibutylcyclohexyloxy)phenol (each isomer), phenyloxyphenol, di(methylphenyloxy)phenol (each isomer), di(ethylphenyloxy)phenol (each isomer), di(propylphenyloxy)phenol (each isomer), di(butylphenyloxy)phenol (each isomer), di(pentylphenyloxy)phenol (each isomer), di(hexylphenyloxy)phenol (each isomer), di(heptylphenyloxy)phenol (each isomer), di(octylphenyloxy)phenol (each isomer), di(nonylphenyloxy)phenol (each isomer), di(decylphenyloxy)phenol (each isomer), dibiphenyloxyphenol (each isomer), bis(dimethylphenyloxy)phenol (each isomer), bis(diethylphenyloxy)phenol (each isomer), bis(dipropylphenyloxy)phenol (each isomer), bis(dibutylphenyloxy)phenol (each isomer), bis(dipentylphenyloxy)phenol (each isomer), bis(dihexylphenyloxy)phenol (each isomer), bis(diheptylphenyloxy)phenol (each isomer), diterphenyloxyphenol (each isomer), di(trimethylphenyloxy)phenol (each isomer), di(triethylphenyloxy)phenol (each isomer), di(tripropylphenyloxy)phenol (each isomer), di(tributylphenyloxy)phenol (each isomer), (phenylmethyloxy)phenol, di(phenylethyloxy)phenol (each isomer), di(phenylpropyloxy)phenol (each isomer), di(phenylbutyloxy)phenol (each isomer), di(phenylpentyloxy)phenol (each isomer), di(phenylhexyloxy)phenol (each isomer), di(phenylheptyloxy)phenol (each isomer), di(phenyloctyloxy)phenol (each isomer), di(phenylnonyloxy)phenol (each isomer), trimethoxyphenol (each isomer), triethoxyphenol (each isomer), tripropyloxyphenol (each isomer), tributyloxyphenol (each isomer), tripentyloxyphenol (each isomer), trihexyloxyphenol (each isomer), triheptyloxyphenol (each isomer), trioctyloxyphenol (each isomer), trinonyloxyphenol (each isomer), tridecyloxyphenol (each isomer), tridodecyloxyphenol (each isomer), trioctadecyloxyphenol (each isomer), tricyclopentyloxyphenol (each isomer), tricyclohexyloxyphenol (each isomer), tricycloheptyloxyphenol (each isomer), tricyclooctyloxyphenol (each isomer), tri(methylcyclopentyloxy)phenol (each isomer), tri(ethylcyclopentyloxy)phenol (each isomer), tri(methylcyclohexyloxy)phenol (each isomer), tri(ethylcyclohexyloxy)phenol (each isomer), tri(propylcyclohexyloxy)phenol (each isomer), tri(butylcyclohexyloxy)phenol (each isomer), tri(pentylcyclohexyloxy)phenol (each isomer), tri(hexylcyclohexyloxy)phenol (each isomer), tri(dimethylcyclohexyloxy)phenol (each isomer), tri(diethylcyclohexyloxy)phenol (each isomer), tri(dibutylcyclohexyloxy)phenol (each isomer), phenyloxyphenol, tri(methylphenyloxy)phenol (each isomer), tri(ethylphenyloxy)phenol (each isomer), tri(propylphenyloxy)phenol (each isomer), tri(butylphenyloxy)phenol (each isomer), tri(pentylphenyloxy)phenol (each isomer), tri(hexylphenyloxy)phenol (each isomer), tri(heptylphenyloxy)phenol (each isomer), tri(octylphenyloxy)phenol (each isomer), tri(nonylphenyloxy)phenol (each isomer), tri(decylphenyloxy)phenol (each isomer), tribiphenyloxyphenol (each isomer), tri(dimethylphenyloxy)phenol (each isomer), tri(diethylphenyloxy)phenol (each isomer), tri(dipropylphenyloxy)phenol (each isomer), tri(dibutylphenyloxy)phenol (each isomer), tri(dipentylphenyloxy)phenol (each isomer), tri(dihexylphenyloxy)phenol (each isomer), tri(diheptylphenyloxy)phenol (each isomer), triterphenyloxyphenol (each isomer), tri(trimethylphenyloxy)phenol (each isomer), tri(triethylphenyloxy)phenol (each isomer), tri(tripropylphenyloxy)phenol (each isomer), tri(tributylphenyloxy)phenol (each isomer), (phenylmethyloxy)phenol, tri(phenylethyloxy)phenol (each isomer), tri(phenylpropyloxy)phenol (each isomer), tri(phenylbutyloxy)phenol (each isomer), tri(phenylpentyloxy)phenol (each isomer), tri(phenylhexyloxy)phenol (each isomer), tri(phenylheptyloxy)phenol (each isomer), tri(phenyloctyloxy)phenol (each isomer), tri(phenylnonyloxy)phenol (each isomer), and naphthol (each isomer).

Among the above described aromatic hydroxy compounds, more preferred examples include aromatic hydroxy compounds in which the number of carbon atoms constituting the $R^{27}$, $R^{28}$, $R^{29}$, $R^{30}$ and $R^{31}$ is from 0 to 13, because it facilitates transfer. Further preferred examples include aromatic hydroxy compounds in which the $R^{27}$, $R^{28}$, $R^{29}$, $R^{30}$ and $R^{31}$ each represent a group containing 0 to 9 carbon atoms, which is selected from a hydrogen atom, a straight chain and/or branched chain alkyl group, a cycloalkyl group, a substituted or unsubstituted aryl group, a straight chain and/or branched chain alkoxy group, a substituted or unsubstituted aryloxy group, and a substituted or unsubstituted aralkyl group.

As described above, from the viewpoint of reactivity in the production of carbamates, an aromatic hydroxy compound having a specific structure is preferably used.

To the contrary, when a group attached to the atom at position α of at least one substituent in ortho position of an aromatic hydroxy compound is a bulky substituent, the rate of generating carbamates is significantly decreased in many cases. Specifically, it is an aromatic hydroxy compound, in which a substituent, wherein the atom at the position α is a tertiary or quaternary carbon atom or a tertiary nitrogen atom, binds to at least one ortho position with respect to the hydroxy group of the aromatic hydroxy compound. Hereinafter, such an aromatic hydroxy compound, the rate of generating carbamates of which is low, is often referred to as a low-active aromatic hydroxy compound.

On the other hand, by utilizing the phenomenon that the rate of generating N-substituted carbamates is different depending on the type of an aromatic hydroxy compound, a method for producing an N-substituted carbamate by using both an active aromatic hydroxy compound and low-active aromatic hydroxy compound can be carried out. This method will be specifically described later.

The low-active aromatic hydroxy compound is an aromatic hydroxy compound represented by the following formula (25):

[Chemical Formula 16]

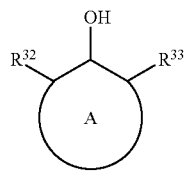

(25)

wherein ring A represents an aromatic hydrocarbon ring optionally having a substituent, and it may be either a single ring or multiple rings, $R^{32}$ and $R^{33}$ independently represent any one group defined in the following (i) to (v), the number of carbon atoms constituting the aromatic hydroxy compound is an integer from 6 to 50, and further, with regard to the $R^{32}$ and $R^{33}$, another portion in the group may bind to the ring A, so as to form a ring structure that is adjacent to A.

(i) a hydrogen atom,
(ii) a halogen atom,
(iii) a group containing 1 to 44 carbon atoms, in which the atom at position α is a nitrogen atom, wherein the nitrogen atom is a tertiary nitrogen atom (which represents a nitrogen atom having no hydrogen atoms), and which does not contain active hydrogen,
(iv) a group containing 1 to 44 carbon atoms, in which the atom at position α is a carbon atom and which does not contain active hydrogen, wherein the carbon atom at the position α is a tertiary or quaternary carbon atom (which represents a carbon atom forming a —CH— bond, or a carbon atom to which hydrogen does not bind); however, when the $R^{32}$ and/or $R^{33}$ form a saturated and/or unsaturated condensed ring structure with the ring A, and when the condensed ring is a 7- or more-membered ring, the carbon atom at the position α may be a primary or secondary carbon atom (which represents a carbon atom forming a methyl group or a —CH$_2$— bond); and in addition, when the carbon atom at the position α forms a double bond with the atom at the position β, the carbon atom at the position α may be quaternary carbon, and the carbon atom at the position α, which forms a triple bond with the atom at the position β, is excluded, and
(v) a group containing 1 to 24 carbon atoms, in which the atom at position α is an oxygen atom, and which does not contain active hydrogen.

In the above formula (25), the term "the atom at position α" is used. This term "the atom at position α" means an atom adjacent to a carbon atom on the aromatic hydrocarbon ring to which the $R^{32}$ and $R^{33}$ groups bind, among atoms constituting the $R^{32}$ and $R^{33}$.

A substituent substituted with the aromatic group of the aromatic hydroxy compound represented by the above formula (25) (excluding $R^{32}$ and $R^{33}$) is selected from a hydrogen atom, a halogen atom, an aliphatic group, and an aromatic group. Examples of such a substituent include a group selected from the group consisting of an acyclic hydrocarbon group and a cyclic hydrocarbon group (e.g. a monocyclic hydrocarbon group, a condensed polycyclic hydrocarbon group, a crosslinked cyclic hydrocarbon group, a spiro hydrocarbon group, a multi-ring hydrocarbon group, a cyclic hydrocarbon group having a side chain, a heterocyclic group, a heterocyclic spiro group, a hetero crosslinked cyclic group, and a heterocyclic group), a group to which one or more groups selected from the above described acyclic hydrocarbon group and the above described cyclic hydrocarbon group bind, and a group to which the above described group binds via a covalent bond with a specific non-metal atom (carbon, oxygen, nitrogen, sulfur, or silicon).

If taking into consideration the unlikeliness of side reactions, among the aforementioned substituents, examples of a substituent that can be preferably used in the present embodiment include: a group selected from the group consisting of an acyclic hydrocarbon group and a cyclic hydrocarbon group (a monocyclic hydrocarbon group, a condensed polycyclic hydrocarbon group, a crosslinked cyclic hydrocarbon group, a spiro hydrocarbon group, a multi-ring hydrocarbon group, and a cyclic hydrocarbon group having a side chain); and a group to which at least one group selected from the above described group binds (wherein the two groups are substituted with each other).

When a composition containing an N-substituted carbamate is transferred at a high temperature, or when an organic amine, a carbonic acid derivative and an aromatic hydroxy compound are reacted to obtain an N-substituted carbamate at a high temperature, it is preferable to use an aromatic hydroxy compound, in which the substituent substituted with the ring A thereof (excluding $R^{32}$ and $R^{33}$) is preferably an inactive substituent. The term "inactive substituent" is used herein to mean a group that does not contain the above described active hydrogen (provided that it may have an aromatic hydroxy group).

Examples of such a substituent substituted with the ring A (excluding $R^{32}$ and $R^{33}$) include: a group selected from the group consisting of an alkyl group, a cycloalkyl group, an aryl group, an aralkyl group, and an ether group (substituted and/or unsubstituted alkyl ether and/or aryl ether and/or aralkyl ether); a group, to which one or more groups selected from the above described group bind; a group selected from groups composed of groups, to which one or more groups selected from the above described group bind via a saturated aliphatic bond and/or an ether bond; and a group which is a halogen atom and in which a total of the number of carbon atoms constituting the ring A and the number of carbon atoms constituting all of the substituents substituted with the ring A can be an integer from 6 to 50.

In the above formula (25), examples of the ring A include a benzene ring, a naphthalene ring, an anthracene ring, a phenanthrene ring, a naphthacene ring, a chrysene ring, a pyrene ring, a triphenylene ring, a pentalene ring, an azulene ring, a heptalene ring, an indacene ring, a biphenylene ring, an acenaphthylene ring, an aceanthrylene ring, and an acephenanthrylene ring. More preferably, it is a structure containing at least one structure selected from a benzene ring and a naphthalene ring.

If considering industrial use, an aromatic hydroxy compound having an easily available benzene ring as a skeleton is preferable. Such an aromatic hydroxy compound is preferably an aromatic hydroxy compound represented by the following formula (26):

[Chemical Formula 17]

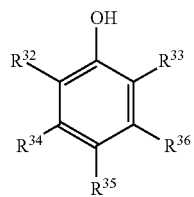

(26)

wherein $R^{32}$ and $R^{33}$ each represent the above-defined group, and $R^{34}$, $R^{35}$ and $R^{36}$ independently represent a group selected from the group consisting of an alkyl group, a cycloalkyl group, an aryl group, an aralkyl group, and an ether group (substituted and/or unsubstituted alkyl ether and/or aryl ether and/or aralkyl ether); a group, to which one or more groups selected from the above described groups bind; a group selected from groups, to which one or more groups selected from the above described group bind via a saturated aliphatic bond and/or an ether bond; a halogen atom; or a hydrogen atom, and in which the total number of carbon atoms constituting the $R^{32}$, $R^{33}$, $R^{34}$, $R^{35}$ and $R^{36}$ is an integer from 0 to 44.

In the above formula (26), preferred $R^{32}$ and $R^{33}$ are groups independently selected from the groups described in the following (i) to (vi):

(i) a hydrogen atom, (ii) a halogen atom, (iii) a group containing 1 to 44 carbon atoms, in which the atom at position α is a nitrogen atom, wherein the nitrogen atom is a tertiary nitrogen atom (which represents a nitrogen atom having no hydrogen atoms), and wherein groups attached to the nitrogen atom at the position α are independently selected from an alkyl group containing 1 to 44 carbon atoms, a cycloalkyl group containing 1 to 44 carbon atoms, a polyoxyalkylene alkyl ether group containing 2 to 44 carbon atoms and having no OH groups at the terminus thereof, an aryl group containing 6 to 44 carbon atoms, an aralkyl group containing 7 to 44 carbon atoms, and a group to which one or more of the above described groups bind, (iv) a substituted or unsubstituted aryl group containing 6 to 44 carbon atoms, which does not contain active hydrogen, (v) a group containing 1 to 44 carbon atoms, in which the atom at position α is a carbon atom and which does not contain active hydrogen, wherein the carbon atom at the position α is a tertiary or quaternary carbon atom (which represents a carbon atom forming a —CH— bond, or a carbon atom to which hydrogen does not bind); however, when the $R^{32}$ and/or $R^{33}$ form a saturated and/or unsaturated condensed ring structure with the ring A, and when the condensed ring is a 7- or more-membered ring, the carbon atom at the position α may be a primary or secondary carbon atom (which represents a carbon atom forming a methyl group or a —CH$_2$— bond); and in addition, when the carbon atom at the position α forms a double bond with the atom at the position β, the carbon atom at the position α may be quaternary carbon, and the carbon atom at the position α, which forms a triple bond with the atom at the position β, is excluded; and further, groups other than a hydrogen atom, which attached to the carbon atom at the position α, are independently selected from an alkyl group containing 1 to 43 carbon atoms, a cycloalkyl group containing 1 to 43 carbon atoms, an alkoxy group containing 1 to 43 carbon atoms, a polyoxyalkylene alkyl ether group containing 2 to 43 carbon atoms and having no OH groups at the terminus thereof, an aryl group containing 6 to 43 carbon atoms, an aralkyl group containing 7 to 43 carbon atoms, an aralkyloxy group containing 7 to 43 carbon atoms, and a group to which one or more of the above described groups bind, and (vi) a group containing 1 to 24 carbon atoms, in which the atom at position α is an oxygen atom and which does not contain active hydrogen, wherein groups attached to the oxygen atom at the position α are independently selected from an alkyl group containing 1 to 44 carbon atoms, a cycloalkyl group containing 1 to 44 carbon atoms, a polyoxyalkylene alkyl ether group containing 2 to 44 carbon atoms and having no OH groups at the terminus thereof, an aralkyl group containing 7 to 44 carbon atoms, and a group to which one or more of the above described groups bind.

More preferred $R^{34}$, $R^{35}$ and $R^{36}$ are groups independently selected from the groups described in the following (vii) to (xi):

(vii) a hydrogen atom, (viii) a halogen atom, (ix) a group containing 1 to 44 carbon atoms, in which the atom at position α is a carbon atom, wherein three groups attached to the carbon atom at the position α are independently selected from an alkyl group containing 1 to 43 carbon atoms, a cycloalkyl group containing 1 to 43 carbon atoms, an alkoxy group containing 1 to 43 carbon atoms, a polyoxyalkylene alkyl ether group containing 2 to 43 carbon atoms and having no OH groups at the terminus thereof, an aryl group containing 6 to 43 carbon atoms, an aralkyl group containing 7 to 43 carbon atoms, an aralkyloxy group containing 7 to 43 carbon atoms, a group to which one or more of the above described groups bind, and a hydrogen atom, (x) an aryl group containing 1 to 44 carbon atoms, which is substituted with a substituent, wherein the substituent is an aryl group optionally substituted with the following integer from 1 to 5 substituents, wherein the substituents are selected from a hydrogen atom, an alkyl group containing 1 to 38 carbon atoms, a cycloalkyl group containing 4 to 38 carbon atoms, an alkoxy group containing 1 to 38 carbon atoms, a polyoxyalkylene alkyl ether group containing 2 to 38 carbon atoms and having no OH groups at the terminus thereof, an aryl group containing 6 to 38 carbon atoms, an aralkyl group containing 7 to 38 carbon atoms, an aralkyloxy group containing 7 to 38 carbon atoms, and a group to which one or more of the above described groups bind, and (xi) a group containing 1 to 44 carbon atoms, in which the atom at position α is an oxygen atom, wherein groups attached to the oxygen atom at the position α are independently selected from an alkyl group containing 1 to 44 carbon atoms, a cycloalkyl group containing 1 to 44 carbon atoms, an alkoxy group containing 1 to 44 carbon atoms, a polyoxyalkylene alkyl ether group containing 2 to 44 carbon atoms and having no OH groups at the terminus thereof, an aryl group containing 6 to 44 carbon atoms, an aralkyl group containing 7 to 44 carbon atoms, an aralkyloxy group containing 7 to 44 carbon atoms, and a group to which one or more of the above described groups bind.

In the above formula (26), the term "the atom at position α" is used. This term "the atom at position α" means an atom adjacent to a carbon atom on the aromatic hydrocarbon ring to which the $R^{32}$, $R^{33}$, $R^{34}$, $R^{35}$ and $R^{36}$ groups bind, among atoms constituting the $R^{32}$, $R^{33}$, $R^{34}$, $R^{35}$ and $R^{36}$.

Examples of such $R^{34}$, $R^{35}$ and $R^{36}$ include:

alkyl groups, and/or cycloalkyl groups, and/or cycloalkyl groups substituted with alkyl groups, and/or alkyl groups substituted with cycloalkyl groups, such as a methyl group, an ethyl group, a propyl group (each isomer), a butyl group (each isomer), a pentyl group (each isomer), a hexyl group (each isomer), a heptyl group (each isomer), an octyl group (each isomer), a nonyl group (each isomer), a decyl group (each isomer), a dodecyl group (each isomer), an octadecyl group (each isomer), cyclopentane, cyclohexane, cycloheptane, cyclooctane, methylcyclopentane (each isomer), ethylcyclopentane (each isomer), methylcyclohexane (each isomer), ethylcyclohexane (each isomer), propylcyclohexane (each isomer), butylcyclohexane (each isomer), pentylcyclohexane (each isomer), hexylcyclohexane (each isomer), dimethylcyclohexane (each isomer), diethylcyclohexane (each isomer), and dibutylcyclohexane (each isomer);

alkoxy groups, and/or cycloalkoxy groups, and/or cycloalkoxy groups substituted with alkyl groups, and/or alkoxy groups substituted with cycloalkyl groups, such as a methoxy group, an ethoxy group, propoxy group (each isomer), a butyloxy group (each isomer), a pentyloxy group (each isomer), a hexyloxy group (each isomer), a heptyloxy group (each isomer), an octyloxy group (each isomer), a nonyloxy group (each isomer), a decyloxy group (each isomer), a dodecyloxy group (each isomer), an octadecyloxy group (each isomer), a cyclopentyloxy group, a cyclohexyloxy group, a cycloheptyloxy group, a cyclooctyloxy group, a methylcyclopentyloxy group (each isomer), an ethylcyclopentyloxy group (each isomer), a methylcyclohexyloxy group (each isomer), an ethylcyclohexyloxy group (each isomer), a propylcyclohexyloxy group (each isomer), a butylcyclohexyloxy group (each isomer), a pentylcyclohexyloxy group (each isomer), a hexylcyclohexyloxy group (each isomer), a dimethylcyclohexyloxy group (each isomer), a diethylcyclohexyloxy group (each isomer), and a dibutylcyclohexyloxy group (each isomer);

substituted or unsubstituted aryl groups, such as a phenyl group, a methylphenyl group (each isomer), an ethylphenyl group (each isomer), a propylphenyl group (each isomer), a butylphenyl group (each isomer), a pentylphenyl group (each isomer), a hexylphenyl group (each isomer), a heptylphenyl group (each isomer), an octylphenyl group (each isomer), a nonylphenyl group (each isomer), a decylphenyl group (each isomer), a biphenyl group (each isomer), a dimethylphenyl group (each isomer), a diethylphenyl group (each isomer), a dipropylphenyl group (each isomer), a dibutylphenyl group (each isomer), a dipentylphenyl group (each isomer), a dihexylphenyl group (each isomer), a diheptylphenyl group (each isomer), a terphenyl group (each isomer), a trimethylphenyl group (each isomer), a triethylphenyl group (each isomer), a tripropylphenyl group (each isomer), and a tributylphenyl group (each isomer);

substituted or unsubstituted aryloxy groups, such as a phenoxy group, a methylphenoxy group (each isomer), an ethylphenoxy group (each isomer), a propylphenoxy group (each isomer), a butylphenoxy group (each isomer), a pentylphenoxy group (each isomer), a hexylphenoxy group (each isomer), a heptylphenoxy group (each isomer), an octylphenoxy group (each isomer), a nonylphenoxy group (each isomer), a decylphenoxy group (each isomer), a phenylphenoxy group (each isomer), a dimethylphenoxy group (each isomer), a diethylphenoxy group (each isomer), a dipropylphenoxy group (each isomer), a dibutylphenoxy group (each isomer), a dipentylphenoxy group (each isomer), a dihexylphenoxy group (each isomer), a diheptylphenoxy group (each isomer), a diphenylphenoxy group (each isomer), a trimethylphenoxy group (each isomer), a triethylphenoxy group (each isomer), a tripropylphenoxy group (each isomer), and a tributylphenoxy group (each isomer); and aralkyl groups such as a phenylmethyl group, a phenylethyl group (each isomer), a phenylpropyl group (each isomer), a phenylbutyl group (each isomer), a phenylpentyl group (each isomer), a phenylhexyl group (each isomer), a phenylheptyl group (each isomer), a phenyloctyl group (each isomer) and a phenylnonyl group (each isomer), and aralkyloxy groups such as a phenylmethoxy group, a phenylethoxy group (each isomer), a phenylpropyloxy group (each isomer), a phenylbutyloxy group (each isomer), a phenylpentyloxy group (each isomer), a phenylhexyloxy group (each isomer), a phenylheptyloxy group (each isomer), a phenyloctyloxy group (each isomer) and a phenylnonyloxy group (each isomer).

Preferred examples of the aromatic hydroxy compound represented by the above formula (25) include the following compounds, and also, specific examples of the aromatic hydroxy compound represented by the above formula (26) include the following compounds.

Specific examples include 2-isopropylphenol (each isomer), 2-tert-butylphenol (each isomer), 2-tert-pentylphenol (each isomer), 2-tert-hexylphenol (each isomer), 2-tert-heptylphenol (each isomer), 2-tert-octylphenol (each isomer), 2-tert-nonylphenol (each isomer), 2-tert-decylphenol (each isomer), 2-tert-dodecylphenol (each isomer), 2-tert-octadecylphenol (each isomer), 2-sec-propylphenol (each isomer), 2-sec-butylphenol (each isomer), 2-sec-pentylphenol (each isomer), 2-sec-hexylphenol (each isomer), 2-sec-heptylphenol (each isomer), 2-sec-octylphenol (each isomer), 2-sec-nonylphenol (each isomer), 2-sec-decylphenol (each isomer), 2-sec-dodecylphenol (each isomer), 2-sec-octadecylphenol (each isomer), 2-phenylphenol, 2,4-di-tert-propylphenol (each isomer), 2,4-di-tert-butylphenol (each isomer), 2,4-di-tert-pentylphenol (each isomer), 2,4-di-tert-hexylphenol (each isomer), 2,4-di-tert-heptylphenol (each isomer), 2,4-di-tert-octylphenol (each isomer), 2,4-di-tert-nonylphenol (each isomer), 2,4-di-tert-decylphenol (each isomer), 2,4-di-tert-dodecylphenol (each isomer), 2,4-di-tert-octadecylphenol (each isomer), 2,4-di-sec-propylphenol (each isomer), 2,4-di-sec-butylphenol (each isomer), 2,4-di-sec-pentylphenol (each isomer), 2,4-di-sec-hexylphenol (each isomer), 2,4-di-sec-heptylphenol (each isomer), 2,4-di-sec-octylphenol (each isomer), 2,4-di-sec-nonylphenol (each isomer), 2,4-di-sec-decylphenol (each isomer), 2,4-di-sec-dodecylphenol (each isomer), 2,4-di-sec-octadecylphenol (each isomer), 2,6-di-tert-propylphenol (each isomer), 2,6-di-tert-butylphenol (each isomer), 2,6-di-tert-pentylphenol (each isomer), 2,6-di-tert-hexylphenol (each isomer), 2,6-di-tert-heptylphenol (each isomer), 2,6-di-tert-octylphenol (each isomer), 2,6-di-tert-nonylphenol (each isomer), 2,6-di-tert-decylphenol (each isomer), 2,6-di-tert-dodecylphenol (each isomer), 2,6-di-tert-octadecylphenol (each isomer), 2,6-di-sec-propylphenol (each isomer), 2,6-di-sec-butylphenol (each isomer), 2,6-di-sec-pentylphenol (each isomer), 2,6-di-sec-hexylphenol (each isomer), 2,6-di-sec-heptylphenol (each isomer), 2,6-di-sec-octylphenol (each isomer), 2,6-di-sec-nonylphenol (each isomer), 2,6-di-sec-decylphenol (each isomer), 2,6-di-sec-dodecylphenol (each isomer), 2,6-di-sec-octadecylphenol (each isomer), 2,4-diphenylphenol, 2,6-diphenylphenol, 2,4,6-tri-tert-propylphenol (each isomer), 2,4,6-tri-tert-butylphenol (each isomer), 2,4,6-tri-tert-pentylphenol (each isomer), 2,4,6-tri-tert-hexylphenol (each isomer), 2,4,6-tri-tert-heptylphenol (each isomer), 2,4,6-tri-tert-octylphenol (each isomer), 2,4,6-tri-tert-nonylphenol (each isomer), 2,4,6-tri-tert-decylphenol (each isomer), 2,4,6-tri-tert-dodecylphenol (each isomer), 2,4,6-tri-tert-octadecylphenol (each isomer), 2,4,6-tri-sec-propylphenol (each isomer), 2,4,6-tri-sec-butylphenol (each isomer), 2,4,6-tri-sec-pentylphenol (each isomer), 2,4,6-tri-sec-hexylphenol (each isomer), 2,4,6-tri-sec-heptylphenol (each isomer), 2,4,6-tri-sec-octylphenol (each isomer), 2,4,6-tri-sec-nonylphenol (each isomer), 2,4,6-tri-sec-decylphenol (each isomer), 2,4,6-tri-sec-dodecylphenol (each isomer), 2,4,6-tri-sec-octadecylphenol (each isomer), (2-methoxy-2-methylethyl)phenol, (2-ethoxy-2-methylethyl)phenol, (2-propoxy-2-methylethyl)phenol (each isomer), (2-butyloxy-2-methylethyl)phenol (each isomer), (2-pentyloxy-2-methylethyl)phenol (each isomer), (2-hexyloxy-2-methylethyl)phenol (each isomer), (2-heptyloxy-2-methylethyl)phenol (each isomer), (2-octyloxy-2-methylethyl)phenol (each isomer), (2-nonyloxy-2-methylethyl)phenol (each isomer), (2-decyloxy-2-methylethyl)phenol (each isomer), (2-dodecyloxy-2-methylethyl)phenol (each isomer), (2-octadecyloxy-2-methylethyl)phenol (each isomer), (2-cyclopentyloxy-2-methylethyl)phenol (each isomer), (2-cyclohexyloxy-2-methylethyl)phenol (each isomer), (2-cycloheptyloxy-2-methylethyl)phenol (each isomer), (2-cyclooctyloxy-2-methylethyl)phenol (each isomer), (2-(methylcyclopentyloxy)-2-methylethyl)phenol (each isomer), (2-(ethylcyclopentyloxy)-2-methylethyl)phenol (each isomer), (2-(methylcyclohexyloxy)-2-methylethyl)phenol (each isomer), (2-(ethylcyclohexyloxy)-2-methylethyl)phenol (each isomer), (2-(propylcyclohexyloxy)-2-methylethyl)phenol (each isomer), (2-(butylcyclohexyloxy)-2-methylethyl)phenol (each isomer), (2-(pentylcyclohexyloxy)-2-methylethyl)phenol (each isomer), (2-(hexylcyclohexyloxy)-2-methylethyl)phenol (each isomer), (2-(dimethylcyclohexyloxy)-2-methylethyl)phenol (each isomer), (2-(diethylcyclohexyloxy)-2-methylethyl)phenol (each isomer), (2-(dibutylcyclohexyloxy)-2-methylethyl)phenol (each isomer), (2-phenoxy-2-methylethyl)phenol (each isomer), (2-(methylphenoxy)-2-methylethyl)phenol (each isomer), (2-(ethylphenoxy)-2-methylethyl)phenol (each isomer), (2-(propylphenoxy)-2-methylethyl)phenol (each isomer), (2-(butylphenoxy)-2-methylethyl)phenol (each isomer), (2-(pentylphenoxy)-2-methylethyl)phenol (each isomer), (2-(hexylphenoxy)-2-methylethyl)phenol (each isomer), (2-(heptylphenoxy)-2-methylethyl)phenol (each isomer), (2-(octylphenoxy)-2-methylethyl)phenol (each isomer), (2-(nonylphenoxy)-2-methylethyl)phenol (each isomer), (2-(decylphenoxy)-2-methylethyl)phenol (each isomer), (2-(phenylphenoxy)-2-methylethyl)phenol (each isomer), (2-(dimethylphenoxy)-2-methylethyl)phenol (each isomer), (2-(diethylphenoxy)-2-methylethyl)phenol (each isomer), (2-(dipropylphenoxy)-2-methylethyl)phenol (each isomer), (2-(dibutylphenoxy)-2-methylethyl)phenol (each isomer), (2-(dipentylphenoxy)-2-methylethyl)phenol (each isomer), (2-(dihexylphenoxy)-2-methylethyl)phenol (each isomer), (2-(diheptylphenoxy)-2-methylethyl)phenol (each isomer), (2-(diphenylphenoxy)-2-methylethyl)phenol (each isomer), (2-(trimethylphenoxy)-2-methylethyl)phenol (each isomer), (2-(triethylphenoxy)-2-methylethyl)phenol (each isomer), (2-(tripropylphenoxy)-2-methylethyl)phenol (each isomer), (2-(tributylphenoxy)-2-methylethyl)phenol (each isomer), (2-(phenylmethoxy)-2-methylethyl)phenol (each isomer), (2-(phenylethoxy)-2-methylethyl)phenol (each isomer), (2-(phenylpropyloxy)-2-methylethyl)phenol (each isomer), (2-(phenylbutyloxy)-2-methylethyl)phenol (each isomer), (2-(phenylpentyloxy)-2-methylethyl)phenol (each isomer), (2-(phenylhexyloxy)-2-methylethyl)phenol (each isomer), (2-(phenylheptyloxy)-2-methylethyl)phenol (each isomer), (2-(phenyloctyloxy)-2-methylethyl)phenol (each isomer), (2-(phenylnonyloxy)-2-methylethyl)phenol (each isomer), (2-methoxy-2-methylpropyl)phenol, (2-ethoxy-2-methylpropyl)phenol, (2-propoxy-2-methylpropyl)phenol (each isomer), (2-butyloxy-2-methylpropyl)phenol (each isomer), (2-pentyloxy-2-methylpropyl)phenol (each isomer), (2-hexyloxy-2-methylpropyl)phenol (each isomer), (2-heptyloxy-2-methylpropyl)phenol (each isomer), (2-octyloxy-2-methylpropyl)phenol (each isomer), (2-nonyloxy-2-methylpropyl)phenol (each isomer), (2-decyloxy-2-methylpropyl)phenol (each isomer), (2-dodecyloxy-2-methylpropyl)phenol (each isomer), (2-octadecyloxy-2-methylpropyl)phenol (each isomer), (2-cyclopentyloxy-2-methylpropyl)phenol (each isomer), (2-cyclohexyloxy-2-methylpropyl)phenol (each isomer), (2-cycloheptyloxy-2-methylpropyl)phenol (each isomer), (2-cyclooctyloxy-2-methylpropyl)phenol (each isomer), (2-(methylcyclopentyloxy)-2-methylpropyl)phenol (each isomer), (2-(ethylcyclopentyloxy)-2-methylpropyl)phenol (each isomer), (2-(methylcyclohexyloxy)-2-methylpropyl)phenol (each isomer), (2-(ethylcyclohexyloxy)-2-methylpropyl)phenol (each isomer), (2-(propylcyclohexyloxy)-2-methylpropyl)phenol (each isomer), (2-

(butylcyclohexyloxy)-2-methylpropyl)phenol (each isomer), (2-(pentylcyclohexyloxy)-2-methylpropyl)phenol (each isomer), (2-(hexylcyclohexyloxy)-2-methylpropyl)phenol (each isomer), (2-(dimethylcyclohexyloxy)-2-methylpropyl)phenol (each isomer), (2-(diethylcyclohexyloxy)-2-methylpropyl)phenol (each isomer), (2-(dibutylcyclohexyloxy)-2-methylpropyl)phenol (each isomer), (2-phenoxy-2-methylpropyl)phenol (each isomer), (2-(methylphenoxy)-2-methylpropyl)phenol (each isomer), (2-(ethylphenoxy)-2-methylpropyl)phenol (each isomer), (2-(propylphenoxy)-2-methylpropyl)phenol (each isomer), (2-(butylphenoxy)-2-methylpropyl)phenol (each isomer), (2-(pentylphenoxy)-2-methylpropyl)phenol (each isomer), (2-(hexylphenoxy)-2-methylpropyl)phenol (each isomer), (2-(heptylphenoxy)-2-methylpropyl)phenol (each isomer), (2-(octylphenoxy)-2-methylpropyl)phenol (each isomer), (2-(nonylphenoxy)-2-methylpropyl)phenol (each isomer), (2-(decylphenoxy)-2-methylpropyl)phenol (each isomer), (2-(phenylphenoxy)-2-methylpropyl)phenol (each isomer), (2-(dimethylphenoxy)-2-methylpropyl)phenol (each isomer), (2-(diethylphenoxy)-2-methylpropyl)phenol (each isomer), (2-(dipropylphenoxy)-2-methylpropyl)phenol (each isomer), (2-(dibutylphenoxy)-2-methylpropyl)phenol (each isomer), (2-(dipentylphenoxy)-2-methylpropyl)phenol (each isomer), (2-(dihexylphenoxy)-2-methylpropyl)phenol (each isomer), (2-(diheptylphenoxy)-2-methylpropyl)phenol (each isomer), (2-(diphenylphenoxy)-2-methylpropyl)phenol (each isomer), (2-(trimethylphenoxy)-2-methylpropyl)phenol (each isomer), (2-(triethylphenoxy)-2-methylpropyl)phenol (each isomer), (2-(tripropylphenoxy)-2-methylpropyl)phenol (each isomer), (2-(tributylphenoxy)-2-methylpropyl)phenol (each isomer), (2-(phenylmethoxy)-2-methylpropyl)phenol (each isomer), (2-(phenylethoxy)-2-methylpropyl)phenol (each isomer), (2-(phenylpropyloxy)-2-methylpropyl)phenol (each isomer), (2-(phenylbutyloxy)-2-methylpropyl)phenol (each isomer), (2-(phenylpentyloxy)-2-methylpropyl)phenol (each isomer), (2-(phenylhexyloxy)-2-methylpropyl)phenol (each isomer), (2-(phenylheptyloxy)-2-methylpropyl)phenol (each isomer), (2-(phenyloctyloxy)-2-methylpropyl)phenol (each isomer), (2-(phenylnonyloxy)-2-methylpropyl)phenol (each isomer), di(2-methoxy-2-methylethyl)phenol (each isomer), di(2-ethoxy-2-methylethyl)phenol (each isomer), di(2-propoxy-2-methylethyl)phenol (each isomer), di(2-butyloxy-2-methylethyl)phenol (each isomer), di(2-pentyloxy-2-methylethyl)phenol (each isomer), di(2-hexyloxy-2-methylethyl)phenol (each isomer), di(2-heptyloxy-2-methylethyl)phenol (each isomer), di(2-octyloxy-2-methylethyl)phenol (each isomer), di(2-nonyloxy-2-methylethyl)phenol (each isomer), di(2-decyloxy-2-methylethyl)phenol (each isomer), di(2-dodecyloxy-2-methylethyl)phenol (each isomer), di(2-octadecyloxy-2-methylethyl)phenol (each isomer), di(2-cyclopentyloxy-2-methylethyl)phenol (each isomer), di(2-cyclohexyloxy-2-methylethyl)phenol (each isomer), di(2-cycloheptyloxy-2-methylethyl)phenol (each isomer), di(2-cyclooctyloxy-2-methylethyl)phenol (each isomer), di(2-(methylcyclopentyloxy)-2-methylethyl)phenol (each isomer), di(2-(ethylcyclopentyloxy)-2-methylethyl)phenol (each isomer), di(2-(methylcyclohexyloxy)-2-methylethyl)phenol (each isomer), di(2-(ethylcyclohexyloxy)-2-methylethyl)phenol (each isomer), di(2-(propylcyclohexyloxy)-2-methylethyl)phenol (each isomer), di(2-(butylcyclohexyloxy)-2-methylethyl)phenol (each isomer), di(2-(pentylcyclohexyloxy)-2-methylethyl)phenol (each isomer), di(2-(hexylcyclohexyloxy)-2-methylethyl)phenol (each isomer), di(2-(dimethylcyclohexyloxy)-2-methylethyl)phenol (each isomer), di(2-(diethylcyclohexyloxy)-2-methylethyl)phenol (each isomer), di(2-(dibutylcyclohexyloxy)-2-methylethyl)phenol (each isomer), di(2-phenoxy-2-methylethyl)phenol (each isomer), di(2-(methylphenoxy)-2-methylethyl)phenol (each isomer), di(2-(ethylphenoxy)-2-methylethyl)phenol (each isomer), di(2-(propylphenoxy)-2-methylethyl)phenol (each isomer), di(2-(butylphenoxy)-2-methylethyl)phenol (each isomer), di(2-(pentylphenoxy)-2-methylethyl)phenol (each isomer), di(2-(hexylphenoxy)-2-methylethyl)phenol (each isomer), di(2-(heptylphenoxy)-2-methylethyl)phenol (each isomer), di(2-(octylphenoxy)-2-methylethyl)phenol (each isomer), di(2-(nonylphenoxy)-2-methylethyl)phenol (each isomer), di(2-(decylphenoxy)-2-methylethyl)phenol (each isomer), di(2-(phenylphenoxy)-2-methylethyl)phenol (each isomer), di(2-(dimethylphenoxy)-2-methylethyl)phenol (each isomer), di(2-(diethylphenoxy)-2-methylethyl)phenol (each isomer), di(2-(dipropylphenoxy)-2-methylethyl)phenol (each isomer), di(2-(dibutylphenoxy)-2-methylethyl)phenol (each isomer), di(2-(dipentylphenoxy)-2-methylethyl)phenol (each isomer), di(2-(dihexylphenoxy)-2-methylethyl)phenol (each isomer), di(2-(diheptylphenoxy)-2-methylethyl)phenol (each isomer), di(2-(diphenylphenoxy)-2-methylethyl)phenol (each isomer), di(2-(trimethylphenoxy)-2-methylethyl)phenol (each isomer), di(2-(triethylphenoxy)-2-methylethyl)phenol (each isomer), di(2-(tripropylphenoxy)-2-methylethyl)phenol (each isomer), di(2-(tributylphenoxy)-2-methylethyl)phenol (each isomer), di(2-(phenylmethoxy)-2-methylethyl)phenol (each isomer), di(2-(phenylethoxy)-2-methylethyl)phenol (each isomer), di(2-(phenylpropyloxy)-2-methylethyl)phenol (each isomer), di(2-(phenylbutyloxy)-2-methylethyl)phenol (each isomer), di(2-(phenylpentyloxy)-2-methylethyl)phenol (each isomer), di(2-(phenylhexyloxy)-2-methylethyl)phenol (each isomer), di(2-(phenylheptyloxy)-2-methylethyl)phenol (each isomer), di(2-(phenyloctyloxy)-2-methylethyl)phenol (each isomer), di(2-(phenylnonyloxy)-2-methylethyl)phenol (each isomer), di(2-methoxy-2-methylpropyl)phenol (each isomer), di(2-ethoxy-2-methylpropyl)phenol (each isomer), di(2-propoxy-2-methylpropyl)phenol (each isomer), di(2-butyloxy-2-methylpropyl)phenol (each isomer), di(2-pentyloxy-2-methylpropyl)phenol (each isomer), di(2-hexyloxy-2-methylpropyl)phenol (each isomer), di(2-heptyloxy-2-methylpropyl)phenol (each isomer), di(2-octyloxy-2-methylpropyl)phenol (each isomer), di(2-nonyloxy-2-methylpropyl)phenol (each isomer), di(2-decyloxy-2-methylpropyl)phenol (each isomer), di(2-dodecyloxy-2-methylpropyl)phenol (each isomer), di(2-octadecyloxy-2-methylpropyl)phenol (each isomer), di(2-cyclopentyloxy-2-methylpropyl)phenol (each isomer), di(2-cyclohexyloxy-2-methylpropyl)phenol (each isomer), di(2-cycloheptyloxy-2-methylpropyl)phenol (each isomer), di(2-cyclooctyloxy-2-methylpropyl)phenol (each isomer), di(2-(methylcyclopentyloxy)-2-methylpropyl)phenol (each isomer), di(2-(ethylcyclopentyloxy)-2-methylpropyl)phenol (each isomer), di(2-(methylcyclohexyloxy)-2-methylpropyl)phenol (each isomer), di(2-(ethylcyclohexyloxy)-2-methylpropyl)phenol (each isomer), di(2-(propylcyclohexyloxy)-2-methylpropyl)phenol (each isomer), di(2-(butylcyclohexyloxy)-2-methylpropyl)phenol (each isomer), di(2-(pentylcyclohexyloxy)-2-methylpropyl)phenol (each isomer), di(2-(hexylcyclohexyloxy)-2-methylpropyl)phenol (each isomer), di(2-(dimethylcyclohexyloxy)-2-methylpropyl)phenol (each isomer), di(2-(diethylcyclohexyloxy)-2-methylpropyl)phenol (each isomer), di(2-(dibutylcyclohexyloxy)-2-methylpropyl)phenol (each isomer), di(2-phenoxy-2-methylpropyl)phenol (each isomer), di(2-(methylphenoxy)-2-methylpropyl)phenol (each isomer), di(2-(ethylphenoxy)-2-methylpropyl)phenol (each isomer), di(2-(propylphenoxy)-2-methylpropyl)phenol (each isomer), di(2-(butylphenoxy)-2-methylpropyl)phenol (each isomer), di(2-(pentylphenoxy)-2-methylpropyl)phenol (each isomer), di(2-(hexylphenoxy)-2-methylpropyl)phenol (each isomer), di(2-(heptylphenoxy)-2-methylpropyl)phenol (each isomer), di(2-(octylphenoxy)-2-methylpropyl)phenol (each isomer), di(2-(nonylphenoxy)-2-methylpropyl)phenol (each isomer), di(2-(decylphenoxy)-2-methylpropyl)phenol (each isomer), di(2-(phenylphenoxy)-2-methylpropyl)phenol (each isomer), di(2-(dimethylphenoxy)-2-methylpropyl)phenol (each isomer), di(2-(diethylphenoxy)-2-methylpropyl)phenol (each isomer), di(2-(dipropylphenoxy)-2-methylpropyl)phenol (each isomer), di(2-(dibutylphenoxy)-2-methylpropyl)phenol (each isomer), di(2-(dipentylphenoxy)-2-methylpropyl)phenol (each isomer), di(2-(dihexylphenoxy)-2-methylpropyl)phenol (each isomer), di(2-(diheptylphenoxy)-2-methylpropyl)phenol (each isomer), di(2-(diphenylphenoxy)-2-methylpropyl)phenol (each isomer), di(2-(trimethylphenoxy)-2-methylpropyl)phenol (each isomer), di(2-(triethylphenoxy)-2-methylpropyl)phenol (each isomer), di(2-(tripropylphenoxy)-2-methylpropyl)phenol (each isomer), di(2-(tributylphenoxy)-2-methylpropyl)phenol (each isomer), di(2-(phenylmethoxy)-2-methylpropyl)phenol (each isomer), di(2-(phenylethoxy)-2-methylpropyl)phenol (each isomer), di(2-(phenylpropyloxy)-2-methylpropyl)phenol (each isomer), di(2-(phenylbutyloxy)-2-methylpropyl)phenol (each isomer), di(2-(phenylpentyloxy)-2-methylpropyl)phenol (each isomer), di(2-(phenylhexyloxy)-2-methylpropyl)phenol (each isomer), di(2-(phenylheptyloxy)-2-methylpropyl)phenol (each isomer), di(2-(phenyloctyloxy)-2-methylpropyl)phenol (each isomer), di(2-(phenylnonyloxy)-2-methylpropyl)phenol (each isomer), tri(2-methoxy-2-methylethyl)phenol (each isomer), tri(2-ethoxy-2-methylethyl)phenol (each isomer), tri(2-propoxy-2-methylethyl)phenol (each isomer), tri(2-butyloxy-2-methylethyl)phenol (each isomer), tri(2-pentyloxy-2-methylethyl)phenol (each isomer), tri(2-hexyloxy-2-methylethyl)phenol (each isomer), tri(2-heptyloxy-2-methylethyl)phenol (each isomer), tri(2-octyloxy-2-methylethyl)phenol (each isomer), tri(2-nonyloxy-2-methylethyl)phenol (each isomer), tri(2-decyloxy-2-methylethyl)phenol (each isomer), tri(2-dodecyloxy-2-methylethyl)phenol (each isomer), tri(2-octadecyloxy-2-methylethyl)phenol (each isomer), tri(2-cyclopentyloxy-2-methylethyl)phenol (each isomer), tri(2-cyclohexyloxy-2-methylethyl)phenol (each isomer), tri(2-cycloheptyloxy-2-methylethyl)phenol (each isomer), tri(2-cyclooctyloxy-2-methylethyl)phenol (each isomer), tri(2-(methylcyclopentyloxy)-2-methylethyl)phenol (each isomer), tri(2-(ethylcyclopentyloxy)-2-methylethyl)phenol (each isomer), tri(2-(methylcyclohexyloxy)-2-methylethyl)phenol (each isomer), tri(2-(ethylcyclohexyloxy)-2-methylethyl)phenol (each isomer), tri(2-(propylcyclohexyloxy)-2-methylethyl)phenol (each isomer), tri(2-(butylcyclohexyloxy)-2-methylethyl)phenol (each isomer), tri(2-(pentylcyclohexyloxy)-2-methylethyl)phenol (each isomer), tri(2-(hexylcyclohexyloxy)-2-methylethyl)phenol (each isomer), tri(2-(trimethylcyclohexyloxy)-2-methylethyl)phenol (each isomer), tri(2-(triethylcyclohexyloxy)-2-methylethyl)phenol (each isomer), tri(2-(tributylcyclohexyloxy)-2-methylethyl)phenol (each isomer), tri(2-phenoxy-2-methylethyl)phenol (each isomer), tri(2-(methylphenoxy)-2-methylethyl)phenol (each isomer), tri(2-(ethylphenoxy)-2-methylethyl)phenol (each isomer), tri(2-(propylphenoxy)-2-methylethyl)phenol (each isomer), tri(2-(butylphenoxy)-2-methylethyl)phenol (each isomer), tri(2-(pentylphenoxy)-2-methylethyl)phenol (each isomer), tri(2-(hexylphenoxy)-2-methylethyl)phenol (each isomer), tri(2-(heptylphenoxy)-2-methylethyl)phenol (each isomer), tri(2-(octylphenoxy)-2-methylethyl)phenol (each isomer), tri(2-(nonylphenoxy)-2-methylethyl)phenol (each isomer), tri(2-(decylphenoxy)-2-methylethyl)phenol (each isomer), tri(2-(phenylphenoxy)-2-methylethyl)phenol (each isomer), tri(2-(trimethylphenoxy)-2-methylethyl)phenol (each isomer), tri(2-(triethylphenoxy)-2-methylethyl)phenol (each isomer), tri(2-(tripropylphenoxy)-2-methylethyl)phenol (each isomer), tri(2-(tributylphenoxy)-2-methylethyl)phenol (each isomer), tri(2-(tripentylphenoxy)-2-methylethyl)phenol (each isomer), tri(2-(trihexylphenoxy)-2-methylethyl)phenol (each isomer), tri(2-(triheptylphenoxy)-2-methylethyl)phenol (each isomer), tri(2-(triphenylphenoxy)-2-methylethyl)phenol (each isomer), tri(2-(trimethylphenoxy)-2-methylethyl)phenol (each isomer), tri(2-(triethylphenoxy)-2-methylethyl)phenol (each isomer), tri(2-(tripropylphenoxy)-2-methylethyl)phenol (each isomer), tri(2-(tributylphenoxy)-2-methylethyl)phenol (each isomer), tri(2-(phenylmethoxy)-2-methylethyl)phenol (each isomer), tri(2-(phenylethoxy)-2-methylethyl)phenol (each isomer), tri(2-(phenylpropyloxy)-2-methylethyl)phenol (each isomer), tri(2-(phenylbutyloxy)-2-methylethyl)phenol (each isomer), tri(2-(phenylpentyloxy)-2-methylethyl)phenol (each isomer), tri(2-(phenylhexyloxy)-2-methylethyl)phenol (each isomer), tri(2-(phenylheptyloxy)-2-methylethyl)phenol (each isomer), tri(2-(phenyloctyloxy)-2-methylethyl)phenol (each isomer), tri(2-(phenylnonyloxy)-2-methylethyl)phenol (each isomer), tri(2-methoxy-2-methylpropyl)phenol (each isomer), tri(2-ethoxy-2-methylpropyl)phenol (each isomer), tri(2-propoxy-2-methylpropyl)phenol (each isomer), tri(2-butyloxy-2-methylpropyl)phenol (each isomer), tri(2-pentyloxy-2-methylpropyl)phenol (each isomer), tri(2-hexyloxy-2-methylpropyl)phenol (each isomer), tri(2-heptyloxy-2-methylpropyl)phenol (each isomer), tri(2-octyloxy-2-methylpropyl)phenol (each isomer), tri(2-nonyloxy-2-methylpropyl)phenol (each isomer), tri(2-decyloxy-2-methylpropyl)phenol (each isomer), tri(2-dodecyloxy-2-methylpropyl)phenol (each isomer), tri(2-octadecyloxy-2-methylpropyl)phenol (each isomer), tri(2-cyclopentyloxy-2-methylpropyl)phenol (each isomer), tri(2-cyclohexyloxy-2-methylpropyl)phenol (each isomer), tri(2-cycloheptyloxy-2-methylpropyl)phenol (each isomer), tri(2-cyclooctyloxy-2-methylpropyl)phenol (each isomer), tri(2-(methylcyclopentyloxy)-2-methylpropyl)phenol (each isomer), tri(2-(ethylcyclopentyloxy)-2-methylpropyl)phenol (each isomer), tri(2-(methylcyclohexyloxy)-2-methylpropyl)phenol (each isomer), tri(2-(ethylcyclohexyloxy)-2-methylpropyl)phenol (each isomer), tri(2-(propylcyclohexyloxy)-2-methylpropyl)phenol (each isomer), tri(2-(butylcyclohexyloxy)-2-methylpropyl)phenol (each isomer), tri(2-(pentylcyclohexyloxy)-2-methylpropyl)phenol (each isomer), tri(2-(hexylcyclohexyloxy)-2-methylpropyl)phenol (each isomer), tri(2-(trimethylcyclohexyloxy)-2-methylpropyl)phenol (each isomer), tri(2-(triethylcyclohexyloxy)-2-methylpropyl)phenol (each isomer), tri(2-(tributylcyclohexyloxy)-2-methylpropyl)phenol (each isomer), tri(2-phenoxy-2-methylpropyl)phenol (each isomer), tri(2-(methylphenoxy)-2-methylpropyl)phenol (each isomer), tri(2-(ethylphenoxy)-2-methylpropyl)phenol (each isomer), tri(2-(propylphenoxy)-2-methylpropyl)phenol (each isomer), tri(2-(butylphenoxy)-2-methylpropyl)phenol (each isomer), tri(2-(pentylphenoxy)-

2-methylpropyl)phenol (each isomer), tri(2-(hexylphenoxy)-2-methylpropyl)phenol (each isomer), tri(2-(heptylphenoxy)-2-methylpropyl)phenol (each isomer), tri(2-(octylphenoxy)-2-methylpropyl)phenol (each isomer), tri(2-(nonylphenoxy)-2-methylpropyl)phenol (each isomer), tri(2-(decylphenoxy)-2-methylpropyl)phenol (each isomer), tri(2-(phenylphenoxy)-2-methylpropyl)phenol (each isomer), tri(2-(trimethylphenoxy)-2-methylpropyl)phenol (each isomer), tri(2-(triethylphenoxy)-2-methylpropyl)phenol (each isomer), tri(2-(tripropylphenoxy)-2-methylpropyl)phenol (each isomer), tri(2-(tributylphenoxy)-2-methylpropyl)phenol (each isomer), tri(2-(tripentylphenoxy)-2-methylpropyl)phenol (each isomer), tri(2-(trihexylphenoxy)-2-methylpropyl)phenol (each isomer), tri(2-(triheptylphenoxy)-2-methylpropyl)phenol (each isomer), tri(2-(triphenylphenoxy)-2-methylpropyl)phenol (each isomer), tri(2-(trimethylphenoxy)-2-methylpropyl)phenol (each isomer), tri(2-(triethylphenoxy)-2-methylpropyl)phenol (each isomer), tri(2-(tripropylphenoxy)-2-methylpropyl)phenol (each isomer), tri(2-(tributylphenoxy)-2-methylpropyl)phenol (each isomer), tri(2-(phenylmethoxy)-2-methylpropyl)phenol (each isomer), tri(2-(phenylethoxy)-2-methylpropyl)phenol (each isomer), tri(2-(phenylpropyloxy)-2-methylpropyl)phenol (each isomer), tri(2-(phenylbutyloxy)-2-methylpropyl)phenol (each isomer), tri(2-(phenylpentyloxy)-2-methylpropyl)phenol (each isomer), tri(2-(phenylhexyloxy)-2-methylpropyl)phenol (each isomer), tri(2-(phenylheptyloxy)-2-methylpropyl)phenol (each isomer), tri(2-(phenyloctyloxy)-2-methylpropyl)phenol (each isomer), tri(2-(phenylnonyloxy)-2-methylpropyl)phenol (each isomer), (dimethylamino)phenol, (diethylamino)phenol, (dipropylamino)phenol (each isomer), (dibutylamino)phenol (each isomer), (dipentylamino)phenol (each isomer), (dihexylamino)phenol (each isomer), (diheptylamino)phenol (each isomer), (dioctylamino)phenol (each isomer), (dinonylamino)phenol (each isomer), (didecylamino)phenol (each isomer), (didodecylamino)phenol (each isomer), (dioctadecylamino)phenol (each isomer), bis(dimethylamino)phenol, bis(diethylamino)phenol, bis(dipropylamino)phenol (each isomer), bis(dibutylamino)phenol (each isomer), bis(dipentylamino)phenol (each isomer), bis(dihexylamino)phenol (each isomer), bis(diheptylamino)phenol (each isomer), bis(dioctylamino)phenol (each isomer), bis(dinonylamino)phenol (each isomer), bis(didecylamino)phenol (each isomer), bis(didodecylamino)phenol (each isomer), bis(dioctadecylamino)phenol (each isomer), (2-phenyl-2-methylethyl)phenol (each isomer), (2-(methylphenyl)-2-methylethyl)phenol (each isomer), (2-(ethylphenyl)-2-methylethyl)phenol (each isomer), (2-(propylphenyl)-2-methylethyl)phenol (each isomer), (2-(butylphenyl)-2-methylethyl)phenol (each isomer), (2-(pentylphenyl)-2-methylethyl)phenol (each isomer), (2-(hexylphenyl)-2-methylethyl)phenol (each isomer), (2-(heptylphenyl)-2-methylethyl)phenol (each isomer), (2-(octylphenyl)-2-methylethyl)phenol (each isomer), (2-(nonylphenyl)-2-methylethyl)phenol (each isomer), (2-(decylphenyl)-2-methylethyl)phenol (each isomer), (2-(biphenyl)-2-methylethyl)phenol (each isomer), (2-(dimethylphenyl)-2-methylethyl)phenol (each isomer), (2-(diethylphenyl)-2-methylethyl)phenol (each isomer), (2-(dipropylphenyl)-2-methylethyl)phenol (each isomer), (2-(dibutylphenyl)-2-methylethyl)phenol (each isomer), (2-(dipentylphenyl)-2-methylethyl)phenol (each isomer), (2-(dihexylphenyl)-2-methylethyl)phenol (each isomer), (2-(diheptylphenyl)-2-methylethyl)phenol (each isomer), (2-(terphenyl)-2-methylethyl)phenol (each isomer), (2-(trimethylphenyl)-2-methylethyl)phenol (each isomer), (2-(triethylphenyl)-2-methylethyl)phenol (each isomer), (2-(tripropylphenyl)-2-methylethyl)phenol (each isomer), (2-(tributylphenyl)-2-methylethyl)phenol (each isomer), di(2-phenyl-2-methylethyl)phenol (each isomer), di(2-(methylphenyl)-2-methylethyl)phenol (each isomer), di(2-(ethylphenyl)-2-methylethyl)phenol (each isomer), di(2-(propylphenyl)-2-methylethyl)phenol (each isomer), di(2-(butylphenyl)-2-methylethyl)phenol (each isomer), di(2-(pentylphenyl)-2-methylethyl)phenol (each isomer), di(2-(hexylphenyl)-2-methylethyl)phenol (each isomer), di(2-(heptylphenyl)-2-methylethyl)phenol (each isomer), di(2-(octylphenyl)-2-methylethyl)phenol (each isomer), di(2-(nonylphenyl)-2-methylethyl)phenol (each isomer), di(2-(decylphenyl)-2-methylethyl)phenol (each isomer), di(2-(biphenyl)-2-methylethyl)phenol (each isomer), di(2-(dimethylphenyl)-2-methylethyl)phenol (each isomer), di(2-(diethylphenyl)-2-methylethyl)phenol (each isomer), di(2-(dipropylphenyl)-2-methylethyl)phenol (each isomer), di(2-(dibutylphenyl)-2-methylethyl)phenol (each isomer), di(2-(dipentylphenyl)-2-methylethyl)phenol (each isomer), di(2-(dihexylphenyl)-2-methylethyl)phenol (each isomer), di(2-(diheptylphenyl)-2-methylethyl)phenol (each isomer), di(2-(terphenyl)-2-methylethyl)phenol (each isomer), di(2-(trimethylphenyl)-2-methylethyl)phenol (each isomer), di(2-(triethylphenyl)-2-methylethyl)phenol (each isomer), di(2-(tripropylphenyl)-2-methylethyl)phenol (each isomer), di(2-(tributylphenyl)-2-methylethyl)phenol (each isomer), tri(2-phenyl-2-methylethyl)phenol (each isomer), tri(2-(methylphenyl)-2-methylethyl)phenol (each isomer), tri(2-(ethylphenyl)-2-methylethyl)phenol (each isomer), tri(2-(propylphenyl)-2-methylethyl)phenol (each isomer), tri(2-(butylphenyl)-2-methylethyl)phenol (each isomer), tri(2-(pentylphenyl)-2-methylethyl)phenol (each isomer), tri(2-(hexylphenyl)-2-methylethyl)phenol (each isomer), tri(2-(heptylphenyl)-2-methylethyl)phenol (each isomer), tri(2-(octylphenyl)-2-methylethyl)phenol (each isomer), tri(2-(nonylphenyl)-2-methylethyl)phenol (each isomer), tri(2-(decylphenyl)-2-methylethyl)phenol (each isomer), tri(2-(biphenyl)-2-methylethyl)phenol (each isomer), tri(2-(dimethylphenyl)-2-methylethyl)phenol (each isomer), tri(2-(diethylphenyl)-2-methylethyl)phenol (each isomer), tri(2-(dipropylphenyl)-2-methylethyl)phenol (each isomer), tri(2-(dibutylphenyl)-2-methylethyl)phenol (each isomer), tri(2-(dipentylphenyl)-2-methylethyl)phenol (each isomer), tri(2-(dihexylphenyl)-2-methylethyl)phenol (each isomer), tri(2-(diheptylphenyl)-2-methylethyl)phenol (each isomer), tri(2-(terphenyl)-2-methylethyl)phenol (each isomer), tri(2-(trimethylphenyl)-2-methylethyl)phenol (each isomer), tri(2-(triethylphenyl)-2-methylethyl)phenol (each isomer), tri(2-(tripropylphenyl)-2-methylethyl)phenol (each isomer), tri(2-(tributylphenyl)-2-methylethyl)phenol (each isomer), (2-phenyl-2-methylpropyl)phenol (each isomer), (2-(methylphenyl)-2-methylpropyl)phenol (each isomer), (2-(ethylphenyl)-2-methylpropyl)phenol (each isomer), (2-(propylphenyl)-2-methylpropyl)phenol (each isomer), (2-(butylphenyl)-2-methylpropyl)phenol (each isomer), (2-(pentylphenyl)-2-methylpropyl)phenol (each isomer), (2-(hexylphenyl)-2-methylpropyl)phenol (each isomer), (2-(heptylphenyl)-2-methylpropyl)phenol (each isomer), (2-(octylphenyl)-2-methylpropyl)phenol (each isomer), (2-(nonylphenyl)-2-methylpropyl)phenol (each isomer), (2-(decylphenyl)-2-methylpropyl)phenol (each isomer), (2-(biphenyl)-2-methylpropyl)phenol (each isomer), (2-(dimethylphenyl)-2-methylpropyl)phenol (each isomer), (2-(diethylphenyl)-2-methylpropyl)phenol (each isomer), (2-(dipropylphenyl)-2-methylpropyl)phenol (each isomer), (2-(dibutylphenyl)-2-methylpropyl)phenol (each isomer), (2-

(dipentylphenyl)-2-methylpropyl)phenol (each isomer), (2-(dihexylphenyl)-2-methylpropyl)phenol (each isomer), (2-(diheptylphenyl)-2-methylpropyl)phenol (each isomer), (2-(terphenyl)-2-methylpropyl)phenol (each isomer), (2-(trimethylphenyl)-2-methylpropyl)phenol (each isomer), (2-(triethylphenyl)-2-methylpropyl)phenol (each isomer), (2-(tripropylphenyl)-2-methylpropyl)phenol (each isomer), (2-(tributylphenyl)-2-methylpropyl)phenol (each isomer), di(2-phenyl-2-methylpropyl)phenol (each isomer), di(2-(methylphenyl)-2-methylpropyl)phenol (each isomer), di(2-(ethylphenyl)-2-methylpropyl)phenol (each isomer), di(2-(propylphenyl)-2-methylpropyl)phenol (each isomer), di(2-(butylphenyl)-2-methylpropyl)phenol (each isomer), di(2-(pentylphenyl)-2-methylpropyl)phenol (each isomer), di(2-(hexylphenyl)-2-methylpropyl)phenol (each isomer), di(2-(heptylphenyl)-2-methylpropyl)phenol (each isomer), di(2-(octylphenyl)-2-methylpropyl)phenol (each isomer), di(2-(nonylphenyl)-2-methylpropyl)phenol (each isomer), di(2-(decylphenyl)-2-methylpropyl)phenol (each isomer), di(2-(biphenyl)-2-methylpropyl)phenol (each isomer), di(2-(dimethylphenyl)-2-methylpropyl)phenol (each isomer), di(2-(diethylphenyl)-2-methylpropyl)phenol (each isomer), di(2-(dipropylphenyl)-2-methylpropyl)phenol (each isomer), di(2-(dibutylphenyl)-2-methylpropyl)phenol (each isomer), di(2-(dipentylphenyl)-2-methylpropyl)phenol (each isomer), di(2-(dihexylphenyl)-2-methylpropyl)phenol (each isomer), di(2-(diheptylphenyl)-2-methylpropyl)phenol (each isomer), di(2-(terphenyl)-2-methylpropyl)phenol (each isomer), di(2-(trimethylphenyl)-2-methylpropyl)phenol (each isomer), di(2-(triethylphenyl)-2-methylpropyl)phenol (each isomer), di(2-(tripropylphenyl)-2-methylpropyl)phenol (each isomer), di(2-(tributylphenyl)-2-methylpropyl)phenol (each isomer), tri(2-phenyl-2-methylpropyl)phenol (each isomer), tri(2-(methylphenyl)-2-methylpropyl)phenol (each isomer), tri(2-(ethylphenyl)-2-methylpropyl)phenol (each isomer), tri(2-(propylphenyl)-2-methylpropyl)phenol (each isomer), tri(2-(butylphenyl)-2-methylpropyl)phenol (each isomer), tri(2-(pentylphenyl)-2-methylpropyl)phenol (each isomer), tri(2-(hexylphenyl)-2-methylpropyl)phenol (each isomer), tri(2-(heptylphenyl)-2-methylpropyl)phenol (each isomer), tri(2-(octylphenyl)-2-methylpropyl)phenol (each isomer), tri(2-(nonylphenyl)-2-methylpropyl)phenol (each isomer), tri(2-(decylphenyl)-2-methylpropyl)phenol (each isomer), tri(2-(biphenyl)-2-methylpropyl)phenol (each isomer), tri(2-(dimethylphenyl)-2-methylpropyl)phenol (each isomer), tri(2-(diethylphenyl)-2-methylpropyl)phenol (each isomer), tri(2-(dipropylphenyl)-2-methylpropyl)phenol (each isomer), tri(2-(dibutylphenyl)-2-methylpropyl)phenol (each isomer), tri(2-(dipentylphenyl)-2-methylpropyl)phenol (each isomer), tri(2-(dihexylphenyl)-2-methylpropyl)phenol (each isomer), tri(2-(diheptylphenyl)-2-methylpropyl)phenol (each isomer), tri(2-(terphenyl)-2-methylpropyl)phenol (each isomer), tri(2-(trimethylphenyl)-2-methylpropyl)phenol (each isomer), tri(2-(triethylphenyl)-2-methylpropyl)phenol (each isomer), tri(2-(tripropylphenyl)-2-methylpropyl)phenol (each isomer), tri(2-(tributylphenyl)-2-methylpropyl)phenol (each isomer), tri(dipropylamino)phenol (each isomer), tri(dibutylamino)phenol (each isomer), tri(dipentylamino)phenol (each isomer), tri(dihexylamino)phenol (each isomer), tri(diheptylamino)phenol (each isomer), tri(dioctylamino)phenol (each isomer), tri(dinonylamino)phenol (each isomer), tri(didecylamino)phenol (each isomer), tri(didodecylamino)phenol (each isomer), and tri(dioctadecylamino)phenol (each isomer).

Among the above described aromatic hydroxy compounds, more preferred examples include aromatic hydroxy compounds in which the number of carbon atoms constituting the $R^{32}$, $R^{33}$, $R^{34}$, $R^{35}$ and $R^{36}$ is from 0 to 13, because it facilitates transfer. Further preferred examples include aromatic hydroxy compounds in which the $R^{32}$, $R^{33}$, $R^{34}$, $R^{35}$ and $R^{36}$ each represent a group containing 0 to 9 carbon atoms, which is selected from a hydrogen atom, a straight chain and/or branched chain alkyl group, a cycloalkyl group, a substituted or unsubstituted aryl group, a straight chain and/or branched chain alkoxy group, a substituted or unsubstituted aryloxy group, and a substituted or unsubstituted aralkyl group.

In addition, the aromatic hydroxy compound forms an N-substituted carbamate, and the N-substituted carbamate is used as an isocyanate precursor. A method for producing an N-substituted carbamate-derived isocyanate from the N-substituted carbamate will be described later, and this is a method of subjecting the N-substituted carbamate to pyrolysis, so as to obtain an aromatic hydroxy compound derived from the N-substituted carbamate, and an isocyanate. If referring to the reaction formula of the aromatic hydroxy compound generated in the above described method, it is an aromatic hydroxy compound used in the production of the N-substituted carbamate. That is to say, the aromatic hydroxy compound represented by the formula (25), or preferably the formula (26), is generated as a by-product together with an isocyanate upon the pyrolysis of the N-substituted carbamate. After completion of the pyrolytic step, in one of the present embodiments, the aromatic hydroxy compound may be separated from the isocyanate by distillation, and the thus separated aromatic hydroxy compound may be then recycled as an aromatic hydroxy compound in the reaction of an organic amine, a carbonic acid derivative and an aromatic hydroxy compound, although it depends on situation. Accordingly, if taking into consideration the production step of the isocyanate, it is necessary to consider the separating property between the aromatic hydroxy compound used as a raw material for the N-substituted carbamate and the isocyanate generated from the N-substituted carbamate. It is difficult to generally define such a separating property. On the basis of the findings that, in general, if the standard boiling points of two components to be separated are 10° C. or more apart from each other, they can be industrially sufficiently separated by distillation, the separating property will be defined as follows. Thus, this definition is a value that is limited to conventionally known separation means, and it is not a definition that constitutes the essence of the present embodiment.

<Compound Having Ureido Group>

A compound having a ureido group is produced by a reaction of an organic amine with a carbonic acid derivative in one of several methods for producing an N-substituted carbamate from an organic amine, urea and a hydroxy compound. In this method, the compound having a ureido group is reacted with a hydroxy compound to produce an N-substituted carbamate.

The compound having a ureido group is a compound represented by the following formula (27):

[Chemical Formula 18]

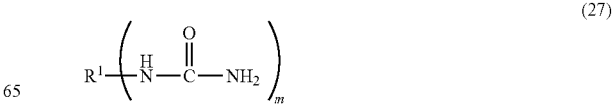

(27)

wherein R¹ represents an organic group containing 1 to 85 carbon atoms, which is substituted with an m number of ureido groups, and m represents an integer between 1 or greater and 10 or less.

The compound having a ureido group represented by the above formula (27) is a compound having a "ureido group" defined in Regulation C-971 of the Nomenclature of IUPAC.

In the above formula (27), R¹ represents an aliphatic group, an aromatic group, and a group formed by binding an aliphatic group to an aromatic group, and thus, R¹ represents a group consisting of an acyclic hydrocarbon group, a cyclic hydrocarbon group (for example, a monocyclic hydrocarbon group, a condensed polycyclic hydrocarbon group, a cross-linked cyclic hydrocarbon group, a spiro hydrocarbon group, a multi-ring hydrocarbon group, a cyclic hydrocarbon group having a side chain, a heterocyclic group, a heterocyclic spiro group, a hetero crosslinked cyclic group, and a heterocyclic group), a group to which at least one selected from the acyclic hydrocarbon group and the cyclic hydrocarbon group binds, and a group to which the above described group binds via a covalent bond with specific non-metal atoms (carbon, oxygen, nitrogen, sulfur, and silicon).

Among these R¹ groups, if taking into consideration the unlikeliness of side reactions, the R¹ group that can be preferably used in the present embodiment is selected from an aliphatic group and an aromatic group, and the R¹ group represents a group selected from the group consisting of an acyclic hydrocarbon group and a cyclic hydrocarbon group (a monocyclic hydrocarbon group, a condensed polycyclic hydrocarbon group, a crosslinked cyclic hydrocarbon group, a spiro hydrocarbon group, a multi-ring hydrocarbon group, and a cyclic hydrocarbon group having a side chain), and a group to which at least one group selected from the aforementioned group binds (wherein the two groups are substituted with each other), wherein the above-mentioned group contains 1 to 85 carbon atoms. If taking into consideration flowability and the like, the R¹ group is preferably a group containing 1 to 70 carbon atoms, and more preferably a group containing 1 to 13 carbon atoms.

Preferred examples of the compound having a ureido group include:

1) an N-substituted aromatic organic monourea, in which the R¹ group represents a group containing 6 to 85 carbon atoms, which contains one or more aromatic rings optionally substituted with aliphatic and/or aromatic groups, the aromatic groups in the R¹ group are substituted with ureido groups, and m is 1, 2) an N-substituted aromatic organic polyurea, in which the R¹ group represents a group containing 6 to 85 carbon atoms, which contains one or more aromatic rings optionally substituted with aliphatic and/or aromatic groups, the aromatic groups in the R¹ group are substituted with ureido groups, and m is 2 or greater, and 3) an N-substituted aliphatic organic polyurea, in which the R¹ group represents an aliphatic group containing 1 to 85 carbon atoms, which is optionally substituted with an aromatic group, and m is 2 or 3. With regard to the above-mentioned organic urea, an organic urea, in which an atom (mainly, a carbon atom) to which a ureido group binds is contained in the aromatic ring, is defined as an N-substituted aromatic organic urea, whereas an organic urea, in which such an atom binds to an atom (mainly, a carbon atom) that is not in the aromatic ring, is defined as an N-substituted aliphatic organic urea.

Moreover, m in the above formula (27) represents an integer from 1 to 10, and when the organic amine of the above formula (1) is used as a starting substance, m is an integer that does not exceed the a of the organic amine represented by the above formula (1).

Specific examples of a preferred compound having a ureido group are as follows.

1) N-substituted aromatic organic monourea

A preferred example of the N-substituted aromatic organic monourea is an N-substituted aromatic organic monourea wherein the R¹ group represents a group containing 6 to 85 carbon atoms, which contains one or more aromatic rings optionally substituted with aliphatic and/or aromatic groups, and the aromatic group in the R¹ group is substituted with a ureido group, and m is 1. The N-substituted aromatic organic monourea is more preferably an N-substituted aromatic organic monourea wherein the R¹ group represents a group containing 6 to 70 carbon atoms and m is 1. Taking into consideration flowability and the like, the N-aromatic organic monourea is further preferably an N-aromatic organic monourea wherein the R¹ group represents a group containing 6 to 13 carbon atoms and m is 1. It is an N-aromatic organic monourea represented by the following formula (28):

[Chemical Formula 19]

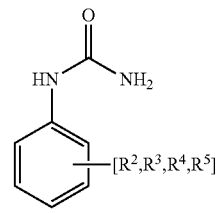

(28)

At least one of the ortho-position and/or para-position of the ureido group of the aromatic organic monourea represented by the above formula (28) is unsubstituted, and each of the R² to R⁵ groups represents a group substituted in any given position at which the aromaticity of the ring is maintained, and the R² to R⁵ groups may independently substitute an aromatic ring, or the R² to R⁵ groups may bind to one another to form a ring together with an aromatic ring, and further, each of the R² to R⁵ groups represents a hydrogen atom, or a group selected from the group consisting of an alkyl group, a cycloalkyl group, an aryl group and an aryl group having a hydroxy group, or a group to which a group selected from the above described groups binds via a saturated aliphatic bond and/or an ether bond, wherein the number of carbon atoms contained in each of the R² to R⁵ groups is an integer from 0 to 7, and the total number of carbon atoms constituting the N-aromatic organic monourea represented by the above formula (28) is from 6 to 13.

A more preferred example of the N-aromatic organic monourea represented by the formula (28) is an N-aromatic organic monourea, wherein the R² to R⁵ groups each represent a hydrogen atom, or a group selected from alkyl groups such as a methyl group and an ethyl group, and examples of such an N-aromatic organic monourea include N-phenyl urea, N-(methylphenyl)urea (each isomer), N-(dimethylphenyl)urea (each isomer), N-(diethylphenyl)urea (each isomer), N-(dipropylphenyl)urea (each isomer), N-naphthyl urea (each isomer), N-(methylnaphthyl)urea (each isomer), N-dimethylnaphthyl urea (each isomer), and N-trimethylnaphthyl urea (each isomer). Of these, N-phenyl urea is more preferable.

2) N-Substituted Aromatic Organic Polyurea

A preferred example of the N-substituted aromatic organic polyurea is an N-substituted aromatic organic polyurea, wherein the $R^1$ group is a group containing 6 to 85 carbon atoms, which contains one or more aromatic rings optionally substituted with aliphatic and/or aromatic groups, the aromatic groups in the $R^1$ group are substituted with ureido groups, and m is 2 or greater. A more preferred example of the N-substituted aromatic organic polyurea is an N-substituted aromatic organic polyurea, wherein the $R^1$ group is a group containing 6 to 70 carbon atoms and m is 2 or greater. If taking into consideration flowability and the like, a further preferred example is an N-aromatic organic polyurea, wherein the $R^1$ group is an aromatic group containing 6 to 13 carbon atoms, which contains one or more aromatic rings, wherein the aromatic rings are further optionally substituted with alkyl groups, aryl groups or aralkyl groups, and m is 2 or greater. Examples of such an aromatic organic polyurea include N,N'-phenylene diurea (each isomer), N,N'-methylphenylene diurea (each isomer), N,N'-methylenediphenylene diurea (each isomer), N,N'-mesitylene diurea (each isomer), N,N'-biphenylene diurea (each isomer), N,N'-diphenylene diurea (each isomer), N,N'-propylenediphenylene diurea (each isomer), N,N'-oxy-diphenylene diurea (each isomer), bis(ureidophenoxyethane) (each isomer), N,N'-xylene diurea (each isomer), N,N'-methoxyphenyl diurea (each isomer), N,N'-ethoxyphenyl diurea (each isomer), N,N'-naphthalene diurea (each isomer), N,N'-methylnaphthalene diurea (each isomer), and polymethylenepolyphenyl polyurea represented by the following formula (29).

[Chemical Formula 20]

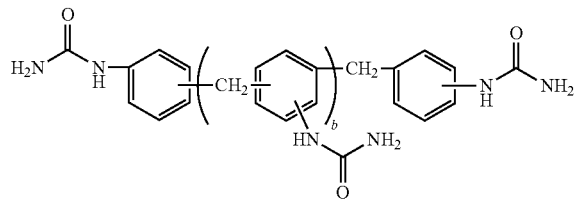

(29)

wherein b represents an integer from 0 to 6.

3) N-Substituted Aliphatic Organic Polyurea

A preferred example of the N-substituted aliphatic organic polyurea is an N-substituted aliphatic organic polyurea, wherein the $R^1$ group of the compound having a ureido group represented by the above formula (27) is an aliphatic group containing 1 to 85 carbon atoms, which is optionally substituted with an aromatic group, and m is 2 or 3. A more preferred example of the N-aliphatic organic polyurea is an N-organic polyurea, wherein the aliphatic group represents an acyclic hydrocarbon group, a cyclic hydrocarbon group, and a group to which at least one group selected from the acyclic hydrocarbon group and the cyclic hydrocarbon group binds (for example, a cyclic hydrocarbon group substituted with an acyclic hydrocarbon group, an acyclic hydrocarbon group substituted with a cyclic hydrocarbon group, etc.). A further preferred example of the N-substituted aliphatic organic polyurea is an N-aliphatic organic polyurea, wherein the $R^1$ group is an aliphatic group, and the aliphatic group represents an acyclic hydrocarbon group, a cyclic hydrocarbon group, and a group to which at least one group selected from the acyclic hydrocarbon group and the cyclic hydrocarbon group binds (for example, a cyclic hydrocarbon group substituted with an acyclic hydrocarbon group, an acyclic hydrocarbon group substituted with a cyclic hydrocarbon group, etc.), each of which contains 1 to 70 carbon atoms, and m is 2 or 3. Taking into consideration flowability necessary for industrial mass production, a most preferred example of the N-substituted aliphatic organic polyurea is an N-aliphatic organic polyurea, wherein the $R^1$ group is an acyclic hydrocarbon group, a cyclic hydrocarbon group, and a group to which at least one group selected from the acyclic hydrocarbon group and the cyclic hydrocarbon group binds (e.g. a cyclic hydrocarbon group substituted with an acyclic hydrocarbon, an acyclic hydrocarbon group substituted with a cyclic hydrocarbon group, etc.), each of which is constituted with carbon atoms and hydrogen atoms and each of which contains 6 to 13 carbon atoms. That is to say, the case is an N-substituted aliphatic organic polyurea, wherein the $R^1$ group is a straight chain and/or branched chain alkyl group, a cycloalkyl group, and a group constituted with the alkyl group and the cycloalkyl group. Examples of such groups include: N-aliphatic diureas, such as N,N'-ethylene diurea, N,N'-propylene diurea (each isomer), N,N'-butylene diurea (each isomer), N,N'-pentamethylene diurea (each isomer), N,N'-hexanemethylene diurea (each isomer), and N,N'-decamethylene diurea (each isomer); N-aliphatic triureas, such as N,N',N"-hexamethylene triurea (each isomer), N,N',N"-nonamethylene triurea (each isomer), and N,N',N"-decamethylene triurea (each isomer); and N-cyclic aliphatic polyureas, such as N,N'-cyclobutylene diurea (each isomer), N,N'-methylenedicyclohexyl diurea (each isomer), 3-ureidomethyl-3,5,5-trimethylcyclohexyl urea (cis and/or trans forms), and methylenebis (cyclohexyl urea) (each isomer).

<N-Substituted Carbamate>

An N-substituted carbamate is a compound produced from an organic amine, a carbonic acid derivative and a hydroxy compound according to the production method used in the present embodiment.

The N-substituted carbamate, which is obtained when alcohol is used as an organic hydroxy compound in the reaction of an organic amine, urea and an organic hydroxy compound, is represented by the following formula (30):

[Chemical Formula 21]

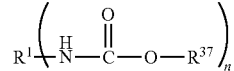

(30)

wherein $R^1$ represents an organic group containing 1 to 85 carbon atoms, which is substituted with an n number of carbamate groups, $R^{37}$ represents a group derived from alcohol, which is a residue obtained by removing from the alcohol one hydroxy group attached to a saturated carbon atom of the alcohol, and n represents an integer between 1 or greater and a or less, or an integer between 1 or greater and m or less, wherein a and m represent the above-defined values.

In the above formula (30), $R^1$ represents an aliphatic group, an aromatic group, and a group formed by binding an aliphatic group to an aromatic group, and thus, $R^1$ represents a group consisting of an acyclic hydrocarbon group, a cyclic hydrocarbon group (for example, a monocyclic hydrocarbon group, a condensed polycyclic hydrocarbon group, a crosslinked cyclic hydrocarbon group, a spiro hydrocarbon group, a multi-ring hydrocarbon group, a cyclic hydrocarbon group having a side chain, a heterocyclic group, a heterocyclic spiro group, a hetero crosslinked cyclic group, and a heterocyclic group), a group to which at least one selected from the acyclic hydrocarbon group and the cyclic hydrocarbon group binds, and a group to which the above described group binds via a covalent bond with specific non-metal atoms (carbon, oxygen, nitrogen, sulfur, and silicon).

Among these $R^1$ groups, if taking into consideration the unlikeliness of side reactions, the $R^1$ group that can be preferably used in the present embodiment is selected from an aliphatic group and an aromatic group, and the $R^1$ group represents a group selected from the group consisting of an acyclic hydrocarbon group and a cyclic hydrocarbon group (a monocyclic hydrocarbon group, a condensed polycyclic hydrocarbon group, a crosslinked cyclic hydrocarbon group, a spiro hydrocarbon group, a multi-ring hydrocarbon group, and a cyclic hydrocarbon group having a side chain), and a group to which at least one group selected from the aforementioned group binds (wherein the two groups are substituted with each other), wherein the above-mentioned group contains 1 to 85 carbon atoms. If taking into consideration flowability and the like, the $R^1$ group is preferably a group containing 1 to 70 carbon atoms, and more preferably a group containing 1 to 13 carbon atoms.

Preferred examples of the N-substituted carbamate constituted with $R^1$ group include:

1) an N-aromatic monocarbamate, in which the $R^1$ group represents a group containing 6 to 85 carbon atoms, which contains one or more aromatic rings, and n is 1, 2) an N-aromatic organic polycarbamate, in which the $R^1$ group represents a group containing 6 to 85 carbon atoms, which contains one or more aromatic rings, and n is 2 or greater, and 3) an N-aliphatic organic polycarbamate, in which the $R^1$ group represents an aliphatic group containing 1 to 85 carbon atoms, and n is 2 or 3. A more preferred aliphatic group is an acyclic hydrocarbon group, a cyclic hydrocarbon group, and a group to which at least one group selected from the acyclic hydrocarbon group and the cyclic hydrocarbon group binds (for example, a cyclic hydrocarbon group substituted with an acyclic hydrocarbon group, an acyclic hydrocarbon group substituted with a cyclic hydrocarbon group, etc.), each of which contains 6 to 70 carbon atoms.

Moreover, n in the above formula (30) represents an integer from 1 to 10, and when the organic amine of the above formula (1) is used as a starting substance, m is an integer that does not exceed the a of the organic amine represented by the above formula (1).

Specific examples of the N-substituted carbamate are as follows.

1) N-Aromatic Organic Monocarbamate

A preferred example of the N-aromatic organic monocarbamate is an N-aromatic organic monocarbamate, wherein the $R^1$ group represents a group containing 6 to 85 carbon atoms, which contains one or more aromatic rings "substituted with carbamate groups," and n is 1. The N-aromatic organic monocarbamate is more preferably an N-aromatic organic monocarbamate, wherein the $R^1$ group represents a group containing 6 to 70 carbon atoms, which contains one or more aromatic rings "substituted with carbamate groups," and n is 1. Taking into consideration flowability and the like, the N-aromatic organic monocarbamate is further preferably an N-aromatic organic monocarbamate, wherein the $R^1$ group represents a group containing 6 to 13 carbon atoms, which contains one or more aromatic rings "substituted with carbamate groups," and n is 1. It is an N-aromatic organic monocarbamate represented by the following formula (31):

[Chemical Formula 22]

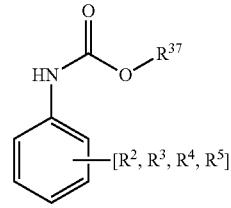

(31)

The $R^1$ group of the N-aromatic organic monocarbamic acid ester represented by the above formula (31) is the above-defined group. The $R^2$ to $R^5$ groups each represent a group substituted in any given position at which the aromaticity of the ring is maintained, and the $R^2$ to $R^5$ groups may independently substitute an aromatic ring, or the $R^2$ to $R^5$ groups may bind to one another to form a ring together with an aromatic ring, and further, each of the $R^2$ to $R^5$ groups represents a hydrogen atom, or a group selected from the group consisting of an alkyl group, a cycloalkyl group, an aryl group and an aryl group having a hydroxy group, or a group to which a group selected from the above described groups binds via a saturated aliphatic bond and/or an ether bond, wherein the number of carbon atoms constituting the N-aromatic organic monocarbamate represented by the formula (31) is from 7 to 63.

A preferred example of the N-aromatic organic monocarbamate represented by the formula (31) is an N-substituted aromatic organic monocarbamate, wherein the $R^2$ to $R^5$ groups are selected from a hydrogen atom and alkyl groups such as a methyl group and an ethyl group.

2) N-Aromatic Organic Polycarbamate

A preferred example of the N-aromatic organic polycarbamate is an N-aromatic organic polycarbamate, wherein the $R^1$ group represents a group containing 6 to 85 carbon atoms, which contains one or more aromatic rings "substituted with carbamate groups," and n is 2 or greater. The N-aromatic organic polycarbamate is more preferably an N-aromatic organic polycarbamate, wherein the $R^1$ group represents a group containing 6 to 70 carbon atoms, which contains one or more aromatic rings "substituted with carbamate groups," and n is 2 or greater. Taking into consideration flowability and the like, the N-aromatic organic polycarbamate is further preferably an N-aromatic organic polycarbamate, wherein the $R^1$ group represents a group containing 6 to 13 carbon atoms, which contains one or more aromatic rings "substituted with carbamate groups" and the aromatic rings are optionally further substituted with alkyl groups, aryl groups or aralkyl groups, and n is 2 or greater.

Moreover, the N-aromatic organic polycarbamate also includes a polymethylenepolyphenyl polycarbamate represented by the following formula (32):

[Chemical Formula 23]

(32)

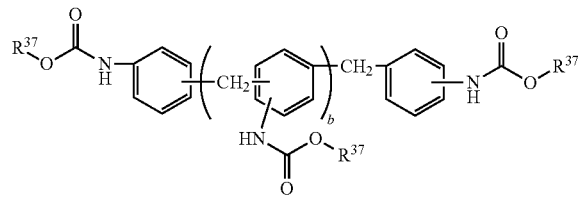

wherein R³⁷ represents the above-defined group, and
b represents an integer from 0 to 6.

3) N-Aliphatic Organic Polycarbamate

A preferred example of the N-aliphatic organic polycarbamate is an N-aliphatic organic polycarbamate, wherein the $R^1$ group of the N-substituted carbamate represented by the formula (30) represents an aliphatic group containing 1 to 85 carbon atoms, and n is 2 or 3. The N-substituted carbamate is more preferably an N-substituted carbamate, wherein the aliphatic group represents an acyclic hydrocarbon group, a cyclic hydrocarbon group, and a group to which at least one group selected from the acyclic hydrocarbon group and the cyclic hydrocarbon group binds (for example, a cyclic hydrocarbon group substituted with an acyclic hydrocarbon group, an acyclic hydrocarbon group substituted with a cyclic hydrocarbon group, etc.). The N-aliphatic organic polycarbamate is further preferably an N-aliphatic organic polycarbamate, wherein the $R^1$ group represents an aliphatic group that is an acyclic hydrocarbon group, a cyclic hydrocarbon group, and a group to which at least one group selected from the acyclic hydrocarbon group and the cyclic hydrocarbon group binds (for example, a cyclic hydrocarbon group substituted with an acyclic hydrocarbon group, an acyclic hydrocarbon group substituted with a cyclic hydrocarbon group, etc.), each of which contains 1 to 70 carbon atoms, and n is an integer of 2 or 3. Taking into consideration flowability necessary for industrial mass production, a most preferred example of the N-aliphatic organic polycarbamate is an N-aliphatic organic polycarbamic acid ester, wherein the $R^1$ group is an acyclic hydrocarbon group, a cyclic hydrocarbon group, and a group to which at least one group selected from the acyclic hydrocarbon group and the cyclic hydrocarbon group binds (e.g. a cyclic hydrocarbon group substituted with an acyclic hydrocarbon group, an acyclic hydrocarbon group substituted with a cyclic hydrocarbon group, etc.), each of which is constituted with carbon atoms and hydrogen atoms and each of which contains 6 to 13 carbon atoms. That is to say, the case is an N-aliphatic organic polycarbamic acid ester, wherein the $R^1$ group is a straight chain and/or branched chain alkyl group, a cycloalkyl group, and a group constituted with the alkyl group and the cycloalkyl group.

Since the specific structure of such an N-substituted carbamate is determined depending on the types of an organic amine used and alcohol that constitutes a hydroxy composition, it is not possible to exemplify all the specific structures, but examples of the specific structure of the N-substituted carbamate include N,N'-hexanediyl-di(carbamic acid methyl ester) (each isomer), N,N'-hexanediyl-di(carbamic acid ethyl ester) (each isomer), N,N'-hexanediyl-di(carbamic acid propyl ester) (each isomer), N,N'-hexanediyl-di(carbamic acid butyl ester) (each isomer), N,N'-hexanediyl-di(carbamic acid pentyl ester) (each isomer), N,N'-hexanediyl-di(carbamic acid hexyl ester) (each isomer), N,N'-hexanediyl-di(carbamic acid heptyl ester) (each isomer), N,N'-hexanediyl-di(carbamic acid octyl ester) (each isomer), N,N'-hexanediyl-di(carbamic acid nonyl ester) (each isomer), N,N'-hexanediyl-di(carbamic acid decyl ester) (each isomer), N,N'-hexanediyl-di(carbamic acid dodecyl ester) (each isomer), N,N'-hexanediyl-di(carbamic acid octadecyl ester) (each isomer), N,N'-methylenediphenylene-di(carbamic acid methyl ester) (each isomer), N,N'-methylenediphenylene-di(carbamic acid ethyl ester) (each isomer), N,N'-methylenediphenylene-di(carbamic acid propyl ester) (each isomer), N,N'-methylenediphenylene-di(carbamic acid butyl ester) (each isomer), N,N'-methylenediphenylene-di(carbamic acid pentyl ester) (each isomer), N,N'-methylenediphenylene-di(carbamic acid hexyl ester) (each isomer), N,N'-methylenediphenylene-di(carbamic acid heptyl ester) (each isomer), N,N'-methylenediphenylene-di(carbamic acid octyl ester) (each isomer), N,N'-methylenediphenylene-di(carbamic acid nonyl ester) (each isomer), N,N'-methylenediphenylene-di(carbamic acid decyl ester) (each isomer), N,N'-methylenediphenylene-di(carbamic acid dodecyl ester) (each isomer), N,N'-methylenediphenylene-di(carbamic acid octadecyl ester) (each isomer), 3-(methoxycarbonylamino-methyl)-3,5,5-trimethylcyclohexyl carbamic acid methyl ester (each isomer), 3-(ethoxycarbonylamino-methyl)-3,5,5-trimethylcyclohexyl carbamic acid ethyl ester (each isomer), 3-(propyloxycarbonylamino-methyl)-3,5,5-trimethylcyclohexyl carbamic acid propyl ester (each isomer), 3-(butyloxycarbonylamino-methyl)-3,5,5-trimethylcyclohexyl carbamic acid butyl ester (each isomer), 3-(pentyloxycarbonylamino-methyl)-3,5,5-trimethylcyclohexyl carbamic acid pentyl ester (each isomer), 3-(hexyloxycarbonylamino-methyl)-3,5,5-trimethylcyclohexyl carbamic acid hexyl ester (each isomer), 3-(heptyloxycarbonylamino-methyl)-3,5,5-trimethylcyclohexyl carbamic acid heptyl ester (each isomer), 3-(octyloxycarbonylamino-methyl)-3,5,5-trimethylcyclohexyl carbamic acid octyl ester (each isomer), 3-(nonyloxycarbonylamino-methyl)-3,5,5-trimethylcyclohexyl carbamic acid nonyl ester (each isomer), 3-(decyloxycarbonylamino-methyl)-3,5,5-trimethylcyclohexyl carbamic acid decyl ester (each isomer), 3-(dodecyloxycarbonylamino-methyl)-3,5,5-trimethylcyclohexyl carbamic acid dodecyl ester (each isomer), 3-(octadecyloxycarbonylamino-methyl)-3,5,5-trimethylcyclohexyl carbamic acid octadecyl ester (each isomer), toluene-di(carbamic acid methyl ester) (each isomer), toluene-di(carbamic acid ethyl ester) (each isomer), toluene-di(carbamic acid propyl ester) (each isomer), toluene-di(carbamic acid butyl ester) (each isomer), toluene-di(carbamic acid pentyl ester) (each isomer), toluene-di(carbamic acid hexyl ester) (each isomer), toluene-di(carbamic acid heptyl ester) (each isomer), toluene-di(carbamic acid octyl ester) (each isomer), toluene-di(carbamic acid nonyl ester) (each isomer), toluene-di(carbamic acid decyl ester) (each isomer), toluene-di(carbamic acid dodecyl ester) (each isomer), toluene-di(carbamic acid octadecyl ester) (each isomer), N,N'-methylenedicyclohexyl-di(carbamic acid methyl ester) (each isomer), N,N'-methylenedicyclohexyl-di(carbamic acid ethyl ester) (each isomer), N,N'-methylenedicyclohexyl-di(carbamic acid propyl ester) (each isomer), N,N'-methylenedicyclohexyl-di(carbamic acid butyl ester) (each isomer), N,N'-methylenedicyclohexyl-di(carbamic acid pentyl ester) (each isomer), N,N'-methylenedicyclohexyl-di(carbamic acid hexyl ester) (each isomer), N,N'-methylenedicyclohexyl-di(carbamic acid heptyl ester) (each isomer), N,N'-methylenedicyclohexyl-di(carbamic acid octyl ester) (each isomer), N,N'-methylenedicyclohexyl-di(carbamic acid nonyl ester) (each isomer), N,N'-methylenedicyclohexyl-di(carbamic acid decyl ester) (each isomer), N,N'-methylenedicyclohexyl-di(carbamic acid dodecyl ester) (each isomer), N,N'-methylenedicyclohexyl-di(carbamic acid octadecyl ester) (each isomer), N-phenyl carbamic acid methyl ester (each isomer), N-phenyl carbamic acid ethyl ester (each isomer), N-phenyl carbamic acid propyl ester (each isomer), N-phenyl carbamic acid butyl ester (each isomer), N-phenyl carbamic acid pentyl ester (each isomer), N-phenyl carbamic acid(hexyl ester (each isomer), N-phenyl carbamic acid heptyl ester (each isomer), N-phenyl carbamic acid octyl ester (each isomer), N-phenyl carbamic acid nonyl ester (each isomer), N-phenyl carbamic acid decyl ester (each isomer), N-phenyl carbamic acid dodecyl ester (each isomer), N-phenyl carbamic acid octadecyl ester (each isomer), N-dimethylphenyl carbamic acid methyl ester (each isomer), N-dimethylphenyl carbamic acid ethyl ester (each isomer), N-dimethylphenyl carbamic acid propyl ester (each isomer), N-dimethylphenyl carbamic acid butyl ester (each isomer), N-dimethylphenyl carbamic acid pentyl ester (each isomer), N-dimethylphenyl carbamic acid hexyl ester (each isomer), N-dimethylphenyl carbamic acid heptyl ester (each isomer), N-dimethylphenyl carbamic acid octyl ester (each isomer), N-dimethylphenyl carbamic acid nonyl ester (each isomer), N-dimethylphenyl carbamic acid decyl ester (each isomer), N-dimethylphenyl carbamic acid dodecyl ester (each isomer), and N-dimethylphenyl carbamic acid octadecyl ester (each isomer).

Next, an N-substituted carbamate obtained when an aromatic hydroxy compound is used as an organic hydroxy compound in an reaction of an organic amine, urea and an organic hydroxy compound is represented by the following formula (33):

[Chemical Formula 24]

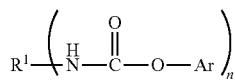

(33)

wherein $R^1$ represents an organic group containing 1 to 85 carbon atoms, which is substituted with an n number of carbamate groups, Ar represents a group derived from an aromatic hydroxy compound, which is a residue obtained by removing from the aromatic hydroxy compound one hydroxy group attached to an aromatic ring of the aromatic hydroxy compound, and n represents an integer between 1 or greater and a or less, or an integer between 1 or greater and m or less, wherein a and m represent the above-defined values.

In the above formula (33), $R^1$ represents an aliphatic group or an aromatic group, and thus, $R^1$ represents a group consisting of an acyclic hydrocarbon group, a cyclic hydrocarbon group (for example, a monocyclic hydrocarbon group, a condensed polycyclic hydrocarbon group, a crosslinked cyclic hydrocarbon group, a spiro hydrocarbon group, a multi-ring hydrocarbon group, a cyclic hydrocarbon group having a side chain, a heterocyclic group, a heterocyclic spiro group, a hetero crosslinked cyclic group, and a heterocyclic group), a group to which at least one selected from the acyclic hydrocarbon group and the cyclic hydrocarbon group binds, and a group to which the above described group binds via a covalent bond with specific non-metal atoms (carbon, oxygen, nitrogen, sulfur, and silicon).

Among these $R^1$ groups, if taking into consideration the unlikeliness of side reactions, the $R^1$ group that can be preferably used in the present embodiment is selected from an aliphatic group and an aromatic group, and the $R^1$ group represents a group selected from the group consisting of an acyclic hydrocarbon group and a cyclic hydrocarbon group (a monocyclic hydrocarbon group, a condensed polycyclic hydrocarbon group, a crosslinked cyclic hydrocarbon group, a spiro hydrocarbon group, a multi-ring hydrocarbon group, and a cyclic hydrocarbon group having a side chain), and a group to which at least one group selected from the aforementioned group binds (wherein the two groups are substituted with each other), wherein the above-mentioned group contains 1 to 85 carbon atoms. If taking into consideration flowability and the like, the $R^1$ group is preferably a group containing 1 to 70 carbon atoms, and more preferably a group containing 1 to 13 carbon atoms.

Preferred examples of the N-substituted carbamate constituted with the above described $R^1$ group include:

1) an N-aromatic organic monocarbamate, in which the $R^1$ group represents a group containing 6 to 85 carbon atoms, which contains one or more aromatic rings "substituted with carbamate groups," and n is 1, 2) an N-aromatic organic polycarbamate, in which the $R^1$ group represents a group containing 6 to 85 carbon atoms, which contains one or more aromatic rings "substituted with carbamate groups," and n is 2 or greater, and 3) an N-aliphatic organic polycarbamate, in which the $R^1$ group represents an aliphatic group containing 1 to 85 carbon atoms, and n is an integer of 2 or 3. A more preferred aliphatic group is an acyclic hydrocarbon group, a cyclic hydrocarbon group, and a group to which at least one group selected from the acyclic hydrocarbon group and the cyclic hydrocarbon group binds (for example, a cyclic hydrocarbon group substituted with an acyclic hydrocarbon group, an acyclic hydrocarbon group substituted with a cyclic hydrocarbon group, etc.), each of which contains 6 to 70 carbon atoms.

Moreover, n in the above formula (33) represents an integer from 1 to 10, and when the organic amine of the above formula (1) is used as a starting substance, n is an integer that does not exceed the a of the organic amine represented by the above formula (1).

Specific examples of the N-substituted carbamate are as follows.

1) N-Aromatic Organic Monocarbamate

A preferred example of the N-aromatic organic monocarbamate is an N-aromatic organic monocarbamate, wherein the $R^1$ group represents a group containing 6 to 85 carbon atoms, which contains one or more aromatic rings, and n is 1. The N-aromatic organic monocarbamate is more preferably an N-aromatic organic monocarbamate, wherein the $R^1$ group represents a group containing 6 to 70 carbon atoms, which contains one or more aromatic rings "substituted with carbamate groups," and n is 1. Taking into consideration flowability and the like, the N-aromatic organic monocarbamate is further preferably an N-aromatic organic monocarbamate, wherein the $R^1$ group represents a group containing 6 to 13 carbon atoms, which contains one or more aromatic rings "substituted with carbamate groups," and n is 1. It is an N-aromatic organic monocarbamate represented by the following formula (34):

[Chemical Formula 25]

(34)

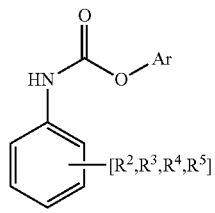

The Ar group of the N-aromatic organic monocarbamate represented by the above formula (34) is the above-defined group. The $R^2$ to $R^5$ groups each represent a group substituted in any given position at which the aromaticity of the ring is maintained, and the $R^2$ to $R^5$ groups may independently substitute an aromatic ring, or the $R^2$ to $R^5$ groups may bind to one another to form a ring together with an aromatic ring, and further, each of the $R^2$ to $R^5$ groups represents a hydrogen atom, or a group selected from the group consisting of an alkyl group, a cycloalkyl group, an aryl group and an aryl group having a hydroxy group, or a group to which a group selected from the above described groups binds via a saturated aliphatic bond and/or an ether bond, wherein the number of carbon atoms constituting the N-aromatic organic monocarbamate represented by the formula (34) is from 7 to 63.

A preferred example of the N-aromatic organic monocarbamate represented by the formula (34) is an N-substituted aromatic organic monocarbamate, wherein the $R^2$ to $R^5$ groups are selected from a hydrogen atom and alkyl groups such as a methyl group and an ethyl group.

2) N-Aromatic Organic Polycarbamate

A preferred example of the N-aromatic organic polycarbamate is an N-aromatic organic polycarbamate, wherein the $R^1$ group represents a group containing 6 to 85 carbon atoms, which contains one or more aromatic rings "substituted with carbamate groups," and n is 2 or greater. The N-aromatic organic polycarbamate is more preferably an N-aromatic organic polycarbamate, wherein the $R^1$ group represents a group containing 6 to 70 carbon atoms, which contains one or more aromatic rings "substituted with carbamate groups," and n is 2 or greater. Taking into consideration flowability and the like, the N-aromatic organic polycarbamate is further preferably an N-aromatic organic polycarbamate, wherein the $R^1$ group represents a group containing 6 to 13 carbon atoms, which contains one or more aromatic rings "substituted with carbamate groups" and the aromatic rings are further substituted with alkyl groups, aryl groups or aralkyl groups, and n is 2 or greater.

Moreover, the N-substituted aromatic organic polycarbamate also includes a polymethylenepolyphenyl polycarbamate represented by the following formula (35):

[Chemical Formula 26]

(35)

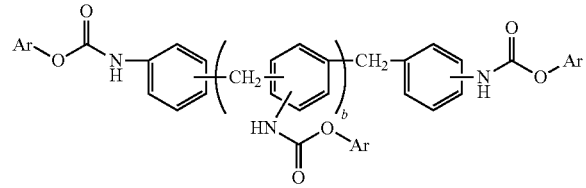

wherein Ar represents the above-defined group, and
b represents an integer from 0 to 6.

3) N-Aliphatic Organic Polycarbamate

A preferred example of the N-aliphatic organic polycarbamate is an N-aliphatic organic polycarbamate, wherein the $R^1$ group of the N-substituted carbamate represented by the formula (33) represents an aliphatic group containing 1 to 85 carbon atoms, and n is 2 or 3. The N-substituted aliphatic organic polycarbamate is more preferably an N-substituted carbamate, wherein the aliphatic group represents an acyclic hydrocarbon group, a cyclic hydrocarbon group, and a group to which at least one group selected from the acyclic hydrocarbon group and the cyclic hydrocarbon group binds (for example, a cyclic hydrocarbon group substituted with an acyclic hydrocarbon group, an acyclic hydrocarbon group substituted with a cyclic hydrocarbon group, etc.). The N-substituted aliphatic organic polycarbamate is further preferably an N-aliphatic organic polycarbamate, wherein the $R^1$ group represents an aliphatic group that is an acyclic hydrocarbon group, a cyclic hydrocarbon group, and a group to which at least one group selected from the acyclic hydrocarbon group and the cyclic hydrocarbon group binds (for example, a cyclic hydrocarbon group substituted with an acyclic hydrocarbon group, an acyclic hydrocarbon group substituted with a cyclic hydrocarbon group, etc.), each of which contains 1 to 70 carbon atoms, and n is an integer of 2 or 3. Taking into consideration flowability necessary for industrial mass production, a most preferred example of the N-substituted aliphatic organic polycarbamate is an N-aliphatic organic polycarbamate, wherein the $R^1$ group is an acyclic hydrocarbon group, a cyclic hydrocarbon group, and a group to which at least one group selected from the acyclic hydrocarbon group and the cyclic hydrocarbon group binds (e.g. a cyclic hydrocarbon group substituted with an acyclic hydrocarbon group, an acyclic hydrocarbon group substituted with a cyclic hydrocarbon group, etc.), each of which is constituted with carbon atoms and hydrogen atoms and each of which contains 6 to 13 carbon atoms. That is to say, the case is an N-aliphatic organic polycarbamate, wherein the $R^1$ group is a straight chain and/or branched chain alkyl group, a cycloalkyl group, and a group constituted with the alkyl group and the cycloalkyl group.

Since the specific structure of such an N-substituted carbamate is determined depending on the types of an organic amine used and an aromatic hydroxy compound that constitutes a hydroxy composition, it is not possible to exemplify all the specific structures, but examples of the specific structure of the N-substituted carbamate include N,N'-hexanediyl-di(carbamic acid phenyl ester), N,N'-hexanediyl-di(carbamic acid(methylphenyl)ester) (each isomer), N,N'-hexanediyl-di(carbamic acid(ethylphenyl)ester) (each isomer), N,N'-hexanediyl-di(carbamic acid(propylphenyl)ester) (each isomer), N,N'-hexanediyl-di(carbamic acid(butylphenyl)ester) (each isomer), N,N'-hexanediyl-di(carbamic acid(pentylphenyl)ester) (each isomer), N,N'-hexanediyl-di(carbamic acid(hexylphenyl)ester) (each isomer), N,N'-hexanediyl-di(carbamic acid(heptylphenyl)ester) (each isomer), N,N'-hexanediyl-di(carbamic acid (octylphenyl)ester) (each isomer), N,N'-hexanediyl-di(carbamic acid(nonylphenyl)ester) (each isomer), N,N'-hexanediyl-di(carbamic acid(decylphenyl)ester) (each isomer), N,N'-hexanediyl-di(carbamic acid(dodecylphenyl)ester) (each isomer), N,N'-hexanediyl-di(carbamic acid(octadecylphenyl)ester) (each isomer), N,N'-hexanediyl-bis(carbamic acid(dimethylphenyl)ester) (each isomer), N,N'-hexanediyl-bis(carbamic acid(diethylphenyl)ester) (each isomer), N,N'-hexanediyl-bis(carbamic acid(dipropylphenyl)ester) (each isomer), N,N'-hexanediyl-bis(carbamic acid (dibutylphenyl)ester) (each isomer), N,N'-hexanediyl-bis(carbamic acid(dipentylphenyl)ester) (each isomer), N,N'-hexanediyl-bis(carbamic acid(dihexylphenyl)ester) (each isomer), N,N'-hexanediyl-bis(carbamic acid(diheptylphenyl)ester) (each isomer), N,N'-hexanediyl-bis(carbamic acid (dioctylphenyl)ester) (each isomer), N,N'-hexanediyl-bis(carbamic acid(dinonylphenyl)ester) (each isomer), N,N'-hexanediyl-bis(carbamic acid(didecylphenyl)ester) (each isomer), N,N'-hexanediyl-bis(carbamic acid(didodecylphenyl)ester) (each isomer), N,N'-hexanediyl-bis(carbamic acid (dioctadecylphenyl)ester) (each isomer), N,N'-methylenediphenylene-di(carbamic acid phenyl ester) (each isomer), N,N'-methylenediphenylene-di(carbamic acid(methylphenyl)ester) (each isomer), N,N'-methylenediphenylene-di(carbamic acid(ethylphenyl)ester) (each isomer), N,N'-methylenediphenylene-di(carbamic acid(propylphenyl)ester) (each isomer), N,N'-methylenediphenylene-di(carbamic acid(butylphenyl)ester) (each isomer), N,N'-methylenediphenylene-di(carbamic acid(pentylphenyl)ester) (each isomer), N,N'-methylenediphenylene-di(carbamic acid(hexylphenyl)ester) (each isomer), N,N'-methylenediphenylene-di(carbamic acid(heptylphenyl)ester) (each isomer), N,N'-methylenediphenylene-di(carbamic acid(octylphenyl)ester) (each isomer), N,N'-methylenediphenylene-di(carbamic acid(nonylphenyl)ester) (each isomer), N,N'-methylenediphenylene-di(carbamic acid(decylphenyl)ester) (each isomer), N,N'-methylenediphenylene-di(carbamic acid(dodecylphenyl)ester) (each isomer), N,N'-methylenediphenylene-di(carbamic acid(octadecylphenyl)ester) (each isomer), N,N'-methylenediphenylene-bis(carbamic acid(dimethylphenyl)ester) (each isomer), N,N'-methylenediphenylene-bis(carbamic acid(diethylphenyl)ester) (each isomer), N,N'-methylenediphenylene-bis(carbamic acid(dipropylphenyl)ester) (each isomer), N,N'-methylenediphenylene-bis(carbamic acid(dibutylphenyl)ester) (each isomer), N,N'-methylenediphenylene-bis(carbamic acid(dipentylphenyl)ester) (each isomer), N,N'-methylenediphenylene-bis(carbamic acid(dihexylphenyl)ester) (each isomer), N,N'-methylenediphenylene-bis(carbamic acid(diheptylphenyl)ester) (each isomer), N,N'-methylenediphenylene-bis(carbamic acid(dioctylphenyl)ester) (each isomer), N,N'-methylenediphenylene-bis(carbamic acid(dinonylphenyl)ester) (each isomer), N,N'-methylenediphenylene-bis(carbamic acid(didecylphenyl)ester) (each isomer), N,N'-methylenediphenylene-bis(carbamic acid(didodecylphenyl)ester) (each isomer), N,N'-methylenediphenylene-bis(carbamic acid(dioctadecylphenyl)ester) (each isomer), 3-(phenoxycarbonylamino-methyl)-3,5,5-trimethylcyclohexyl carbamic acid phenyl ester, 3-((methylphenoxy)carbonylamino-methyl)-3,5,5-trimethylcyclohexyl carbamic acid(methylphenyl)ester) (each isomer), 3-((ethylphenoxy)carbonylamino-methyl)-3,5,5-trimethylcyclohexyl carbamic acid(ethylphenyl)ester (each isomer), 3-((propylphenoxy)carbonylamino-methyl)-3,5,5-trimethylcyclohexyl carbamic acid(propylphenyl)ester (each isomer), 3-((butylphenoxy)carbonylamino-methyl)-3,5,5-trimethylcyclohexyl carbamic acid(butylphenyl)ester (each isomer), 3-((pentylphenoxy)carbonylamino-methyl)-3,5,5-trimethylcyclohexyl carbamic acid(pentylphenyl)ester (each isomer), 3-((hexylphenoxy)carbonylamino-methyl)-3,5,5-trimethylcyclohexyl carbamic acid(hexylphenyl)ester (each isomer), 3-((heptylphenoxy)carbonylamino-methyl)-3,5,5-trimethylcyclohexyl carbamic acid(heptylphenyl)ester (each isomer), 3-((octylphenoxy)carbonylamino-methyl)-3,5,5-trimethylcyclohexyl carbamic acid(octylphenyl)ester (each isomer), 3-((nonylphenoxy)carbonylamino-methyl)-3,5,5-trimethylcyclohexyl carbamic acid(nonylphenyl)ester (each isomer), 3-((decylphenoxy)carbonylamino-methyl)-3,5,5-trimethylcyclohexyl carbamic acid(decylphenyl)ester (each isomer), 3-((dodecylphenoxy)carbonylamino-methyl)-3,5,5-trimethylcyclohexyl carbamic acid(dodecylphenyl)ester (each isomer), 3-((octadecylphenoxy)carbonylamino-methyl)-3,5,5-trimethylcyclohexy carbamic acid(octadecylphenyl)ester (each isomer), 3-((dimethylphenoxy)carbonylamino-methyl)-3,5,5-trimethylcyclohexyl carbamic acid(dimethylphenoxy)ester (each isomer), 3-((diethylphenoxy)carbonylamino-methyl)-3,5,5-trimethylcyclohexyl carbamic acid(diethylphenyl)ester (each isomer), 3-((dipropylphenoxy)carbonylamino-methyl)-3,5,5-trimethylcyclohexyl carbamic acid(dipropylphenyl)ester (each isomer), 3-((dibutylphenoxy)carbonylamino-methyl)-3,5,5-trimethylcyclohexyl carbamic acid(dibutylphenyl)ester (each isomer), 3-((dipentylphenoxy)carbonylamino-methyl)-3,5,5-trimethylcyclohexyl carbamic acid(dipentylphenyl)ester (each isomer), 3-((dihexylphenoxy)carbonylamino-methyl)-3,5,5-trimethylcyclohexyl carbamic acid(dihexylphenyl)ester (each isomer), 3-((diheptylphenoxy)carbonylamino-methyl)-3,5,5-trimethylcyclohexyl carbamic acid(diheptylphenyl)ester (each isomer), 3-((dioctylphenoxy)carbonylamino-methyl)-3,5,5-trimethylcyclohexyl carbamic acid (dioctylphenyl)ester (each isomer), 3-((dinonylphenoxy)carbonylamino-methyl)-3,5,5-trimethylcyclohexyl carbamic acid(dinonylphenyl)ester (each isomer), 3-((didecylphenoxy)carbonylamino-methyl)-3,5,5-trimethylcyclohexyl carbamic acid(didecylphenyl)ester (each isomer), 3-((didodecylphenoxy)carbonylamino-methyl)-3,5,5-trimethylcyclohexyl carbamic acid(didodecylphenyl)ester (each isomer), 3-((dioctadecylphenoxy)carbonylamino-methyl)-3,5,5-trimethylcyclohexyl carbamic acid(dioctadecylphenyl) ester (each isomer), toluene-di(carbamic acid phenyl ester) (each isomer), toluene-di(carbamic acid(methylphenyl)ester) (each isomer), toluene-di(carbamic acid(ethylphenyl)ester) (each isomer), toluene-di(carbamic acid(propylphenyl)ester) (each isomer), toluene-di(carbamic acid (butylphenyl)ester) (each isomer), toluene-di(carbamic acid (pentylphenyl)ester) (each isomer), toluene-di(carbamic acid(hexylphenyl)ester) (each isomer), toluene-di(carbamic acid(heptylphenyl)ester) (each isomer), toluene-di(carbamic acid(octylphenyl)ester) (each isomer), toluene-di(carbamic acid(nonylphenyl)ester) (each isomer), toluene-di(carbamic acid(decylphenyl)ester) (each isomer), toluene-di(carbamic acid(dodecylphenyl)ester) (each isomer), toluene-di(carbamic acid(octadecylphenyl)ester) (each isomer), toluene-bis(carbamic acid(dimethylphenyl)ester) (each isomer), toluene-bis(carbamic acid(diethylphenyl)ester) (each isomer), toluene-bis(carbamic acid(dipropylphenyl)ester) (each isomer), toluene-bis(carbamic acid(dibutylphenyl)ester) (each isomer), toluene-bis(carbamic acid(dipentylphenyl)ester) (each isomer), toluene-bis(carbamic acid(dihexylphenyl)ester) (each isomer), toluene-bis(carbamic acid(diheptylphenyl)ester) (each isomer), toluene-bis(carbamic acid (dioctylphenyl)ester) (each isomer), toluene-bis(carbamic acid(dinonylphenyl)ester) (each isomer), toluene-bis(carbamic acid(didecylphenyl)ester) (each isomer), toluene-bis (carbamic acid(didodecylphenyl)ester) (each isomer), toluene-bis(carbamic acid(dioctadecylphenyl)ester) (each isomer), N,N'-methylenedicyclohexyl-di(carbamic acid phenyl ester) (each isomer), N,N'-methylenedicyclohexyl-di (carbamic acid(methylphenyl)ester) (each isomer), N,N'-methylenedicyclohexyl-di(carbamic acid(ethylphenyl)ester) (each isomer), N,N'-methylenedicyclohexyl-di(carbamic acid(propylphenyl)ester) (each isomer), N,N'-methylenedicyclohexyl-di(carbamic acid(butylphenyl)ester) (each isomer), N,N'-methylenedicyclohexyl-di(carbamic acid(pentylphenyl)ester) (each isomer), N,N'-methylenedicyclohexyl-di(carbamic acid(hexylphenyl)ester) (each isomer), N,N'-methylenedicyclohexyl-di(carbamic acid(heptylphenyl)ester) (each isomer), N,N'-methylenedicyclohexyl-di(carbamic acid(octylphenyl)ester) (each isomer), N,N'-methylenedicyclohexyl-di(carbamic acid(nonylphenyl)ester) (each isomer), N,N'-methylenedicyclohexyl-di(carbamic acid(decylphenyl)ester) (each isomer), N,N'-methylenedicyclohexyl-di(carbamic acid(dodecylphenyl)ester) (each isomer), N,N'-methylenedicyclohexyl-di(carbamic acid(octadecylphenyl)ester) (each isomer), N,N'-methylenedicyclohexyl-bis(carbamic acid(dimethylphenyl)ester) (each isomer), N,N'-methylenedicyclohexyl-bis(carbamic acid(diethylphenyl)ester) (each isomer), N,N'-methylenedicyclohexyl-bis(carbamic acid(dipropylphenyl)ester) (each isomer), N,N'-methylenedicyclohexyl-bis(carbamic acid(dibutylphenyl)ester) (each isomer), N,N'-methylenedicyclohexyl-bis(carbamic acid(dipentylphenyl)ester) (each isomer), N,N'-methylenedicyclohexyl-bis(carbamic acid(dihexylphenyl)ester) (each isomer), N,N'-methylenedicyclohexyl-bis(carbamic acid(diheptylphenyl)ester) (each isomer), N,N'-methylenedicyclohexyl-bis(carbamic acid(dioctylphenyl)ester) (each isomer), N,N'-methylenedicyclohexyl-bis(carbamic acid(dinonylphenyl)ester) (each isomer), N,N'-methylenedicyclohexyl-bis(carbamic acid(didecylphenyl)ester) (each isomer), N,N'-methylenedicyclohexyl-bis(carbamic acid(didodecylphenyl)ester) (each isomer), N,N'-methylenedicyclohexyl-bis(carbamic acid(dioctadecylphenyl)ester) (each isomer), N-phenyl carbamic acid phenyl ester, N-phenyl carbamic acid(methylphenyl)ester (each isomer), N-phenyl carbamic acid(ethylphenyl)ester (each isomer), N-phenyl carbamic acid(propylphenyl)ester (each isomer), N-phenyl carbamic acid(butylphenyl)ester (each isomer), N-phenyl carbamic acid(pentylphenyl)ester (each isomer), N-phenyl carbamic acid(hexylphenyl)ester (each isomer), N-phenyl carbamic acid(heptylphenyl)ester (each isomer), N-phenyl carbamic acid(octylphenyl)ester (each isomer), N-phenyl carbamic acid(nonylphenyl)ester (each isomer), N-phenyl carbamic acid(decylphenyl)ester (each isomer), N-phenyl carbamic acid(dodecylphenyl)ester (each isomer), N-phenyl carbamic acid(octadecylphenyl)ester (each isomer), N-phenyl carbamic acid(dimethylphenyl)ester (each isomer), N-phenyl carbamic acid(diethylphenyl)ester (each isomer), N-phenyl carbamic acid(dipropylphenyl)ester (each isomer), N-phenyl carbamic acid(dibutylphenyl)ester (each isomer), N-phenyl carbamic acid(dipentylphenyl)ester (each isomer), N-phenyl carbamic acid(dihexylphenyl)ester (each isomer), N-phenyl carbamic acid(diheptylphenyl)ester (each isomer), N-phenyl carbamic acid(dioctylphenyl)ester (each isomer), N-phenyl carbamic acid(dinonylphenyl)ester (each isomer), N-phenyl carbamic acid(didecylphenyl)ester (each isomer), N-phenyl carbamic acid(didodecylphenyl)ester (each isomer), N-phenyl carbamic acid(dioctadecylphenyl)ester (each isomer), N-dimethylphenyl carbamic acid phenyl ester (each isomer), N-dimethylphenyl carbamic acid(methylphenyl)ester (each isomer), N-dimethylphenyl carbamic acid(ethylphenyl)ester (each isomer), N-dimethylphenyl carbamic acid(propylphenyl)ester (each isomer), N-dimethylphenyl carbamic acid(butylphenyl)ester (each isomer), N-dimethylphenyl carbamic acid(pentylphenyl)ester (each isomer), N-dimethylphenyl carbamic acid(hexylphenyl)ester (each isomer), N-dimethylphenyl carbamic acid(heptylphenyl)ester (each isomer), N-dimethylphenyl carbamic acid(octylphenyl)ester (each isomer), N-dimethylphenyl carbamic acid(nonylphenyl)ester (each isomer), N-dimethylphenyl carbamic acid(decylphenyl)ester (each isomer), N-dimethylphenyl carbamic acid(dodecylphenyl)ester (each isomer), N-dimethylphenyl carbamic acid(octadecylphenyl)ester (each isomer), N-dimethylphenyl carbamic acid(dimethylphenyl)ester (each isomer), N-dimethylphenyl carbamic acid(diethylphenyl)ester (each isomer), N-dimethylphenyl carbamic acid(dipropylphenyl)ester (each isomer), N-dimethylphenyl carbamic acid(dibutylphenyl)ester (each isomer), N-dimethylphenyl carbamic acid(dipentylphenyl)ester (each isomer), N-dimethylphenyl carbamic acid(dihexylphenyl)ester (each isomer), N-dimethylphenyl carbamic acid(diheptylphenyl)ester (each isomer), N-dimethylphenyl carbamic acid(dioctylphenyl)ester (each isomer), N-dimethylphenyl carbamic acid(dinonylphenyl)ester (each isomer), N-dimethylphenyl carbamic acid(didecylphenyl)ester (each isomer), N-dimethylphenyl carbamic acid(didodecylphenyl)ester (each isomer), and N-dimethylphenyl carbamic acid(dioctadecylphenyl)ester (each isomer).

<Isocyanate>

Isocyanate is a compound of interest produced by the method of the present embodiment, which is represented by the following formula (36):

[Chemical Formula 27]

$$R^1 (\text{—NCO})_p \tag{36}$$

wherein $R^1$ represents an organic group containing 1 to 85 carbon atoms, which is substituted with a p number of ureido groups, and p represents an integer from 1 to 10.

The compound having a ureido group represented by the above formula (36) is a compound having an "isocyanate group" defined in Regulation C-971 of the Nomenclature of IUPAC.

In the above formula (36), $R^1$ represents an aliphatic group, an aromatic group, and a group formed by binding an aliphatic group to an aromatic group, and thus, $R^1$ represents a group consisting of an acyclic hydrocarbon group, a cyclic hydrocarbon group (for example, a monocyclic hydrocarbon group, a condensed polycyclic hydrocarbon group, a crosslinked cyclic hydrocarbon group, a spiro hydrocarbon group, a multi-ring hydrocarbon group, a cyclic hydrocarbon group having a side chain, a heterocyclic group, a heterocyclic spiro group, a hetero crosslinked cyclic group, and a heterocyclic group), a group to which at least one selected from the acyclic hydrocarbon group and the cyclic hydrocarbon group binds, and a group to which the above described group binds via a covalent bond with specific non-metal atoms (carbon, oxygen, nitrogen, sulfur, and silicon).

Among these $R^1$ groups, if taking into consideration the unlikeliness of side reactions, the $R^1$ group that can be preferably used in the present embodiment is selected from an aliphatic group and an aromatic group, and the $R^1$ group represents a group selected from the group consisting of an acyclic hydrocarbon group and a cyclic hydrocarbon group (a monocyclic hydrocarbon group, a condensed polycyclic hydrocarbon group, a crosslinked cyclic hydrocarbon group, a spiro hydrocarbon group, a multi-ring hydrocarbon group, and a cyclic hydrocarbon group having a side chain), and a group to which at least one group selected from the aforementioned group binds (wherein the two groups are substituted with each other), wherein the above-mentioned group contains 1 to 85 carbon atoms. If taking into consideration flowability and the like, the $R^1$ group is preferably a group containing 1 to 70 carbon atoms, and more preferably a group containing 1 to 13 carbon atoms.

Preferred examples of the isocyanate include:

1) an aromatic monoisocyanate, in which the $R^1$ group represents a group containing 6 to 85 carbon atoms, which contains one or more aromatic rings optionally substituted with aliphatic and/or aromatic groups, the aromatic groups in the $R^1$ group are substituted with isocyanate groups, and p is 1, 2) an aromatic organic polyisocyanate, in which the $R^1$ group represents a group containing 6 to 85 carbon atoms, which contains one or more aromatic rings optionally substituted with aliphatic and/or aromatic groups, the aromatic groups in the $R^1$ group are substituted with isocyanate groups, and p is 2 or greater, and 3) an aliphatic organic polyisocyanate, in which the $R^1$ group represents an aliphatic group containing 1 to 85 carbon atoms, which is optionally substituted with an aromatic group, and p is 2 or 3. With regard to the above-mentioned isocyanate, an isocyanate, in which an atom (mainly, a carbon atom) to which an isocyanate group binds is contained in the aromatic ring, is referred to as an aromatic organic isocyanate, whereas an isocyanate, in which such an atom binds to an atom (mainly, a carbon atom) that is not in the aromatic ring, is referred to as an aliphatic organic isocyanate.

Moreover, p in the above formula (36) represents an integer from 1 to 10, and when the organic amine of the above formula (1) is used as a starting substance, p is an integer that does not exceed the a of the organic amine represented by the above formula (1).

Specific examples of a preferred compound having an isocyanate group are as follows.

1) Aromatic Organic Monoisocyanate

A preferred example of the aromatic organic monoisocyanate is an aromatic organic monoisocyanate, wherein the $R^1$ group represents a group containing 6 to 85 carbon atoms, which contains one or more aromatic rings optionally substituted with aliphatic and/or aromatic groups, and the aromatic group in the $R^1$ group is substituted with an isocyanate group, and p is 1. The aromatic organic monoisocyanate is more preferably an aromatic organic monoisocyanate, wherein the $R^1$ group represents a group containing 6 to 70 carbon atoms and p is 1. Taking into consideration flowability and the like, the aromatic organic monoisocyanate is further preferably an aromatic organic monoisocyanate, wherein the $R^1$ group represents a group containing 6 to 13 carbon atoms and p is 1. It is an aromatic organic monoisocyanate represented by the following formula (37):

[Chemical Formula 28]

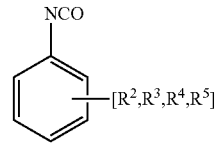

(37)

At least one of the ortho-position and/or para-position of the isocyanate group of the aromatic organic monoisocyanate represented by the above formula (37) is unsubstituted, and each of the $R^2$ to $R^5$ groups represents a group substituted in any given position at which the aromaticity of the ring is maintained, and the $R^2$ to $R^5$ groups may independently substitute an aromatic ring, or the $R^2$ to $R^5$ groups may bind to one another to form a ring together with an aromatic ring, and further, each of the $R^2$ to $R^5$ groups represents a hydrogen atom, or a group selected from the group consisting of an alkyl group, a cycloalkyl group, an aryl group and an aryl group having a hydroxy group, or a group to which a group selected from the above described groups binds via a saturated aliphatic bond and/or an ether bond, wherein the number of carbon atoms contained in each of the $R^2$ to $R^5$ groups is an integer from 0 to 7, and the total number of carbon atoms constituting the aromatic organic monoisocyanate represented by the above formula (37) is from 6 to 13.

A preferred example of the aromatic organic monoisocyanate represented by the formula (37) is an aromatic organic monoisocyanate, wherein the $R^2$ to $R^5$ groups each represent a hydrogen atom, or a group selected from alkyl groups such as a methyl group and an ethyl group, and examples of such an aromatic organic monoisocyanate include phenyl isocyanate, (methylphenyl) isocyanate (each isomer), (dimethylphenyl) isocyanate (each isomer), (diethylphenyl) isocyanate (each isomer), (dipropylphenyl) isocyanate (each isomer), naphthylisocyanate (each isomer), (methylnaphthyl) isocyanate (each isomer), dimethylnaphthylisocyanate (each isomer), and trimethylnaphthylisocyanate (each isomer). Of these, phenyl isocyanate is more preferable.

2) Aromatic Organic Polyisocyanate

A preferred example of the aromatic organic polyisocyanate is an aromatic organic polyisocyanate, wherein the $R^1$ group is a group containing 6 to 85 carbon atoms, which contains one or more aromatic rings optionally substituted with aliphatic and/or aromatic groups, the aromatic groups in the $R^1$ group are substituted with isocyanate groups, and p is 2 or greater. A more preferred example of the aromatic organic polyisocyanate is an aromatic organic polyisocyanate, wherein the $R^1$ group is a group containing 6 to 70 carbon atoms and p is 2 or greater. If taking into consideration flowability and the like, a further preferred example is an aromatic organic polyisocyanate, wherein the $R^1$ group is an aromatic group containing 6 to 13 carbon atoms, which contains one or more aromatic rings, wherein the aromatic rings are further optionally substituted with alkyl groups, aryl groups or aralkyl groups, and p is 2 or greater. Examples of such an aromatic organic polyisocyanate include phenylene diisocyanate (each isomer), methylphenylene diisocyanate (each isomer), methylenediphenylene diisocyanate (each isomer), mesitylene diisocyanate (each isomer), biphenylene diisocyanate (each isomer), diphenylene diisocyanate (each isomer), propylenediphenylene diisocyanate (each isomer), diphenylene diisocyanate (each isomer), bis (isocyanato phenoxyethane) (each isomer), xylene diisocyanate (each isomer), methoxyphenyl diisocyanate (each isomer), ethoxyphenyl diisocyanate (each isomer), naphthalene diisocyanate (each isomer), methylnaphthalene diisocyanate (each isomer), and polymethylenepolyphenyl polyisocyanate represented by the following formula (38):

[Chemical Formula 29]

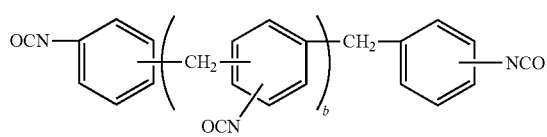

(38)

wherein b represents an integer from 0 to 6.

3) Aliphatic Organic Polyisocyanate

A preferred example of the aliphatic organic polyisocyanate is an aliphatic organic polyisocyanate, wherein the $R^1$ group of the compound having an isocyanate group represented by the above formula (36) is an aliphatic group containing 1 to 85 carbon atoms, which is optionally substituted with an aromatic group, and p is 2 or 3. A more preferred example of the aliphatic organic polyisocyanate is an aliphatic organic polyisocyanate, wherein the aliphatic group represents an acyclic hydrocarbon group, a cyclic hydrocarbon group, and a group to which at least one group selected from the acyclic hydrocarbon group and the cyclic hydrocarbon group binds (for example, a cyclic hydrocarbon group substituted with an acyclic hydrocarbon group, an acyclic hydrocarbon group substituted with a cyclic hydrocarbon group, etc.). A further preferred example of the aliphatic organic polyisocyanate is an aliphatic organic polyisocyanate, wherein the $R^1$ group is an aliphatic group, and the aliphatic group represents an acyclic hydrocarbon group, a cyclic hydrocarbon group, and a group to which at least one group selected from the acyclic hydrocarbon group and the cyclic hydrocarbon group binds (for example, a cyclic hydrocarbon group substituted with an acyclic hydrocarbon group, an acyclic hydrocarbon group substituted with a cyclic hydrocarbon group, etc.), each of which contains 1 to 70 carbon atoms, and p is 2 or 3. Taking into consideration flowability necessary for industrial mass production, a most preferred example of the aliphatic organic polyisocyanate is an aliphatic organic polyisocyanate, wherein the $R^1$ group is an acyclic hydrocarbon group, a cyclic hydrocarbon group, and a group to which at least one group selected from the acyclic hydrocarbon group and the cyclic hydrocarbon group binds (e.g. a cyclic hydrocarbon group substituted with an acyclic hydrocarbon group, an acyclic hydrocarbon group substituted with a cyclic hydrocarbon group, etc.), each of which is constituted with carbon atoms and hydrogen atoms and each of which contains 6 to 13 carbon atoms. That is to say, the case is an aliphatic organic polyisocyanate, wherein the $R^1$ group is a straight chain and/or branched chain alkyl group, a cycloalkyl group, and a group constituted with the alkyl group and the cycloalkyl group. Examples of such groups include: aliphatic diisocyanates, such as ethylene diisocyanate, propylene diisocyanate (each isomer), butylene diisocyanate (each isomer), pentamethylene diisocyanate (each isomer), hexanemethylene diisocyanate (each isomer), and decamethylene diisocyanate (each isomer); aliphatic triisocyanates, such as hexamethylene triisocyanate (each isomer), nonamethylene triisocyanate (each isomer), and decamethylene triisocyanate (each isomer); and substituted cyclic aliphatic polyisocyanates, such as cyclobutylene diisocyanate (each isomer), methylenedicyclohexyl diisocyanate (each isomer), 3-isocyanatomethyl-3,5,5-trimethylcyclohexyl isocyanate (cis and/or trans forms), and methylene bis(cyclohexylisocyanate) (each isomer).

<<Preferred Method for Producing Isocyanate-1>>

The method for producing an isocyanate of the present embodiment uses, as raw materials, an organic primary amine, urea and an organic hydroxy compound, wherein the method comprises the following Step (1) to Step (3), and further comprises the following Step (4) and Step (5).

Step (1): a carbamation step of generating an N-substituted carbamate from an organic primary amine, urea and an organic hydroxy compound according to a carbamation reaction, and then recovering a first gaseous phase component containing the urea and/or a compound having a carbonyl group derived from the urea, the organic hydroxy compound, and ammonia;

Step (2): a condensation step of condensing the first gaseous phase component with a condenser;

Step (3): an isocyanate production step of producing an isocyanate by subjecting the N-substituted carbamate to pyrolysis;

Step (4): an ammonia absorption step of allowing a second gaseous phase component containing ammonia as a main component, which has been recovered as a gaseous phase component from the condenser, to be absorbed by absorption water, thereby generating gas-absorbed water; and Step (5): an ammonia stripping step of heating the gas-absorbed water to separate the ammonia from the gas-absorbed water.

Hereinafter, each of these steps will be described.

<Step (1): Carbamation Step>

Step (1) is a carbamation step of generating a carbamate from an organic primary amine, urea and an organic hydroxy compound used as raw materials according to a carbamation reaction, and then recovering a gaseous phase component containing the urea and/or isocyanic acid, the organic hydroxy compound, and ammonia (a first gaseous component).

Step (1) of the present embodiment may broadly include the following two methods:

(1)': A method of carrying out Step (A), wherein an organic primary amine, urea and an organic hydroxy compound are "simultaneously" reacted to produce an N-substituted carbamate, and (1)": A method, in which a step of producing an N-substituted carbamate from an organic primary amine, urea and an organic hydroxy compound is divided, namely, an organic primary amine is reacted with urea to produce a compound having a ureido group in Step (a), and then, in the subsequent Step (b), the compound having a ureido group is reacted with an organic hydroxy compound to produce an N-substituted carbamate.

In the production method for the present embodiment, the method (1)' may be combined with the method (1)".

(Step (A): a step of producing a carbamate by simultaneously reacting an organic primary amine, a carbonic acid derivative and an organic hydroxy compound)

The term "simultaneously" is used in the method (1)' to mean that a step of producing an N-substituted carbamate is not divided in the case of the method (1)', whereas the step is divided in the case of the method (1)", and thus, the term "simultaneously" does not necessarily mean that an organic primary amine, urea and an organic hydroxy compound are completely simultaneously reacted.

Reaction conditions, under which an organic primary amine, urea and an organic hydroxy compound are reacted to produce an N-substituted carbamate, are different depending on the type of a compound to be reacted, and the organic hydroxy compound is used at a stoichiometric ratio of 1:1 to 500:1 with respect to the amino group of the used organic primary amine. Since a complicatedly substituted carbonyl compound and the like are easily generated if the amount of the used organic hydroxy compound is small, it is preferable to use a largely excessive amount of organic hydroxy compound. If taking into consideration the size of a reaction vessel, the organic hydroxy compound is used at a stoichiometric ratio of preferably 1:1 to 200:1, more preferably 1.5:1 to 100:1, and further preferably 2:1 to 50:1 with respect to the aforementioned amino group.

Urea is used at a stoichiometric ratio of 1:1 to 100:1 with respect to the amino group of the organic primary amine. Since a complicatedly substituted carbonyl compound and the like are easily generated if the amount of the used urea is small, it is preferable to use an excessive amount of urea. However, if a largely excessive amount of urea is used, there may be a case in which such a complicatedly substituted carbonyl compound would be easily generated, or in which unreacted urea would remain and enormous efforts would be required for the separation and recovery of urea (as described later). Accordingly, the urea is used at a stoichiometric ratio of preferably 1.1:1 to 10:1, and more preferably 1.5:1 to 5:1 with respect to the aforementioned amino group.

The reaction temperature is preferably in a range of 100° C. to 350° C., although it depends on the reactivity of the used organic primary amine, urea and organic hydroxy compound. If the reaction temperature is lower than 100° C., it is not preferable because since the organic hydroxy compound strongly binds to ammonia generated as a by-product, the reaction would progress slowly, or almost no reaction would occur, or the amount of a complicatedly substituted carbonyl compound increases. On the other hand, if the reaction temperature is higher than 350° C., it is not preferable either, because the decomposition of urea and side reactions attended therewith would significantly take place, or the organic hydroxy compound would be dehydrogenated, or the decomposition reaction, degeneration reaction and the like of an N-substituted carbamate as a product are easily take place. From such a viewpoint, the reaction temperature is more preferably in a range of 120° C. to 320° C., and further preferably in a range of 140° C. to 300° C.

The reaction pressure is different depending on the composition of a reaction system, a reaction temperature, a method for removing ammonia, a reaction vessel, etc., and the reaction can be carried out under a reduced pressure, under an ordinary pressure, or under a compressed pressure. In general, the reaction is preferably carried out in a pressure range of 0.01 kPa to 10 MPa (absolute pressure). If taking into consideration facilitation of industrial production, a reduced pressure or an ordinary pressure is preferable, and a pressure in a range of 0.1 kPa to 1.5 MPa (absolute pressure) is more preferable.

In the Step (A), the reaction of generating an N-substituted carbamate is mainly carried out in a liquid phase in many cases. Thus, the organic hydroxy compound is preferably present in the form of a liquid phase component under the reaction conditions. On the other hand, as described later, since the organic hydroxy compound and a compound having a carbonyl group derived from urea (which will be described in detail later) are introduced as gaseous phase components into a condenser and they are then condensed in the condenser, it is preferable that the organic hydroxy compound be also present in a gaseous phase component under the reaction conditions. Accordingly, the reaction conditions are determined, such that a portion of the organic hydroxy compound is present as a liquid phase component and another portion thereof is present as a gaseous phase component. When an organic hydroxy composition constituted with a plurality of organic hydroxy compounds is used, the reaction conditions are determined, such that at least one organic hydroxy compound is present as a liquid phase component. Since such reaction conditions (reaction temperature and pressure) are closely associated with the properties of the used organic hydroxy compound, and particularly, with correlation between temperature and vapor pressure, the properties (correlation between temperature and vapor pressure) of the used organic hydroxy compound have previously been measured or searched, and the results are used as indicators for determining the reaction conditions. It is to be noted that the fact that correlation between temperature and the vapor pressure of a substance increases depending on the purity of the substance, and the type or amount of a coexisting compound, is common knowledge to a person skilled in the art, and thus, it is apparent that not only the above described properties of the organic hydroxy compound (correlation between temperature and vapor pressure), but the type of a coexisting compound and the amount thereof should also be considered.

As a result of the intensive studies conducted by the present inventors, it was found that the reaction of generating an N-substituted carbamate from an organic primary amine, urea and an organic hydroxy compound is an equilibrium reaction, and thus, the reaction largely lies on the original system. Accordingly, in order to increase the yield of the N-substituted carbamate, it is necessary to carry out the reaction, while ammonia generated as a by-product is removed from the reaction system as much as possible. Ammonia is removed, so that the concentration of the ammonia in the reaction solution becomes preferably 1000 ppm or less, more preferably 300 ppm or less, further preferably 100 ppm or less, and most preferably 10 ppm or less. As such a method for removing ammonia, a reaction distillation method, a method using inert gas, membrane separation, a method involving adsorptive separation, and the like can be applied. For example, the reaction distillation method is a method for separating ammonia, which has been successively generated as a result of the reaction, in a gaseous state by distillation. In order to increase the distillation efficiency of ammonia, distillation can be carried out, while boiling a solvent or the organic hydroxy compound. In addition, the method using inert gas is a method of accompanying ammonia successively generated as a result of the reaction in a gaseous state with inert gas, so as to separate the ammonia from the reaction system. A method of using inert gas such as nitrogen, helium, argon, carbon dioxide, methane, ethane or propane, singly or in combination, and introducing the inert gas into the reaction system, is preferable. As adsorbents used in the method involving adsorptive separation, adsorbents that can be used under temperature conditions in which the present reaction is carried out, such as silica, alumina, various types of zeolites, and diatomaceous earths, can be used. These methods for removing ammonia from the reaction system may be applied, either singly or in combination of multiple types of methods.

In the present reaction, for the purpose of increasing the reaction rate for example, a catalyst can be used. Examples of the catalyst that is preferably used herein include basic catalysts such as the methylate, ethylate and butylate (each isomer) of lithium, sodium, potassium, calcium and barium; simple substances of rare earth elements, antimony and bismuth, and the oxides, sulfides and salts of these elements, boron as a simple substance and boron compounds; the metals of copper elements, zinc elements, aluminum elements, carbon elements and titanium elements in the periodic table, and the metal oxides and sulfides thereof, and the carbides and nitrides of carbon elements, titanium elements, vanadium elements and chromium elements, other than carbon in the periodic table. In the case of using such a catalyst, the amount used is not particularly limited. The catalyst can be used at a stoichiometric ratio of 0.0001:1 to 100:1 with respect to the amount of the amino group of the organic primary amine. If a catalyst is added, it becomes necessary to remove the catalyst in many cases. Thus, the reaction is preferably carried out without adding catalysts. When a catalyst is used, such a catalyst may be removed after completion of the reaction. Since there is a case in which the catalyst would affect a compound generated in the step of the present embodiment, the catalyst is preferably separated or removed during the process of subjecting the N-substituted carbamate to pyrolysis to obtain an isocyanate and then purifying the isocyanate. If the isocyanate is preserved in a state in which it coexists with the above described catalyst, an unfavorable phenomenon such as discoloration may occur. As a method for removing the catalyst, a known method can be applied. Methods such as membrane separation, distillation separation, or crystallization can be preferably applied. For the aforementioned reason, the catalyst is preferably removed not only in Step (A). The catalyst is more preferably removed at every completion of a step in which the catalyst is used. As methods for removing the catalyst, the aforementioned known methods can be preferably applied.

The reaction time (which is a retention time in the case of a continuous reaction) is different depending on the composition of a reaction system, a reaction temperature, a method for removing ammonia, a reaction apparatus, a reaction pressure, and the like. It is generally 0.01 to 100 hours. The reaction time can be determined based on the amount of an N-substituted carbamate as a compound of interest generated. For example, the reaction solution is sampled, the content of an N-substituted carbamate in the reaction solution is then quantified, it is then confirmed that the N-substituted carbamate can be obtained at a yield of 10% or more with respect to the used organic amine, and thereafter, the reaction may be terminated, or alternatively, the reaction may also be terminated after it has been confirmed that the yield is 90% or more.

In the present reaction, it is not necessary to always use a reaction solvent, but for the purpose of facilitation of reaction operations, etc., the following suitable reaction solvents are preferably used:

alkanes, such as pentane (each isomer), hexane (each isomer), heptane (each isomer), octane (each isomer), nonane (each isomer), and decane (each isomer);

aromatic hydrocarbons and alkyl-substituted aromatic hydrocarbons, such as benzene, toluene, xylene (each isomer), ethylbenzene, diisopropylbenzene (each isomer), dibutylbenzene (each isomer), and naphthalene;

nitrile compounds, such as acetonitrile and benzonitrile;

aromatic compounds substituted with a halogen or a nitro group, such as chlorobenzene, dichlorobenzene (each isomer), bromobenzene, dibromobenzene (each isomer), chloronaphthalene, bromonaphthalene, nitrobenzene, and nitronaphthalene;

polycyclic hydrocarbon compounds, such as diphenyl, substituted diphenyl, diphenylmethane, terphenyl, anthracene, and dibenzyltoluene (each isomer);

aliphatic hydrocarbons, such as cyclohexane, cyclopentane, cyclooctane, and ethylcyclohexane;

ketones, such as methyl ethyl ketone and acetophenone;

esters, such as dibutyl phthalate, dihexyl phthalate, dioctyl phthalate, and benzylbutyl phthalate;

ethers and thioethers, such as tetrahydrofuran, 1,4-dioxane, 1,2-dimethoxyethane, diphenyl ether, and diphenyl sulfide;

ketone compounds, such as acetone and methyl ethyl ketone;

ester compounds, such as ethyl acetate and ethyl benzoate; and sulfoxides, such as dimethyl sulfoxide and diphenyl sulfoxide. Needless to say, the organic hydroxy compound used in an excessive amount in the present reaction is also preferably used as a reaction solvent.

The present reaction is carried out in a system, which has a gaseous phase containing an organic hydroxy compound, a compound having a carbonyl group derived from urea, and ammonia generated as a by-product in the reaction, and a liquid phase in which the reaction is carried out. There is a case in which the reaction would take place also in the gaseous phase, depending on the reaction conditions, but a major part of the reaction is carried out in the liquid phase. During the reaction, the content of the liquid phase in a reaction vessel, in which the reaction is carried out, is preferably 50% or less. When the reaction is continuously carried out over a long period of time, there is a case in which polymeric by-products may be generated depending on fluctuations in operating conditions (temperature, pressure, etc.) and the like. If the content of the liquid phase in the reaction vessel is high, adhesion and/or accumulation of such polymeric by-products to the reaction vessel can be avoided. However, if the content of the liquid phase is too high, there is a case in which the efficiency of removing ammonia generated as a by-product would be deteriorated, thereby causing a decrease in the yield of an N-substituted carbamate. Thus, the content of the liquid phase with respect to the gaseous phase is preferably 50% or less, more preferably 30% or less, and further preferably 20% or less (wherein the content of the liquid phase means the ratio of the liquid phase volume to the volume of a reaction tank portion in the case of a tank-type reaction vessel, or the volume of plates lower than a feed plate (excluding a column bottom portion and a reboiler portion) in the case of a column-type reaction vessel, or the volume of a thin film distillation apparatus in the case of a thin film distillation apparatus).

The type of a reaction vessel in which the present reaction is carried out is not particularly limited, as long as it comprises a condenser, and a known reaction vessel can be used. Tank-type and/or column-type reaction vessels, which comprise a condenser, are preferably used. Materials for the reaction vessel are not particularly limited. Known materials can be used. Examples of the material that can be used herein include glass, stainless steel, carbon steel, Hastelloy, a glass-lined base material, and a base material coated with Teflon (registered trademark). SUS304, SUS316, SUS316L, and the like are inexpensive, and thus, they can be preferably used. Instrumentation apparatuses such as a flowmeter and a thermometer, and known processing apparatuses such as a reboiler, a pump and a condenser may be added, as necessary. Heating may be carried out by known methods such as steam and a heater. For cooling, known methods such as natural cooling, the use of cooling water, and the use of brine can be used. Other steps may also be added, as necessary. For example, steps and apparatuses, such as a step of removing the generated ammonia, a step of purifying the organic primary amine, a step of dissolving the urea into the organic hydroxy compound, a step of dissolving the organic hydroxy compound, a step of separating and/or purifying the organic hydroxy compound, a step of purifying an N-substituted carbamate from the generated reaction solution, a step of burning or discarding by-products, etc., may be added, to such an extent that they seem to be conceived of by persons skilled in the art and engineers in the present technical field.

(Step (a) and Step (b): a method for producing an N-substituted carbamate, which comprises reacting a compound having a ureido group with an organic hydroxy compound)

As described above, the method for producing an N-substituted carbamate of the present embodiment may broadly include the following two methods:

(1)': A method for "simultaneously" reacting an organic primary amine, urea and an organic hydroxy compound to produce an N-substituted carbamate, and (1)'': A method, in which a step of producing an N-substituted carbamate by reacting an organic primary amine, urea and an organic hydroxy compound is divided, namely, an organic primary amine is reacted with urea to produce a compound having a ureido group in a first step (Step (a)), and then, in the subsequent second step (Step (b)), the compound having a ureido group is reacted with an organic hydroxy compound to produce an N-substituted carbamate.

Hereinafter, the method (1)'' will be described.

The present inventors consider that the reaction of generating an N-substituted carbamate in Step (A) is formed by a combination of the following various reactions. It is to be noted that an organic primary amine having two amino groups is used as an organic primary amine in the following explanation for convenience sake. Needless to say, organic primary amines other than the organic primary amine exemplified herein can also be used.

The present reaction consists of a reaction of generating a compound having a ureido group from an organic primary amine and urea (e.g. the following formula (39)) and a reaction of generating an N-substituted carbamate from the compound having a ureido group and an organic hydroxy compound (e.g. the following formula (40)).

[Chemical Formula 30]

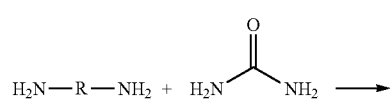
(39)

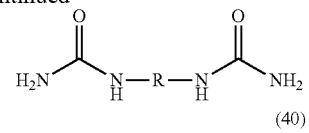
(40)

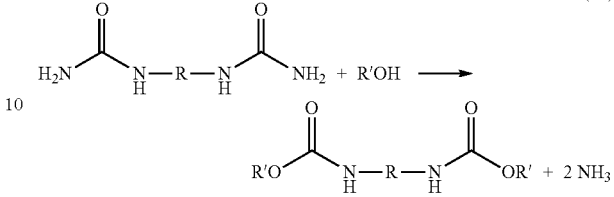

wherein R independently represents an organic group substituted with two substituents.

In the reaction of generating a compound having a ureido group, represented by the above formula (39), there is a case in which side reactions, such as a reaction of generating a compound having a ureylene group from a compound having a ureido group represented by the following formula (41) and an organic primary amine, or a reaction of generating a compound having a biuret group by condensation of a compound having a ureido group represented by the following formula (42), may occur.

[Chemical Formula 31]

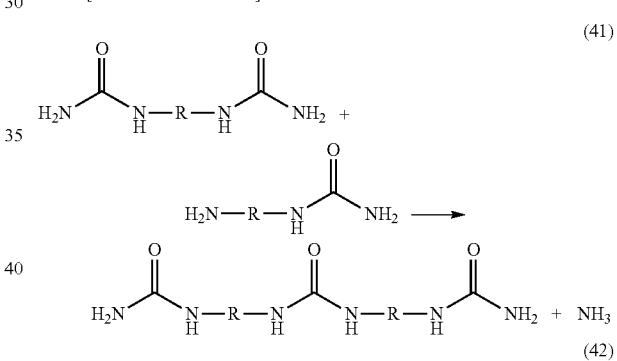
(41)

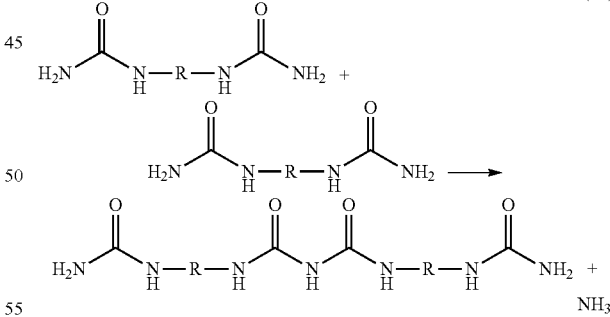
(42)

wherein R independently represents an organic group substituted with two substituents.

It is assumed that the compound having a ureylene group reacts with urea and an organic hydroxy compound to generate an N-substituted carbamate, as shown in the following formula (43), and that, for example, the compound having a biuret group reacts with an organic hydroxy compound, as shown in the following formula (44), to generate an N-substituted carbamate.

[Chemical Formula 32]

(43)

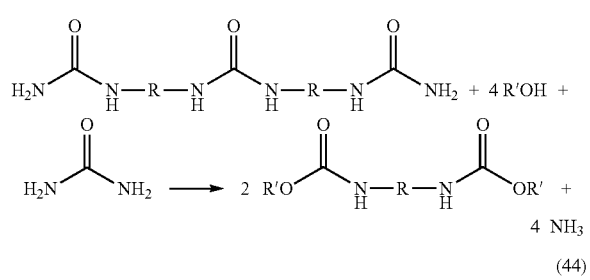

(44)

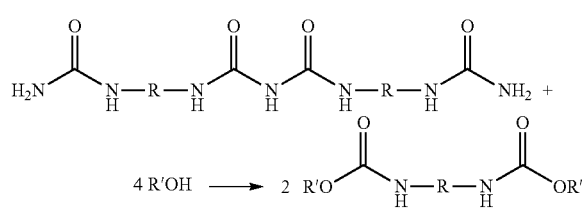

wherein R independently represents an organic group substituted with two substituents, and R'OH represents a monovalent hydroxy compound.

Hence, in the above described method (1)', an N-substituted carbamate is produced through production of various intermediates. As a result of the studies conducted by the present inventors, it was found that in particular, the rate of generating an N-substituted carbamate by the reaction of the above formula (43) or (44) is lower than that by the reaction of the above formula (40). That is to say, this means that if the N-substituted carbamates would like to be obtained at a certain level of yield, the reaction time would be prolonged because the reaction of the above formula (43) or (44) is slow. If the reaction time is prolonged, the previously generated N-substituted carbamate should be preserved under the reaction temperature conditions for a long period of time, and thus, there has been a case in which a heat degeneration reaction would occur on the previously generated N-substituted carbamate and the yield of the N-substituted carbamates would be reduced. On the other hand, when the reaction is terminated in a short time in order to avoid the heat degeneration reaction of the N-substituted carbamate, there have been many cases in which compounds generated as intermediates, such as a compound having a ureylene group (e.g. a compound on the right-hand side of the above formula (41)) or a compound having a biuret bond (e.g. a compound on the right-hand side of the above formula (42)), would remain in large quantities, and in which the yield of N-substituted carbamates would be reduced. Moreover, there has also been a case in which an N-substituted carbamate generated by the relatively quick reaction represented by the above formula (40) would be reacted with the amine terminus (—NH$_2$ group) of an unreacted organic primary amine, so as to generate a compound having a ureylene group (e.g. the reaction of the following formula (45)):

[Chemical Formula 33]

(45)

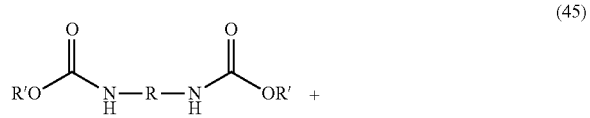

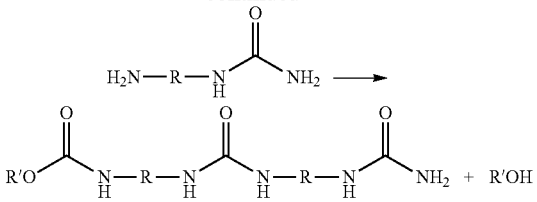

wherein R independently represents an organic group substituted with two substituents, and R'OH represents a hydroxy compound.

As such, there has been a case in which the method for "simultaneously" reacting an organic primary amine, urea and an organic hydroxy compound to produce an N-substituted carbamate could not produce N-substituted carbamates at a sufficient yield, depending on reaction conditions, compounds used in the reaction, etc.

This problem can be often solved by the above described method (1)", namely, a method, in which a step of producing an N-substituted carbamate by reacting an organic primary amine, urea and an organic hydroxy compound is divided, and specifically, an organic primary amine is reacted with urea to produce a compound having a ureido group in a first step (Step (a)), and then, in the subsequent second step (Step (b)), the compound having a ureido group is reacted with an organic hydroxy compound to produce an N-substituted carbamate. Needless to say, the important step in the present method is Step (a), and surprisingly, in the Step (a), the reaction of the above formula (39) is preferentially performed by determining the ratio between an organic amine and urea in a specific range in a system in which the organic amine, the urea and the organic hydroxy compound are present, so that a compound having a ureido group can be selectively produced.

The method corresponding to (1)" above, which is preferably carried out in the method of the present embodiment, is a method for producing an N-substituted carbamate by performing the following Step (a) and Step (b) in this order.

Step (a): a step of reacting an organic primary amine with urea to obtain a reaction mixture containing a compound having a ureido group, and Step (b): a step of reacting the compound having a ureido group obtained in the Step (a) with an organic hydroxy compound to produce an N-substituted carbamate.

Hereinafter, Step (a) and Step (b) will be described.

(Step (a))

Step (a) is a step of reacting an organic primary amine with urea to obtain a reaction mixture containing a compound having a ureido group.

Reaction conditions for carrying out the reaction of the organic primary amine with the urea are different depending on the types of compounds to be reacted. The number of urea groups used is 1 to 100 times larger than the number of amino groups of the organic primary amine used. If the amount of urea used is small, complicatedly substituted carbonyl compounds and the like assumed to be caused by the above formula (41), such as compounds having a ureylene group, are easily generated. Accordingly, it is preferable to use an excessive amount of urea.

In addition, it is assumed that an excessive amount of urea present in the reaction system of Step (a) has the effect of stabilizing the generated compound having a ureido group. A compound having a biuret bond (e.g. a compound on the right-hand side of the following formula (42)) or a compound having a biuret terminus is generated in the process of producing the compound having a ureido group, depending on reaction conditions. In order to generate a compound of interest having a ureido group with high selectivity, it is necessary to suppress generation of the aforementioned compounds. There is a close relationship between urea present in the reaction system and the amount of the compounds generated, and there is a tendency that the amount of the generated compound is reduced as the amount of urea is increased.

Thus, in order to generate a compound having a ureido group with high selectivity, it is preferable to use an excessive amount of urea. However, if a largely excessive amount of urea is used, there is a case in which the size of a reaction vessel would be enlarged and industrial production would become difficult, or it would cause problems to the aftermentioned separation and recovery of urea. Accordingly, the number of urea groups is more preferably 1.1 to 10 times, and further preferably 1.5 to 5 times larger than the number of amino groups of the organic primary amine used.

Furthermore, taking into consideration the above described role of urea, it is necessary to pay attention on operations performed during the reaction. That is, in order to maintain a condition in which the number of urea groups in the reaction system is always larger than the number of amino groups of the organic primary amine (if possible, the number of urea groups is much larger), there is preferably applied, for example, a method which comprises previously dissolving the total amount of used urea in a reaction solvent (the details will be described later) to prepare a mixed solution, and then adding an organic primary amine to the mixed solution.

Next, the concentration of ammonia in the system will be described. It is to be noted that the preferred range of the concentration of ammonia described herein indicates the concentration of ammonia in a reaction solution obtained after a compound having a ureido group has been generated to a certain extent (for example, at a yield of 5% or more with respect to organic amine), and thus, it does not indicate the concentration of ammonia at the initial stage of the reaction.

The reaction of generating an N-substituted carbamate (e.g. the reaction of the above formula (40)) is an equilibrium reaction, and thus, the equilibrium largely lies on the original system. However, the reaction of generating a compound having a ureido group (the reaction of the above formula (39)) is a reaction in which the equilibrium largely lies on the generation system, or it is an irreversible reaction, and thus this reaction hardly depends on the concentration of ammonia in the system. Accordingly, generation of an N-substituted carbamate by the reaction of the generated compound having a ureido group with an aromatic hydroxy compound (the reaction of the above formula (40)) can be suppressed and the compound having a ureido group can be selectively generated by retaining the concentration of ammonia in the reaction solution of Step (a) to a certain level or higher, and further, side reactions can be suppressed and the compound having a ureido group can be obtained with high selectivity by retaining the concentration of ammonia at a certain level or higher. The concentration of ammonia providing the aforementioned effects is preferably 10 ppm or higher, more preferably 100 ppm or higher, further preferably 300 ppm or higher, and most preferably 1000 ppm or higher.

The Step (a) can be carried out in a reaction temperature range of 30° C. to 250° C. A high temperature is preferably applied in order to increase the reaction rate. On the other hand, there is a case in which an unfavorable reaction (e.g. the decomposition reaction of urea and complicated side reactions caused by the aforementioned decomposition reaction) occurs at a high temperature and as a result, complicatedly substituted urea compounds or carbonyl compounds may be generated. Thus, the reaction temperature is in a range, more preferably of 50° C. to 200° C., and further preferably of 70° C. to 180° C. In order to keep the reaction temperature constant, a reaction vessel, in which the Step (a) is carried out, may be equipped with a known cooling device and/or heating device.

The reaction pressure is different depending on the type of a compound used, the composition of a reaction system, the reaction temperature, the reaction apparatus, etc. In general, the reaction pressure is preferably in a range of 0.01 kPa to 10 MPa (absolute pressure). If taking into consideration facilitation of industrial production, the reaction pressure is more preferably in a range of 0.1 kPa to 5 MPa (absolute pressure).

The reaction time (which is a retention time, when the reaction is a continuous reaction) is not particularly limited. It is generally 0.001 to 100 hours, preferably 0.01 to 80 hours, and more preferably 0.1 to 50 hours. Otherwise, the reaction solution is sampled, and it is then confirmed by, for example, liquid chromatography that a desired amount of compound having a ureido group has been generated, so that the reaction can be terminated. The Step (a) is a step of producing a compound having a ureido group. If large quantities of amino groups derived from unreacted organic primary amines are present in the Step (a), a compound having a ureylene group and the like are generated in Step (b) following the Step (a), and thereby, the amount of an N-substituted carbamate generated would not only be reduced, but adhesion of the aforementioned compound to the reaction vessel and the consolidation thereof would take place in many cases. Accordingly, it is preferable that, in the Step (a), a compound having a ureido group be generated at a yield as high as possible, and that the amounts of the amino groups derived from the organic primary amines be reduced. Specifically, it is preferable to continue the reaction, until the ratio of the number of the amino groups derived from the organic primary amines to the number of ureido groups constituting the compounds having ureido groups becomes preferably 0.25 or less, more preferably 0.1 or less, and further preferably 0.05 or less.

In the present embodiment, a catalyst can be used, as necessary. Examples of such a catalyst that can be used herein include: organic metal compounds and inorganic metal compounds, such as tin, lead, copper, and titanium; and basic catalysts, such as the alcoholates of alkali metals and alkali earth metals, which include the methylate, ethylate and butylate (each isomer) of lithium, sodium, potassium, calcium and barium.

From the viewpoint of a decrease in the viscosity of a reaction solution and/or the achievement of a homogeneous reaction solution, the reaction in the Step (a) is preferably carried out in the presence of a solvent. Examples of such a reaction solvent that can be preferably used herein include: alkanes, such as pentane (each isomer), hexane (each isomer), heptane (each isomer), octane (each isomer), nonane (each isomer), and decane (each isomer);

aromatic hydrocarbons and alkyl-substituted aromatic hydrocarbons, such as benzene, toluene, xylene (each isomer), ethylbenzene, diisopropylbenzene (each isomer), dibutylbenzene (each isomer), and naphthalene;

nitrile compounds, such as acetonitrile and benzonitrile;

aromatic compounds substituted with a halogen or a nitro group, such as chlorobenzene, dichlorobenzene (each isomer), bromobenzene, dibromobenzene (each isomer), chloronaphthalene, bromonaphthalene, nitrobenzene, and nitronaphthalene;

polycyclic hydrocarbon compounds, such as diphenyl, substituted diphenyl, diphenylmethane, terphenyl, anthracene, and dibenzyltoluene (each isomer);

aliphatic hydrocarbons, such as cyclohexane, cyclopentane, cyclooctane, and ethylcyclohexane;

ketones, such as methyl ethyl ketone and acetophenone;

esters, such as dibutyl phthalate, dihexyl phthalate, dioctyl phthalate, and benzyl butyl phthalate;

ethers and thioethers, such as tetrahydrofuran, 1,4-dioxane, 1,2-dimethoxyethane, diphenyl ether, and diphenyl sulfide;

ketone compounds, such as acetone and methyl ethyl ketone;

ester compounds, such as ethyl acetate and ethyl benzoate;

sulfoxides such as dimethyl sulfoxide and diphenyl sulfoxide;

water; and hydroxy compounds such as alcohol and aromatic hydroxy compounds. From the viewpoint of the solubility of the compound having a ureido group as a product, the reaction solvent is preferably water or an organic hydroxy compound (alcohol or an aromatic hydroxy compound). These solvents can be used singly or in the form of a mixture of two or more types.

The present organic hydroxy compound may be completely identical to, or may be partially identical to, or may be different from the organic hydroxy compound used in Step (b). In order to facilitate operations, the present organic hydroxy compound is preferably identical to the organic hydroxy compound used in Step (b). As described below, the reaction of Step (a) is carried out in the presence of an aromatic hydroxy compound. It is more preferable that the reaction of Step (a) be carried out in the presence of alcohol or an aromatic hydroxy compound, and that an aromatic hydroxy compound be then added to the reaction system.

The above-mentioned reaction solvent can be used in any given amount. When alcohol is used as such a reaction solvent, it can be used in an amount 1 to 100 times, at a stoichiometric ratio, as large as the amount of the amino group of the organic primary amine. In order to improve the flowability of a reaction solution and to efficiently promote the reaction, alcohol is preferably used in an excessive amount with respect to the amount of the amino group of the organic primary amine. However, if an extremely large amount of alcohol is used, there is a risk of requiring a large reaction vessel, etc. Thus, the reaction solvent may be used in an amount range, more preferably 5 to 50 times, and further preferably 8 to 20 times, as large as the amount of the amino group of the organic primary amine.

Moreover, when an aromatic hydroxy compound is used as a reaction solvent in Step (a), it can be used in an amount 1 to 100 times, at a stoichiometric ratio, as large as the amount of the amino group of the organic primary amine. In order to improve the flowability of a reaction solution and to efficiently promote the reaction, an aromatic hydroxy compound is preferably used in an excessive amount with respect to the amount of the amino group of the organic primary amine. However, if an extremely large amount of aromatic hydroxy compound is used, there is a risk of requiring a large reaction vessel, etc. Thus, the reaction solvent may be used in an amount range, more preferably 2 to 50 times, and further preferably 3 to 20 times, as large as the amount of the amino group of the organic primary amine.

If taking into consideration the solubility of a compound having a ureido group generated, among the alcohol represented by the above formula (17) and organic hydroxy compounds such as the aromatic hydroxy compound represented by the above formula (18), the aromatic hydroxy compound is preferably used. For example, Japanese Patent Application Laid-Open No. 6-41045 describes that polyhexamethylene-urea generated as a result of the reaction of urea with hexamethylenediamine is hardly dissolved in n-butanol. In this respect, the aromatic hydroxy compound is excellent in terms of the property of dissolving various reaction products including a compound having a ureido group as a typical example in many cases. Moreover, the aromatic hydroxy compound also has the effect of promoting the reaction of an organic primary amine with urea. The mechanism of providing such an effect has not yet been elucidated. In general, urea tends to obtain an association state through a hydrogen bond. The present inventors have assumed that the aromatic hydroxy compound would have an acidic hydroxy group, and that the hydroxy group would suppress association among urea molecules and would facilitate the approach of an amine to the reaction point of urea (which is assumed to be carbon constituting the carbonyl group of urea).

When an aromatic hydroxy compound is used as a reaction solvent, it may be used singly, or may be used in the form of a mixture with other solvents. The amount of the aromatic hydroxy compound used is determined in the above described values. Even when Step (a) is carried out in the presence of alcohol and an aromatic hydroxy compound is then added to the reaction system, the aromatic hydroxy compound is used within the above described range. At that time, with regard to the amount of alcohol used in the reaction of Step (a) as well, alcohol is used at a stoichiometric ratio of the above described aromatic hydroxy compound to the organic primary amine. When water is used in Step (a), it is preferably used with an aromatic hydroxy composition and/or alcohol. Water can be used alone as a solvent, but there is a case in which it is necessary to remove water after completion of Step (a). If the aforementioned amount of aromatic hydroxy compound is added after completion of Step (a), there is a case in which a water phase is separated from an organic phase or in which an aromatic hydroxy compound or a compound having a ureido group is consolidated, and as a result, there is a case in which a homogeneous solution cannot be supplied upon implementation of Step (b) or in which a pump or a pipe for transfer is clogged. Accordingly, when water alone is used as a solvent in Step (a), the water is removed before or after addition of the aromatic hydroxy compound. The amount of water removed depends on the compounds used and the composition thereof. Water is removed such that the water remains in a range of 10 ppm to 10 wt %, preferably 10 ppm to 5 wt %, and further preferably 10 ppm to 2 wt %, in the reaction solution after the removal of the water (or in the mixed solution). As a method for removing water, a known method for removing water can be applied. For example, a method for removing water by performing distillation under a reduced pressure or an ordinary pressure, a method of using an adsorbent such as zeolite, a method of adding a hydrolytic compound such as acetal and then removing water by a hydrolysis reaction, and a method for removing water by using a compound that reacts with water, such as N,N-dicyclohexylcarbodiimide, are preferably applied. A method involving distillation is further preferable. When water is used as a solvent together with an aromatic hydroxy composition and/or alcohol in Step (a), the water is used in the reaction in a range of 10 ppm to 10 wt %, preferably 10 ppm to 5 wt %, and further preferably 10 ppm to 2 wt %. The present inventors have found that, in the reaction of Step (a), the reaction rate is surprisingly improved by the presence of water. Therefore, the coexistence of water in the reaction is a preferable method. This effect has not yet been clarified in detail, but the inventors have assumed that water would provide the effect of enhancing the nucleophilicity of an organic primary amine.

The type of a reaction apparatus used to carry out the present reaction is not particularly limited, and a known reaction vessel can be used. For example, conventionally known reaction vessels, such as an agitation tank, a pressurized agitation tank, a depressurized agitation tank, a column-type reaction vessel, a distillation column, a packed column, a thin film distiller, and a tube-type reaction vessel can be used in combination, as appropriate, depending on a reaction method or reaction conditions. In addition, the reaction may be either a batch-type reaction or a continuous flow-type reaction, and the reaction apparatus may be selected depending on each reaction form. From the viewpoint of efficient implementation of the reaction, the continuous flow-type reaction is preferable, and high efficiency can be obtained by circulating a raw material solution through a tubular flow channel (pipe) having a small inside diameter in many cases. In such a case, the thickness and length of the flow channel are important, and they can be determined, as appropriate, based on the amount of a compound having a ureido group produced, the area of a thermally-conductive surface with respect to the volume of a hollow interior, and a necessary retention time (reaction time). The anterior portion of a single flow channel can be used in a supply step, and the posterior portion thereof can be used in a reaction step. In this case, a portion in which a solution supplied to the flow channel is able to reach a desired temperature can be considered to be a portion used in the reaction step, and the other portion can be considered to be a portion used in the supply step.

Materials for the reaction vessel are not particularly limited. Known materials can be used. Examples of the material that can be used herein include glass, stainless steel, carbon steel, Hastelloy, a glass-lined base material, and a base material coated with Teflon (registered trademark). SUS304, SUS316, SUS316L, and the like are inexpensive, and thus, they can be preferably used. Instrumentation apparatuses such as a flowmeter and a thermometer, and known processing apparatuses such as a mechanism of retaining pressure, a reboiler, a pump and a condenser may be added, as necessary. Heating may be carried out by known methods such as steam and a heater. For cooling, known methods such as natural cooling, the use of cooling water, and the use of brine can be used. Other steps may also be added, as necessary. For example, steps and apparatuses, such as a step of removing the generated ammonia, a step of purifying the organic primary amine, a step of dissolving the urea into the aromatic hydroxy compound, a step of dissolving the aromatic hydroxy compound, a step of separating alcohol, a step of separating and/or purifying the aromatic hydroxy compound, a step of purifying a compound having a ureido group from the generated reaction solution, a step of burning or discarding by-products, etc., may be added, to such an extent that they seem to be conceived of by persons skilled in the art and engineers in the present technical field.

As described above, from the viewpoint of selective production of a compound having a ureido group in Step (a), it is preferable that a certain amount of ammonia be dissolved in the reaction solution. On the other hand, in the after-mentioned Step (b), it is preferable to remove ammonia. Accordingly, when the reaction solution obtained after production of the compound having a ureido group in Step (a) is used as a raw material in Step (b), a method of previously separating ammonia from the reaction solution is also preferable. The separation method is not particularly limited, and for example, the reaction solution is supplied to a depressurized vessel to promptly separate a gaseous phase portion from a liquid phase portion, and the liquid phase portion comprising the compound having a ureido group can be then recovered and used.

The compound having a ureido group obtained by the above described reaction is represented by the above formula (27).

When a reaction solvent is used in Step (a), the reaction solvent may be removed from the reaction solution of Step (a) before performing Step (b), or Step (b) may be directly carried out without removing the reaction solvent. In particular, it is preferable that the hydroxy compound used as a reaction solvent in Step (a) be directly used as a portion of a hydroxy compound in Step (b).

(Step (b))

Step (b) is a step of reacting the compound having a ureido group obtained in Step (a) with an organic hydroxy compound to produce an N-substituted carbamate.

When an organic hydroxy compound is used as a reaction solvent in Step (a) and it is identical to an organic hydroxy compound used in Step (b), Step (b) can be directly carried out by using the reaction solution obtained in Step (a).

When the reaction solvent used in Step (a) is different from a hydroxy composition in Step (b), a hydroxy compound may be newly added to the reaction solution obtained in Step (a), and Step (b) may be then carried out. Alternatively, one or more organic hydroxy compounds may be newly added to the reaction solution obtained in Step (a), and a part or the whole of the reaction solvent used in Step (a) may be then separated, and Step (b) may be then carried out. Otherwise, after a part or the whole of the reaction solvent used in Step (a) has been removed, an organic hydroxy compound may be newly added to the reaction solution, and Step (b) may be then carried out. The added organic hydroxy compound comprises at least one of the alcohol represented by the above formula (17) and the aromatic hydroxy compound represented by the above formula (18). Among such organic hydroxy compounds, the active aromatic hydroxy compound represented by the above formula (25) is more preferable, and the active aromatic hydroxy compound represented by the above formula (26) is further preferable. The method for separating the reaction solvent used in Step (a) is not particularly limited, and a known method such as distillation separation, membrane separation, or extraction separation can be applied, and among others, distillation separation is preferable.

The organic hydroxy compound used in Step (b) is preferably the aromatic hydroxy compound represented by the above formula (18), and more preferably the active aromatic hydroxy compound represented by the above formula (25) or the above formula (26).

Reaction conditions, which are applied to the reaction of a compound having a ureido group with an organic hydroxy compound to produce an N-substituted carbamate in Step (b), are different depending on the type of a compound to be reacted, and the amount of the organic hydroxy compound is within a range in which the number of the organic hydroxy compounds is set at a stoichiometric ratio of 1:1 to 500:1 with respect to the number of ureido groups in the used compound having ureido groups. Since a complicatedly substituted carbonyl compound and a high-molecular-weight compound having a carbonyl bond in a molecule thereof are easily generated if the aforementioned stoichiometric ratio is less than 1:1, it is preferable to use a largely excessive amount of an organic hydroxy compound. If taking into consideration the size of a reaction vessel, the organic hydroxy compound is used at a stoichiometric ratio of preferably 1:1 to 100:1, more preferably 2:1 to 50:1, and further preferably 3:1 to 20:1 with respect to the aforementioned ureido groups.

The reaction temperature is preferably in a range of 100° C. to 350° C., although it depends on the reactivity of the used compound. If the reaction temperature is lower than 100° C., it is not preferable because since the organic hydroxy compound strongly binds to ammonia generated as a by-product, the reaction would progress slowly, or almost no reaction would occur, or the amount of a complicatedly substituted carbonyl compound increases. On the other hand, if the reaction temperature is higher than 350° C., it is not preferable either, because the compound having a ureido group would be decomposed, or the organic hydroxy compound would be dehydrogenated, or the decomposition reaction, degeneration reaction and the like of an N-substituted carbamate as a product are easily take place. From such a viewpoint, the reaction temperature is more preferably in a range of 120° C. to 320° C., and further preferably in a range of 140° C. to 300° C.

The reaction pressure is different depending on the composition of a reaction system, a reaction temperature, a method for removing ammonia, a reaction vessel, etc. In general, the reaction is preferably carried out in a pressure range of 0.01 Pa to 10 MPa (absolute pressure). If taking into consideration facilitation of industrial production, a pressure in a range of 0.1 Pa to 5 MPa (absolute pressure) is preferable, and if taking into consideration the removal of gaseous ammonia from the system, a pressure in a range of 0.1 Pa to 1.5 MPa (absolute pressure) is more preferable.

In the Step (b), the reaction of generating an N-substituted carbamate is mainly carried out in a liquid phase in many cases. Thus, the organic hydroxy compound is preferably present in the form of a liquid phase component under the reaction conditions. On the other hand, as described later, in Step (2), since the organic hydroxy compound and urea and/or a compound having a carbonyl group derived from the compound having a ureido group (which will be described in detail later) are introduced as gaseous phase components into a condenser and they are then condensed in the condenser, it is preferable that the organic hydroxy compound be also present as a gaseous phase component under the reaction conditions. Accordingly, the reaction conditions are determined, such that a portion of the organic hydroxy compound is present as a liquid phase component and another portion thereof is present as a gaseous phase component. When a plurality of organic hydroxy compounds are used, the reaction conditions are determined such that at least one organic hydroxy compound is present as a liquid phase component. Since such reaction conditions (reaction temperature and pressure) are closely associated with the properties of the used organic hydroxy compound, and particularly, with correlation between temperature and vapor pressure, the properties (correlation between temperature and vapor pressure) of the used hydroxy composition have previously been measured or searched, and the results are used as indicators for determining the reaction conditions. It is to be noted that the fact that correlation between temperature and the vapor pressure of a substance increases depending on the purity of the substance, and the type or amount of a coexisting compound, is common knowledge to a person skilled in the art, and thus, it is apparent that not only the above described properties of the organic hydroxy compound (correlation between temperature and vapor pressure), but the type of a coexisting compound and the amount thereof should also be considered.

As described above, since the reaction of generating an N-substituted carbamate is an equilibrium reaction and thus the reaction largely lies on the original system, it is preferable to carry out the reaction, while ammonia generated as a by-product is removed from the reaction system as much as possible. Ammonia is removed, so that the concentration of the ammonia in the reaction solution becomes preferably 1000 ppm or less, more preferably 300 ppm or less, further preferably 100 ppm or less, and most preferably 10 ppm or less. As such a method for removing ammonia, a reaction distillation method, a method using inert gas, membrane separation, a method involving adsorptive separation, and the like can be applied. For example, the reaction distillation method is a method for separating ammonia, which has been successively generated as a result of the reaction, in a gaseous state by distillation. In order to increase the distillation efficiency of ammonia, distillation can be carried out, while boiling a solvent or the organic hydroxy compound. In addition, the method using inert gas is a method of accompanying ammonia successively generated as a result of the reaction in a gaseous state with inert gas, so as to separate the ammonia from the reaction system. A method of using inert gas such as nitrogen, helium, argon, carbon dioxide, methane, ethane or propane, singly or in combination, and introducing the inert gas into the reaction system, is preferable. These methods for removing ammonia from the reaction system may be applied, either singly or in combination of multiple types of methods.

In the present reaction, for the purpose of increasing the reaction rate for example, a catalyst can be used. Examples of the catalyst that is preferably used herein include basic catalysts such as the methylate, ethylate and butylate (each isomer) of lithium, sodium, potassium, calcium and barium; simple substances of rare earth elements, antimony and bismuth, and the oxides, sulfides and salts of these elements, boron as a simple substance and boron compounds; the metals of copper elements, zinc elements, aluminum elements, carbon elements and titanium elements in the periodic table, and the metal oxides and sulfides thereof, and the carbides and nitrides of carbon elements, titanium elements, vanadium elements and chromium elements, other than carbon in the periodic table. In the case of using such a catalyst, the amount used is not particularly limited. The catalyst can be used at a stoichiometric ratio of 0.0001:1 to 100:1 with respect to the amount of ureido group of the compound having a ureido group.

The reaction time (which is a retention time in the case of a continuous reaction) is different depending on the composition of a reaction system, a reaction temperature, a method for removing ammonia, a reaction apparatus, a reaction pressure, and the like. It is generally 0.01 to 100 hours. The reaction time can be determined based on the amount of an N-substituted carbamate as a compound of interest generated. For example, the reaction solution is sampled, the content of an N-substituted carbamate in the reaction solution is then quantified, it is then confirmed that the N-substituted carbamate can be obtained at a yield of 10% or more with respect to the compound having a ureido group, and thereafter, the reaction may be terminated, or alternatively, the reaction may also be terminated after it has been confirmed that the yield is 90% or more. The yield is preferably 50% or more, more preferably 80% or more, and further preferably 90% or more.

In the present reaction, it is not necessary to always use a reaction solvent, but for the purpose of facilitation of reaction operations, etc., the following suitable reaction solvents can be preferably used:

alkanes, such as pentane (each isomer), hexane (each isomer), heptane (each isomer), octane (each isomer), nonane (each isomer), and decane (each isomer);

aromatic hydrocarbons and alkyl-substituted aromatic hydrocarbons, such as benzene, toluene, xylene (each isomer), ethylbenzene, diisopropylbenzene (each isomer), dibutylbenzene (each isomer), and naphthalene;

nitrile compounds, such as acetonitrile and benzonitrile;

aromatic compounds substituted with a halogen or a nitro group, such as chlorobenzene, dichlorobenzene (each isomer), bromobenzene, dibromobenzene (each isomer), chloronaphthalene, bromonaphthalene, nitrobenzene, and nitronaphthalene;

polycyclic hydrocarbon compounds, such as diphenyl, substituted diphenyl, diphenylmethane, terphenyl, anthracene, and dibenzyltoluene (each isomer);

aliphatic hydrocarbons, such as cyclohexane, cyclopentane, cyclooctane, and ethylcyclohexane;

ketones, such as methyl ethyl ketone and acetophenone;

esters, such as dibutyl phthalate, dihexyl phthalate, dioctyl phthalate, and benzylbutyl phthalate;

ethers and thioethers, such as tetrahydrofuran, 1,4-dioxane, 1,2-dimethoxyethane, diphenyl ether, and diphenyl sulfide;

ketone compounds, such as acetone and methyl ethyl ketone;

ester compounds, such as ethyl acetate and ethyl benzoate; and sulfoxides, such as dimethyl sulfoxide and diphenyl sulfoxide. These solvents can be used singly or in the form of a mixture of two or more types. Needless to say, the organic hydroxy compound used in an excessive amount in the present reaction is also preferably used as a reaction solvent.

The present reaction is carried out in a system, which has a gaseous phase containing an organic hydroxy compound, a compound having a carbonyl group derived from urea, and ammonia generated as a by-product in the reaction, and a liquid phase in which the reaction is carried out. Although a major part of the reaction is carried out in the liquid phase, there is also a case in which the reaction would take place also in the gaseous phase, depending on the reaction conditions. During the reaction, the content of the liquid phase in a reaction vessel, in which the reaction is carried out, is preferably 50% or less. When the reaction is continuously carried out over a long period of time, there is a case in which polymeric by-products may be generated depending on fluctuations in operating conditions (temperature, pressure, etc.). If the content of the liquid phase in the reaction vessel is high, adhesion and/or accumulation of such polymeric by-products to the reaction vessel can be avoided. However, if the content of the liquid phase is too high, there is a case in which the efficiency of removing ammonia generated as a by-product would be deteriorated, thereby causing a decrease in the yield of an N-substituted carbamate. Thus, the content of the liquid phase with respect to the gaseous phase is preferably 50% or less, more preferably 30% or less, and further preferably 20% or less (wherein the content of the liquid phase means the ratio of the liquid phase volume to the volume of a reaction tank portion in the case of a tank-type reaction vessel, or the volume of plates lower than a feed plate (excluding a column bottom portion and a reboiler portion) in the case of a column-type reaction vessel, or the volume of a thin film distillation apparatus in the case of a thin film distillation apparatus).

The type of a reaction apparatus in which the present reaction is carried out is not particularly limited, as long as it comprises a condenser, and a known reaction vessel can be used. Tank-type and/or column-type reaction vessels, which comprise a condenser, are preferably used.

As described above, the present reaction is preferably carried out in a system which has a gaseous phase containing an organic hydroxy compound, a compound having a carbonyl group derived from urea, and ammonia generated as a by-product in the reaction, and a liquid phase in which the reaction is mainly carried out, under reaction conditions wherein the content of the liquid phase in a reaction vessel in which the reaction is carried out is 50% or less. Regarding the reaction vessel in which the reaction is carried out, a reaction vessel which complies with the present reaction conditions is selected.

Specifically, conventionally known reaction vessels, such as an agitation tank, a pressurized agitation tank, a depressurized agitation tank, a column-type reaction vessel, a distillation column, a packed column, and a thin film distiller, can be used in combination, as appropriate. The type of a condenser comprised in the reaction vessel is not particularly limited, and a known condenser can be used. For example, conventionally known condensers, such as a multitubular cylindrical condenser, a double-tube condenser, a single-tube condenser, and an air-cooled condenser, can be used in combination, as appropriate. The condenser may be equipped inside the reaction vessel, or it may also be equipped outside the reaction vessel and may be connected with the reaction vessel via a pipe. Considering the type of the reaction vessel or condenser, a method for handling a condensate, and the like, various forms can be adopted.

Materials for the reaction vessel and the condenser are not particularly limited, and known materials can be used. Examples of the material that can be used herein include glass, stainless steel, carbon steel, Hastelloy, a glass-lined base material, and a base material coated with Teflon (registered trademark). SUS304, SUS316, SUS316L, and the like are inexpensive, and thus, they can be preferably used. Instrumentation apparatuses such as a flowmeter and a thermometer, and known processing apparatuses such as a reboiler, a pump and a condenser may be added, as necessary. Heating may be carried out by known methods such as steam and a heater. For cooling, known methods such as natural cooling, the use of cooling water, and the use of brine can be used. Other steps may also be added, as necessary. For example, steps and apparatuses, such as a step of removing the generated ammonia, a step of purifying the organic primary amine, a step of dissolving the urea into the organic hydroxy compound, a step of separating and/or purifying the organic hydroxy compound, a step of purifying an N-substituted carbamate from the generated reaction solution, a step of burning or discarding by-products, etc., may be added, to such an extent that they seem to be conceived of by persons skilled in the art and engineers in the present technical field.

When alcohol is used as an organic hydroxy compound, the N-substituted carbamate obtained by the above described reaction is represented by the above formula (30). On the other hand, when an aromatic hydroxy compound is used as an organic hydroxy compound, the N-substituted carbamate obtained by the above described reaction is represented by the above formula (33).

(Step (c): Production of N-Unsubstituted Carbamate)

In step (a), or in the above described Step (A), an N-unsubstituted carbamate can be used instead of urea. The N-unsubstituted carbamate is the compound represented by the above formula (15), and it can be produced by the following Step (c). Accordingly, the following Step (c) may be combined with the aforementioned steps, so as to create the method for producing an N-substituted carbamate of the present embodiment.

Step (c): a step of reacting an organic hydroxy compound with urea to produce an N-unsubstituted carbamate.

Hereinafter, Step (c) will be described.

The organic hydroxy compound used in Step (c) may be one or more organic hydroxy compounds. Alcohol and/or aromatic hydroxy compound can be used as such an organic hydroxy compound. The organic hydroxy compound may be identical to or different from the organic hydroxy compound used in Step (a), and it may also be identical to or different from the organic hydroxy compound used in Step (b), and it may further be identical to or different from the organic hydroxy compound used in Step (A).

When the organic hydroxy compound is alcohol, the alcohol is preferably represented by the above formula (17), and when the organic hydroxy compound is an aromatic hydroxy compound, the aromatic hydroxy compound is preferably represented by the above formula (18). The organic hydroxy compound used herein has both a role as a reaction solvent used in Step (c), and a role of reacting with urea to generate an N-unsubstituted carbamate. In particular, in the case of an aromatic hydroxy compound, as with the reaction of generating an N-substituted carbamate, the reaction rate in the reaction of generating the N-unsubstituted carbamate tends to depend on the structure of the aromatic hydroxy compound. If taking into consideration reactivity with urea, the aromatic hydroxy compound represented by the above formula (25) is preferable, and the aromatic hydroxy compound represented by the above formula (26) is more preferable.

Regarding reaction conditions applied in Step (c), known methods (see, for example, Japanese Patent Application Laid-Open No. 5-310677) can be referred.

The amount ratio between the urea and the organic hydroxy compound used in the reaction of the step (c) is different depending on the types of compounds to be used. Preferably, the organic hydroxy compound is used at a stoichiometric ratio of 5:1 or more with respect to the urea. When the organic hydroxy compound is used at a stoichiometric ratio of 5:1 or less with respect to the urea, the yield of an N-unsubstituted carbamate would be deteriorated or it would take a long period of time for the reaction in many cases. The upper limit of the amount of the organic hydroxy compound to the urea is not limited. However, if a largely excessive amount of organic hydroxy compound is used, it results in a decrease in the production efficiency of an N-unsubstituted carbamate. Thus, with respect to the upper limit, the organic hydroxy compound is generally used at the above described stoichiometric ratio of 100:1 or less with respect to the urea.

Since equilibrium largely lies on the original system in the reaction of the organic hydroxy compound with the urea, ammonia generated as a by-product as a result of the reaction is preferably removed from the reaction system. One of preferred embodiments is a reaction distillation method. In order to increase the efficiency of removing ammonia, the reaction can be carried out while boiling the organic hydroxy compound. For the same purpose, it is also possible to use a solvent having a standard boiling point lower than that of the organic hydroxy compound used, and to carry out the reaction at the boiling point of the solvent. The thus boiled organic hydroxy compound or solvent is separated from ammonia according to a known method such as distillation, and the ammonia is then removed from the system. Examples of such a solvent include hydrocarbons such as pentane, hexane, cyclohexane, heptane, benzene, toluene and xylene, halogenated hydrocarbons such as dichloromethane, chloroform and carbon tetrachloride, ketones such as acetone and methyl ethyl ketone, and ethers such as tetrahydrofuran and dioxane.

As another preferred embodiment of removing ammonia generated as a by-product in the reaction system, a method using inert gas is also applied. Specifically, a method of accompanying ammonia successively generated as a result of the reaction in a gaseous state with inert gas, so as to separate the ammonia from the reaction system. Examples of such inert gas include nitrogen, helium, argon, carbon dioxide, methane, ethane, and propane.

A further preferred embodiment of removing ammonia generated as a by-product in the reaction system is a method of adsorbing ammonia on an adsorbent to separate it from the reaction system. The type of an adsorbent used herein is not particularly limited, as long as it has ability to adsorb ammonia at a temperature used and under conditions used. Examples of such an adsorbent include silica, alumina, zeolite, and diatomaceous earth.

The reaction temperature applied in the step (c) is in a range, preferably of 120° C. to 250° C., and more preferably of 130° C. to 240° C. At a temperature lower than the above described range, the reaction rate is low, and it takes a long period of time for obtaining a high yield. Thus, it is not adequate for industrial use. On the other hand, at a temperature higher than the above described range, a yield is decreased due to side reactions in many cases, and thus, it is not preferable.

The reaction pressure is different depending on conditions such as the composition of a reaction system, a reaction temperature, a method for removing ammonia, and a reaction apparatus. The reaction is generally carried out in a range of 0.01 kPa to 5 MPa (absolute pressure).

The type of a reaction apparatus used to carry out the present reaction is not particularly limited, and a known reaction vessel can be used. For example, conventionally known reaction vessels, such as an agitation tank, a pressurized agitation tank, a depressurized agitation tank, a column-type reaction vessel, a distillation column, a packed column, and a thin film distiller, can be used in combination, as appropriate. Materials used for the reaction vessel are not particularly limited, either. Known materials can be used. Examples of the material that can be used herein include glass, stainless steel, carbon steel, Hastelloy, a glass-lined base material, and a base material coated with Teflon (registered trademark). SUS304, SUS316, SUS316L, and the like are inexpensive, and thus, they can be preferably used. Instrumentation apparatuses such as a flowmeter and a thermometer, and known processing apparatuses such as a reboiler, a pump and a condenser may be added, as necessary. Heating may be carried out by known methods such as steam and a heater. For cooling, known methods such as natural cooling, the use of cooling water, and the use of brine can be used. Other steps may also be added, as necessary. For example, steps and apparatuses, such as a step of removing the generated ammonia, a step of dissolving the urea into the aromatic hydroxy compound, a step of dissolving the aromatic hydroxy compound, a step of separating alcohol, a step of separating and/or purifying the aromatic hydroxy compound, a step of burning or discarding by-products, etc., may be added, to such an extent that they seem to be conceived of by persons skilled in the art and engineers in the present technical field. Moreover, there is preferably used an apparatus comprising a distillation column, a partial condenser and the like, with which ammonia is separated from an organic hydroxy compound or a solvent, and the organic hydroxy compound or the solvent is then returned to the reaction system.

The use of a catalyst is not essential in the reaction of the step (c). However, a catalyst can be used for the purpose of decreasing the reaction temperature or increasing the reaction rate. Examples of such a catalyst that is preferably used herein include: rare earth elements, antimony and bismuth as simple substances, and the oxides, sulfides and chlorides of these elements; boron as a simple substance and boron compounds; the metals of copper elements, zinc elements, aluminum elements, carbon elements and titanium elements in the periodic table, and the oxides and sulfides thereof; and the carbides and nitrides of carbon elements, titanium elements, vanadium elements and chromium elements, other than carbon in the periodic table. In the case of using such a catalyst, the amount ratio between the catalyst and urea is not particularly limited. The catalyst is used at a weight ratio from 0.0001:1 to 0.1:1 with respect to the weight of the urea.

For the purpose of decreasing the viscosity of a reaction solution and/or preparing a reaction solution as a homogeneous system, a reaction solvent may also be used in the reaction of the step (c). Examples of such a reaction solvent that can be preferably used herein include: alkanes, such as pentane (each isomer), hexane (each isomer), heptane (each isomer), octane (each isomer), nonane (each isomer), and decane (each isomer); aromatic hydrocarbons and alkyl-substituted aromatic hydrocarbons, such as benzene, toluene, xylene (each isomer), ethylbenzene, diisopropylbenzene (each isomer), dibutylbenzene (each isomer), and naphthalene; nitrile compounds, such as acetonitrile and benzonitrile; aromatic compounds substituted with a halogen or a nitro group, such as chlorobenzene, dichlorobenzene (each isomer), bromobenzene, dibromobenzene (each isomer), chloronaphthalene, bromonaphthalene, nitrobenzene, and nitronaphthalene; polycyclic hydrocarbon compounds, such as diphenyl, substituted diphenyl, diphenylmethane, terphenyl, anthracene, and dibenzyltoluene (each isomer); aliphatic hydrocarbons, such as cyclohexane, cyclopentane, cyclooctane, and ethylcyclohexane; ketones, such as methyl ethyl ketone and acetophenone; esters, such as dibutyl phthalate, dihexyl phthalate, dioctyl phthalate, and benzylbutyl phthalate; ethers and thioethers, such as tetrahydrofuran, 1,4-dioxane, 1,2-dimethoxyethane, diphenyl ether, and diphenyl sulfide; ketone compounds, such as acetone and methyl ethyl ketone; ester compounds, such as ethyl acetate and ethyl benzoate; and sulfoxides, such as dimethyl sulfoxide and diphenyl sulfoxide. Needless to say, the organic hydroxy compound used in an excessive amount in Step (c) is also preferably used as a reaction solvent.

The thus produced reaction solution of Step (c), which contains an N-unsubstituted carbamate, can be directly used in the reaction of the Step (a) or the reaction of the Step (A). Alternatively, the N-unsubstituted carbamate can be separated from the reaction solution, and the separated N-unsubstituted carbamate can be then used in the reaction of the Step (a) or in the reaction of the Step (A). Furthermore, after a reaction solvent used in the Step (a) and the like have been added to the reaction solution of the Step (c), a part or all of, the reaction solvent used in the Step (c), an excess or unreacted organic hydroxy compound, excess or unreacted urea, etc. may be extracted from the reaction solution of the Step (c), and thereafter, it may be then used in the Step (a). For separation of the N-unsubstituted carbamate, the reaction solvent, the organic hydroxy compound and the urea, known methods such as distillation separation, crystallization or membrane separation can be applied.

(Method for Producing an N-Substituted Carbamate, Wherein an Aromatic Hydroxy Composition Comprising an Active Aromatic Hydroxy Compound and a Low-Active Aromatic Hydroxy Compound is Used)

A method for producing an N-substituted carbamate, wherein an aromatic hydroxy composition comprising an active aromatic hydroxy compound and a low-active aromatic hydroxy compound is used as an organic hydroxy compound, will be described. The present method is preferably applied to the above described Step (A) and Step (b).

As in the case of the after-mentioned Step (2), in the method for producing an N-substituted carbamate of the present embodiment, wherein an aromatic hydroxy compound is used as a raw material, gas containing an aromatic hydroxy compound and a compound having a carbonyl group derived from urea is condensed with a condenser, in order to recover a compound having a carbonyl group derived from a carbonic acid derivative in the form of a homogeneous solution. Thus, the aromatic hydroxy composition preferably contains an aromatic hydroxy compound that is easily vaporized to a certain extent under the reaction conditions. On the other hand, since the organic primary amine, the urea and the aromatic hydroxy compound are mainly reacted in a liquid phase so as to generate an N-substituted carbamate, the aromatic hydroxy compound is preferably present in a liquid form under the reaction conditions. Accordingly, as described above, it is preferable that the aromatic hydroxy compound be present both as a liquid phase component and as a gaseous phase component under the reaction conditions. It is also possible to use an aromatic hydroxy composition comprising a plurality of aromatic hydroxy compounds each having a different standard boiling point, so that aromatic hydroxy compounds having a main component in a gaseous phase can be used together with other types of aromatic hydroxy compounds having a main component in a liquid phase.

In such a case, if all of the plurality of aromatic hydroxy compounds each having a different standard boiling point reacted with an organic primary amine and urea so as to generate N-substituted carbamates, a plurality of aromatic hydroxy compounds would be generated together with isocyanates when the isocyanates are produced by pyrolysis of the N-substituted carbamates, and as a result, separation of the aromatic hydroxy compounds would become complicated in many cases. Hence, there is preferably applied a method for producing an N-substituted carbamate having an ester group derived from an active aromatic hydroxy compound with high selectivity, by using the active aromatic hydroxy compound in combination with a low-active aromatic hydroxy compound. Further, if aromatic hydroxy compounds are selected such that the standard boiling point of the active aromatic hydroxy compound becomes highest in the aromatic hydroxy composition, the concentration of the active aromatic hydroxy compound becomes high in a liquid phase in which the reaction of generating an N-substituted carbamate mainly takes place, and as a result, it becomes possible to generate an N-substituted carbamate derived from the active aromatic hydroxy compound with higher selectivity. The low-active aromatic hydroxy compound having a standard boiling point lower than that of the active aromatic hydroxy compound is preferably introduced as a gaseous phase component into a condenser in Step (2), and it is then condensed together with a compound having a carbonyl group derived from a carbonic acid derivative by using the condenser. As such, when aromatic hydroxy compounds each having a different standard boiling point are used in combination, a difference in the standard boiling point between an aromatic hydroxy compound that is mainly present in a liquid phase and an aromatic hydroxy compound that is condensed mainly as a gaseous phase component together with a compound having a carbonyl group derived from a carbonic acid derivative by using a condenser is preferably 5° C. or higher, and more preferably 10° C. or higher. In particular, it is effective if aromatic hydroxy compounds are combined such that the standard boiling point of the active aromatic hydroxy compound is higher than the standard boiling point of the low-active aromatic hydroxy compound preferably by 5° C. or higher, and more preferably by 10° C. or higher.

In the case of using an aromatic hydroxy composition comprising such a plurality of aromatic hydroxy compounds, the ratio of the amount of the active aromatic hydroxy compound to the amount of the low-active aromatic hydroxy compound in the aromatic hydroxy composition is preferably 0.01:1 to 100:1, more preferably 0.05:1 to 20:1, and further preferably 0.1:1 to 10:1, at a stoichiometric ratio.

(Step (d): A Step of Reacting a Compound Having a Ureylene Group with a Carbonic Acid Derivative)

In the method for producing an N-substituted carbamate of the present embodiment, the following Step (d) can be carried out as well as Step (1).

Step (d): a step of reacting a compound having a ureylene group and/or a biuret bond with a carbonic acid derivative.

As described above, in the production of an N-substituted carbamate, there is a case in which the reactions represented by, for example, the formulae (41) and (42) may take place. As described above, these compounds are converted to N-substituted carbamates by the reactions represented by, for example, the formulae (43) and (44). However, depending on reaction conditions applied during the production of N-substituted carbamates, there is a case in which a polymeric compound would be generated as a result of the reactions represented by the above formulae (41) and (42), and it would be precipitated from the reaction solution, and further it would adhere to the reaction vessel. Step (d) is a step of reacting compounds having a ureylene group (e.g. the compound on the right-hand side of the above formula (41)) or compounds having a biuret group (e.g. the compound on the right-hand side of the above formula (42)), which are generated by such reactions, with a carbonic acid derivative (the compound represented by the above formula (13)), so as to obtain N-substituted carbamates. Preferably, the aforementioned compound is allowed to react with a carbonic acid derivative having a carbonyl group (—C(=O)—) under heating them at a temperature higher than the thermal dissociation temperature of a ureylene group and/or a biuret group, so as to obtain a carbonyl compound.

The Step (d) is preferably carried out in the coexistence of an organic hydroxy compound. The organic hydroxy compound may be either the alcohol represented by the above formula (17), or the aromatic hydroxy compound represented by the above formula (18).

The reaction of Step (d) will be described by using a compound having a ureylene group as an example.

[Chemical Formula 34]

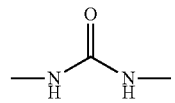

(46)

In Step (d), the compound having a ureylene group represented by the above formula (46) is allowed to react with a carbonic acid derivative under heating them at a temperature higher than the thermal dissociation temperature of the ureylene group of the aforementioned compound. The reaction mechanism of this reaction has not been elucidated, but the present inventors have assumed as follows. It is to be noted that, in the present specification, only reaction formulae regarding a ureylene group portion will be described in order to simplify the descriptions of the reaction.

First, by heating the compound having a ureylene group represented by the above formula (46) to a temperature higher than the thermal dissociation temperature of the ureylene group of the compound, the ureylene group represented by the above formula (46) induces a thermal dissociation reaction, so that it is dissociated into a compound having an isocyanate group (—NCO group) and into a compound having an amino group (—NH$_2$ group) (the following formula (47)).

[Chemical Formula 35]

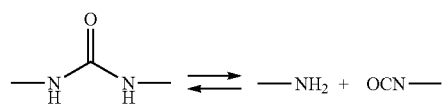

(47)

The compound having an amino group (—NH$_2$ group) reacts with a carbonic acid derivative having a carbonyl group (—C(=O)—), so as to obtain a carbonyl compound containing a group represented by the following formula (48):

[Chemical Formula 36]

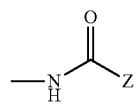

(48)

wherein Z represents a group attached to the carbon atom of the carbonyl group (—C(=O)—) of the carbonic acid derivative.

On the other hand, the compound having an isocyanate group (—NCO group) reacts with a compound derived from the carbonic acid derivative generated as a result of the above described reaction of the compound having an amino group (—NH$_2$ group) with the carbonic acid derivative, so as to obtain the carbonyl compound containing the group represented by the above formula (48).

In addition, when the reaction in the step (d) is carried out in the coexistence of an organic hydroxy compound, the compound having an isocyanate group (—NCO group)

reacts with the organic hydroxy compound, so as to obtain a carbonyl compound containing a group represented by the following formula (49):

[Chemical Formula 37]

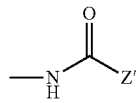
(49)

wherein Z' represents a residue obtained by removing the hydrogen atom of one hydroxy group (—OH) from the organic hydroxy compound.

Hereinafter, the specific reaction mechanism of the present reaction will be described.

When the carbonic acid derivative is, for example, the carbonic acid ester represented by the above formula (16), the carbonic acid ester and a compound having an amino group are subjected to a reaction represented by the following formula (50), so as to generate the carbonyl compound represented by the above formula (48):

[Chemical Formula 38]

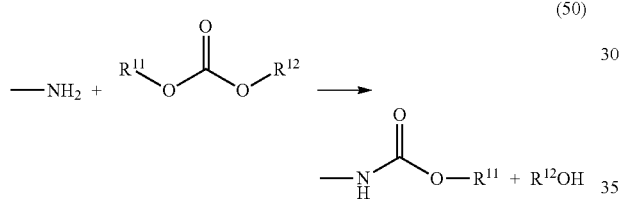
(50)

wherein $R^{11}$ and $R^{12}$ each represent a group defined by the above formula (16).

On the other hand, the compound having an isocyanate group (—NCO group) reacts with a hydroxy compound generated as a result of the reaction of the above formula (52) (which is $R^{12}OH$, the second item on the right-hand side of the above formula (50)), and/or, when the reaction is carried out in the coexistence of an organic hydroxy compound, with the organic hydroxy compound, according to a reaction represented by the following formula (51), so as to generate the carbonyl compounds represented by the above formula (48) and/or the above formula (49):

[Chemical Formula 39]

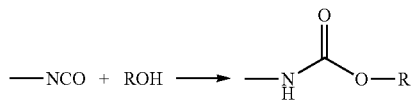
(51)

wherein ROH represents a hydroxy compound ($R^{12}OH$) generated as a result of the reaction of the above formula (52), and/or when the reaction is carried out in the coexistence of an organic hydroxy compound, ROH represents that organic hydroxy compound.

Moreover, when the carbonic acid derivative is, for example, the N-unsubstituted carbamate represented by the above formula (15), the N-unsubstituted carbamate and a compound having an amino group are subjected to reactions represented by the following formula (52) and/or the following formula (53), so as to generate the carbonyl compound represented by the above formula (48):

[Chemical Formula 40]

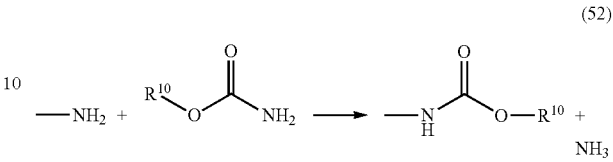
(52)

[Chemical Formula 41]

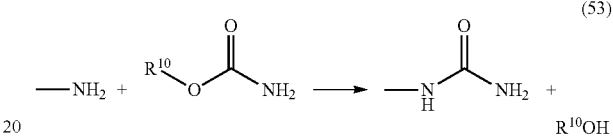
(53)

On the other hand, the compound having an isocyanate group (—NCO group) reacts with ammonia ($NH_3$) generated as a result of the reaction of the above formula (52), and/or with an organic hydroxy compound ($R^{10}OH$) generated as a result of the reaction of the above formula (53), and/or when the reaction is carried out in the coexistence of an organic hydroxy compound, with that organic hydroxy compound, so as to generate the carbonyl compounds represented by the above formula (48) and/or the above formula (49) (the following formulae (54) and (55)):

[Chemical Formula 42]

(54)

[Chemical Formula 43]

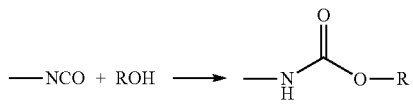
(55)

wherein ROH represents the organic hydroxy compound ($R^{10}OH$) generated as a result of the reaction of the above formula (53), and/or when the reaction is carried out in the coexistence of an organic hydroxy compound, ROH represents that organic hydroxy compound.

Moreover, when the carbonic acid derivative is urea, the carbonyl compound represented by the above formula (48) is generated as a result of a reaction represented by the following formula (56):

[Chemical Formula 44]

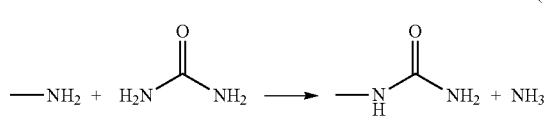
(56)

Furthermore, when the carbonic acid derivative is a phosgene, the carbonyl compound represented by the above formula (48) is generated as a result of a reaction represented by the following formula (57):

[Chemical Formula 45]

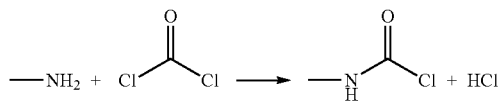

(57)

On the other hand, the compound having an isocyanate group (—NCO group) reacts with hydrogen chloride (HCl) generated as a result of the above formula (57), and/or when the reaction is carried out in the coexistence of a hydroxy compound, with that hydroxy compound, so as to generate the carbonyl compounds represented by the above formula (48) and/or the above formula (49) (the following formulae (58) and (59)):

[Chemical Formula 46]

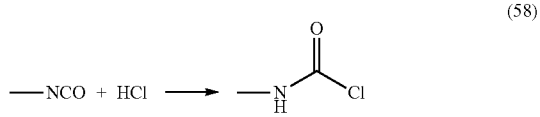

(58)

[Chemical Formula 47]

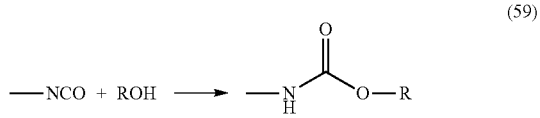

(59)

wherein ROH represents a hydroxy compound when the reaction is carried out in the coexistence of the hydroxy compound.

As described above, it is assumed that, in the method for producing a carbonyl compound of the present embodiment, two types of compounds each having a carbonyl group represented by the above formula (48) will be produced from a single compound having a ureylene group (wherein only one type of compound will be produced depending on the type of a product to be reacted). According to the production method of the present embodiment, by heating the compound having a ureylene group to a temperature that is higher than the thermal dissociation temperature, the thermal dissociation reaction of the ureylene group is induced, and a compound having an amino group is thereby generated, and thereafter, a carbonic acid derivative is allowed to react with the compound having an amino group, so as to obtain a compound having a carbonyl group.

In addition, by appropriately selecting a carbonic acid derivative or an organic hydroxy compound used as a solvent in the above described reaction of a carbonic acid derivative with a compound having a ureylene group, an N-substituted carbamate can also be produced.

The term "the thermal dissociation temperature of a ureylene group" is used in the present embodiment to mean a temperature at which the thermal dissociation of the compound having a ureylene group represented by the above formula (46) progresses. In general, in a method for measuring the weight of a sample as a temperature function while changing or maintaining the temperature of the sample according to certain program, it is measured as a temperature that causes a reduction in the weight of the compound. When a sample is heated at a rate of temperature rise of 10° C./min under the current of inert gas such as nitrogen, helium or argon, a temperature at which a weight reduction of 3%, and more clearly, of 5% occurs with respect to the weight of the added sample, is defined as a thermal dissociation temperature.

In this case, depending on the types of compounds used, the above described "weight reduction" is not only a weight reduction caused by the thermal dissociation of a ureylene group (—NHCONH—) constituting the compound represented by the above formula (46), but also a weight reduction caused by the thermal dissociation of functional groups other than the ureylene group constituting the above described compound. If taking into consideration the gist of the present embodiment, a weight reduction caused by the thermal dissociation of the ureylene group is preferably adopted. In this case, as a method for determining which groups are thermally dissociated, the ureylene group or the functional groups other than the ureylene group constituting the above compound, a method comprising introducing exhaust gas from a thermogravimetric apparatus into a mass spectroscope and then analyzing component contained in the exhaust gas can be applied. Moreover, depending on the types of compounds used, there is a case in which even if the thermal dissociation of the ureylene group occurs, the thermal dissociation reaction is not observed in the form of a weight reduction because the molecular weight of a thermal dissociation product is large (because the boiling point of such a thermal dissociation product is high in many cases). In such a case, according to methods such as differential thermal analysis or differential scanning calorimetry, a temperature at which an endothermic reaction attended with the thermal dissociation reaction is observed can be defined as a thermal dissociation temperature. In order to ensure higher accuracy, a method of combining such differential thermal analysis or differential scanning calorimetry with a thermogravimetric apparatus can also be applied. Furthermore, the thermal dissociation reaction of the urea bond during heating is observed using a near-infrared spectrophotometer, a Raman spectrophotometer, etc., the urea bond is then quantified, and a temperature at which a weight reduction of 3%, and more clearly, of 5% occurs with respect to the weight of the added sample, can be defined as a thermal dissociation temperature.

The reaction of the compound having a ureylene group represented by the above formula (46) with a carbonic acid derivative is carried out in a state in which they are heated to a temperature higher than the thermal dissociation temperature of the ureylene group of the compound having a ureylene group represented by the above formula (46). The "thermal dissociation temperature" is a temperature as defined above, and it is preferably between 100° C. or higher and 350° C. or lower. If the thermal dissociation temperature is too low, the thermal dissociation reaction rate becomes low, and as a result, the reaction efficiency is deteriorated. In contrast, if the thermal dissociation temperature is too high, it induces denaturation reactions of isocyanate groups or amino groups generated as a result of the thermal dissociation reaction. Accordingly, the thermal dissociation temperature is more preferably between 120° C. or higher and 330° C. or lower, and further preferably between 140° C. or higher and 300° C. or lower.

The amount of a carbonic acid derivative used depends on the type of the carbonic acid derivative or reaction conditions. The number of the carbonic acid derivatives is preferably 5 or less with respect to the number of the ureylene groups of the compound having ureylene groups in many cases. In order to increase the reaction rate so as to achieve high reaction efficiency, the amount of the carbonic acid derivative is preferably large. However, if a largely excessive amount of carbonic acid derivative is used, there may be a case in which it induces side reactions such as N-alkylation. Accordingly, the number of the carbonic acid derivatives is set at preferably 3 or less, and more preferably 2 or less, with respect to the number of the ureylene groups of the compound having ureylene groups.

The reaction of the compound having a ureylene group with the carbonic acid derivative is preferably carried out in the presence of a solvent. The type of such a solvent is not particularly limited, as long as it is a compound that is able to dissolve the compound having a ureylene group and the carbonic acid derivative and is stable at a reaction temperature. The same solvents as those described in the section <Step (1)>, or alcohols and aromatic hydroxy compounds described in the section <Organic hydroxy compound>, can be used. In particular, aromatic hydroxy compounds are preferably used, in that the compound having a ureylene group is highly soluble therein and in that the aromatic hydroxy compounds have a high effect of stabilizing a compound having an amino group generated as a result of the thermal dissociation reaction of the ureylene group.

The Step (d) may also be carried out by using a compound having a ureylene group, which is contained in the reaction solution obtained in the Step (1) (i.e. which is generated as a by-product in the Step (1)), after completion of the production of an N-substituted carbamate from an organic primary amine, urea and an organic hydroxy compound, as described in the Step (1). Alternatively, as described later, an N-substituted carbamate is produced from the reaction of an organic primary amine, urea and an organic hydroxy compound, and at the same time, the Step (d) may be carried out, so that an N-substituted carbamate may be produced from the reaction of a compound having a ureylene group generated as a by-product with a carbonic acid derivative. In such a case, a solvent used in the reaction of the organic primary amine with the urea, or an organic hydroxy compound that is used in an excessive amount, can be used as a solvent.

The present reaction is carried out under any condition of a compressed pressure, an ordinary pressure, and a reduced pressure. Moreover, the present reaction is preferably carried out in an inert gas atmosphere, such as nitrogen, argon, helium or neon.

As a reaction apparatus, conventionally known reaction vessels, such as an agitation tank, a pressurized agitation tank, a depressurized agitation tank, a column-type reaction vessel, a distillation column, a packed column, and a thin film distiller, can be used in combination, as appropriate. In order to keep the reaction temperature constant, a known cooling device and/or heating device may be equipped. In addition, materials used for the reaction vessel are not particularly limited. Known materials can be used. Examples of the material that can be used herein include glass, stainless steel, carbon steel, Hastelloy, a glass-lined base material, and a base material coated with Teflon (registered trademark).

From the viewpoint of an increase in the reaction efficiency, the Step (d) in the method for producing a carbonyl compound of the present embodiment is preferably carried out in a distillation column.

The type of the distillation column may be either a packed column or a plate column. It can be selected depending on a reaction form or reaction conditions.

In addition, the Step (d) in the method for producing a carbonyl compound of the present embodiment is preferably carried out by using a distillation column comprising a supply port A, a supply port B, and a discharge port C, which will be described later.

The distillation column preferably comprises a reboiler used for afterheating and vaporizing raw materials and the like to be distilled, and a condenser used for cooling, condensing and recovering a distillate, as well as a column part as a main body. The distillation column more preferably comprises a condenser. The type of a condenser comprised in the distillation column is not particularly limited. A known condenser can be used. For example, conventionally known condensers such as a multitubular cylindrical condenser, a double-tube condenser, a single-tube condenser, and an air-cooled condenser, can be used in combination, as appropriate. The condenser may be equipped inside the distillation column, or it may also be equipped outside the distillation column and may be connected with the distillation column via a pipe. Considering the type of the distillation column or condenser, a method for handling a condensate, and the like, various forms can be adopted.

Materials for the distillation column and the condenser are not particularly limited. Known materials can be used. Examples of the material that can be used herein include glass, stainless steel, carbon steel, Hastelloy, a glass-lined base material, and a base material coated with Teflon (registered trademark). SUS304, SUS316, SUS316L, and the like are inexpensive, and thus, they can be preferably used. Instrumentation apparatuses such as a flowmeter and a thermometer, and known processing apparatuses such as a reboiler, a pump and a condenser may be added, as necessary. Heating may be carried out by known methods such as steam and a heater. For cooling, known methods such as natural cooling, the use of cooling water, and the use of brine can be used. Other steps may also be added to the method for producing a carbonyl compound of the present embodiment, as necessary. For example, steps and apparatuses, such as a step of removing the generated ammonia, a step of dissolving the carbonic acid derivative in the organic hydroxy compound, a step of melting the organic hydroxy compound, etc., may be added, to such an extent that they can be conceived of in the present technical field.

In the method of the present embodiment, as shown in the above formulae (50), (52) and (53), there are many cases in which compounds that can be low-boiling components (ammonia and an organic hydroxy compound) are often generated in the reaction system, and thus, in order to advantageously carry out the reaction, a method of carrying out the reaction while removing such low-boiling components is also preferably applied. Accordingly, a method of carrying out Step (d) by using a distillation column (which is also referred to as a "reaction distillation column") is preferably adopted.

Hereinafter, a method for producing a carbonyl compound from a compound having a ureylene group by using a reaction distillation column will be given as an example.

In the present embodiment, a preferably used reaction distillation column is a distillation column comprising a supply port A, a supply port B, and a discharge port C.

Herein, the supply port A is preferably a supply port for supplying raw material components containing the compound having a ureylene group, and/or raw material components containing a raw material (a precursor of the compound having a ureylene group) for producing the compound having a ureylene group. The raw material components are preferably an organic primary amine and urea, which are precursors of the compound having a ureylene group, and are also preferably compounds having a ureido group represented by the above formula (27).

The raw materials to be supplied via the supply port A further preferably contain an organic hydroxy compound.

The supply port B is preferably a supply port for supplying a carbonic acid derivative to be reacted with the compound having a urea bond. It is more preferable to supply a hydroxy compound via the supply port B to the distillation column.

The discharge port C is preferably a discharge port for discharging a mixture containing a carbonyl compound generated as a result of the reaction of the compound having a urea bond with the carbonic acid derivative under heating them at a temperature higher than the thermal dissociation temperature of the urea bond.

In the Step (d) of the present embodiment, it is preferable that the raw material components to be supplied via the supply port A be the following combinations (i) to (iii), and that the mixture recovered via the discharge port C contain an N-substituted carbamate and an organic hydroxy compound.

combination (i): an organic primary amine, urea, and an organic hydroxy compound, combination (ii): an organic hydroxy compound and a compound having a ureido group, and combination (iii): the reaction solution of Step (1), which contains a compound having a ureylene group.

The raw material components of the above described combination (i) may be supplied via one supply port A in the form of a mixture of an organic primary amine, urea and an organic hydroxy compound. Alternatively, two types of mixtures, namely, a mixture of an organic primary amine and an organic hydroxy compound, and a mixture of urea and an organic hydroxy compound may be prepared, and these mixtures may be then supplied via two or more supply ports A.

When the raw material components of the above described combination (i) are supplied via the supply port A to the distillation column, as a carbonic acid derivative to be supplied via the supply port B, any one of the above described urea, carbonic acid ester, N-unsubstituted carbamate and phosgene may be used. Preferably, at least one compound selected from urea, a carbonic acid ester, and an N-unsubstituted carbamate, is used. If taking into consideration easy availability for industrial use or easy recyclability after the recovery of the carbonic acid derivative with the condenser of Step (2), the same urea as that contained in the raw material components of the above described combination (i) is preferably used. Moreover, the carbonic acid derivative is preferably supplied via the supply port B in the form of a mixture of the carbonic acid derivative and an organic hydroxy compound. If taking into consideration easy recyclability after the recovery of the organic hydroxy compound with the condenser of Step (2), the organic hydroxy compound used at that time is preferably an organic hydroxy compound of the same type as that contained in the raw material components of the above described combination (i).

The compound having a ureido group in the raw material components of the above described combination (ii) is more preferably the compound having a ureido group produced by steps including the above described Step (a), or Step (a) and Step (c). As stated above, there may be a case in which a compound having a ureylene group is generated in the above described Step (a). However, the compound having a ureylene group contained in the raw material components has no problems.

When the raw material components of the above described combination (ii) are supplied via the supply port A to the distillation column, as a carbonic acid derivative to be supplied via the supply port B, any one of the above described urea, carbonic acid ester, N-unsubstituted carbamate and phosgene may be used. Preferably, at least one compound selected from urea, a carbonic acid ester, and an N-unsubstituted carbamic acid ester, is used. If taking into consideration easy availability for industrial use or easy recyclability after the recovery of the carbonic acid derivative with a condenser comprised in the distillation column, the same urea as that contained in the raw material components of the above described combination (i) is preferably used. Moreover, the carbonic acid derivative is preferably supplied via the supply port B in the form of a mixture of the carbonic acid derivative and an organic hydroxy compound. If taking into consideration easy recyclability after the recovery of the organic hydroxy compound with the condenser of Step (2), the organic hydroxy compound used at that time is preferably an organic hydroxy compound of the same type as that contained in the raw material components of the above described combination (i).

When the reaction solution of Step (1) containing a compound having a ureylene group, which is the raw material component of the above described combination (iii), is supplied via the supply port A to the distillation column, as a carbonic acid derivative to be supplied via the supply port B, any one of the above described urea, carbonic acid ester, N-unsubstituted carbamate and phosgene may be used. Preferably, at least one compound selected from urea, a carbonic acid ester, and an N-unsubstituted carbamic acid ester, is used. If taking into consideration easy availability for industrial use or easy recyclability after the recovery of the carbonic acid derivative with a condenser comprised in the distillation column, the same urea as that contained in the raw material components of the above described combination (i) is preferably used. Moreover, the carbonic acid derivative is preferably supplied via the supply port B in the form of a mixture of the carbonic acid derivative and an organic hydroxy compound. If taking into consideration easy recyclability after the recovery of the organic hydroxy compound with the condenser of Step (2), the organic hydroxy compound used at that time is preferably an organic hydroxy compound of the same type as that contained in the raw material components of the above described combination (i).

The case of supplying a mixture containing a compound having a ureylene group via a supply port A (that is, the case of carrying out Step (d) after Step (1)) will be described.

The compound having a ureylene group supplied via the supply port A to the distillation column is preferably supplied in the form of a mixture of the aforementioned compound and a solvent. A method of melting the compound having a ureylene group and then supplying it via a supply port A in the state of a liquid can also be adopted. However, the compound having a ureylene group has a high melting point in many cases, and in such cases, the compound having a ureylene group must be retained at a high temperature in order to melt it. When the compound having a ureylene group is retained at a high temperature, unpredictable side reactions may occur in some cases. Thus, the compound having a ureylene group is preferably supplied in the form of a mixture of the compound and a solvent. The type of a solvent used herein is not particularly limited. Examples of such a solvent include:

alkanes such as hexane, heptane, octane, nonane, and decane;

aromatic hydrocarbons such as benzene, toluene, xylene, ethylbenzene, diisopropylbenzene, dibutylbenzene, and naphthalene;

aromatic compounds substituted with a halogen or a nitro group, such as chlorobenzene, dichlorobenzene, bromobenzene, dibromobenzene, chloronaphthtalene, bromonaphthalene, nitrobenzene, and nitronaphthalene;

polycyclic hydrocarbon compounds such as diphenyl, substituted diphenyl, diphenylmethane, terphenyl, anthracene, and dibenzyltoluene;

aliphatic hydrocarbons such as cyclohexane, cyclopentane, cyclooctane, and ethylcyclohexane;

alicyclic alcohols such as cyclohexanol, cyclopentanol, and cyclooctanol;

ketones such as methyl ethyl ketone and acetophenone;

esters such as dibutyl phthalate, dihexyl phthalate, dioctyl phthalate, and benzylbutyl phthalate;

ethers and thioethers, such as diphenyl ether and diphenyl sulfide; and sulfoxides such as dimethyl sulfoxide and diphenyl sulfoxide. The solvent can be selected depending on the types of compounds to be used (a compound having a ureylene group, a carbonic acid derivative, etc.) or reaction conditions.

Moreover, as a solvent used for the compound having a ureylene group, the above described organic hydroxy compound (alcohol or an aromatic hydroxy compound) is more preferably used. Unexpectedly, these compounds have an effect of moderately stabilizing the ureylene group of the compound having a ureylene group. In many cases, an aromatic hydroxy compound tends to have a higher effect of stabilizing the ureylene group. The reason why the organic hydroxy compound has such an effect has not been clarified. The present inventors have assumed that the organic hydroxy compound would be located close to the urea bond due to a hydrogen bond, so that it could suppress the approach of compounds each having a ureylene group and it could thereby suppress a side reaction between the compounds each having a ureylene group.

The amount of a solvent used is different depending on the types of compounds to be used or reaction conditions. If taking into consideration the solubility of compounds to be used, the solvent is used at a stoichiometric ratio of 1:1 or greater, and more preferably 5:1 or greater, with respect to the number of ureylene groups in the compound having a ureylene group. On the other hand, if taking into consideration the size of a reaction vessel, the solvent is used at a stoichiometric ratio of 500:1 or less, and more preferably 300:1 or less.

The carbonic acid derivative supplied via the supply port B to the distillation column is preferably supplied in the form of a mixture of the derivative and a solvent. A method of melting the carbonic acid derivative and then supplying it via the supply port B in the state of a liquid can also be adopted. However, in many cases, the carbonic acid derivative has a high melting point, and in such cases, the carbonic acid derivative tends to induce a pyrolytic reaction around the melting point. Thus, when the carbonic acid derivative is retained at a high temperature in order to melt it, there is a case in which the carbonic acid derivative disappears as a result of the pyrolytic reaction. Accordingly, it is preferable that a suitable solvent be used, and that a carbonic acid derivative that is in the state of a solution be supplied to the reaction distillation column. The type of a solvent used is not particularly limited. There can be used the same solvents as those exemplified above as solvents used for supplying the compound having a urea bond via the supply port A. Among them, an organic hydroxy compound is preferably used. Such an organic hydroxy compound has not only the effect of highly dissolving a carbonic acid derivative in many cases, but it unexpectedly has the effect of moderately stabilizing the carbonic acid derivative. In many cases, an aromatic hydroxy compound tends to have a higher effect of stabilizing the carbonic acid derivative. The reason why the organic hydroxy compound has such an effect has not been clarified. The present inventors have assumed that the organic hydroxy compound would be located close to the carbonyl group of the carbonic acid derivative due to a hydrogen bond, so that it could suppress the approach of carbonic acid derivatives and it could thereby suppress a side reaction between the carbonic acid derivatives. The amount of a solvent used is different depending on the types of compounds to be used or reaction conditions. The solvent is used at a stoichiometric ratio of 1:1 or greater, and more preferably 2:1 or greater, with respect to the amount of the carbonic acid derivative.

In the distillation column, the temperature of the position of the supply port B through which the carbonic acid derivative is to be supplied (in the same plate in a plate column, whereas in the same theoretical plate in a packed column) is set, preferably higher than the thermal dissociation temperature of the ureylene group of the compound represented by the above formula (46), more preferably 5° C. or more higher than the thermal dissociation temperature of the ureylene group of the compound represented by the above formula (46), and further preferably 10° C. or more higher than the thermal dissociation temperature of the ureylene group of the compound represented by the above formula (1). It is assumed that, by setting the temperature of the position of the supply port B, namely, the temperature of the position through which the carbonic acid derivative is to be supplied, at a temperature higher than the thermal dissociation temperature of a ureylene group, as described above, the ureylene group of the compound having a ureylene group can be subjected to thermal dissociation, and as a result, the generated compound having an amino group can be allowed to react with the carbonic acid derivative. In the present reaction, it is important to allow a carbonic acid derivative to coexist with a system in which a ureylene group is subjected to thermal dissociation, as described above. A method, which comprises setting the temperature of the position in which the supply port B is disposed in the reaction distillation column higher than the thermal dissociation temperature of the ureylene group and then supplying the carbonic acid derivative via the supply port B, is one of methods that satisfy the aforementioned conditions.

The reaction pressure in the distillation column is different depending on the composition of a reaction system, the temperature, a method for removing ammonia, the reaction apparatus, etc. The reaction pressure can be set to a reduced pressure, an ordinary pressure, or a compressed pressure. In general, the reaction pressure is preferably in a range of 0.01 kPa to 10 MPa (absolute pressure). If taking into consideration facilitation of industrial production, a reduced pressure or an ordinary pressure is preferable, and further, a pressure in a range of 0.01 kPa to 100 kPa (absolute pressure) is preferable, a pressure in a range of 0.03 kPa to 80 kPa is more preferable, and a pressure in a range of 0.05 kPa to 50 kPa is further preferable.

In the reaction carried out in the distillation column, for the purpose of increasing the reaction rate for example, a catalyst can be used. Examples of such a catalyst that can be preferably used herein include: basic catalysts such as the methylate, ethylate and butylate of lithium, sodium, potassium, calcium and barium; simple substances of rare earth elements, antimony and bismuth, and the oxides, sulfides and salts of these elements; boron as a simple substance and boron compounds; the metals of copper elements, zinc elements, aluminum elements, carbon elements and titanium elements in the periodic table, and the metal oxides and sulfides thereof; and the carbides and nitrides of carbon elements, titanium elements, vanadium elements and chromium elements, other than carbon in the periodic table. There are many cases in which if such a catalyst is used, the catalyst must be then removed. Thus, the reaction is preferably carried out without using such catalysts. In the case of using a catalyst, it may be removed after completion of the reaction. As a method for removing a catalyst, a known method can be applied. Methods such as membrane separation, distillation separation, or crystallization can be preferably applied.

The reaction time in the distillation column (which is a retention time in the case of a continuous reaction) is different depending on the composition of a reaction system, a reaction temperature, a reaction apparatus, a reaction pressure, and the like. It is generally 0.01 to 100 hours. The reaction time can be determined based on the amount of the generated N-substituted carbamate that is a compound of interest. For example, the reaction solution is sampled, it is then confirmed that the N-substituted carbamate of interest can be obtained at a desired yield, for example, at a yield of 90% or more, and thereafter, the reaction can be terminated. When a carbonic acid derivative is supplied via a single supply port B and the reaction is then performed, if a compound of interest cannot be obtained at a sufficiently desired yield, then, a method of establishing supply ports B in multiple positions in the reaction distillation column, and then performing both the thermal dissociation reaction of the urea bond of the compound having a ureylene group and the reaction of the generated amino group with the carbonic acid derivative at multiple sites in the reaction distillation column may also be adopted.

As shown in the above formulae (52) and (56), when an N-unsubstituted carbamate and/or urea are used as a carbonic acid derivative(s), ammonia is generated. The generated ammonia would react with a compound of interest and as a result, it would decrease the yield of the compound of interest in many cases. Thus, it is preferable to promptly remove such ammonia from the reaction system, so as to prevent ammonia from remaining in the reaction distillation column. The range of a preferred pressure is as described above. From the aforementioned viewpoint as well, the reaction pressure is preferably a reduced pressure or an ordinary pressure.

In order to increase the distillation efficiency of ammonia, the reaction is preferably carried out, while boiling a solvent. There can also be adopted a method, which comprises introducing inert gas into the reaction distillation column and then accompanying ammonia successively generated as a result of the reaction in a gaseous state with the inert gas, so as to separate the ammonia from the reaction system. As such inert gas, nitrogen, helium, argon, carbon dioxide, methane, ethane or propane can be used singly or in combination.

As adsorbents used in the method involving adsorptive separation, adsorbents that can be used under temperature conditions in which the present reaction is carried out, such as silica, alumina, various types of zeolites, and diatomaceous earths, can be used. These methods for removing ammonia from the reaction system may be applied, either singly or in combination of multiple methods.

A single distillation column may comprise at least one supply port A, or may comprise a plurality of supply ports A.

The position in which the supply port A is equipped is a plate that is one or more plates higher than the lowest plate of the distillation column (one or more plates higher than the lowest plate at a theoretical plate in a packed column), preferably three or more plates higher than the lowest plate thereof (three or more plates higher than the lowest plate at a theoretical plate in a packed column), and more preferably five or more plates higher than the lowest plate thereof (five or more plates higher than the lowest plate at a theoretical plate in a packed column).

A single distillation column may comprise at least one supply port B. Otherwise, a single distillation column may comprise a plurality of supply ports B, and a carbonic acid derivative may be supplied via such a plurality of supply ports B. It is preferable to supply a mixture of a carbonic acid derivative and an organic hydroxy compound via the plurality of supply ports B to the distillation column.

In a distillation column, at least one supply port B is disposed in the same position as that in which the supply port A is disposed, or at a position lower than that of the supply port A (the same plate as that in which the supply port A is disposed, or a plate lower than that in which the supply port A is disposed, in a plate column; and the theoretical plate as that in which the supply port A is disposed, or a theoretical plate lower than that in which the supply port A is disposed, in a packed column). Preferably, the supply port B is disposed at a position one or more plates lower than that of the supply port A (one or more plates lower than the supply port A at a theoretical plate in a packed column), preferably three or more plates lower than that of the supply port A (three or more plates lower than the supply port A at a theoretical plate in a packed column), and more preferably five or more plates lower than that of the supply port A (five or more plates lower than the supply port A at a theoretical plate in a packed column).

The supply port C is disposed in the same position as that in which the supply port B is disposed, or at a position lower than that of the supply port B (the same plate as that in which the supply port B is disposed, or a plate lower than that in which the supply port B is disposed, in a plate column; and the theoretical plate as that in which the supply port B is disposed, or a theoretical plate lower than that in which the supply port B is disposed, in a packed column). Preferably, the supply port C is disposed at a position one or more plates lower than that of the supply port B (one or more plates lower than the supply port B at a theoretical plate in a packed column), preferably three or more plates lower than that of the supply port B (three or more plates lower than the supply port B at a theoretical plate in a packed column), and more preferably five or more plates lower than that of the supply port B (five or more plates lower than the supply port B at a theoretical plate in a packed column).

Even in the case of the combinations (i) and (ii), the routine can be performed by the same method as that described above.

(Step (e): Transesterification Step)

The N-substituted carbamate produced by the above described method (Step (A), and/or Step (a) and Step (b)) can be preferably used in the production of an isocyanate by the pyrolysis of the N-substituted carbamate. The N-substituted carbamate more preferably used in the production of the isocyanate is an N-substituted carbamate in which a carbamate group is derived from an aromatic hydroxy compound. For convenience of explanation, the N-substituted carbamate, in which a carbamate group is derived from an aromatic hydroxy compound, is referred to as "N-substituted aromatic carbamate," whereas the N-substituted carbamate, in which a carbamate group is derived from alcohol, is referred to as "N-substituted aliphatic carbamate". This is because, as compared with the N-substituted aliphatic carbamate, the N-substituted aromatic carbamate easily induces a pyrolytic reaction, and it tends to be easily decomposed into the corresponding isocyanate and an aromatic hydroxy compound.

The N-substituted carbamate obtained by the above described production method may be converted to either an N-substituted aromatic carbamate or an N-substituted aliphatic carbamate, depending on the type of an organic hydroxy compound used. When an N-substituted aliphatic carbamate is obtained by the above described production method, it is converted to an easily pyrolyzed N-substituted aromatic carbamate by the below-mentioned Step (e), and the obtained N-substituted aromatic carbamate can be then used in the reaction of an isocyanate. It is to be noted that since the present step is a step of converting the ester group of an N-substituted aliphatic carbamate to another group, it is also referred to as a "transesterification step" in the present embodiment.

Step (e): a step of reacting an N-substituted aliphatic carbamate with an aromatic hydroxy compound to produce an N-substituted aromatic carbamate having an ester group derived from the aromatic hydroxy compound.

In the Step (e), alcohol derived from an N-substituted aliphatic carbamate is generated. Hereinafter, the Step (e) will be described.

Referring to known methods (see, for example, WO2008/059953), the Step (e) can be carried out by applying various methods, depending on the types of compounds to be used and the like.

Reaction conditions for the Step (e) are different depending on the type of a compound to be reacted. An aromatic hydroxy compound is used at a stoichiometric ratio of 2:1 to 1000:1 with respect to ester groups constituting the N-substituted aliphatic carbamate used as a raw material. In order to complete the reaction at an early stage, the aromatic hydroxy compound is preferably used in an excessive amount with respect to ester groups constituting the N-substituted aliphatic carbamate used as a raw material. If taking into consideration the size of a reaction vessel, the aromatic hydroxy compound is used at a stoichiometric ratio of more preferably 2:1 to 100:1, and further preferably 5:1 to 50:1, with respect to ester groups constituting the N-substituted aliphatic carbamate used as a raw material.

The reaction temperature is generally in a range of 100° C. to 300° C. In order to increase the reaction rate, the reaction temperature is preferably high. On the other hand, there is a case in which side reactions easily occur at a high temperature. Thus, the reaction temperature is preferably in a range of 150° C. to 250° C. In order to keep the reaction temperature constant, the above described reaction vessel may be equipped with a known cooling device and/or heating device. The reaction pressure is different depending on the type of a compound used or the reaction temperature. The reaction pressure may be any one of a reduced pressure, an ordinary pressure and a compressed pressure. In general, the reaction pressure is in a range of 20 to $1 \times 10^6$ Pa. The reaction time (which is a retention time when a continuous reaction method is applied) is not particularly limited. It is generally 0.001 to 100 hours, preferably 0.01 to 50 hours, and more preferably 0.1 to 30 hours. In addition, it is also possible that the reaction solution is collected, and that it is then confirmed by liquid chromatography or the like that a desired amount of N-substituted aromatic carbamate of interest has been generated, so that the reaction can be terminated.

In the Step (e), a catalyst is not always necessary. However, the use of such a catalyst to decrease the reaction temperature or to complete the reaction at an early stage has no problems. The catalyst is used at a weight percentage of 0.01% to 30%, and more preferably 0.5% to 20%, with respect to the weight of the N-substituted aliphatic carbamate. Examples of such a catalyst include Lewis acids, transition metal compounds for generating such Lewis acids, organic tin compounds, and compounds of copper element metal, zinc and iron element metal. Specific examples include:

Lewis acids represented by $AlX_3$, $TiX_3$, $TiX_4$, $VOX_3$, $VX_5$, $ZnX_2$, $FeX_3$, and $SnX_4$ (wherein X represents a halogen, an acetoxy group, an alkoxy group, or an aryloxy group), and transition metal compounds for generating such Lewis acids;

organic tin compounds represented by $(CH_3)_3SnOCOCH_3$, $(C_2H_5)SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(CH_3)_2$, $(C_2H_5)_3SnOH$, $PhSnOH$, $Bu_2SnO$, $(C_8H_{17})_2SnO$, $Bu_2SnCl_2$, $BuSnO(OH)$ and the like;

compounds of copper element metals such as $CuCl$, $CuCl_2$, $CuBr$, $CuBr_2$, $CuI$, $CuI_2$, $Cu(OAc)_2$, $Cu(acac)_2$, copper olefinate, $Bu_2Cu$, $(CH_3O)_2Cu$, $AgNO_3$, $AgBr$, silver picrate, and $AgC_6H_6ClO_4$;

zinc compounds such as $Zn(acac)_2$; and compounds of iron element metals such as $Fe(C_{10}H_8)(CO)_5$, $Fe(CO)_5$, $Fe(C_4H_6)(CO)_3$, $Co(mesitylene)_2(PEt_2Ph_2)$, $CoC_5F_5(CO)_7$, and ferrocene (wherein Bu represents a butyl group, Ph represents a phenyl group, acac represents an acetylacetone chelate ligand). In addition, amines such as 1,4-diazabicyclo[2,2,2]octane, triethylenediamine and triethylamine are suitably used, and among others, organic metal catalysts such as dibutyltin dilaurate, lead octoate and stanaoctoate are preferably used. These compounds may be used singly or in the form of a mixture of two or more types.

In the present embodiment, it is not necessary to always use a reaction solvent, but for the purpose of facilitation of reaction operations, etc., appropriate inactive solvents can be used. Examples of such an reaction solvent that can be used herein include:

alkanes, such as hexane (each isomer), heptane (each isomer), octane (each isomer), nonane (each isomer), and decane (each isomer);

aromatic hydrocarbons and alkyl-substituted aromatic hydrocarbons, such as benzene, toluene, xylene (each isomer), ethylbenzene, diisopropylbenzene (each isomer), dibutylbenzene (each isomer), and naphthalene;

aromatic compounds substituted with a halogen or a nitro group, such as chlorobenzene, dichlorobenzene (each isomer), bromobenzene, dibromobenzene (each isomer), chloronaphthalene, bromonaphthalene, nitrobenzene, and nitronaphthalene;

polycyclic hydrocarbon compounds, such as diphenyl, substituted diphenyl, diphenylmethane, terphenyl, anthracene, and dibenzyltoluene (each isomer);

aliphatic hydrocarbons, such as cyclohexane, cyclopentane, cyclooctane, and ethylcyclohexane;

ketones, such as methyl ethyl ketone and acetophenone;

esters, such as dibutyl phthalate, dihexyl phthalate, dioctyl phthalate, and benzylbutyl phthalate;

ethers and thioethers, such as diphenyl ether and diphenyl sulfide;

sulfoxides, such as dimethyl sulfoxide and diphenyl sulfoxide; and silicon oil. These solvents can be used singly or in the form of a mixture of two or more types.

The transesterification reaction in the present embodiment is an equilibrium reaction. Accordingly, in order to efficiently carry out the transesterification, the reaction is preferably promoted, while removing the generated alcohol (which is alcohol derived from the N-substituted aliphatic carbamate as a raw material) from the reaction system. Accordingly, if an aromatic hydroxy compound is selected such that the standard boiling point of the aromatic hydroxy compound used in the transesterification becomes higher than the standard boiling point of the alcohol derived from the N-substituted aliphatic carbamate as a raw material, it results in that the compound having the lowest standard boiling point in the reaction system can be the alcohol derived from the N-substituted aliphatic carbamate as a raw material, and as a result, it becomes easy to remove a product from the reaction system.

Moreover, in order to efficiently carry out the transesterification, it is preferably carried out according to a continuous method. That is to say, it is preferable that the N-substituted aliphatic carbamate as a raw material and the aromatic hydroxy compound be continuously supplied into a reaction vessel to carry out the transesterification, that the generated alcohol derived from the N-substituted aliphatic carbamate as a raw material be removed in the form of a gaseous component from the reaction vessel, and that the generated reaction solution containing the N-substituted aliphatic carbamate and the aromatic hydroxy compound be continuously removed from the bottom portion of the reaction vessel.

Materials for the reaction vessel and line, in which the transesterification step is carried out, are not particularly limited, as long as they do not affect starting materials or reaction substances, and thus, known materials can be used. SUS304, SUS316, SUS316L, and the like are inexpensive, and thus, they can be preferably used. The form of the reaction vessel is not particularly limited. Known reaction vessels such as tank-type and column-type reaction vessels can be used. Various types of known methods, such as a method of using a reaction vessel containing any one of an agitation tank, a multi-stage agitation tank, a distillation column, a multi-stage distillation column, a multitubular reaction vessel, a continuous multi-stage distillation column, a packed column, a thin film evaporator, a reaction vessel containing a support therein, a forced-circulation reaction vessel, a falling-film evaporator, a falling-drop evaporator, a trickle phase reaction vessel and a bubble column, or a method of combining these devices, are used. From the viewpoint of efficient deviation of equilibrium to the generation system side, a method of using a thin film evaporator or a column-type reaction vessel is preferable. In addition, a structure having a large gas-liquid contact area for promptly transferring to the gaseous phase, the generated alcohol derived from the N-substituted aliphatic carbamate as a raw material, is preferable.

The multi-stage distillation column is a distillation column having a multi-stage in the number of theoretical plates in distillation is two or more. The type of such a multi-stage distillation column is not particularly limited, as long as it enables continuous distillation. Any type of multi-stage distillation column can be used, as long as it is generally used as a multi-stage distillation column. Examples of the multi-stage distillation column include: plate-column type distillation columns, which use a tray such as a bubble cap tray, a perforated plate tray, a valve tray, or a countercurrent tray; and packed column-type distillation columns, which are filled with various types of fillers such as a Raschig ring, a Lessing ring, a pall ring, a Berl saddle, an intalox saddle, a Dixon packing, a McMahon packing, Heli-Pack, a Sulzer packing, or Melapack. The type of a packed column that can be used is not particularly limited, as long as it was a packed column filled with the above described known filler. Moreover, a plate column-packed column, mixed column-type comprising both a plate column portion and a portion filled with a filler is also preferably used.

A line for supplying inert gas and/or a liquid-state inactive solvent from the lower portion of the reaction vessel may be equipped into the reaction vessel, separately. Otherwise, when the mixed solution containing the N-substituted aromatic carbamate of interest and the aromatic hydroxy compound comprises the N-substituted aliphatic carbamate as a raw material, a line for re-circulating a part or the whole of the mixed solution in the reaction vessel may also be equipped. When the above described inactive solvent is used, it may be a gaseous and/or liquid solvent.

Gaseous components containing the alcohol derived from the N-substituted aliphatic carbamate as a raw material, which have been removed from the reaction vessel, are preferably purified by a known method such as a distillation column, and the resultant can be then recycled as alcohol in Step (A) and/or Step (a) and/or Step (b) and/or Step (c).

<Step (2): A Step of Condensing a Gaseous Phase Component>

Step (2) is a condensation step of condensing a gaseous phase component (first gaseous phase component) containing urea and/or a compound having a carbonyl group derived from the urea, an organic hydroxy compound, and ammonia, which have been recovered in Step (1), by using a condenser comprised in a reaction vessel, in which the carbamation step is carried out.

The type of the condenser is not particularly limited, and a known condenser can be used. For example, conventionally known condensers, such as a multitubular cylindrical condenser, a double-tube condenser, a single-tube condenser, and an air-cooled condenser, can be used in combination, as appropriate. The condenser may be equipped inside the reaction vessel, or it may also be equipped outside the reaction vessel and may be connected with the reaction vessel via a pipe. Considering the type of the reaction vessel or condenser, a method for handling a condensate, and the like, various forms can be adopted.

Materials for the reaction vessel and condenser are not particularly limited. Known materials can be used. Examples of the material that can be used herein include glass, stainless steel, carbon steel, Hastelloy, a glass-lined base material, and a base material coated with Teflon (registered trademark). SUS304, SUS316, SUS316L, and the like are inexpensive, and thus, they can be preferably used. Instrumentation apparatuses such as a flowmeter and a thermometer, and known processing apparatuses such as a reboiler, a pump and a condenser may be added, as necessary. Heating may be carried out by known methods such as steam and a heater. For cooling, known methods such as natural cooling, the use of cooling water, and the use of brine can be used. Other steps or apparatuses, which seem to be conceived of by persons skilled in the art and engineers in the present technical field, may also be added, as necessary.

The method for producing an N-substituted carbamate of the present embodiment is a method for producing an N-substituted carbamate, which comprises reacting an organic primary amine, urea and an organic hydroxy compound in a reaction vessel comprising a condenser. In the present reaction, a gaseous phase component, which comprises urea and/or compound having a carbonyl group derived from urea, an organic hydroxy compound, and ammonia generated as a by-product in the reaction, is generated. In Step (2), the gaseous phase component is introduced into a condenser comprised in a reaction vessel in which a carbamation step (Step (1)) is carried out, and a part or the whole of the organic hydroxy compound, and a part or the whole of the urea and/or the compound having a carbonyl group derived from urea, are condensed. In this operation, the amount of the organic hydroxy compound to be condensed is set at a stoichiometric ratio of 1:1 or greater with respect to the amount of the compound having a carbonyl group derived from urea to be condensed, and moreover, the ratio between the number of carbonyl groups (—C(=O)—) contained in the compound having a carbonyl group derived from urea, which is contained in ammonia recovered as gas from the condenser, and the number of ammonia molecules is preferably 1:1 or less.

In the present embodiment, the "compound having a carbonyl group derived from urea" used as a component to be condensed with a condenser is a compound having a carbonyl group derived from urea that is used in the reaction of an organic primary amine, urea and an organic hydroxy compound, and it includes urea itself used as a raw material (an unreacted product, and/or an excess obtained when excessively used with respect to the organic primary amine), a compound in which urea is reacted with an organic hydroxy compound, and a compound reacting with urea. It is difficult to identify all of the compounds having a carbonyl group derived from urea. Specific examples of the compound having a carbonyl group derived from urea include urea and an N-unsubstituted carbamate, which are used as raw materials, urea compounds generated as by-products, such as isocyanic acid, biuret, isocyanurate and a urea polymer, an N-unsubstituted carbamate in which the carbamate group is derived from an organic hydroxy compound, and a carbonic acid ester in which the ester group is derived from an organic hydroxy compound. The compound having a carbonyl group derived from urea can be quantified by a method for detecting a carbonyl group contained in the compound according to methods such as infrared spectrophotometry, near-infrared spectrophotometry, Raman spectrophotometry or ultraviolet spectrophotometry. Alternatively, it can also be quantified by a method for specifically analyzing the generated compound according to methods such as gas chromatography, liquid chromatography or NMR. Many of these compounds each having a carbonyl group derived from urea have a high melting point, and thus they tend to be easily precipitated. Among the aforementioned compounds having a carbonyl group derived from urea, the most attention should be paid particularly to urea because the amount of urea generated (the amount to be detected) is large and the melting point thereof is 135° C.

In the condensation operations, the amount of the organic hydroxy compound to be condensed is set at a stoichiometric ratio of 1:1 or greater with respect to the amount of the compound having a carbonyl group derived from urea to be condensed, so that the obtained mixture can be a homogeneous liquid mixture in the condenser. Accordingly, it does not only facilitate the handling of the mixture, but the occurrence of problems, such as adhesion and/or accumulation of solid components to the condenser, can be avoided. Moreover, as described later, it is also effective for reducing the amount of the compound having a carbonyl group derived from urea, which is contained in ammonia recovered from the condenser, to be a specific amount or less. The amount of the organic hydroxy compound to be condensed is set at a stoichiometric ratio of more preferably 2:1 or greater, and further preferably 3:1 or greater, with respect to the amount of the compound having a carbonyl group derived from urea to be condensed. In order to set the amount of the organic hydroxy compound to be condensed with respect to the amount of the compound having a carbonyl group derived from urea to be condensed into the aforementioned range, the condenser is preferably retained at a temperature that is lower than the standard boiling point of the organic hydroxy compound by 90° C. or more, at which the organic hydroxy compound is not solidified.

The above described mixture of the organic hydroxy compound and the compound having a carbonyl group derived from urea, which has been condensed with the condenser, may be circulated inside a reaction vessel, and may be recycled in the reaction of an organic primary amine, urea and an organic hydroxy compound. Alternatively, the mixture may be recovered, and the hydroxy compound and/or the compound having a carbonyl group derived from urea may be then recycled in the reaction of an organic primary amine, urea and an organic hydroxy compound. Otherwise, it may be recycled in a step of producing an N-unsubstituted carbamate (which is the above described Step (c)).

When such condensed components are recycled, the amount of ammonia contained in the organic hydroxy compound and the compound having a carbonyl group derived from urea is preferably 5000 ppm or less. Even if the condensed components contain more than 5000 ppm of ammonia, they can be recycled in the reaction of an organic primary amine, urea and an organic hydroxy compound. However, as described above, since the reaction of an organic primary amine, urea and an organic hydroxy compound is an equilibrium reaction, in order to efficiently carry out the reaction, it is necessary to remove ammonia as a product from the system. If the amount of ammonia contained in the organic hydroxy compound and the compound having a carbonyl group derived from urea to be recycled is too large, the amount of the ammonia removed is also increased in the reaction. As a result, there is a case in which ammonia is introduced into the reaction system in an amount that is larger than the amount of ammonia that can be removed at a unit time (which depends on the capacity of the reaction vessel for urethane production, reaction conditions, etc.), in which the concentration of ammonia in the reaction solution cannot be decreased to a preferred range (the above described range), and in which the yield of an N-substituted carbamate is decreased. Accordingly, the amount of ammonia contained in the organic hydroxy compound and the compound having a carbonyl group derived from urea, which are recycled in the reaction, is preferably small. However, in order to decrease the amount of ammonia to the minimum, enormous efforts are required. From such a viewpoint, the amount of ammonia contained in the organic hydroxy compound and the compound having a carbonyl group derived from urea is more preferably 3000 ppm or less, and further preferably 2000 ppm or less.

As described above, various compounds may be recovered as compounds having a carbonyl group derived from a carbonic acid derivative. Even if the mixture of the organic hydroxy compound and the compound having a carbonyl group derived from urea comprises such compounds, it does not cause problems to the recycling of the condensed components.

<Step (3): A Step of Producing an Isocyanate by Performing a Pyrolytic Reaction of an N-Substituted Carbamate>

Step (3) is a step of subjecting an N-substituted carbamate to a pyrolytic reaction to produce an isocyanate. After the production of an isocyanate, if low-boiling components comprising the isocyanate and an organic hydroxy compound are separated, the after-mentioned residual liquid (first residual liquid) remains.

As described above, among N-substituted carbamates, the pyrolytic temperature of an N-substituted aromatic carbamate can be set lower than that of an N-substituted aliphatic carbamate, and thus, it is preferable to use the N-substituted aromatic carbamate in Step (3).

The reaction temperature applied to the pyrolysis of an N-substituted carbamate is generally in a range of 100° C. to 300° C. In order to increase the reaction rate, the reaction temperature is preferably high. On the other hand, there is a case in which the above described side reactions would be caused by the N-substituted carbamate and/or the isocyanate generated as a product at a high temperature. Thus, the reaction temperature is preferably in a range of 150° C. to 250° C. In order to keep the reaction temperature constant, the above described reaction vessel may be equipped with a known cooling device and/or heating device. The reaction pressure is different depending on the type of a compound used or the reaction temperature. The reaction pressure may be any one of a reduced pressure, an ordinary pressure and a compressed pressure. In general, the reaction pressure is in a range of 20 to $1 \times 10^6$ Pa. The reaction time (which is a retention time when a continuous reaction method is applied) is not particularly limited. It is generally 0.001 to 100 hours, preferably 0.005 to 50 hours, and more preferably 0.01 to 10 hours.

In the present embodiment, a catalyst is not always necessary. However, the use of such a catalyst to decrease the reaction temperature or to complete the reaction at an early stage has no problems. The catalyst is used at a weight percentage of 0.01% to 30%, and more preferably 0.5% to 20%, with respect to the weight of the N-substituted carbamate. Examples of such a catalyst include Lewis acids, transition metal compounds for generating such Lewis acids, organic tin compounds, and compounds of copper element metal, zinc and iron element metal. Specific examples include:

Lewis acids represented by $AlX_3$, $TiX_3$, $TiX_4$, $VOX_3$, $VX_5$, $ZnX_2$, $FeX_3$, and $SnX_4$ (wherein X represents a halogen, an acetoxy group, an alkoxy group, or an aryloxy group), and transition metal compounds for generating such Lewis acids;

organic tin compounds represented by $(CH_3)_3SnO$-$COCH_3$, $(C_2H_5)SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(CH_3)_2$, $(C_2H_5)_3SnOH$, $PhSnOH$, $Bu_2SnO$, $(C_8H_{17})_2SnO$, $Bu_2SnCl_2$, $BuSnO(OH)$ and the like;

compounds of copper element metals such as $CuCl$, $CuCl_2$, $CuBr$, $CuBr_2$, $CuI$, $CuI_2$, $Cu(OAc)_2$, $Cu(acac)_2$, copper olefinate, $Bu_2Cu$, $(CH_3O)_2Cu$, $AgNO_3$, $AgBr$, silver picrate, and $AgC_6H_6ClO_4$;

zinc compounds such as $Zn(acac)_2$; and compounds of iron element metals such as $Fe(C_{10}H_8)(CO)_5$, $Fe(CO)_5$, $Fe(C_4H_6)(CO)_3$, $Co(mesitylene)_2(PEt_2Ph_2)$, $CoC_5F_5(CO)_7$, and ferrocene (wherein Bu represents a butyl group, Ph represents a phenyl group, acac represents an acetylacetone chelate ligand). In addition, amines such as 1,4-diazabicyclo[2,2,2]octane, triethylenediamine and triethylamine are suitably used, and among others, organic metal catalysts such as dibutyltin dilaurate, lead octoate and stanaoctoate are preferably used. These compounds may be used singly or in the form of a mixture of two or more types.

Moreover, when a catalyst is used in any step in the production of the N-substituted carbamate, there is a case in which the residue of the catalyst and the like would be supplied to the pyrolysis step. Even if such a catalyst residue and the like are present, there are no problems in many cases.

In Step (3), it is not necessary to always use a reaction solvent in addition to an aromatic hydroxy compound, but for the purpose of facilitation of reaction operations, etc., appropriate inactive solvents can be used. Examples of such an reaction solvent that can be used herein include: alkanes, such as hexane (each isomer), heptane (each isomer), octane (each isomer), nonane (each isomer), and decane (each isomer); aromatic hydrocarbons and alkyl-substituted aromatic hydrocarbons, such as benzene, toluene, xylene (each isomer), ethylbenzene, diisopropylbenzene (each isomer), dibutylbenzene (each isomer), and naphthalene; aromatic compounds substituted with a halogen or a nitro group, such as chlorobenzene, dichlorobenzene (each isomer), bromobenzene, dibromobenzene (each isomer), chloronaphthalene, bromonaphthalene, nitrobenzene, and nitronaphthalene; polycyclic hydrocarbon compounds, such as diphenyl, substituted diphenyl, diphenylmethane, terphenyl, anthracene, and dibenzyltoluene (each isomer); aliphatic hydrocarbons, such as cyclohexane, cyclopentane, cyclooctane, and ethylcyclohexane; ketones, such as methyl ethyl ketone and acetophenone; esters, such as dibutyl phthalate, dihexyl phthalate, dioctyl phthalate, and benzylbutyl phthalate; ethers and thioethers, such as diphenyl ether and diphenyl sulfide; sulfoxides, such as dimethyl sulfoxide and diphenyl sulfoxide; and silicon oil. These solvents can be used singly or in the form of a mixture of two or more types.

When the N-substituted carbamate is retained at a high temperature for a long period of time, it may induce side reactions, such as a reaction of generating a compound containing a ureylene group according to a reaction of removing a carbonic acid ester from two molecules of N-substituted carbamate, or a reaction of generating an allophanate group according to a reaction with an isocynate group generated as a result of the pyrolysis of the N-substituted carbamate, in some cases. Accordingly, the time at which the N-substituted carbamate and the isocyanate are retained at a high temperature is preferably as short as possible. Therefore, the pyrolytic reaction is preferably carried out by a continuous method. The continuous method is a method comprising continuously supplying a mixture containing the N-substituted carbamate to a reaction vessel, so as to subject it to a pyrolytic reaction, and then continuously removing the generated isocyanate and organic hydroxy compound from the pyrolytic reaction vessel. In the continuous method, a low-boiling component generated as a result of the pyrolytic reaction of an N-substituted carbamate is preferably recovered as a gaseous phase component from the upper portion of the pyrolytic reaction vessel, and the residue is recovered as a liquid phase component from the bottom portion of the pyrolytic reaction vessel. All of compounds existing in the pyrolytic reaction vessel may be recovered as gaseous phase components. However, the presence of a liquid phase component in the pyrolytic reaction vessel provides an effect of dissolving a polymeric compound generated as a side reaction that is induced by the N-substituted carbamate and/or isocyanate, thereby preventing the polymeric compound from adhering and/or accumulating to the pyrolytic reaction vessel. An isocyanate and an organic hydroxy compound are generated as a result of the pyrolytic reaction of an N-substituted carbamate. At least one of these compounds is recovered as a gaseous phase component. Which compound is recovered as a gaseous phase component depends on pyrolytic reaction conditions and the like.

Herein, the expression "low-boiling component generated as a result of the pyrolytic reaction of an N-substituted carbamate" is used in the present embodiment to mean an aromatic hydroxy compound and/or an isocyanate generated as a result of the pyrolytic reaction of the N-substituted carbamate, and particularly means a compound that can be present in the form of gas under conditions in which the present pyrolytic reaction is carried out.

For example, a method comprising recovering an isocyanate and an organic hydroxy compound generated as a result of the pyrolytic reaction as gaseous phase components, and also recovering a liquid phase component containing an N-substituted carbamate, can be adopted. In the present method, the isocyanate and the organic hydroxy compound may be recovered from the pyrolytic reaction vessel, separately. The recovered gaseous phase component containing an isocyanate is supplied, preferably in the form of a gaseous phase, to a distillation apparatus for purifying and separating the isocyanate. It is also possible to convert the recovered gaseous phase component containing an isocyanate to a liquid phase using a condenser or the like, and to supply it to a distillation apparatus. However, the apparatus becomes complicated, or enormous energy is required in many cases. Thus, it is not favorable. When the liquid phase component contains an N-substituted carbamate, a part or the whole of the liquid phase component is preferably supplied to the upper portion of the pyrolytic reaction vessel, and the N-substituted carbamate is again subjected to a pyrolytic reaction. Herein, when the pyrolytic reaction vessel is a distillation column for example, the term "the upper portion of the pyrolytic reaction vessel" is used herein to mean a plate that is two or more plates higher than the bottom of the column at a theoretical plate. When the pyrolytic reaction vessel is a thin film distillation apparatus, it means a portion higher than the portion to be heated. When a part or the whole of the liquid phase component is supplied to the upper portion of the pyrolytic reaction vessel, the liquid phase component is transferred, while retaining it preferably at 50° C. to 180° C., more preferably 70° C. to 170° C., and further preferably 100° C. to 150° C.

Moreover, a method comprising recovering, for example, an organic hydroxy compound, from an isocyanate and an organic hydroxy compound generated as a result of the pyrolytic reaction, as a gaseous phase component, and recovering a mixture containing the isocyanate as a liquid phase component from the bottom portion of the pyrolytic reaction vessel can be adopted. In this case, the liquid phase component is supplied to a distillation apparatus, and an isocyanate is then recovered. When the liquid phase component contains an N-substituted carbamate, a part or the whole of the mixture containing the N-substituted carbamate is preferably supplied to the upper portion of the pyrolytic reaction vessel, and the N-substituted carbamate is again subjected to a pyrolytic reaction. When a part or the whole of the liquid phase component is supplied to the upper portion of the pyrolytic reaction vessel, the liquid phase component is transferred, while retaining it preferably at 50° C. to 180° C., more preferably 70° C. to 170° C., and further preferably 100° C. to 150° C.

As stated above, in the pyrolytic reaction, the liquid phase component is preferably recovered from the bottom portion of the pyrolytic reaction vessel. This is because by allowing the liquid phase component to be present in the pyrolytic reaction vessel, the above described polymeric by-products generated as a result of side reactions caused by the N-substituted carbamate and/or the isocyanate can be dissolved, and they can be discharged as liquid phase components from the pyrolytic reaction vessel, and thus because it has an effect of reducing the amount of the polymeric compound adhering and/or accumulating to the pyrolytic reaction vessel.

When the liquid phase component contains the N-substituted carbamate, a part or the whole of the liquid phase component may be supplied to the upper portion of the pyrolytic reaction vessel, and the N-substituted carbamate may be subjected to a pyrolytic reaction again. However, if this step is repeatedly carried out, there is a case in which polymeric by-products are accumulated in the liquid phase component. In such a case, a part or the whole of the liquid phase component is removed from the reaction system, so that the amounts of the accumulated polymeric by-products can be reduced, or they can be maintained in a certain concentration. The liquid phase component removed from the reaction system contains an organic hydroxy compound in many cases. Such an organic hydroxy compound can be recovered from the liquid phase component according to a method such as distillation, and it can be used in Step (1). Also, the liquid phase component can be recycled in Step (1).

The type of the pyrolytic reaction vessel is not particularly limited. In order to efficiently recover the gaseous phase component, a known distillation apparatus is preferably used. For example, various types of known methods such as a method of using a reaction vessel containing any one of a distillation column, a multi-stage distillation column, a multitubular reaction vessel, a continuous multi-stage distillation column, a packed column, a thin film evaporator, a reaction vessel containing a support therein, a forced-circulation reaction vessel, a falling-film evaporator and a falling-drop evaporator, and a method of combining these devices, are used. From the viewpoint of the prompt removal of a low-boiling component from the reaction system, a method of using a tubular reaction vessel is preferable, and a method of using a reaction vessel such as a tubular thin film evaporator or a tubular falling-film evaporator is more preferable. A structure having a large gas-liquid contact area for promptly transferring the generated low-boiling component to the gaseous phase is preferable.

Materials for the pyrolytic reaction vessel and the line are not particularly limited, as long as they do not affect the N-substituted carbamate, an organic hydroxy compound and an isocyanate generated as products, and the like. Thus, known materials may be used. SUS304, SUS316, SUS316L, and the like are inexpensive, and thus, they can be preferably used.

There is a case in which the recovered isocyanate contains an organic hydroxy compound and the like, depending on reaction conditions, conditions for recovering the isocyanate, a reaction apparatus, etc. In such a case, operations such as distillation can be further carried out, and an isocyanate with a desired purity can be obtained.

In general, the reactivity of an organic hydroxy compound with an isocyanate is high, and thus, there are many cases in which an N-substituted carbamate is generated as a reaction of separating the two compounds by distillation. Accordingly, in such a case, there can be applied a method which comprises performing the distillation separation in a multi-stage distillation column, and supplying a mixture comprising the organic hydroxy compound and the isocyanate to an inactive site formed in the distillation column.

<Step (f): Precondensation Step>

In Step (3), an N-substituted carbamate is subjected to a pyrolytic reaction to produce an isocyanate. Such an isocyanate is highly reactive with active hydrogen (e.g. a hydroxy group of alcohol and a hydroxy group of an aromatic hydroxy compound), and it is in an equilibrium state represented by the following formula (60):

[Chemical Formula 48]

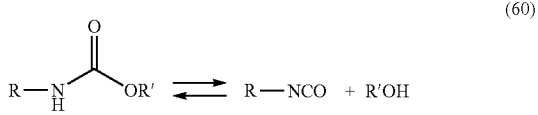

(60)

wherein R and R' each represent an organic group.

In the above formula (60), a pyrolytic reaction of a monofunctional N-substituted carbamate is shown, but a person skilled in the art could readily understand that the same reaction as described above progresses even using a polyfunctional N-substituted carbamate.

When the reaction solution containing an N-substituted carbamate and an organic hydroxy compound obtained in the above described Step (1) is directly used as a raw material in Step (3), since the organic hydroxy compound used in an excessive amount in Step (1) is present, the equilibrium represented by the above formula (60) lies on the left-hand side, and thereby the pyrolytic reaction tends to hardly progress. Accordingly, it is preferable to separate the organic hydroxy compound from the reaction solution. However, the organic hydroxy compound has a role of a solvent, which retains the N-substituted carbamate in the form of a solution and facilitates the handling of the N-substituted carbamate, such as transfer. Therefore, depending on the composition of the reaction solution, it cannot be necessarily said that it is preferable to separate all of organic hydroxy compounds.

From the aforementioned viewpoint, it is preferable to moderately separate the organic hydroxy compound from the reaction solution obtained in Step (1) and to use it in Step (3).

In Step (f), the temperature applied to the separation of the organic hydroxy compound depends on the composition of the reaction solution used. It is preferably in a range of 100° C. to 300° C. The pressure is preferably a reduced pressure, and the reaction is carried out in a pressure range of 20 to $1 \times 10^6$ Pa. If the temperature is too high, it is not preferable because the pyrolytic reaction of an N-substituted carbamate is induced. On the other hand, in a system in which a largely excessive amount of organic hydroxy compound is present, as described above, the pyrolytic reaction of an N-substituted carbamate hardly progresses. Accordingly, certain extents of high-temperature conditions can be determined. However, the degeneration reaction of the N-substituted carbamate should be considered, and thus, it is not preferable to retain the compound at a too high temperature for a long period of time. Therefore, it is necessary to distill the organic hydroxy compound away from the reaction solution in a short time.

The method for separating the organic hydroxy compound applied at that time is not particularly limited, and a known method can be adopted. For example, methods such as a distillation method, membrane separation or adsorptive separation can be applied. Among these methods, a distillation method is preferable.

As a device for carrying out the distillation method, a known device can be used, and both of tank-type and/or column-type reaction vessels can be used. For example, various types of known methods such as a method of using a distiller containing any one of a distillation column, a multi-stage distillation column, a continuous multi-stage distillation column, a packed column, a thin film evaporator, a falling-film evaporator and a falling-drop evaporator, and a method of combining these devices, are used. From the viewpoint of the prompt removal of an organic hydroxy compound, a method of using a tubular reaction vessel is preferable, and a method of using a reaction vessel such as a tubular thin film evaporator or a tubular falling-film evaporator is more preferable. A structure having a large gas-liquid contact area for promptly transferring the vaporized organic hydroxy compound to the gaseous phase is preferable.

The materials for the distiller and the line are not particularly limited, as long as they do not affect the N-substituted carbamate, the organic hydroxy compound and the like contained in the reaction solution, and known materials may be used. Examples of the material that can be used herein include glass, stainless steel, carbon steel, Hastelloy, a glass-lined base material, and a base material coated with Teflon (registered trademark). SUS304, SUS316, SUS316L, and the like are inexpensive, and thus, they can be preferably used. Instrumentation apparatuses such as a flowmeter and a thermometer, and known processing apparatuses such as a reboiler, a pump and a condenser may be added, as necessary. Heating may be carried out by known methods such as steam and a heater. For cooling, known methods such as natural cooling, the use of cooling water, and the use of brine can be used. Other steps may also be added, as necessary. In addition, it is preferable that a heat exchanger be prepared, and that the vapor of the organic hydroxy compound obtained in the precondensation step be introduced into the heat exchanger to perform a heat exchange reaction with a heat medium or water (water vapor), so as to recover and/or recycle the heat.

<Step (4): Ammonia Absorption Step>

Step (4) is a step of allowing a gaseous phase component (a second gaseous phase component) containing ammonia as a main component, which has been recovered as a gaseous phase component from the condenser in Step (2), to be absorbed by absorption water, thereby generating gas-absorbed water.

The gaseous phase component containing ammonia as a main component is used herein to mean a gaseous phase component recovered after completion of the condensation of a gaseous phase component containing urea and/or a compound having a carbonyl group derived from the urea, the organic hydroxy compound, and ammonia, described in the section of Step (2), by using a condenser comprised in a reaction vessel in which the carbamation step is carried out, and preferably, the ratio between the number of carbonyl groups (—C(=O)—) contained in the compound having a carbonyl group derived from urea, which is contained in ammonia recovered as gas from the condenser, and the number of ammonia molecules, is preferably 1:1 or less. Compounds comprised in the gaseous phase component are the same as those described in the above described section <Step (2)>.

It is to be noted that the gaseous phase component absorbed by absorption water in Step (4) may contain ammonia generated in the above described Step (a) and Step (c).

Gas-absorbed water is generated by allowing water to come into contact with the above described gaseous phase component containing ammonia as a main component.

The type of the water is not particularly limited, and all types of water, such as pure water or ion exchange water, can be used. It is also possible to use a part or the whole of the water obtained after ammonia has been separated from gas-absorbed water in the after-mentioned Step (5). In addition, as described later, the water may contain ammonia. The water may contain products generated as a result of side reactions caused by the method for producing an isocyanate of the present embodiment or the used raw materials themselves. That is, the "absorption water" may be either pure water or an aqueous solution in which a certain substance is dissolved.

For example, when carbon dioxide generated as a result of the pyrolysis of urea used as a raw material is contained in a gaseous phase component, the carbon dioxide is absorbed by water in the Step (4), although it depends on conditions. After such gas-absorbed water has been transferred to Step (5) and ammonia has been separated therefrom, the liquid phase component may contain a carbonate derived from the carbon dioxide, and the water can be used as water in the Step (4). In such a case, the carbonate is a compound containing carbonate ion ($CO_3^{2-}$), and it is not particularly limited. The carbonate is considered to be present in the form of an inorganic carbonate, an organic carbonate, etc. Examples of the inorganic carbonate include carbonates of alkaline metals (e.g. lithium carbonate, sodium carbonate, and potassium carbonate), carbonates of alkaline-earth metals (e.g. magnesium carbonate and calcium carbonate), and carbonates of transition metals (e.g. copper carbonate, iron carbonate, and silver carbonate). Examples of the organic carbonate include amine salts such as alkanolamine salts. Examples of the alkanolamine salts include a carbonate of monoethanolamine, a carbonate of diethanolamine, a carbonate of triethanolamine, a carbonate of N-methylethanolamine, a carbonate of N-methyldiethanolamine, a carbonate of N-ethyldiethanolamine, a carbonate of N,N-dimethylethanolamine, a carbonate of N,N-diethylethanolamine, a carbonate of 2-amino-2-methyl-1-propanol, and a carbonate of diisopropanolamine. When the inorganic carbonate is used as a carbonate, examples include inorganic hydroxides (for example, hydroxides of alkaline metals (e.g. lithium hydroxide, sodium hydroxide, and potassium hydroxide) and hydroxides of alkaline-earth metals (e.g. magnesium hydroxide and potassium hydroxide)).

Moreover, as in the case of the above described carbon dioxide, there are no problems, even if an organic primary amine, a hydroxy compound, an N-unsubstituted carbamate and the like are contained in water as by-products caused by the method for producing an isocyanate of the present embodiment, the raw materials used, and the like.

The mixing ratio between a gaseous phase component containing ammonia as a main component and water depends on the conditions applied in the Step (4) or the composition of the gaseous phase component. Water is preferably used in a range of 1.2 kg to 200 kg with respect to 1 kg of the gaseous phase component. Since a large amount of ammonia can be efficiently removed from the gaseous phase component containing ammonia as a main component by using a large amount of water, the amount of the residual gaseous phase component can be reduced, so that the load on pressure-controlling devices (decompression devices such as a vacuum pump used under a reduced pressure, and intensifying devices such as a compressor and a pressure keeping valve used under high pressure) can also be reduced. On the other hand, if an extremely large amount of water is used, it causes a problem that a device for generating gas-absorbed water is enlarged. From such a viewpoint, the amount of water used is more preferably in a range of 2 kg to 150 kg, and further preferably in a range of 5 kg to 100 kg.

The temperature applied during the generation of gas-absorbed water is not particularly limited, as long as it is a temperature at which the water can be treated as a liquid (wherein a solid may be partially contained in the water). If taking into consideration the after-mentioned Step (5) of heating gas-absorbed water to separate ammonia therefrom, the temperature applied in Step (4) is desirably at least lower than the temperature applied in Step (5), and it is preferably 1° C. to 60° C., more preferably 3° C. to 40° C., and further preferably 5° C. to 30° C.

The pressure applied during the generation of gas-absorbed water is not particularly limited, and any pressure conditions, such as a compressed pressure, an ordinary pressure and a reduced pressure, can be selected. The pressure is preferably equivalent to the pressure applied in Step (2). In fact, there are many cases in which pressure loss during the supply of water through a pipe or pressure loss caused by instrumentation devices established in the pipe, such as a pressure gage, would take place, and thus, strictly speaking, it cannot be said that the same pressure is always applied, but it means that operations for increasing or decreasing pressure are not carried out.

The device for contacting the gaseous phase component containing ammonia as a main component with water is not particularly limited, and all types of devices may be used. Specifically, conventionally known reaction vessels, such as an agitation tank, a pressurized agitation tank, a depressurized agitation tank, a column-type reaction vessel, a plate column, and a packed column, can be used in combination, as appropriate. Materials for the device are not particularly limited. Known materials can be used. Examples of the material that can be used herein include glass, stainless steel, carbon steel, Hastelloy, a glass-lined base material, and a base material coated with Teflon (registered trademark). SUS304, SUS316, SUS316L, and the like are inexpensive, and thus, they can be preferably used. Instrumentation apparatuses such as a flowmeter and a thermometer, and known processing apparatuses such as a reboiler, a pump and a condenser may be added, as necessary. Heating may be carried out by known methods such as steam and a heater. For cooling, known methods such as natural cooling, the use of cooling water, and the use of brine can be used. Moreover, devices such as a solid-liquid separator, a liquid-liquid separator and a filter can be added, as necessary.

When a liquid obtained after the recovery of ammonia in Step (5) is used as absorption water, the gas-absorbed water obtained in Step (4) may comprise components contained in the aforementioned absorption water. Furthermore, the gas-absorbed water may also comprise a compound contained in the gaseous phase component containing ammonia as a main component, which has been recovered as a gaseous phase component from the condenser used in Step (2). Specifically, the gas-absorbed water preferably comprises ammonia, urea and/or isocyanic acid, an organic hydroxy compound, and water. Further, the gas-absorbed water may also comprise organic primary amines used as raw materials in the method for producing an isocyanate of the present embodiment, carbonic acid derivatives generated during the production of the isocyanate, such as an N-unsubstituted carbamate or a carbonic acid ester, compounds having a ureido group, and biuret, triuret, carbon dioxide (carbonate), ammonium carbamate and the like, which are derived from an N-substituted carbamate and urea.

<Step (5): Ammonia Stripping Step>

Step (5) is an ammonia stripping step of heating gas-absorbed water generated in Step (4) to separate ammonia from the gas-absorbed water.

The gas-absorbed water is transferred to a device in which the ammonia stripping step is carried out. The temperature applied in the separation of gaseous ammonia from the gas-absorbed water is not particularly limited. Since ammonia is dissolved in the gas-absorbed water, in order to convert the ammonia to a gaseous component, it is adequate that the temperature is as high as possible, and it is preferably in a range of 60° C. to 110° C. Moreover, the present temperature is preferably at least higher than the temperature applied in Step (4). The gas-absorbed water is heated to the boiling point thereof (or a temperature close to the boiling point thereof), so as to obtain gaseous ammonia. At this time, the pressure may be a compressed pressure, an ordinary pressure or a reduced pressure, and it is preferably an ordinary pressure, or an ordinary or compressed pressure in a range in which a device for retaining the pressure is not necessary.

The heating of the absorption water may be carried out at any point in the Step (5). The heating operation may be carried out in a part or the whole of a device for generating gaseous ammonia, which will be described later. Otherwise, a heating device may be established on a portion of a pipe for supplying the gas-absorbed water to the aforementioned device, which is close to the device, and the gas-absorbed water may be heated immediately before being supplied to the device.

The pressure applied in the ammonia stripping step is not particularly limited. Since ammonia is generated from the gas-absorbed water according to gas-liquid equilibrium, a reduced pressure system is preferably used for the purpose of promptly discharging gaseous ammonia from the system. In addition, in association with the above described temperature, it is preferable that the temperature be set at a temperature higher than the boiling point of the gas-absorbed water under an ordinary pressure, and that gaseous ammonia be generated under a compressed pressure (or under a slightly compressed pressure).

The device for generating gaseous ammonia is not particularly limited, and all types of devices may be used. Specifically, conventionally known reaction vessels, such as an agitation tank, a pressurized agitation tank, a depressurized agitation tank, a column-type reaction vessel, a plate column, and a packed column, can be used in combination, as appropriate. Materials for the device are not particularly limited. Known materials can be used. Examples of the material that can be used herein include glass, stainless steel, carbon steel, Hastelloy, a glass-lined base material, and a base material coated with Teflon (registered trademark). SUS304, SUS316, SUS316L, and the like are inexpensive, and thus, they can be preferably used. Instrumentation apparatuses such as a flowmeter and a thermometer, and known processing apparatuses such as a reboiler, a pump and a condenser may be added, as necessary. Heating may be carried out by known methods such as steam and a heater. For cooling, known methods such as natural cooling, the use of cooling water, and the use of brine can be used. Moreover, devices such as a solid-liquid separator, a liquid-liquid separator and a filter can be added, as necessary.

The device for generating gaseous ammonia needs to comprise a discharge port for recovering gaseous ammonia. The discharge port may be established on any portion of the device, unless it is immersed in a liquid phase. The discharge port is preferably established on the highest portion of the device, viewing from the height direction (for example, a column top portion in the case of a distillation column, and a tank top portion in the case of agitation tank).

As described above, when gas-absorbed water is generated in Step (4), there are many cases in which various compounds, which are caused by the method for producing an isocyanate and are derived from raw materials and by-products, are contained in the gas-absorbed water. Specifically, the gas-absorbed water may comprise an organic primary amine, urea and an organic hydroxy compound used as raw materials in the method for producing an isocyanate of the present embodiment, carbonic acid derivatives generated during the production of the isocyanate, such as an N-unsubstituted carbamate or a carbonic acid ester, compounds having a ureido group, and biuret, triuret, carbon dioxide (carbonate), ammonium carbamate and the like, which are derived from an N-substituted carbamate and urea. Moreover, ammonia may remain in the liquid phase.

These compounds contained in the gas-absorbed water may be recovered as gaseous phase components together with ammonia in the Step (5), or may be recovered as liquid phase components. Whether the compounds are recovered as gaseous phase components or liquid phase components can be determined by the above described devices and conditions (temperature, pressure, etc.), and it can be arbitrarily determined while considering the properties of components contained in the gas-absorbed water.

On the other hand, when the recovery of high-purity ammonia in Step (5) is desired, it is preferable to recover as small as possible amounts of components to the gaseous phase, other than ammonia, contained in the gas-absorbed water obtained in Step (4).

After the generation of ammonia, water may be directly discarded, or it may be discarded after active components have been recovered from the water. Alternatively, the water may be directly recycled as absorption water in Step (4), or after active components have been recovered from the water, it may be recycled as absorption water in Step (4).

When the water is used as a part or the whole of the absorption water in Step (4), in order to avoid the accumulation and/or precipitation of the compounds contained in the water in the reaction system, the following steps may be further established, depending on the properties of the contained compounds.

<Organic Hydroxy Compound Separation Step>

As described above, a liquid phase component obtained after the separation of ammonia in the ammonia stripping step may comprise an organic hydroxy compound in some cases. Examples of such an organic hydroxy compound include alcohol and aromatic hydroxy compounds, which are used in the production of an N-substituted carbamate.

These organic hydroxy compounds are not necessarily dissolved in water. In the case of alcohol, methanol, ethanol and propanol are well dissolved in water. However, for example, 1-butanol only has a solubility of approximately 7.7 g in 100 mL of water at 20° C. Thus, as the number of carbon atoms contained in alcohol increases, the solubility of the alcohol in water tends to be decreased. On the other hand, in the case of aromatic hydroxy compounds, phenol is well dissolved in water. However, for example, p-cresol only has a solubility of approximately 1.9 g in 100 mL of water at 25° C. Thus, as the number of carbon atoms contained in an aromatic hydroxy compound increases, the solubility of the aromatic hydroxy compound in water tends to be decreased. In the case of the production of an N-substituted carbamate of the present embodiment, since it is necessary to set the reaction temperature at high (for example, 200° C. or higher) in order to generate the N-substituted carbamate, it is preferable to use an organic hydroxy compound having a relatively high boiling point. Boiling point is a value specific to each compound, and thus it cannot be easily assumed from the structure of the compound. However, in general, an organic hydroxy compound containing many carbon atoms tends to have a high boiling point. Accordingly, in the method for producing an N-substituted carbamate of the present embodiment, an organic hydroxy compound containing many carbon atoms is used in many cases. When a liquid phase component obtained after the separation of ammonia in the ammonia stripping step comprises an organic hydroxy compound, the liquid phase component comprises water. The organic hydroxy compound is separated from the water according to phase separation in many cases, and further, such a system is preferable. What is more, when they are separated from each other according to phase separation, it is preferable to select an organic hydroxy compound and operating conditions (temperature and pressure) in the ammonia stripping step, under which the two phases are present in the form of a liquid.

When a liquid phase component obtained after the separation of ammonia in the ammonia stripping step comprises an organic hydroxy compound, as described above, the liquid phase component may be used as absorption water in Step (4). However, if the liquid phase component is continuously used, accumulation of organic hydroxy compounds in the liquid phase component would progress, and there is a case in which the efficiency is significantly decreased in Step (4) and Step (5). Accordingly, it is preferable that the present method further comprise an organic hydroxy compound separation step of separating the organic hydroxy compound contained in the liquid phase component from an aqueous solution (water phase).

The method of carrying out the organic hydroxy compound separation step is not particularly limited. A known method such as distillation separation, liquid separation, membrane separation, or extraction separation can be applied, as appropriate.

As described above, when the organic hydroxy compound is separated from the aqueous solution according to phase separation in the liquid phase component obtained after the separation of ammonia in the ammonia stripping step, a method according to liquid separation is preferably applied. The type of the method according to liquid separation is not particularly limited, unless it goes against the gist of the present embodiment. For example, the liquid phase component is placed in a liquid-liquid separator, and is then left at rest. Then, one phase or both of two phases, after completion of the phase separation, are discharged from the liquid-liquid separator. The liquid-liquid separator is not particularly limited, and a known liquid-liquid separator can be used. Such a liquid-liquid separator may comprise a liquid-level gauge, a partition plate and the like therein, as necessary. Alternatively, in order to keep the temperature thereof constant, the liquid-liquid separator may comprise a heater or a cooler. In general, an organic hydroxy compound and water have low solubility, but they are dissolved in each other in almost all cases. In general, since a liquid having a lower temperature has lower solubility, in order to efficiently separate the organic hydroxy compound from the water, the temperature applied to liquid-liquid separation is preferably set at as low as possible, as long as both the organic hydroxy compound and the water can be present in the form of a liquid.

In addition, in a liquid phase component obtained after the separation of ammonia in the ammonia stripping step, when an organic hydroxy compound is not separated from an aqueous solution according to phase separation, a method according to distillation separation is preferably applied. The method according to distillation separation is not particularly limited, unless it goes against the gist of the present embodiment. For example, the liquid phase component is supplied to a distillation column, and operating conditions, such as temperature and pressure, under which an organic hydroxy compound can be separated from water according to distillation separation, are arbitrarily determined, so that the two components can be separated from each other.

<Liquid Phase Blow-Down Step>

As described in the above sections <Step (4)> and <Step (5)>, there are many cases in which the liquid phase component in Step (4) and Step (5) comprises various compounds derived from the method for producing an isocyanate of the present embodiment. If the liquid phase component obtained after the separation of ammonia in Step (5) or the water phase that has undergone the above described <organic hydroxy compound separation step> is repeatedly used as absorption water in Step (4), there is a case in which various compounds derived from the method for producing an isocyanate of the present embodiment are accumulated in the liquid phase component or the water phase, thereby causing problems such as precipitation of the compounds in the system. In order to avoid such problems, it is preferable to discharge a portion of the liquid phase component or the water phase from the system of the present embodiment, as appropriate. Moreover, in order to keep the amount of the liquid phase component or the water phase component in the system constant, it is also preferable to add water or the like to the system, as appropriate. The discharged liquid phase component may be discarded after active components have been recovered, or it may be directly discarded. Taking into consideration operational situation, the place in the system in which the liquid phase component or the water phase is discharged, and the amount and/or frequency of discharge, can be arbitrarily determined.

<Absorption Water Recycling Pre-Treatment Step>

The absorption water recycling pre-treatment step is a step of pre-treating the liquid phase component after the separation of ammonia in Step (5) or the water phase that has undergone the above described <organic hydroxy compound separation step> in order to use them as a part or the whole of the absorption water in Step (4). Specifically, it is a step of cooling the water phase depending on the operating conditions in Step (4), or adding ammonia, as necessary.

The liquid phase component after the separation of ammonia in Step (5) or the water phase that has undergone the above described <organic hydroxy compound separation step> is preferably used as absorption water in the above described Step (4). There is a case in which even the water phase that has undergone the <organic hydroxy compound separation step> may contain an organic hydroxy compound. For example, when the organic hydroxy compound is separated from water by using a liquid-liquid separator, although the organic hydroxy compound and the water generally have low solubility, they are dissolved in each other in almost all cases, as described above. Thus, even in a case in which the separation has been carried out at a low temperature, there are many cases in which a small amount of organic hydroxy compound remains in the water phase. As described in the section of Step (4), in order to increase the efficiency of absorbing ammonia, it is necessary to set the temperature of absorption water at low. However, if the temperature of the water is set at low when it is used as absorption water in Step (4), there may be a case in which such a small amount of organic hydroxy compound contained in the water would be aggregated and precipitated. In such a case, the solubility of the organic hydroxy compound can be increased by allowing the water to contain a small amount of ammonia. The reason why such a small amount of ammonia provides such effects has not been clarified. In particular, when the organic hydroxy compound is an aromatic hydroxy compound, it exhibits acidity in many cases. Thus, the present inventors have assumed that ammonium salts would be formed as a result of addition of ammonia, and that the ammonia salts would provide the effect of improving solubility in water. The amount of ammonia added can be determined, as appropriate, depending on the type of the organic hydroxy compound contained or operating conditions (temperature, pressure, etc.) in Step (4). Moreover, the ammonia used at that time may be a portion of the ammonia recovered in Step (5), and it may be added in the form of either gaseous ammonia or ammonia water.

<Use of Recovered Ammonia>

In the present embodiment, the ammonia separated in the above described Step (5) has high purity. In general, ammonia is produced from nitrogen and hydrogen according to a Haber-Bosch process. Hydrogen is produced by the steam-reforming of hydrocarbon or the like in many cases, and thus, there is a case in which hydrocarbon contained in hydrogen as a raw material would be contained in ammonia. In particular, methane is a hydrocarbon compound having the lowest boiling point, and thus, there is a case in which, for example, 1000 ppm to 5000 ppm of methane would be contained in ammonia through the hydrogen used as a raw material. In addition, since nitrogen existing in air is used as nitrogen as a raw material, there is a case in which components contained in the air would be contained in ammonia. There is a case in which, for example, 1000 ppm to 5000 ppm of argon would be contained in ammonia. On the other hand, since ammonia recovered by the method of the present embodiment is produced without using hydrogen as a raw material, it substantially contains neither hydrocarbon compounds including methane as a typical example, nor rare gas components such as argon. With regard to ammonia recovered in Step (5) (ammonia stripping step), the amount of either methane or argon contained in the ammonia can be set at 0.05 wt % or less. The ammonia recovered by the method of the present embodiment can be recovered in various forms. It is preferable to recover the ammonia in the form of liquid ammonia. Moreover, ammonia can be used as a cooling medium in absorption type refrigerators, an oil detergent for woolen goods, or a coagulant for fresh gum, or can also be used for the production of various types of ammonium salts, the treatment of NOx generated in a thermal power station and the like, the production of photographic emulsion, etc. Moreover, the ammonia is converted to liquid ammonia according to a method such as cryogenic separation, and it can be then used as a raw material for nitrogen fertilizers, a raw material for synthetic fibers (caprolactam or aclyronitrile), a raw material for urea, the treatment of NOx generated in a thermal power station and the like, as a cooling medium in refrigerators, etc. Furthermore, the recovered ammonia is burned to recover heat, and the thus recovered heat can be used as a heat source in the carbamation step and/or the isocyanate production step. In all of the use methods, the method for treating ammonia is not particularly limited, and a known method can be used, as appropriate.

In order to industrially produce urea, as shown in the following formula (61), first, ammonia is allowed to react with carbon dioxide, for example, so as to produce ammonium carbamate:

[Chemical Formula 49]

$$2NH_3 + CO_2 \rightarrow NH_2COONH_4 \quad (61)$$

The reaction of ammonia with carbon dioxide may be carried out according to a known method, and the reaction conditions (mixing method, temperature, pressure, etc.) are determined, as appropriate, depending on purpose and intended use.

Subsequently, in this method, the obtained ammonium carbamate is subjected to a dehydration reaction, so as to decompose it into urea and water, as shown in the following formula (60):

[Chemical Formula 50]

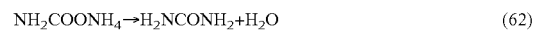

$$NH_2COONH_4 \rightarrow H_2NCONH_2 + H_2O \quad (62)$$

The dehydration reaction of ammonium carbamate may be carried out according to a known method, and the reaction conditions (temperature, pressure, etc.) are determined, as appropriate, depending on purpose and intended use.

It is to be noted that water generated as a by-product (discharged) in the aforementioned dehydration reaction can be used as water for absorbing ammonia in the production of gas-absorbed water.

The urea produced by the above described method is preferably used as a part or the whole of the raw material in the carbamation step.

<<Preferred Method for Producing Isocyanate-2>>

As an alternative method of the above described method for producing an isocyanate comprising Step (1) to Step (5), a method for producing an isocyanate comprising Step (1) to Step (3) and Step (4)' is also preferably carried out.

<Step (4)': Production of Ammonium Sulfate>

Step (4)' is an ammonia absorption step of allowing a gaseous phase component containing ammonia as a main component (a second gaseous phase component), which has been discharged from the condenser in Step (2), to be absorbed by sulfuric acid water, thereby generating ammonium sulfate.

The gaseous phase component containing ammonia as a main component means herein a gaseous phase component, which is recovered, after a gaseous phase component containing urea and/or a compound having a carbonyl group derived from the urea, an organic hydroxy compound, and ammonia, as described in the section of Step (2), has been condensed with a condenser comprised in a reaction vessel in which the carbamation step is carried out. It is preferably a gaseous phase component, in which the ratio between the number of carbonyl groups (—C(=O)—) contained in the compound having a carbonyl group derived from the urea, which is contained in ammonia recovered as gas, and the number of ammonia molecules is 1:1 or less. The compounds contained in the gaseous phase component are the same as the compounds described in the section of the above described <Step (2)>.

It is to be noted that the gaseous phase component absorbed by sulfuric acid water in Step (4)' may contain the ammonia generated in the above described Step (a) and Step (c).

Ammonium sulfate is generated by allowing sulfuric acid water (an aqueous solution of sulfuric acid) to come into contact with the above described gaseous phase component containing ammonia as a main component.

The mixing ratio between a gaseous phase component containing ammonia as a main component and sulfuric acid water depends on the conditions applied in the Step (4)' or the composition of the gaseous phase component. The mixing ratio can be determined while taking into consideration the concentration of the sulfuric acid water or the solubility of the generated ammonium sulfate, so that sulfuric acid ($H_2SO_4$) can be used at a stoichiometric ratio of preferably 0.5:1 to 10:1, more preferably 0 7:1 to 7:1, and further preferably 1:1 to 5:1, with respect to the ammonia contained in the gaseous phase component.

The pressure applied when Step (4)' is carried out is not particularly limited, and any pressure conditions, such as a compressed pressure, an ordinary pressure and a reduced pressure, can be selected. The pressure is preferably equivalent to the pressure applied in Step (2). In fact, there are many cases in which pressure loss during the supply of water through a pipe or pressure loss caused by instrumentation devices established in the pipe, such as a pressure gage, would take place, and thus, strictly speaking, it cannot be said that "the same pressure as the pressure applied in Step (2)" is applied, but it particularly means that operations for increasing or decreasing pressure are not carried out.

The device for contacting the gaseous phase component containing ammonia as a main component with the sulfuric acid water is not particularly limited, and all types of devices may be used. Specifically, conventionally known reaction vessels, such as an agitation tank, a pressurized agitation tank, a depressurized agitation tank, a column-type reaction vessel, a plate column, and a packed column, can be used in combination, as appropriate. Materials for the reaction vessel are not particularly limited, as long as they have sufficient corrosion resistance to the sulfuric acid water. Examples of the material that can be used herein include glass, stainless steel, carbon steel, Hastelloy, a glass-lined base material, a base material coated with Teflon (registered trademark), a base material coated with polyethylene, and a base material coated with polypropylene. SUS304, SUS316, SUS316L, and the like are inexpensive, and thus, they can be preferably used. Instrumentation apparatuses such as a flowmeter and a thermometer, and known processing apparatuses such as a reboiler, a pump and a condenser may be added, as necessary. Heating may be carried out by known methods such as steam and a heater. For cooling, known methods such as natural cooling, the use of cooling water, and the use of brine can be used. Moreover, devices such as a solid-liquid separator, a liquid-liquid separator and a filter can be added, as necessary.

The ammonium sulfate obtained in Step (4)' can be used as a nitrogenous fertilizer, or as a raw material for synthetic fertilizer.

<<Preferred Method for Producing Isocyanate-3>>

As an alternative method of the above described method for producing an isocyanate comprising Step (1) to Step (5), a method for producing an isocyanate comprising Step (1) to Step (3) and Step (6) to Step (8) can also be preferably carried out.

Step (1): a carbamation step of generating an N-substituted carbamate from an organic primary amine, urea and an organic hydroxy compound according to a carbamation reaction, and then recovering a first gaseous phase component containing urea and/or a compound having a carbonyl group derived from the urea, an organic hydroxy compound, and ammonia, Step (2): a condensation step of condensing the first gaseous phase component with a condenser, Step (3): an isocyanate production step of producing an isocyanate by subjecting the N-substituted carbamate to pyrolysis, Step (6): a regeneration step of allowing a part or the whole of the first residual liquid, from which low-boiling components containing the isocyanate and the organic hydroxy compound obtained in the isocyanate production step have been separated, to react with a carbonic acid derivative and an organic hydroxy compound, Step (7): a separation step of subjecting a reaction solution in the regeneration step to a pyrolytic reaction, so as to separate the generated isocyanate from a second residual liquid containing a non-regeneratable by-product, and Step (8): a blow-down step of heating the first residual liquid and/or the second residual liquid to recover low-boiling components containing an organic hydroxy compound, recycling the low-boiling components to at least one of the Steps (1), (3) and (6), and removing high-boiling components containing non-regeneratable by-products from the system.

Hereinafter, each of Steps (6), (7) and (8) will be described.

<Step (6): Regeneration Step>

Step (6) is a step of allowing a part or the whole of the residual liquid (first residual liquid) obtained in Step 3, from which low-boiling components containing an isocyanate and an organic hydroxy compound have been separated, to react with a carbonic acid derivative (e.g. urea) and an organic hydroxy compound.

There are many cases in which liquid phase components obtained after the recovery of an isocyanate generated by subjecting an N-substituted carbamate to a pyrolytic reaction in Step (3) may comprise polymeric by-products generated as a result of side reactions induced by the N-substituted carbamate and/or the isocyanate. There is a case in which the polymeric by-product would be a compound having a ureylene group for the reason that it is generated, for example, by a reaction represented by the following formula (63):

[Chemical Formula 51]

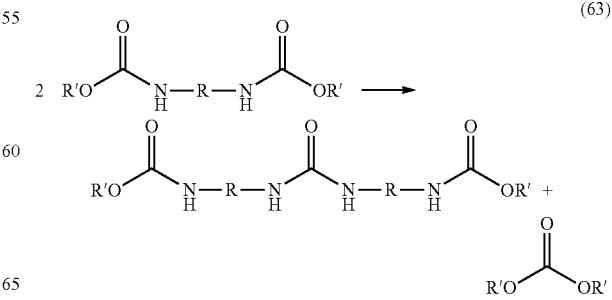

wherein R and R' independently represent an organic group substituted with two substituents.

The liquid phase component recovered in Step (3) may be supplied to the upper portion of the pyrolytic reaction vessel, and the N-substituted carbamate contained therein may be subjected to a pyrolytic reaction again. Alternatively, an organic hydroxy compound may be recovered from the liquid phase component according to a method such as distillation, and may be then recycled in Step (A) and/or Step (a) and/or Step (b) and/or Step (c) and/or Step (e). Otherwise, the two above methods may also be carried out. However, if an extremely large amount of liquid phase component intends to be recycled, the size of a reaction apparatus or the like in the recycling step may be enlarged, or the composition of a reaction system may not be stabilized, so that the reaction conditions should be changed frequently to create suitable reaction conditions. Accordingly, it is preferable to carry out the recycling of the liquid phase component in another step (namely, in Step (6)).

In Step (6), a part or the whole of the residual liquid obtained in Step 3, from which low-boiling components containing an isocyanate and an organic hydroxy compound have been separated, is allowed to react with urea and an organic hydroxy compound. The reaction in the Step (6) can be carried out by the same method as that in the above described Step (d).

As described above, the liquid phase component obtained in Step (3) contains a compound having a ureylene group or a compound having a biuret group in many cases. Step (6) is a step of reacting a compound having a ureylene group (e.g. a compound of the following formula (64)) or a compound having a biuret group (e.g. a compound of the following formula (65)), which are generated by such reactions, with urea, so as to obtain an N-substituted carbamate. Preferably, the aforementioned compound is allowed to react with urea having a carbonyl group (—C(=O)—) under heating them at a temperature higher than the thermal dissociation temperature of a ureylene group and/or a biuret group, so as to obtain an N-substituted carbamate.

[Chemical Formula 52]

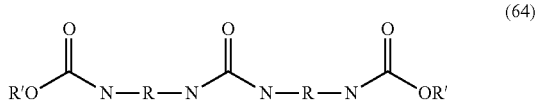
(64)

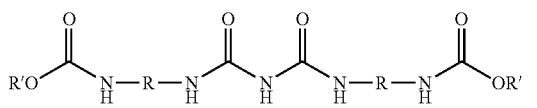
(65)

wherein R and R' independently represent an organic group.

The Step (6) is preferably carried out in the coexistence of an organic hydroxy compound. When the liquid phase component recovered in Step (3) contains an organic hydroxy compound in an amount sufficient for being used in Step (6), it can be directly used. On the other hand, when the liquid phase component does not contain a sufficient amount of organic hydroxy compound, a necessary amount of organic hydroxy compound can be newly added. The organic hydroxy compound may be either the alcohol represented by the above formula (17) or the aromatic hydroxy compound represented by the above formula (18). In addition, as necessary, a carbonic acid derivative such as urea or an organic primary amine is added to the liquid phase component recovered in Step (3), and the obtained mixture can be then used in Step (6).

The reaction in the Step (6) is the same as that in Step (d), and thus, the same method as that in Step (d) may be carried out. The reaction of the compound having a ureylene group represented by the above formula (46) with a carbonic acid derivative is carried out in a state in which they are heated to a temperature higher than the thermal dissociation temperature of the ureylene group of the compound having a ureylene group represented by the above formula (46). The "thermal dissociation temperature" is a temperature as defined above, and it is preferably between 100° C. or higher and 350° C. or lower. If the thermal dissociation temperature is too low, the thermal dissociation reaction rate becomes low, and as a result, the reaction efficiency is deteriorated. In contrast, if the thermal dissociation temperature is too high, it induces denaturation reactions of isocyanate groups or amino groups generated as a result of the thermal dissociation reaction. Accordingly, the thermal dissociation temperature is more preferably between 120° C. or higher and 330° C. or lower, and further preferably between 140° C. or higher and 300° C. or lower.

The amount of a carbonic acid derivative used depends on the type of the carbonic acid derivative or reaction conditions. The number of the carbonic acid derivatives is preferably 5 or less with respect to the number of the ureylene groups of the compound having ureylene groups in many cases. In order to increase the reaction rate so as to achieve high reaction efficiency, the amount of the carbonic acid derivative is preferably large. However, if a largely excessive amount of carbonic acid derivative is used, there may be a case in which it induces side reactions such as N-alkylation. Accordingly, the number of the carbonic acid derivatives is set at preferably 3 or less, and more preferably 2 or less, with respect to the number of the ureylene groups of the compound having ureylene groups.

The reaction of the compound having a ureylene group with the carbonic acid derivative is preferably carried out in the presence of a solvent. The type of such a solvent is not particularly limited, as long as it is a compound that is able to dissolve the compound having a ureylene group and the carbonic acid derivative and is stable at a reaction temperature. The same solvents as those described in the section <Step (1)>, or alcohols and aromatic hydroxy compounds described in the section <Organic hydroxy compound>, can be used. In particular, aromatic hydroxy compounds are preferably used, in that the compound having a ureylene group is highly soluble therein and in that the aromatic hydroxyl compounds have a high effect of stabilizing a compound having an amino group generated as a result of the thermal dissociation reaction of the ureylene group.

The present reaction is carried out under any condition of a compressed pressure, an ordinary pressure, and a reduced pressure. Moreover, the present reaction is preferably carried out in an inert gas atmosphere, such as nitrogen, argon, helium or neon.

As a reaction apparatus, conventionally known reaction vessels, such as an agitation tank, a pressurized agitation tank, a depressurized agitation tank, a column-type reaction vessel, a distillation column, a packed column, and a thin film distiller, can be used in combination, as appropriate. In order to keep the reaction temperature constant, a known cooling device and/or heating device may be equipped. In addition, materials used for the reaction vessel are not particularly limited. Known materials can be used. Examples of the material that can be used herein include glass, stainless steel, carbon steel, Hastelloy, a glass-lined base material, and a base material coated with Teflon (registered trademark).

In the present embodiment, from the viewpoint of an increase in the reaction efficiency, the Step (6) is preferably carried out by using a distillation column. Regarding a method of carrying out the Step (6) by using a distillation column, the same method as that in the above described Step (d) can be adopted.

<Step (7): Separation of Residual Liquid Comprising Non-Regeneratable by-Products>

Step (7) is a step of subjecting the reaction solution in Step (6) to a pyrolytic reaction, so as to separate the generated isocyanate from a residual liquid (a second residual liquid) containing a non-regeneratable by-product. Specifically, the N-substituted carbamate regenerated in the above described Step (6) is subjected to a pyrolytic reaction to generate an isocyanate and an organic hydroxy compound, and thereafter, the isocyanate is separated from a residual liquid containing a non-regeneratable by-product. In the Step (7), the same method as that applied in the above described Step (3) can be applied.

The residual liquid recovered in Step (7) contains various by-products that are assumed to be generated as a result of a complicated combination of the reactions, for example, represented by the following formulae (66) to (69) (wherein only functional group portions are described).

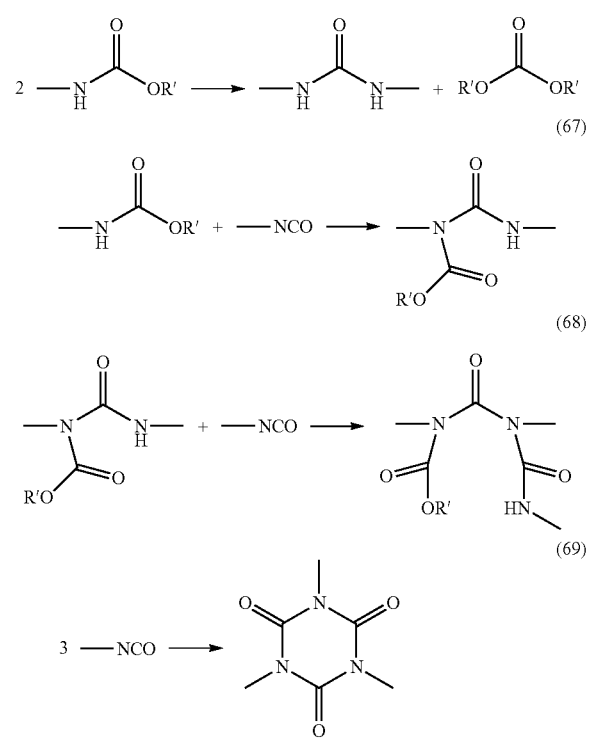

wherein R' represents an organic group.

In the above formulae (66) to (69), only the functional group portions are described. When an organic primary amine containing two or more functional groups is used as a raw material, each terminal functional group independently induces the reactions as represented by the above formulae (66) to (69). Accordingly, the by-products thereof include various binding modes, and have a wide range of molecular weight. The bond itself represented on the right-hand side of each of the above formulae (66) to (69) is likely to be thermally dissociated under reaction conditions, under which Step (7) is carried out. In the case of a compound in which a plurality of molecules bind to one another according to various binding modes, a molecule generated as a result of the thermal dissociation has a high molecular weight and a high boiling point. Accordingly, there is a case in which the compound is recovered as a non-regeneratable component. The bond represented on the right-hand side of the formula (69) has an extremely high thermal dissociation temperature (e.g. 350° C. or higher), and thus, it is not renewable in many cases.

When the pyrolytic reaction takes place in Step (7), a liquid phase component comprising such a non-regeneratable by-product can be treated as a liquid phase component having a relatively low viscosity because it is sufficiently heated. However, there is a case in which such a liquid phase component has a high viscosity when it is discharged from the reaction vessel in which the pyrolytic reaction takes place and is then cooled. Accordingly, the liquid phase component in Step (7) is preferably treated in a temperature range in which the liquid phase component exhibits a sufficiently low viscosity. In addition, it is also preferable to add a solvent or the like to such an extent that the liquid phase component exhibits a sufficiently low viscosity even when it is cooled. A preferred solvent used at that time is an organic hydroxy compound, and particularly, an aromatic hydroxy compound. The same operation as described above can also be carried out on a liquid phase component recovered in Step (3).

The residual liquid recovered in Step (7) may be subjected to the pyrolytic reaction in Step (7), or may be subjected to Step (8) as described later. The viscosity of the residual liquid is preferably 1000 mPa·s or less, when the residual liquid is transferred to Step (8). The viscosity means herein a viscosity under conditions in which the residual liquid is transferred to Step (8). Thus, the viscosity may be actually measured by establishing a viscometer in a pipe for transferring the residual liquid. Alternatively, the residual liquid may be sampled, and the viscosity thereof under transferring conditions may be then measured, separately. At that time, a viscometer capable of performing a simple measurement, such as a B-type viscometer, can be used. Moreover, it is also preferable for the residual liquid recovered in Step (3) to have a viscosity of 1000 mPa·s or less, when it is transferred to Step (8).

<Step (8): Recovery of Organic Hydroxy Compound from Residual Liquid and Blow-Down>

Step (8) is a blow-down step of heating the residual liquid obtained in Step (3) and/or Step (7) to recover low-boiling components containing an organic hydroxy compound, recycling the low-boiling components to at least one of the Steps (1), (3) and (6), and removing high-boiling components containing non-regeneratable by-products from the system.

There is a case in which the residual liquid obtained in Step (3) and/or Step (7) contains an organic hydroxy compound at a time point at which it is discharged from a reaction vessel in which Step (3) and/or Step (7) are carried out. Otherwise, as described above, there is also a case in which such an organic hydroxy compound is added to the liquid phase component in order to decrease the viscosity thereof. Moreover, the residue (which is —OR' in the above formulae (67) and (68)) of the organic hydroxy compound is contained in the bond represented on the right-hand side of each of the above formulae (67) and (68), and it is likely that such a residue will be recovered as an organic hydroxy compound (R'OH) by heating it to a high temperature. It is necessary to remove (blow-down) a non-regeneratable component from the reaction system in order to prevent the accumulation thereof in the system. However, if an organic hydroxy compound, as well as such a non-regeneratable component, is removed, it would lead to an increase in waste materials or the waste of resources. Thus, these organic hydroxy compounds are preferably recovered.

Specifically, the residual liquid obtained in Step (3) and/or Step (7) is heated by using at least one device selected from the group consisting of:

(a) a paddle type dryer comprising a forced transfer device;

(b) an extruder comprising a degassing function; and (c) a vertical thin film evaporator comprising a forced transfer device.

In a paddle type dryer, which comprises a forced transfer machine and does not have a cooling zone, the residual liquid cannot be separated into a heating zone and a cooling zone, and thus, a drastic decrease in the temperature that is much more than 100° C., as described, for example, in U.S. Pat. No. 5,962,728, does not occur. Instead, the temperature of a residue is increased in a process in which the residue is passed through the device, and a temperature gradient in the process in which the residue is passed through the device is changed, while it does not exceed 50° C., and preferably, there is not a substantial temperature change in the process in which the residue is passed through the device. Such a paddle type dryer is configured substantially horizontally, and in this case, the residue is generally transferred through one or two mixing shafts and kneading shafts equipped in the device. These devices include a particle bed reaction vessel, a kneading dryer, and a kneading reaction vessel.

Heating is carried out through a wall according to any given method. Preferably, heating is carried out not only through the outer wall of the device, but also through an internal structure, such as a cleaning hook, a segment plate, and a kneading shaft.

The section, in which the residue supplied to a paddle type dryer is heated, is preferably between 10% or more and 70% or less, more preferably between 20% or more and 60% or less, and particularly preferably between 30% or more and 50% or less, with respect to the entire length of the paddle type dryer.

In the present embodiment, as a transfer device that can be used herein for the forced transfer of the residue after the organic hydroxy compound has been decreased, a screw, and preferably, a twin screw can be used.

Moreover, the paddle type dryer is preferably operated together with a device for condensing the vapor of the organic hydroxy compound, and thereby, the separated organic hydroxy compound can be recovered.

In the present embodiment, the effective volume of the paddle type dryer is filled with preferably 25% to 90% of, more preferably 30% to 80% of, further preferably 40% to 75% of, and particularly preferably 50% to 70% of residue.

In the case of an extruder comprising a degassing function, the residual liquid obtained in Step (3) and/or (7) is extruded against an orifice plate or a slot plate under a reduced pressure. The residue is blended by being kneaded in the extruder, and an organic hydroxy compound is separated. The organic hydroxy compound is condensed, as appropriate, and it can be then recycled.

In the case of a vertical thin film evaporator comprising a forced transfer device, the residue on the heated surface is applied and extended as a thin film, and as a result, an easily volatile organic hydroxy compound can be separated. In addition, as necessary, inert gas such as nitrogen can be passed through the residue under separation conditions. There is a case in which after the separation of the organic hydroxy compound, the residue had high viscosity at a time point at which it reached the lower terminus of the thin film evaporator, and in such a case, the residue can be discharged from the bottom of the column, by using a suitable forced transfer system such as a screw or a shaft.

<Washing of Device>

In the production of an isocyanate of the present embodiment, there may be a case in which a polymeric by-product and the like would be generated, and as a result, conditions for operating the reaction device would be changed, or when such operation is carried out for a long period of time, such a polymeric by-product would adhere to the device.

In such a case, the inside (particularly, the wall surface) of the concerned device is washed with an acid that is a good solvent for the polymeric by-product, so that the inside of the reaction vessel can be maintained clean.

The type of an acid used in the washing is not particularly limited, as long as it dissolves the polymeric by-product. Either an organic acid or an inorganic acid may be used. Preferably, an organic acid is used. Examples of such an organic acid include carboxylic acid, sulfonic acid, sulfinic acid, an aromatic hydroxy compound, enols, thiophenols, imides, oximes, and aromatic sulfonamides. Preferably, carboxylic acid and an aromatic hydroxy compound are used. Examples of such carboxylic acid include saturated or unsaturated aliphatic monocarboxylic acid compounds such as formic acid, acetic acid, propionic acid, n-butyric acid, isobutyric acid, valeric acid, isovaleric acid, 2-methylbutanoic acid, pivalic acid, hexanoic acid, isocaproic acid, 2-ethylbutanoic acid, 2,2-dimethylbutanoic acid, heptanoic acid (each isomer), octanoic acid (each isomer), nonanoic acid (each isomer), decanoic acid (each isomer), undecanoic acid (each isomer), dodecanoic acid (each isomer), tetradecanoic acid (each isomer), hexadecanoic acid (each isomer), acrylic acid, crotonoic acid, isocrotonoic acid, vinyl acetate, metacrylic acid, angelic acid, tiglic acid, allyl acetate, or undecenoic acid (each isomer), saturated or unsaturated aliphatic dicarboxylic acids such as oxalic acid, malonic acid, succinic acid, glutaric acid, adipic acid, heptanedioic acid (each isomer), octanedioic acid (each isomer), nonanedioic acid (each isomer), decanedioic acid (each isomer), maleic acid, fumaric acid, methyl maleate, methyl fumarate, pentenedioic acid (each isomer), itaconic acid, or allyl malonate, saturated or unsaturated aliphatic tricarboxylic acid compounds such as 1,2,3-propanetricarboxylic acid, 1,2,3-propenetricarboxylic acid, or 2,3-dimethylbutane-1,2,3-tricarboxylic acid, aromatic cartoxylic acid compounds such as benzoic acid, methyl benzoate (each isomer), ethyl benzoate (each isomer), propyl benzoate (each isomer), dimethyl benzoate (each isomer), or trimethyl benzoate (each isomer), aromatic dicarboxylic acid compounds such as phthalic acid, isophthalic acid, terephthalic acid, or methyl isophthalate (each isomer), and aromatic tricarboxylic acid compounds such as hemimellitic acid, trimellitic acid, or trimesic acid. As aromatic hydroxy compounds, those described in the above section "Aromatic hydroxy compound" can be used.

When such an aromatic hydroxy compound is used as an acid for washing, from the viewpoint of washing effect, the standard boiling point of the aromatic hydroxy compound preferably has a difference in boiling point of 10° C. or higher from the standard boiling point of the generated isocyanate.

EXAMPLES

Example 1

The apparatus shown in FIG. 1 was used. The apparatus shown in FIG. 1 is an apparatus for carrying out a carbamation step, step of separating a gaseous phase component containing ammonia as a main component, a step of producing gas-absorbed water, an ammonia separation step, a urea production step, and an isocyanate production step.

A mixture of 7.2 kg of hexamethylenediamine, 7.5 kg of urea (wherein 5.3 kg out of 7.5 kg of the urea was produced in the after-mentioned urea production equipment 107), and 261.9 kg of 4-(1,1,3,3-tetramethylbutyl)phenol was supplied at a rate of approximately 92.2 kg/Hr through a line 1 to a continuous multistage distillation column 101. A mixture of 4-(1,1,3,3-tetramethylbutyl)phenol and urea, which had been obtained in a condenser 103, was supplied at a rate of approximately 9.56 kg/Hr through a line 4 to the continuous multistage distillation column 101. The continuous multistage distillation column 101 was a device for carrying out a carbamation step, and by heating the device with a reboiler 111, the column bottom temperature thereof was set at 250° C., and the column top pressure thereof was set at 5 kPa. A reaction solution was discharged at a rate of approximately 90.7 kg/Hr from the bottom portion of the continuous multistage distillation column 101, and was then supplied through a line 5 to a pyrolysis device 102. The pyrolysis device 102 was a thin film evaporator for generating hexamethylene diisocyanate as a result of the pyrolytic reaction of a carbamate, and the internal pressure thereof was set at 1 kPa. The pyrolysis device 102 was heated to 250° C. by being heated from the outside thereof. A gaseous phase component generated in the pyrolysis device 102 was supplied through a line 7 to a separation column 109, and 4-(1,1,3,3-tetramethylbutyl)phenol was then separated from hexamethylene diisocyanate. Heat necessary for distillation separation was supplied from a reboiler 112. 4-(1,1,3,3-Tetramethylbutyl)phenol was recovered from the column bottom of the separation column 109 through a line 18. A component recovered from the column top of the separation column 109 was supplied through a condenser 114 and a line 20 to a purification column 110, and hexamethylene diisocyanate was then purified by distillation. Heat necessary for the purification by distillation was supplied from a reboiler 113. From the column top of the purification column 110, hexamethylene diisocyanate was recovered at a rate of approximately 2.4 kg/Hr through a condenser 115 and a line 2. A component remaining at the column bottom of the purification column 110 was discharged through a line 19. A portion of a liquid phase component recovered from the bottom portion of the pyrolysis device 102 was blown down from the system through a line 8, and the remaining liquid phase component was supplied to the pyrolysis device 102 again through a line 6.

On the other hand, a gaseous phase component recovered from the column top of a continuous multistage distillation column 101 was supplied to a condenser 103 through a line 3. As a result of the analysis of the gaseous phase component, it was found that the gaseous phase component was a mixture comprising 4-(1,1,3,3-tetramethylbutyl)phenol, ammonia and urea as main components. The condenser 103 was a device for carrying out a step of recovering urea and/or isocyanic acid, and then separating a gaseous phase component containing ammonia as a main component therefrom, and it was a vertical shell-and-tube condenser. Hot water (90° C.) was supplied to the shell side, so that the gaseous phase component was condensed. The condensed component was a mixture of 4-(1,1,3,3-tetramethylbutyl)phenol and urea (which contained 2100 ppm of ammonia), and the mixture was supplied to the continuous multistage distillation column again through a line 4, as described above.

An uncondensed gaseous phase component was a gaseous phase component containing ammonia as a main component, and the gaseous phase component was supplied to a gas absorption column 104 through a line 9. The gas absorption column 104 was a packed column filled with Heli-Pack No. 5. The internal pressure thereof was set at 3 kPa, and ammonia was then absorbed by supplying water (10° C.) at a rate of 40.0 kg/Hr to the gas absorption column through a line 13. From the column top of the gas absorption column 104, a trace amount of ammonia (less than 0.5% with respect to the ammonia recovered from the bottom portion of the gas absorption column 104) and water were recovered as gaseous phase components through a line 10, and the gaseous phase components were then supplied to a urea production equipment 107 through a vacuum device (water seal vacuum pump) 106 and a line 11 under an ordinary pressure.

On the other hand, from the bottom portion of the gas absorption column 104, a mixed solution of water and ammonia was recovered at a rate of 41.26 kg/Hr, and it was then supplied to a stripping column 105 (wherein ammonia was separated by heating gas-absorbed water) through a line 12. The stripping column 105 was a packed column filled with Heli-Pack No. 5, the internal pressure thereof was an ordinary pressure, and the temperature of the column bottom portion thereof was adjusted to 100° C. with a reboiler 116 comprised in the stripping column 105. The generated ammonia was discharged from the column top, and entrained components such as water were then condensed in a condenser 117, and the components were then supplied to urea production equipment 107 through a line 14. Carbon dioxide was supplied through a line 17 to the equipment, and urea was then produced in the urea production equipment 107. Urea was produced at a rate of approximately 1.75 kg/Hr. The urea in the urea production equipment 107 can be recovered from the urea production equipment through a line 15 and can be then used.

Example 2

(Carbamation Step)

Figure 2:
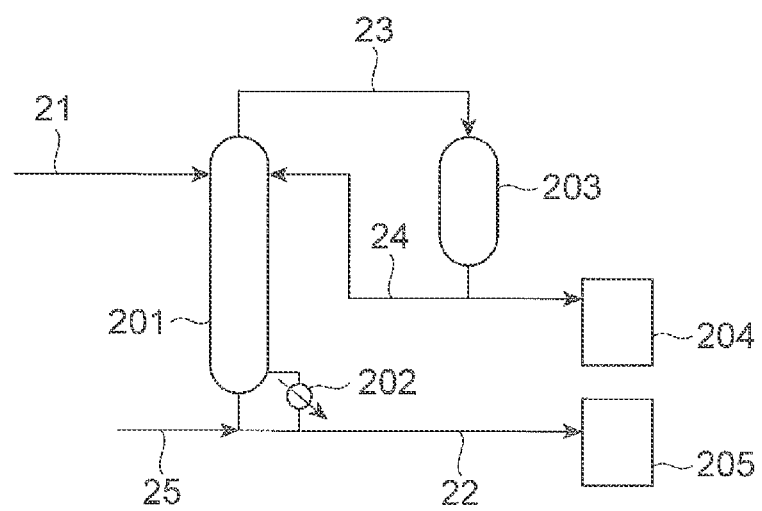
FIG. 2 is a schematic view of an apparatus according to the method for producing an isocyanate of the present embodiment.

By using the apparatus shown in FIG. 2, a carbamation step was carried out. A mixture of 11.3 kg of 1-amino-3-aminomethyl-3,5,5-trimethylcyclohexane, 15.1 kg of urea, and 220.3 kg of 1-butanol was supplied at a rate of approximately 20 kg/Hr through a line 21 to a continuous multistage distillation column 201. A mixture of 1-butanol and urea, which had been obtained in a condenser 203, was supplied at a rate of approximately 3.5 kg/Hr through a line 24 to the continuous multistage distillation column 201. An excess condensed component was recovered in a reservoir 204. The continuous multistage distillation column 201 was a device for carrying out a carbamation step, and by heating the device with a reboiler 202, the column bottom temperature thereof was set at 220° C., and the column top pressure thereof was set at 1.2 MPa. A reaction solution was discharged from the bottom portion of the continuous multistage distillation column 201, and it was then recovered in a reservoir 205 through a line 22.

(Precondensation Step)

Subsequently, by using the apparatus shown in FIG. 3, a precondensation step was carried out. The reaction solution recovered in the reservoir 205 in the carbamation step was supplied at a rate of approximately 21 kg/Hr to a thin film evaporator 301 through a line 31. Regarding the thin film evaporator 301, the jacket temperature was set at 130° C., and the internal pressure was set at 70 kPa. The gaseous phase component generated in thin film evaporator 301 was condensed in a condenser 302, and was then recovered in a reservoir 304. The recovered product was 1-butanol. On the other hand, a liquid phase component in the thin film evaporator 301 was recovered at a rate of approximately 10 kg/Hr in a reservoir 303 through a line 32.

(Pyrolysis Step)

Figure 4:
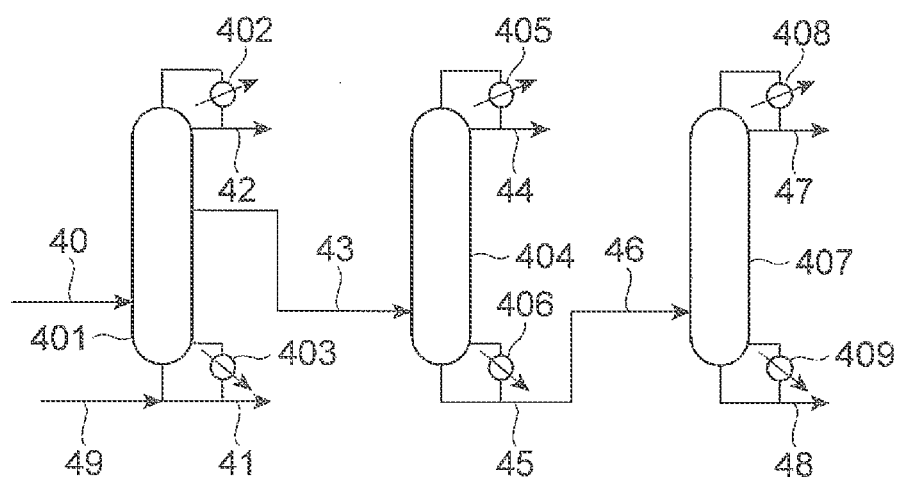
FIG. 4 is a schematic view of an apparatus according to the method for producing an isocyanate of the present embodiment.

By using the apparatus shown in FIG. 4, a pyrolysis step was carried out. A pyrolysis device 401 was a multistage distillation column for generating isophorone diisocyanate by performing the pyrolytic reaction of an N-substituted carbamate. The column top pressure thereof was set at 25 kPa, and the substance was then heated with a reboiler 403, and a total reflux condition of dibenzyl ether was created. The liquid recovered in the reservoir 303 in the precondensation step was supplied thereto at a rate of approximately 5 kg/Hr through a line 40, and the dibenzyl ether was supplied thereto through a line 49. A low-boiling component was discharged from the column top, and it was supplied to a condenser 402 and was then recovered through a line 42. A high-boiling component was recovered through a line 41. A fraction containing isophorone diisocyanate was recovered through a line 43 established at the middle stage of the pyrolysis device 401, and was then supplied to a separation column 404. In the separation column 404, a low-boiling component containing 1-butanol was subjected to distillation separation, and the low-boiling component was supplied to a condenser 405 and was then recovered through a line 44. Heat necessary for distillation separation was supplied from a reboiler 406. A liquid recovered from the column bottom was supplied to a separation column 407 through a line 45 and a line 46. In the separation column 407, a high-boiling component was subjected to distillation separation, and was then recovered through a line 48. In the separation column 407, heat necessary for the distillation separation was supplied from a reboiler 409. A gaseous phase component recovered from the column top was condensed in a condenser 408, and isophorone diisocyanate was then recovered through a line 47.

(Recovery of Gaseous Phase Component)

On the other hand, the gaseous phase component recovered from the column top of a continuous multistage distillation column 201 shown in FIG. 2 was supplied to a condenser 203 through a line 23. As a result of the analysis of the gaseous phase component, it was found that the gaseous phase component was a mixture comprising 1-butanol, ammonia and urea as main components. The condenser 203 was a device for carrying out a step of recovering 1-butanol and urea and/or isocyanic acid, and then separating a gaseous phase component containing ammonia as a main component therefrom, and it was a vertical shell-and-tube condenser, and a cooling medium (0° C.) was supplied to the shell side thereof, so that the gaseous phase component was condensed. The condensed component was a mixture of 1-butanol and urea, and as described above, the mixture was supplied to the continuous multistage distillation column 201 again through a line 24.

(Absorption Step and Stripping Step)

Figure 5:
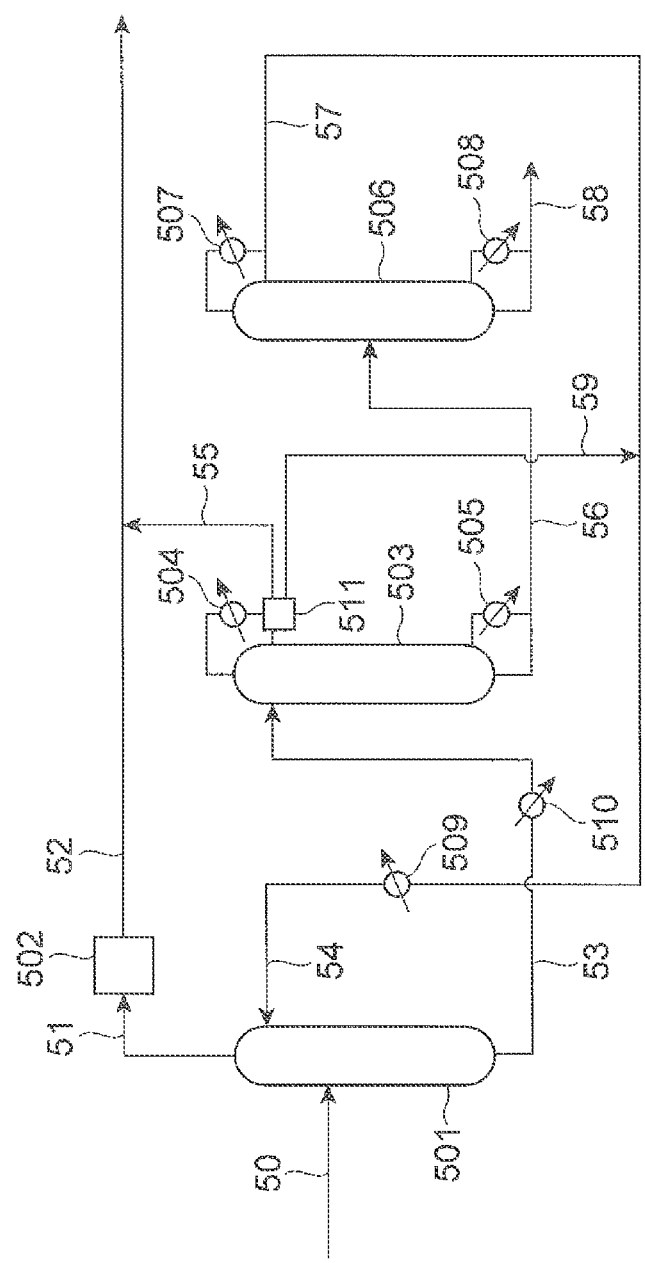
FIG. 5 is a schematic view of an apparatus according to the method for producing an isocyanate of the present embodiment.

The apparatus shown in FIG. 5 was used. An uncondensed gaseous phase component was a gaseous phase component containing ammonia as a main component, and the gaseous phase component was supplied to a gas absorption column 501 through a line 50. The gas absorption column 501 was a packed column, and ammonia water (5° C.) was supplied thereto at a rate of approximately 20 kg/Hr through a line 54, so as to absorb ammonia. A trace amount of ammonia (less than 0.5% with respect to the ammonia recovered from the bottom portion of the gas absorption column 501) and water were recovered as gaseous phase components from the column top of the gas absorption column 501 through a line 51, and thereafter, the gaseous phase components were supplied to a pump 502 for pressure regulation, and were then discharged through a line 52.

On the other hand, from the bottom portion of the gas absorption column 501, a mixed solution comprising water, ammonia and 1-butanol was recovered, and it was then supplied to a stripping column 503 (wherein ammonia was separated by heating gas-absorbed water) through a line 53. The gas-absorbed water was heated in a preheater 510 in the mid-course. The stripping column 503 was a packed column filled with Heli-Pack, the internal pressure thereof was an ordinary pressure, and the temperature of the column bottom portion thereof was adjusted to 105° C. with a reboiler 505 comprised in the stripping column 503. After entrained components such as water had been condensed in a condenser 504, the generated ammonia was recovered through a line 55. The ammonia was analyzed by gas chromatography. As a result, it was found that the contents of methane and argon in the ammonia were less than a lower detection limit (0.05 wt %).

(Separation of 1-Butanol)

Continuously, the apparatus shown in FIG. 5 was used. A liquid present at the column bottom of a stripping column 503 was a mixture comprising 1-butanol, water and a small amount of ammonia. The mixture was supplied to a distillation column 506 through a line 56, and 1-butanol and water were subjected to distillation separation. Heat necessary for distillation separation was supplied from a reboiler 508. The gaseous phase component recovered from the column top of the distillation column 506 was condensed in a condenser 507, and water (containing a small amount of ammonia) was then recovered. The water was passed through lines 57 and 54, and in the mid-course, ammonia water recovered in a gas-liquid separator 511 was added to the water through a line 59, so as to adjust the concentration of ammonia. The mixed solution was adjusted to a temperature of 5° C. in a cooler 509, and was then circulated to the absorption column 501.

Example 3

(Carbamation Step)

The same method as that in the carbamation step of Example 2 was carried out, with the exceptions that 21 kg of 4,4'-dicyclohexylmethanediamine was used instead of 1-amino-3-aminomethyl-3,5,5-trimethylcyclohexane, that 16.5 kg of urea was used, that 250 kg of 2,4-xylenol was used instead of 1-butanol, and that the column bottom temperature was set at 240° C. A reaction solution was discharged from the bottom portion of the continuous multistage distillation column 201 shown in FIG. 2, and was then recovered in a reservoir 205 through a line 22.

(Precondensation Step)

Figure 3:
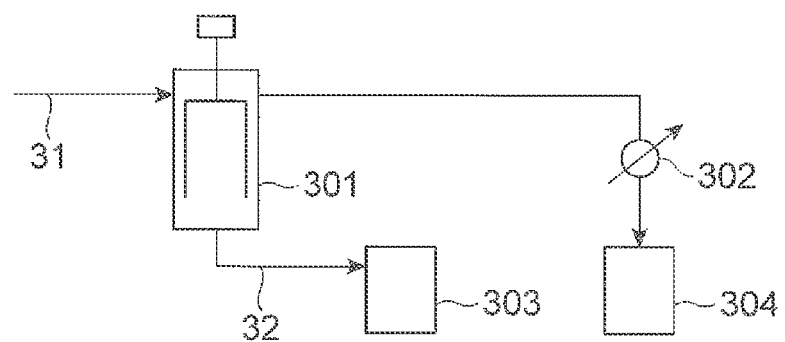
FIG. 3 is a schematic view of an apparatus according to the method for producing an isocyanate of the present embodiment.

The same method as that in the precondensation step of Example 2 was carried out, with the exceptions that the jacket temperature of the thin film evaporator 301 shown in FIG. 3 was set at 150° C., and that the internal pressure was set at 10 kPa. A liquid phase component was recovered at a rate of approximately 10 kg/Hr from the bottom portion of the thin film evaporator 301.

(Pyrolysis Step)

By using the apparatus shown in FIG. 4, a pyrolysis step was carried out. The pyrolysis device 401 was a multistage distillation column for generating 4,4'-dicyclohexylmethane diisocyanate by performing the pyrolytic reaction of an N-substituted carbamate. The same method as that in the pyrolysis step of Example 2 was carried out, with the exceptions that the internal pressure was set at 15 kPa, and that fluorene was used instead of dibenzyl ether. A low-boiling component containing 2,4-xylenol was subjected to distillation separation in a separation column 404, and a high-boiling component was subjected to distillation separation in a separation column 407, so that 4,4'-dicyclohexylmethane diisocyanate was recovered through a line 47.

(Recovery of Gaseous Phase Component)

On the other hand, a gaseous phase component recovered from the column top of a continuous multistage distillation column 201 shown in FIG. 2 was supplied to a condenser 203 through a line 23. As a result of the analysis of the gaseous phase component, it was found that the gaseous phase component was a mixture comprising 2,4-xylenol, ammonia and urea as main components. The condenser 203 was a device for carrying out a step of recovering 2,4-xylenol, and urea and/or isocyanic acid, and then separating a gaseous phase component containing ammonia as a main component, and it was a vertical shell-and-tube condenser. Hot water (approximately 80° C.) was supplied to the shell side, so that the gaseous phase component was condensed. The condensed component was a mixture of 2,4-xylenol and urea, and the mixture was supplied to the continuous multistage distillation column 201 again through a line 24, as described above.

(Absorption Step, Step of Separating 2,4-Xylenol, and Stripping Step)

Figure 6:
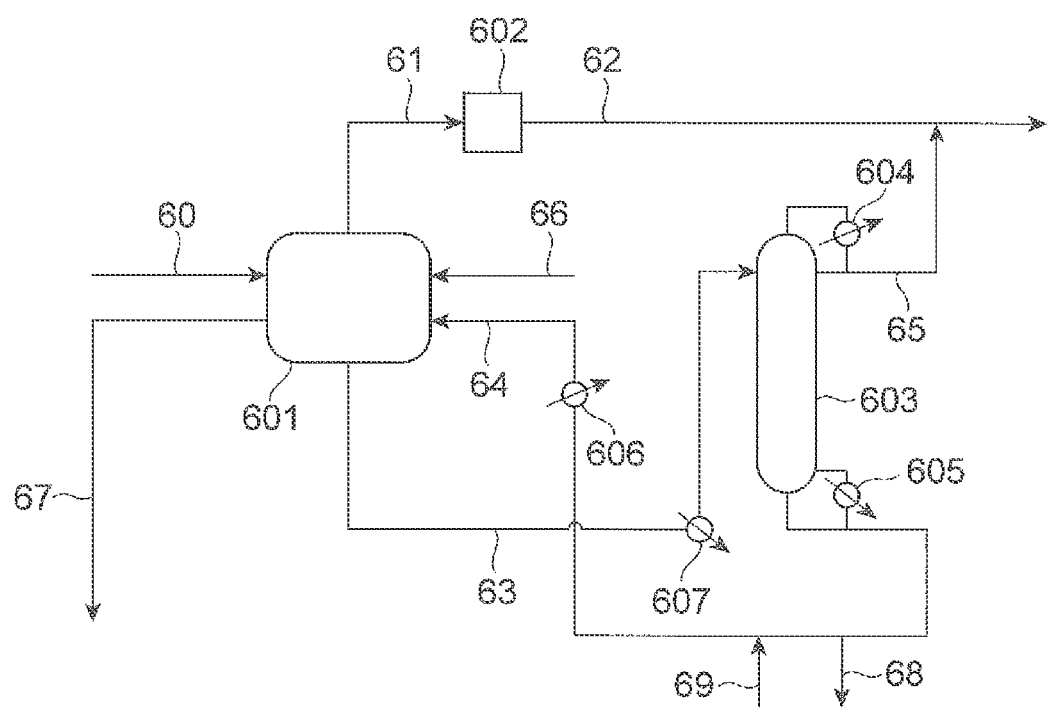
FIG. 6 is a schematic view of an apparatus according to the method for producing an isocyanate of the present embodiment.

The apparatus shown in FIG. 6 was used. An uncondensed gaseous phase component was a gaseous phase component containing ammonia as a main component, and the gaseous phase component was supplied to a gas absorption and/or liquid-liquid separation device 601 through a line 60. The gas absorption and/or liquid-liquid separation device 601 was a decanter. Water (5° C.) was supplied at a rate of approximately 22 kg/Hr to the device through a line 64, and ammonia was then absorbed in a state in which the tip of the line 60 was immersed in the water phase. On the other hand, toluene was supplied at a rate of approximately 11 kg/Hr to the device through a line 66, and 2,4-xylenol was then extracted from the uncondensed gaseous phase component. An organic phase containing toluene as a main component was recovered through a line 67, and toluene was then separated from 2,6-xylenol in a distillation column thereof. Thus, toluene and 2,6-xylenol were each recycled. From the column top of the gas absorption and/or liquid-liquid separation device 601, a trace amount of ammonia (less than 0.5% with respect to the ammonia recovered from the bottom portion of the gas absorption and/or liquid-liquid separation device 601), water and toluene were recovered as a gaseous phase component through a line 61. The gaseous phase component was supplied to a pump 602 for pressure regulation, and was then discharged through a line 62.

On the other hand, from the bottom portion of the gas absorption and/or liquid-liquid separation device 601, a mixed solution comprising water and ammonia was recovered, and it was then supplied to a stripping column 603 (wherein ammonia was separated by heating gas-absorbed water) through a line 63. The gas-absorbed water was heated in a preheater 607 in the mid-course. The stripping column 603 was a packed column filled with Heli-Pack, the internal pressure thereof was an ordinary pressure, and the temperature of the column bottom portion thereof was adjusted to 105° C. with a reboiler 605 comprised in the stripping column 603. After entrained components such as water had been condensed in a condenser 604, the generated ammonia was recovered through a line 65. The ammonia was analyzed by gas chromatography. As a result, it was found that the contents of methane and argon in the ammonia were less than a lower detection limit (0.05 wt %).

A portion of water recovered from the bottom portion of the stripping column 603 was discharged through a line 68, and at the same time, the same amount of water was supplied through a line 69, so that the absorbed solution was blown down. Thereafter, the resulting solution was cooled to 5° C. in a cooler 606, and was then circulated to the gas absorption and/or liquid-liquid separation device 601 through a line 64. The water recovered through the line 68 contained urea.

Example 4

(Carbamation Step)

The same method as that in the carbamation step of Example 2 was carried out, with the exceptions that 8.5 kg of aniline was used instead of 1-amino-3-aminomethyl-3,5,5-trimethylcyclohexane, that 13.2 kg of urea was used, that 180 kg of 2,4-di-tert-amylphenol was used instead of 1-butanol, and that the column bottom temperature was set at 250° C. A reaction solution was discharged from the bottom portion of the continuous multistage distillation column 201 shown in FIG. 2, and was then recovered in a reservoir 205 through a line 22. The recovered solution was directly subjected to a pyrolysis step, without performing a precondensation step.

(Pyrolysis Step)

Figure 7:
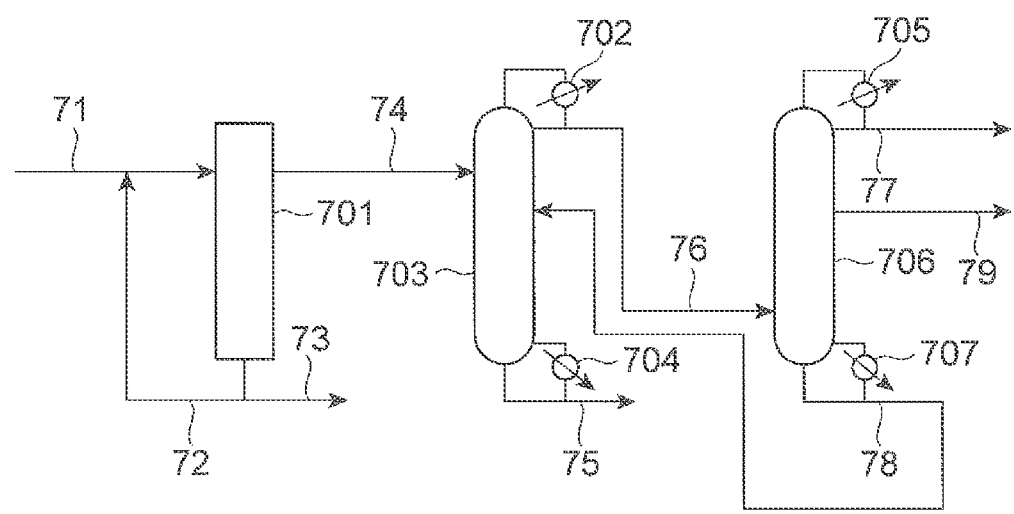
FIG. 7 is a schematic view of an apparatus according to the method for producing an isocyanate of the present embodiment.

By using the apparatus shown in FIG. 7, a pyrolysis step was carried out. The pyrolysis device 701 was a falling-film-type reaction vessel for generating phenyl isocyanate by performing the pyrolytic reaction of an N-substituted carbamate. The internal pressure thereof was set at 1 kPa, and the jacket temperature thereof was set at 250° C., and the column top pressure of a separation column 703 was set at 0.5 kPa, and a total reflux condition of dodecane was created. Necessary heat was supplied from a reboiler 704. The reaction solution obtained in the carbamation step was supplied at a rate of approximately 10 kg/Hr to the device through a line 71, and the generated gaseous phase component was then supplied to the separation column 703 through a line 74. Approximately a half of a liquid phase component recovered from the bottom portion of the pyrolysis device 701 was supplied to the pyrolysis device 701 again through a line 72, and the remaining liquid phase component was recovered through a line 73. To the separation column 703, the gaseous phase component generated as a result of the pyrolysis was supplied through a line 74, and at the same time, dodecane was also supplied thereto at a rate of approximately 1 kg/Hr through a line 78. A gaseous phase component recovered from the column top of the separation column 703 was condensed in a condenser 702, so as to prepare a mixed solution of phenyl isocyanate and dodecane. The mixed solution was supplied to a separation column 706 through a line 76. A high-boiling component containing 2,4-di-tert-amylphenol was recovered from the column bottom of the separation column 703 through a line 75. Phenyl isocyanate was distilled in the separation column 706. Heat necessary for distillation separation was supplied from a reboiler 707. A gaseous phase component was recovered from the column top, and was then condensed in a condenser 705. Thereafter, phenyl isocyanate was recovered through a line 77.

(Recovery of Gaseous Phase Component)

On the other hand, a gaseous phase component recovered from the column top of a continuous multistage distillation column 201 shown in FIG. 2 was supplied to a condenser 203 through a line 23. As a result of the analysis of the gaseous phase component, it was found that the gaseous phase component was a mixture comprising 2,4-di-tert-amylphenol, ammonia and urea as main components. The condenser 203 was a device for carrying out a step of recovering 2,4-di-tert-amylphenol, and urea and/or isocyanic acid, and then separating a gaseous phase component containing ammonia as a main component, and it was a vertical shell-and-tube condenser. Hot water (approximately 25° C.) was supplied to the shell side, so that the gaseous phase component was condensed. The condensed component was a mixture of 2,4-di-tert-amylphenol and urea, and the mixture was supplied to the continuous multistage distillation column 201 again through a line 24, as described above.

(Absorption Step, Step of Separating 2,4-Di-Tert-Amylphenol, and Stripping Step)

The apparatus shown in FIG. 6 was used. The same method as that of Example 3 was carried out, with the exceptions that the temperature of water supplied through a line 64 was set at 25° C., and that toluene was not supplied through a line 66. An organic phase containing 2,4-di-tert-amylphenol as a main component was recovered through a line 67, and a trace amount of water contained in the organic phase was removed, so that the residue was used as 2,4-di-tert-amylphenol. From the column top of the gas absorption and/or liquid-liquid separation device 601, a trace amount of ammonia (less than 0.5% with respect to the ammonia recovered from the bottom portion of the gas absorption and/or liquid-liquid separation device 601) and water were recovered as gaseous phase components through a line 61.

Ammonia generated in a stripping column 603 was recovered through a line 65.

A portion of water recovered from the bottom portion of the stripping column 603 was discharged through a line 68, and at the same time, the same amount of water was supplied through a line 69, so that the absorbed solution was blown down. Thereafter, the resulting solution was circulated to the gas absorption and/or liquid-liquid separation device 601 through a line 64. The water recovered through the line 68 contained urea.

Example 5

(Carbamation Step)

The same method as that in the carbamation step of Example 2 was carried out, with the exceptions that 9.8 kg of 2,4-toluenediamine was used instead of 1-amino-3-aminomethyl-3,5,5-trimethylcyclohexane, that 10.3 kg of urea was used, that 80 kg of phenol was used instead of 1-butanol, that the column bottom temperature was set at 230° C. and the column top pressure was set at 0.2 MPa, and that phenol was supplied for concentration regulation through a line 25 at the column bottom. A reaction solution was discharged from the bottom portion of the continuous multistage distillation column 201 shown in FIG. 2, and was then recovered in a reservoir 205 through a line 22.

(Precondensation Step)

The same method as that in the precondensation step of Example 2 was carried out, with the exceptions that the jacket temperature of the thin film evaporator 301 shown in FIG. 3 was set at 150° C., and that the internal pressure was set at 10 kPa. A liquid phase component was recovered at a rate of approximately 10 kg/Hr from the bottom portion of the thin film evaporator 301.

(Pyrolysis Step)

By using the apparatus shown in FIG. 4, a pyrolysis step was carried out. The pyrolysis device 401 was a multistage distillation column for generating 2,4-toluene diisocyanate by performing the pyrolytic reaction of an N-substituted carbamate. The same method as that in the pyrolysis step of Example 2 was carried out, with the exceptions that the internal pressure was set at 15 kPa, and that diphenyl ether was used instead of dibenzyl ether. A low-boiling component containing phenol was subjected to distillation separation in a separation column 404, and a high-boiling component was subjected to distillation separation in a separation column 407, so that 2,4-toluene diisocyanate was recovered through a line 47.

(Recovery of Gaseous Phase Component)

On the other hand, a gaseous phase component recovered from the column top of a continuous multistage distillation column 201 shown in FIG. 2 was supplied to a condenser 203 through a line 23. As a result of the analysis of the gaseous phase component, it was found that the gaseous phase component was a mixture comprising phenol, ammonia and urea as main components. The condenser 203 was a device for carrying out a step of recovering phenol, and urea and/or isocyanic acid, and then separating a gaseous phase component containing ammonia as a main component, and it was a vertical shell-and-tube condenser. Hot water (approximately 40° C.) was supplied to the shell side, so that the gaseous phase component was condensed. The condensed component was a mixture of phenol and urea, and the mixture was supplied to the continuous multistage distillation column 201 again through a line 24, as described above.

(Absorption Step and Stripping Step)

By using the apparatus shown in FIG. 5, the same methods as those in the absorption step and the stripping step of Example 2 were carried out with the exception that water (10° C.) was supplied at a rate of approximately 30 kg/Hr to the device through a line 54. The generated ammonia was recovered through a line 55.

(Separation of Phenol)

Continuously, by using the apparatus shown in FIG. 5, the method as that of Example 2 was carried out. Water (containing a small amount of ammonia) was recovered from the column top of a distillation column 506. The water was circulated to an absorption column 501 through lines 57 and 54. Phenol was recovered from the column bottom of the distillation column 506 through a line 58, and it was recycled as a raw material for the carbamation step.

Example 6

(Carbamation Step)

The same method as that in the carbamation step of Example 2 was carried out, with the exceptions that 12.7 kg of hexamethylenediamine was used instead of 1-amino-3-aminomethyl-3,5,5-trimethylcyclohexane, that 13.8 kg of urea was used, that 220 kg of phenol was used instead of 1-butanol, that the column bottom temperature was set at 230° C. and the column top pressure was set at 0.2 MPa, and that phenol was supplied for concentration regulation through a line 25 at the column bottom. A reaction solution was discharged from the bottom portion of the continuous multistage distillation column 201 shown in FIG. 2, and was then recovered in a reservoir 205 through a line 22.

(Precondensation Step)

The same method as that in the precondensation step of Example 2 was carried out, with the exceptions that the jacket temperature of the thin film evaporator 301 shown in FIG. 3 was set at 150° C., and that the internal pressure was set at 5 kPa. A liquid phase component was recovered at a rate of approximately 11 kg/Hr from the bottom portion of the thin film evaporator 301.

(Pyrolysis step)

By using the apparatus shown in FIG. 4, a pyrolysis step was carried out. The pyrolysis device 401 was a multistage distillation column for generating hexamethylene diisocyanate by performing the pyrolytic reaction of an N-substituted carbamate. The same method as that in the pyrolysis step of Example 2 was carried out, with the exceptions that the internal pressure was set at 10 kPa, and that benzylbutyl phthalate was used instead of dibenzyl ether. A low-boiling component containing phenol was subjected to distillation separation in a separation column 404, and a high-boiling component was subjected to distillation separation in a separation column 407, so that hexamethylene diisocyanate was recovered through a line 47.

(Recovery of Gaseous Phase Component)

On the other hand, a gaseous phase component recovered from the column top of a continuous multistage distillation column 201 shown in FIG. 2 was supplied to a condenser 203 through a line 23. As a result of the analysis of the gaseous phase component, it was found that the gaseous phase component was a mixture comprising phenol, ammonia and urea as main components. The condenser 203 was a device for carrying out a step of recovering phenol, and urea and/or isocyanic acid, and then separating a gaseous phase component containing ammonia as a main component, and it was a vertical shell-and-tube condenser. Hot water (approximately 40° C.) was supplied to the shell side, so that the gaseous phase component was condensed. The condensed component was a mixture of phenol and urea, and the mixture was supplied to the continuous multistage distillation column 201 again through a line 24, as described above.

(Absorption Step and Stripping Step)

Figure 8:
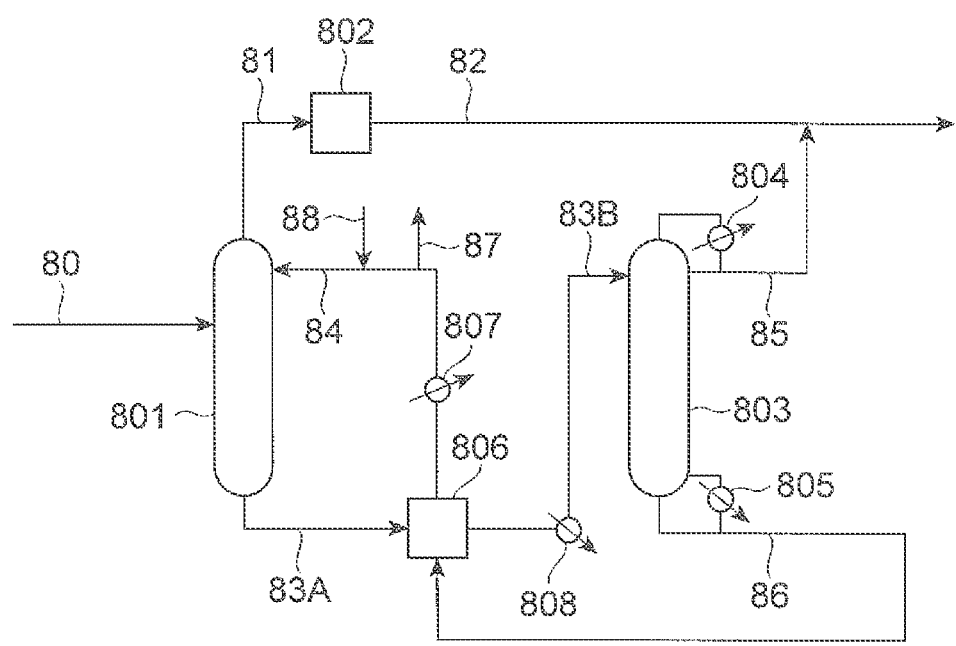
FIG. 8 is a schematic view of an apparatus according to the method for producing an isocyanate of the present embodiment.

The apparatus shown in FIG. 8 was used. An uncondensed gaseous phase component was a gaseous phase component containing ammonia as a main component, and the gaseous phase component was supplied to a gas absorption column 801 through a line 80. The gas absorption column 801 was a packed column. Ammonia was absorbed by supplying water (10° C.) at a rate of 25 kg/Hr through a line 84 to the gas absorption column. From the column top of the gas absorption column 801, a trace amount of ammonia (less than 0.5% with respect to the ammonia recovered from the bottom portion of the gas absorption column 801) and water were recovered as gaseous phase components through a line 81, and thereafter, the gaseous phase components were supplied to a pump used for pressure regulation, and were then discharged through a line 82.

On the other hand, from the bottom portion of the gas absorption column 801, a mixed solution of water, ammonia and phenol was recovered, and it was then supplied to a stripping column 803 (wherein ammonia was separated by heating gas-absorbed water) through lines 83A and 83B. In the mid-course, heat exchange was carried out in a heat exchanger 806 between a mixed solution recovered from the column bottom of the stripping column 803 through a line 86 and an absorbed solution recovered from the column bottom of the absorption column 801 through a line 83, and thereafter, gas-absorbed water was heated in a preheater 808. The stripping column 803 was a packed column filled with Heli-Pack, the internal pressure thereof was an ordinary pressure, and the temperature of the column bottom portion thereof was adjusted to 105° C. with a reboiler 805 comprised in the stripping column 803. After entrained components had been condensed in a condenser 804, the generated ammonia was recovered through a line 85.

On the other hand, water recovered from the bottom portion of the stripping column 803 contained phenol and urea. A portion of the water was discharged through a line 87, and at the same time, the same amount of water was supplied through a line 88, so that the absorbed solution was blown down. Thereafter, the resulting solution was cooled to 10° C. in a cooler 807, and was then circulated to the absorption column 801 through a line 84. The water containing phenol and urea recovered through the line 87 was subjected to distillation separation, so that phenol containing urea was separated from water. The thus separated components were recycled as a raw material for carbamation and absorption water, respectively.

Example 7

(Carbamation Step)

Figure 9:
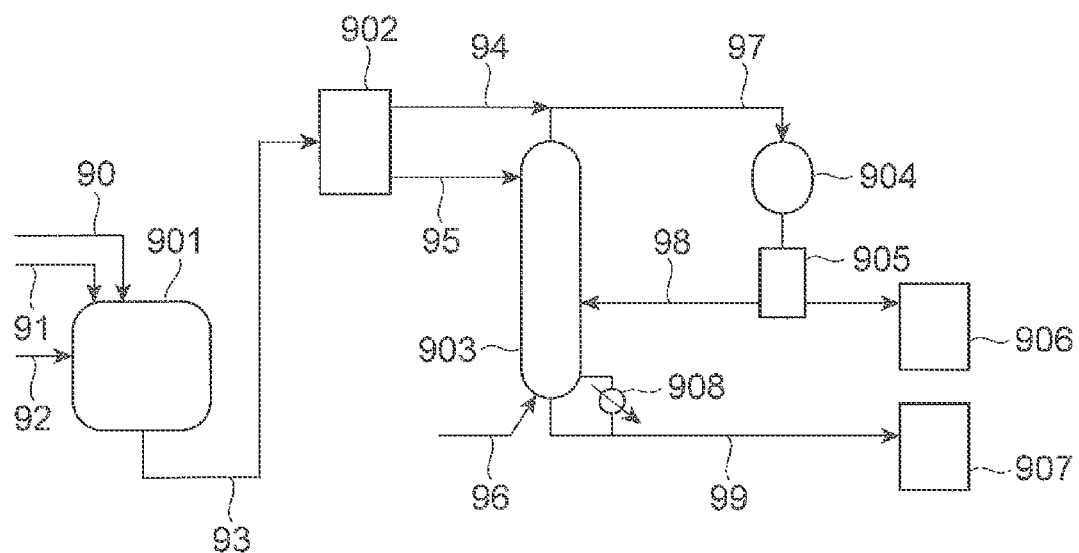
FIG. 9 is a schematic view of an apparatus according to the method for producing an isocyanate of the present embodiment.

By using the apparatus shown in FIG. 9, a carbamation step was carried out. 2.85 kg of urea and 26.0 kg of 2-isopropylphenol were supplied to a stirring tank 901 through lines 90 and 91, respectively. They were heated to 130° C. to prepare a homogeneous solution, and thereafter, 1.05 kg of hexamethylenediamine was supplied at a rate of approximately 0.3 kg/Hr to the stirring tank 901 through a line 92. A total amount of hexamethylenediamine was supplied thereto, and the obtained mixture was then stirred for 2 hours. Thereafter, the reaction solution was analyzed, and as a result, it was found that 1,6-hexamethylenediurea was generated at a yield of approximately 95% with respect to hexamethylenediamine. The reaction solution was supplied to a multistage distillation column 903 through a line 93 and a line 95. In the mid-course, ammonia was separated from the reaction solution in a gas-liquid separator 902, and was then discharged through a line 94.

The multistage distillation column 903 is a distillation column comprising CASCADE MINI-RINGS (registered trademark) as a filler. In advance, 4-phenylphenol had been added to the column bottom thereof, and a mixed solution of urea and 2-isopropylphenol (urea concentration: approximately 6.8 weight %) had been added to a reservoir 905. The column bottom temperature was set at 250° C., and the inside of the column was placed under a total reflux condition. To this column, the reaction solution obtained after gas-liquid separation was added at a rate of approximately 1.5 kg/Hr through a line 95, and 4-phenylphenol was supplied at a rate of approximately 2.5 kg/Hr through a line 96 present at the column bottom portion. A mixed solution of 2-isopropylphenol and urea obtained in a condenser 904 was supplied to the column through a line 98. An excess mixed solution was recovered in a reservoir 906. The reaction solution was discharged from the bottom portion of the multistage distillation column 903, and was then recovered in a reservoir 907 through a line 99.

(Precondensation Step)

Subsequently, by using the apparatus shown in FIG. 3, a precondensation step was carried out. The reaction solution recovered in the reservoir 907 in the carbamation step was supplied at a rate of approximately 15 kg/Hr to a thin film evaporator 301 through a line 31. Regarding the thin film evaporator 301, the jacket temperature was set at 180° C., and the internal pressure was set at 2 kPa. A gaseous phase component generated in the thin film evaporator 301 was condensed in a condenser 302, and was then recovered in a reservoir 304. The recovered product was 4-phenylphenol. On the other hand, a liquid phase component in the thin film evaporator 301 was recovered at a rate of approximately 3 kg/Hr in a reservoir 303 through a line 32.

(Pyrolysis Step)

By using the apparatus shown in FIG. 7, a pyrolysis step was carried out. The same method as that in the pyrolysis step of Example 4 was carried out, with the exceptions that the internal pressure was set at 1 kPa, that the jacket temperature was set at 250° C., that the column top pressure of a separation column 703 was set at 0.5 kPa, that hexadecane was used instead of dodecane to create a total reflux condition, and that the reaction solution recovered in a reservoir 303 through a line 71 was supplied at a rate of approximately 3 kg/Hr to the column, and hexadecane was supplied instead of dodecane at a rate of approximately 0.5 kg/Hr to the column through a line 78. A solution recovered from the column top of the separation column 703 was supplied to a separation column 706, and hexamethylene diisocyanate was then recovered through a line 79 established at the middle stage of the separation column 706.

(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising 2-isopropylphenol, ammonia and urea as main components. The condenser 904 was a device for carrying out a step of recovering 2-isopropylphenol, and urea and/or isocyanic acid, and then separating a gaseous phase component containing ammonia as a main component, and it was a vertical shell-and-tube condenser. Hot water (approximately 15° C.) was supplied to the shell side, so that the gaseous phase component was condensed. The condensed component was a mixture of 2-isopropylphenol and urea, and the mixture was supplied to the multistage distillation column 903 again through a line 98, as described above.

(Absorption Step, Step of Separating 2-Isopropylphenol, and Stripping Step)

Figure 10:
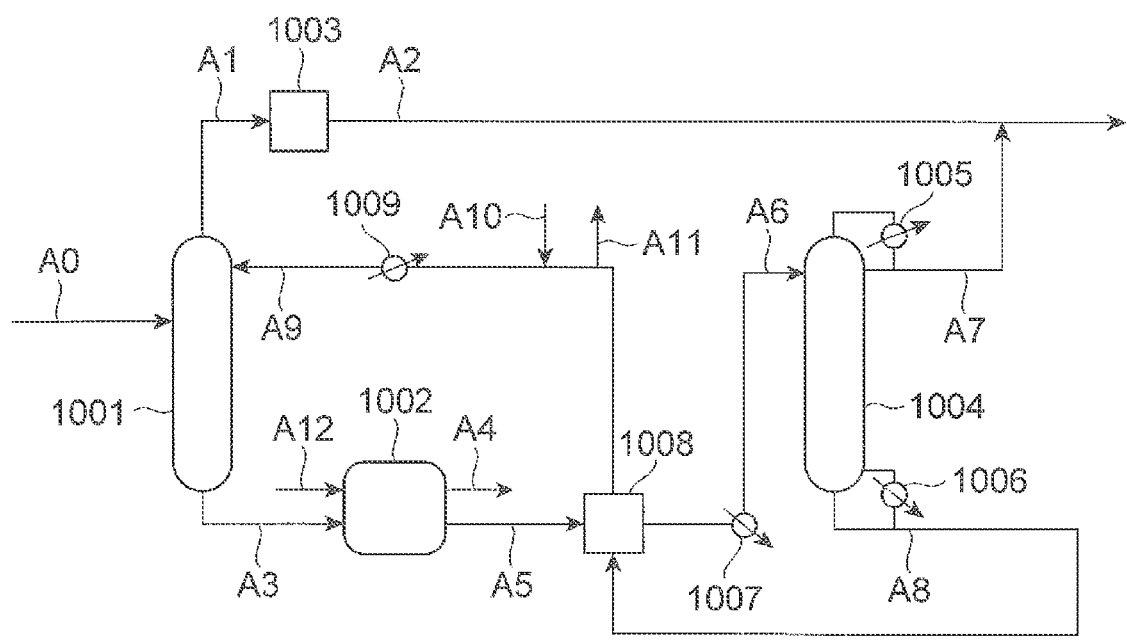
FIG. 10 is a schematic view of an apparatus according to the method for producing an isocyanate of the present embodiment.

The apparatus shown in FIG. 10 was used. An uncondensed gaseous phase component was a gaseous phase component containing ammonia as a main component, and the gaseous phase component was supplied to a gas absorption column 1001 through a line A0. The gas absorption column 1001 was a packed column. Water (15° C.) was supplied at a rate of approximately 10 kg/Hr to the column through a line A9. From the column top of the gas absorption column 1001, a trace amount of ammonia (less than 0.5% with respect to the ammonia recovered from the bottom portion of the gas absorption column 1001) and water were recovered as gaseous phase components through a line A1. Thereafter, the gaseous phase components were supplied to a pump 1003 for pressure regulation, and were then discharged through a line A2. A solution containing ammonia was recovered from the bottom portion of the gas absorption column 1001 through a line A3, and it was then supplied to a liquid-liquid separator 1002. The liquid-liquid separator 1002 was a decanter. In the separator 1002, 2-isopropylphenol was separated from the solution containing ammonia, and an organic phase consisting of the 2-isopropylphenol was recovered through a line A4. The 2-isopropylphenol was recycled as a raw material for the carbamation step. On the other hand, a water phase was discharged from a line A5, and it was passed through a heat exchanger 1008 connecting with a line A8, a preheater 1007 and a line A6, and was then supplied to a stripping column 1004. The stripping column 1004 was a packed column filled with Heli-Pack, the internal pressure thereof was an ordinary pressure, and the temperature of the column bottom portion thereof was adjusted to 105° C. with a reboiler 1006 comprised in the stripping column 1004. After entrained components such as water had been condensed in a condenser 1005, the generated ammonia was recovered through a line A7. The ammonia was analyzed by gas chromatography. As a result, it was found that the contents of methane and argon in the ammonia were less than a lower detection limit (0.05 wt %).

Water recovered from the bottom portion of a stripping column 1004 was passed through a line A8, a heat exchanger 1008 and a cooler 1009, and was then supplied to an absorption column 1001 through a line A9. A portion of the water was discharged through a line A11, and at the same time, the same amount of water was supplied through a line A10, so that the absorbed solution was blown down. The water recovered through the line A11 contained urea.

Example 8

(Carbamation Step)

By using the apparatus shown in FIG. 9, a carbamation step was carried out. The same method as that of Example 7 was carried out, with the exceptions that 5.3 kg of urea was used, that 43.0 kg of 4-dodecylphenol was used instead of 2-isopropylphenol, and that 3.5 kg of 1-amino-3-aminomethyl-3,5,5-trimethylcyclohexane was used instead of hexamethylenediamine, so as to obtain a reaction solution containing 1-ureido-(3-aminocarbonylaminomethyl)-3,5,5-trimethylcyclohexane.

After 4-dodecylphenol had previously been added to the column bottom of a multistage distillation column 903, the column bottom temperature was set at 250° C., and the inside of the column was placed under a total reflux condition of 4-dodecylphenol. To this column, the reaction solution obtained after gas-liquid separation was added at a rate of approximately 2.0 kg/Hr through a line 95, and a line 98 was then closed. 4-Dodecylphenol was supplied at a rate of approximately 2.5 kg/Hr through a line 96 present at the column bottom portion. A mixed solution of 4-dodecylphenol and urea was obtained in a condenser 904. A reaction solution was discharged from the bottom portion of the multistage distillation column 903, and was then recovered in a reservoir 907 through a line 99. This reaction solution contained a polymer having a urea bond, as well as an N-substituted carbamate that was a compound of interest in the present step. The yield of the N-substituted carbamate was found to be approximately 53% with respect to 1-amino-3-aminomethyl-3,5,5-trimethylcyclohexane.

(Carbamate Regeneration Step)

Figure 11:
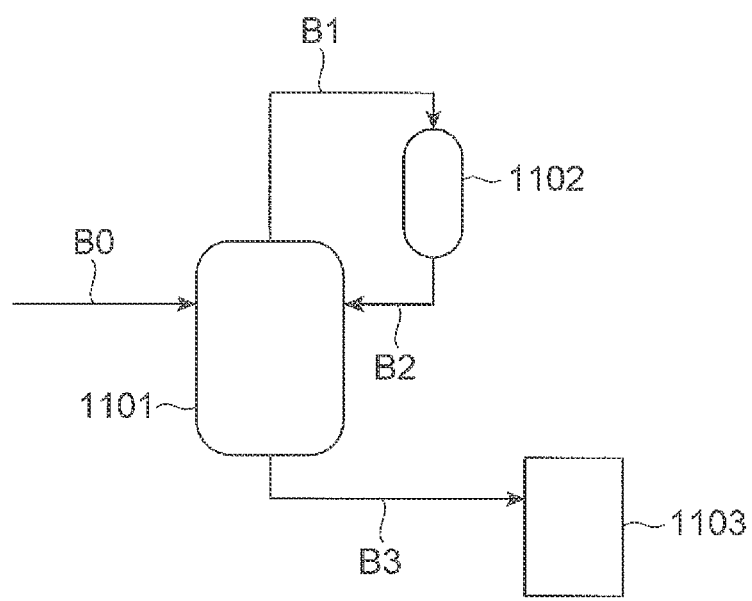
FIG. 11 is a schematic view of an apparatus according to the method for producing an isocyanate of the present embodiment.

The apparatus shown in FIG. 11 was used. 2.7 kg of urea was added to a stirring tank 1101, and the reaction solution recovered in the reservoir 907 was supplied through a line B0 to the tank. The stirring tank 1101 was heated to 220° C., and the pressure of the inside thereof was reduced to 10 kPa.

The generated gaseous phase component was discharged through a line B1, and was then condensed in a condenser 1102. The obtained condensate was supplied to the stirring tank 1101 again through a line B2. After a reaction had been performed for 5 hours, the reaction solution was recovered in a reservoir 1103 through a line B3. The yield of an N-substituted carbamate contained in the reaction solution was found to be approximately 92% with respect to 1-amino-3-aminomethyl-3,5,5-trimethylcyclohexane.

(Precondensation Step)

Subsequently, by using the apparatus shown in FIG. 3, a precondensation step was carried out. The reaction solution recovered in the reservoir 1103 in the above described step was supplied at a rate of approximately 15 kg/Hr to a thin film evaporator 301 through a line 31. Regarding the thin film evaporator 301, the jacket temperature was set at 190° C., and the internal pressure was set at 2 kPa. A gaseous phase component generated in the thin film evaporator 301 was condensed in a condenser 302, and was then recovered in a reservoir 304. The recovered product was 4-dodecylphenol. On the other hand, a liquid phase component in the thin film evaporator 301 was recovered at a rate of approximately 3 kg/Hr in a reservoir 303 through a line 32.

(Pyrolysis Step)

Figure 12:
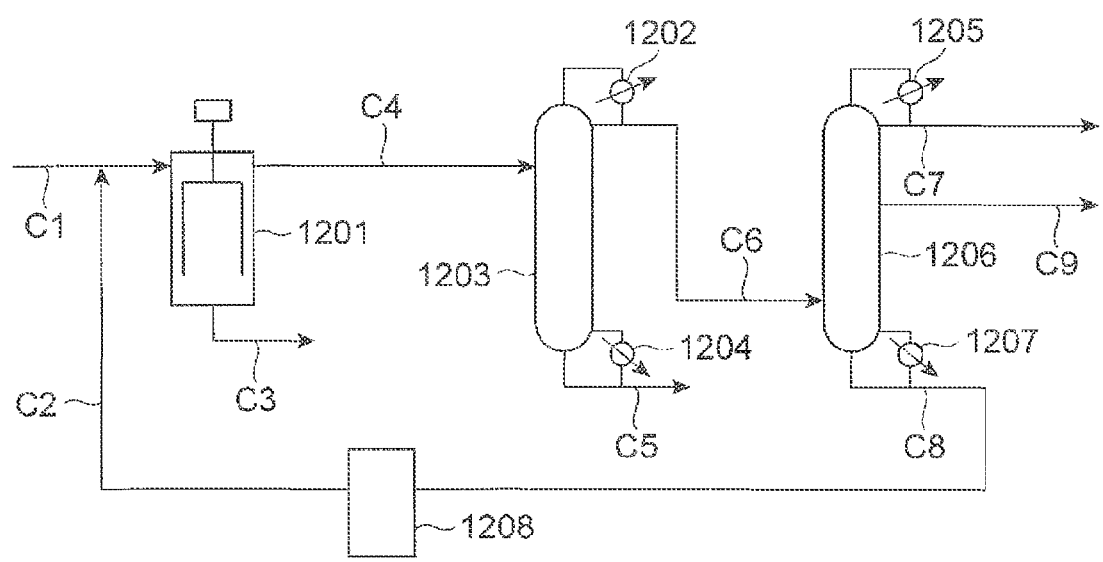
FIG. 12 is a schematic view of an apparatus according to the method for producing an isocyanate of the present embodiment.

By using the apparatus shown in FIG. 12, a pyrolysis step was carried out. The internal pressure of a thin film evaporator 1201 was set at 1 kPa, and the jacket temperature was set at 250° C. The column top pressure of a separation column 1203 was set at 0.5 kPa, and a total reflux condition was created by using NeoSK-OIL 1300. The reaction solution recovered in the reservoir 303 was supplied at a rate of approximately 3 kg/Hr to the apparatus through a line C1, and NeoSK-OIL 1300 was supplied at a rate of approximately 1 kg/Hr to the apparatus through a line C2. In the thin film evaporator 1201, the pyrolysis of an N-substituted carbamate was carried out. A liquid phase component was recovered through a line C3, and a gaseous phase component containing isophorone diisocyanate was recovered through a line C4, and was then supplied to the separation column 1203. Heat necessary for the distillation separation in the separation column 1203 was supplied from a reboiler 1204, and a column bottom component was recovered through a line C5. The gaseous phase component recovered from the column top of the separation column 1203 was condensed in a condenser 1202, so as to recover isophorone diisocyanate and NeoSK-OIL 1300. They were supplied to a separation column 1206 through a line C6, and were then subjected to distillation separation in the separation column 1206. Heat necessary for distillation separation was supplied from a reboiler 1207. From a line C9 established at the middle stage of the separation column 1206, isophorone diisocyanate was recovered. Meanwhile, NeoSK-OIL 1300 separated at the column bottom portion of the separation column 1206 was recovered in a reservoir 1208 through a line C8, and was then supplied to the thin film evaporator 1201 again through the line C2. A gaseous phase component recovered from the column top of the separation column 1206 was condensed in a condenser 1205, and was then recovered through a line C7.

(Recovery of Gaseous Phase Component)

On the other hand, the gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising 4-dodecylphenol, ammonia and urea as main components. The condenser 904 was a device for carrying out a step of recovering 4-dodecylphenol and urea and/or isocyanic acid, and then separating a gaseous phase component containing ammonia as a main component therefrom, and it was a vertical shell-and-tube condenser. Hot water (approximately 15° C.) was supplied to the shell side thereof, so that the gaseous phase component was condensed. The condensed component was a mixture of 4-dodecylphenol and urea.

(Absorption Step, Step of Separating 4-Dodecylphenol, and Stripping Step)

The apparatus shown in FIG. 10 was used, and the same method as that of Example 7 was carried out. An organic phase consisting of 4-dodecylphenol was recovered through a line A4, and was then recycled as a raw material for the carbamation step. In addition, ammonia was recovered through a line A7.

Water recovered from the bottom portion of a stripping column 1004 was passed through a line A8, a heat exchanger 1008 and the like, and was then supplied to an absorption column 1001 through a line A9. A portion of the water was discharged through a line A11, and at the same time, the same amount of water was supplied through a line A10, so that the absorbed solution was blown down. The water recovered through the line A11 contained urea.

Example 9

(Production of N-Unsubstituted Carbamate)

Figure 13:
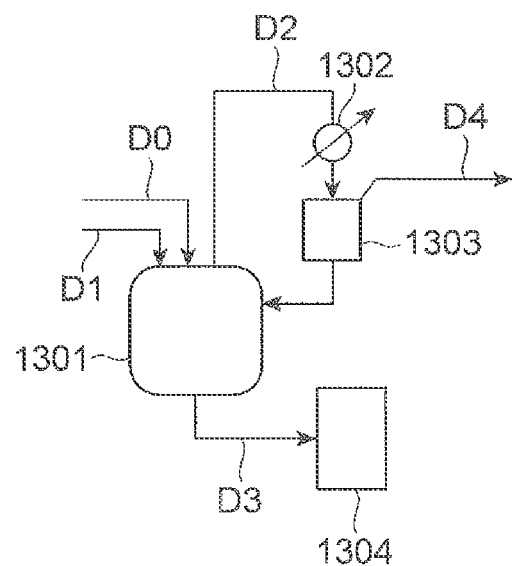
FIG. 13 is a schematic view of an apparatus according to the method for producing an isocyanate of the present embodiment.

By using the apparatus shown in FIG. 13, an N-unsubstituted carbamate was produced. 3.1 kg of urea was added to a stirring tank 1301 through a line D0, and 48.6 kg of phenol was added thereto through a line D1. The stirring tank 1301 was heated to 200° C., and the reaction was then carried out while stirring. A gaseous phase component was discharged through a line D2, and was then condensed in a condenser 1302. The condensate was passed through a gas-liquid separator 1303, and was then supplied to the stirring tank 1301. A gaseous phase component containing ammonia as a main component separated in the gas-liquid separator 1303 was discharged through a line D4, and was then used in the after-mentioned absorption step. After the reaction had been carried out for approximately 5 hours, the reaction solution was discharged through a line D3, and was then recovered in a reservoir 1304. The reaction solution contained phenyl carbamate, and the yield of the phenyl carbamate was found to be approximately 70% with respect to urea.

(Carbamation Step)

By using the apparatus shown in FIG. 9, a carbamation step was carried out. The same method as that of Example 7 was carried out, with the exceptions that the reaction solution recovered in the reservoir 1304 in the above described step was used instead of urea and 2-isopropylphenol, and that 2.2 kg of 1-amino-3-aminomethyl-3,5,5-trimethylcyclohexane was used instead of hexamethylenediamine, so as to obtain a reaction solution containing 1-ureido-(3-aminocarbonylaminomethyl)-3,5,5-trimethylcyclohexane.

After phenol had previously been added to the column bottom of a multistage distillation column 903, the column bottom temperature was set at 220° C., and the inside of the column was placed under a total reflux condition of phenol. The pressure at the column top was approximately 0.2 MPa. To this column, the reaction solution obtained after gas-liquid separation was added at a rate of approximately 2.0 kg/Hr through a line 95, and the same method as that of Example 7 was then carried out with the exception that phenol was used instead of 4-dodecylphenol. The reaction solution was recovered in a reservoir 907 through a line 99. The reaction solution contained a polymer having a urea bond, as well as an N-substituted carbamate that was a compound of interest in the present step. The yield of the N-substituted carbamate was found to be approximately 72% with respect to 1-amino-3-aminomethyl-3,5,5-trimethylcyclohexane.

(Carbamate Regeneration Step)

The apparatus shown in FIG. 11 was used, and the same method as that in the carbamate regeneration step of Example 8 was carried out, with the exceptions that 2.8 kg of diphenyl carbonate was used instead of urea, that the stirring tank 1101 was heated to 220°, and that the internal pressure of the tank was set at 0.2 MPa. After a reaction had been performed for 3 hours, the reaction solution was recovered in a reservoir 1103 through a line B3. The yield of an N-substituted carbamate contained in the reaction solution was found to be approximately 97% with respect to 1-amino-3-aminomethyl-3,5,5-trimethylcyclohexane.

(Precondensation Step)

By using the apparatus shown in FIG. 3, the same method as that in the precondensation step of Example 8 was carried out.

(Pyrolysis Step)

By using the apparatus shown in FIG. 4, the same method as that of Example 6 was carried out, and isophorone diisocyanate was then recovered through a line 47.

(Recovery of Gaseous Phase Component)

On the other hand, the gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising phenol, ammonia and urea as main components. The condenser 904 was a device for carrying out a step of recovering phenol and urea and/or isocyanic acid, and then separating a gaseous phase component containing ammonia as a main component therefrom, and it was a vertical shell-and-tube condenser. Hot water (40° C.) was supplied to the shell side thereof, so that the gaseous phase component was condensed. The condensed component was a mixture of phenol and urea.

(Absorption Step, Step of Separating Phenol, and Stripping Step)

The apparatus shown in FIG. 10 was used, and the same method as that of Example 7 was carried out with the exception that toluene was supplied at a rate of approximately 1 kg/Hr to the apparatus through a line A12. A mixed solution containing phenol and toluene was recovered through a line A4, and it was then subjected to distillation separation in the distillation column. The thus obtained phenol and toluene were recycled as a raw material for the carbamation step and as a solution fed to the line A12, respectively. In addition, ammonia was recovered through a line A7.

Water recovered from the bottom portion of a stripping column 1004 was passed through a line A8, a heat exchanger 1008 and the like, and was then supplied to an absorption column 1001 through a line A9. A portion of the water was discharged through a line A11, and at the same time, the same amount of water was supplied through a line A10, so that the absorbed solution was blown down. The water recovered through the line A11 contained urea.

Example 10

(Carbamation Step)

By using the apparatus shown in FIG. 9, a carbamation step was carried out. The same method as that of Example 7 was carried out, with the exceptions that 1.8 kg of urea was used, that 39.0 kg of 3-methyl-1-butanol was used instead of 2-isopropylphenol, and that 1.1 kg of hexamethylenediamine was used, so as to obtain a reaction solution containing 1,6-hexamethylenediurea.

Subsequently, after 3-methyl-1-butanol had previously been added to the column bottom of a multistage distillation column 903, the column bottom temperature was set at 200° C., the column top pressure was set at 1.3 MPa, and the inside of the column was placed under a total reflux condition of 3-methyl-1-butanol. To this column, the reaction solution obtained after gas-liquid separation was added at a rate of approximately 1.0 kg/Hr through a line 95, and 3-methyl-1-butanol was then supplied at a rate of approximately 3.1 kg/Hr to the column through a line 96 present at the column bottom portion. Moreover, a mixed solution of 3-methyl-1-butanol and urea obtained in a condenser 904 was supplied to the column through a line 98. A reaction solution was discharged from the bottom portion of the multistage distillation column 903, and was then recovered in a reservoir 907 through a line 99.

(Precondensation Step)

Figure 14:
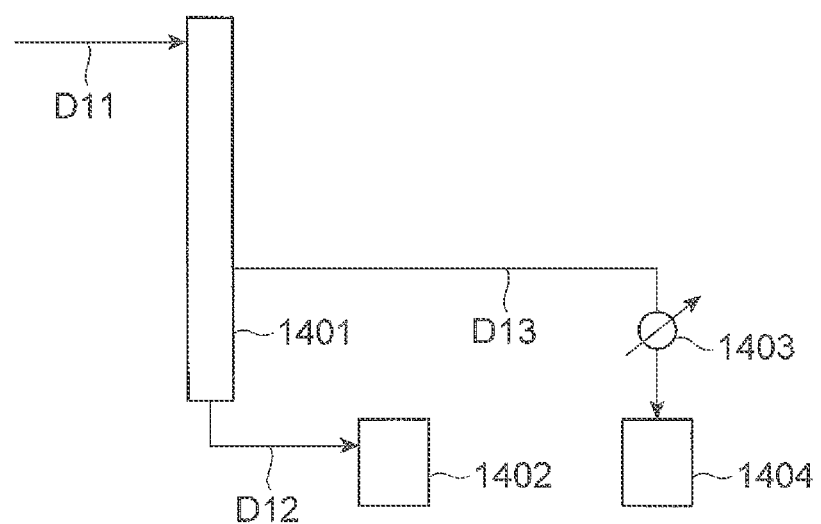
FIG. 14 is a schematic view of an apparatus according to the method for producing an isocyanate of the present embodiment.

Subsequently, by using the apparatus shown in FIG. 14, a precondensation step was carried out. The reaction solution recovered in the reservoir 907 in the carbamation step was supplied at a rate of approximately 10 kg/Hr to a preconcentrator 1401 through a line D11. The preconcentrator 1401 was a falling-film-type evaporator. The jacket temperature thereof was set at 150° C., and the internal pressure thereof was set at 80 kPa. A gaseous phase component generated in the preconcentrator 1401 was passed through a line D13, was then condensed in a condenser 1403, and was then recovered in a reservoir 1404. The recovered product was a mixture of 3-methyl-1-butanol and (3-methylbutyl)carbamate. On the other hand, a liquid phase component in the preconcentrator 1401 was recovered at a rate of approximately 1 kg/Hr in a reservoir 1402 through a line D12. As a result of the analysis of the solution recovered in the reservoir 1402, it was found that 1,6-hexanediyl-di((3-methylbutyl)carbamate) was generated at a yield of 95% with respect to 1,6-hexanediyl-di((3-methylbutyl)carbamate).

(Transesterification Step)

Figure 15:
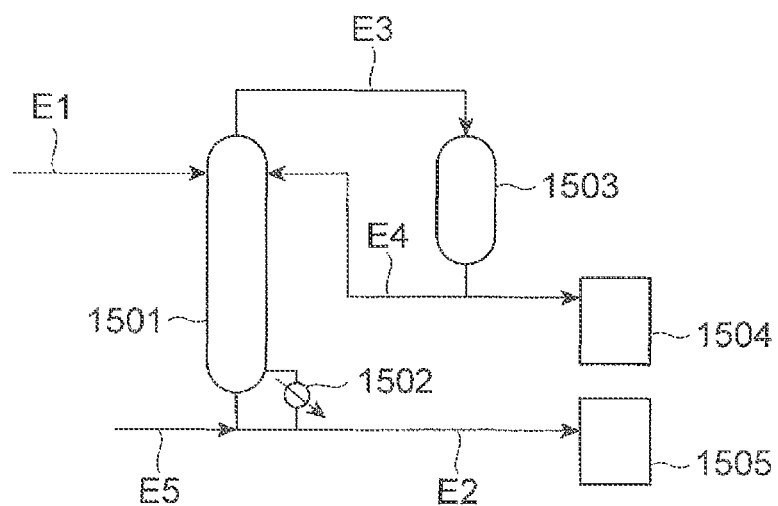
FIG. 15 is a schematic view of an apparatus according to the method for producing an isocyanate of the present embodiment.

By using the apparatus shown in FIG. 15, an transesterification step was carried out. A continuous multistage distillation column 1501 was a packed column filled with Raschig ring. After 4-nonylphenol had previously been supplied to the column bottom portion thereof, the inside of the column was placed under a total reflux condition of 4-nonylphenol. Necessary heat was supplied from a reboiler 1502 to the column. The column bottom temperature was 220° C. The solution recovered in the reservoir 1402 in the precondensation step was supplied at a rate of approximately 1 kg/Hr to the column through a line E1, and 4-nonylphenol was supplied at a rate of approximately 2 kg/Hr to the column through a line E5. At the same time at which the supply of the reaction solution was initiated from the line E1, a line E4 was closed. From the column top, a gaseous phase component containing 3-methyl-1-butanol as a main component was discharged, and it was passed through a line E3, was then condensed in a condenser 1503, and was then recovered in a reservoir 1504. On the other hand, from the column bottom portion, the reaction solution was discharged. It was passed through a line E2, and was then recovered at a rate of approximately 2.1 kg/Hr in a reservoir 1505. The solution recovered in the reservoir 1505 was analyzed. As a result, it was found that 1,6-hexanediyl-di ((4-nonylphenyl)carbamate) was generated at a yield of 95% with respect to 1,6-hexanediyl-di((3-methylbutyl)carbamate).
(Pyrolysis Step)

Figure 16:
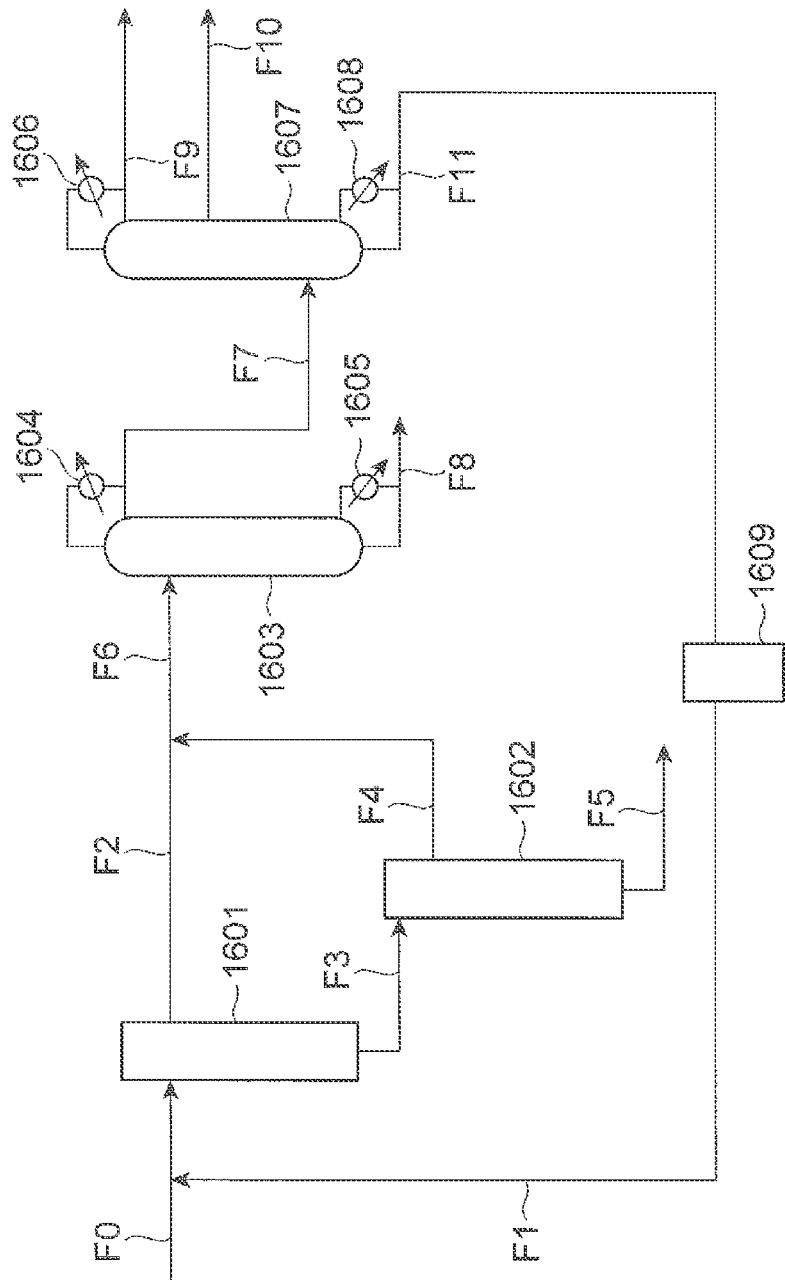
FIG. 16 is a schematic view of an apparatus according to the method for producing an isocyanate of the present embodiment.

By using the apparatus shown in FIG. 16, a pyrolysis step was carried out. Pyrolytic reaction vessels 1601 and 1602 were both thin film evaporators. The internal pressure thereof was set at 1 kPa, and the jacket temperature thereof was set at 250° C. The column top pressure of a separation column 1603 was set at 0.5 kPa, and a total reflux condition of hexadecane was created. A reaction solution recovered in a reservoir 1505 was supplied at a rate of approximately 2.1 kg/Hr to the vessel through a line F0, and hexadecane was supplied thereto at a rate of approximately 1 kg/Hr through a line F1. A liquid phase component contained in the pyrolytic reaction vessel 1601 was continuously supplied to the pyrolytic reaction vessel 1602 through a line F3. A liquid phase component recovered from the bottom portion of the pyrolytic reaction vessel 1602 was recovered through a line F5. A gaseous phase component generated in the pyrolytic reaction vessel was discharged from the pyrolytic reaction vessel through lines F2 and F3, and were then supplied to a separation column 1603 through lines F6 and F4. Heat necessary for distillation separation was supplied from a reboiler 1605, and a component present at the column bottom was recovered through a line F8. From the column top of the separation column 1603, a component containing hexamethylene diisocyanate was recovered, and was then condensed in a condenser 1604. Thereafter, the condensate was supplied to a separation column 1607 through a line F7. Heat necessary for distillation separation was supplied from a reboiler 1608. Hexamethylene diisocyanate was subjected to distillation separation in the separation column 1607, and it was then recovered through a line F10 established at the middle stage of the separation column 1607. A gaseous phase component recovered from the column top of the separation column 1607 was condensed in a condenser 1606, and was then recovered through a line F9. A component containing hexadecane recovered from the column bottom of the separation column 1607 was recovered in a reservoir 1609 through a line F11, and was then recycled through the line F1.
(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising 3-methyl-1-butanol, ammonia and urea as main components. The condenser 904 was a device for carrying out a step of recovering 3-methyl-1-butanol, and urea and/or isocyanic acid, and then separating a gaseous phase component containing ammonia as a main component therefrom, and it was a vertical shell-and-tube condenser. A cooling medium (approximately −5° C.) was supplied to the shell side, so that the gaseous phase component was condensed. The condensed component was a mixture comprising 3-methyl-1-butanol and urea.
(Absorption Step, Step of Separating 3-Methyl-1-Propanol, and Stripping Step)

Figure 17:
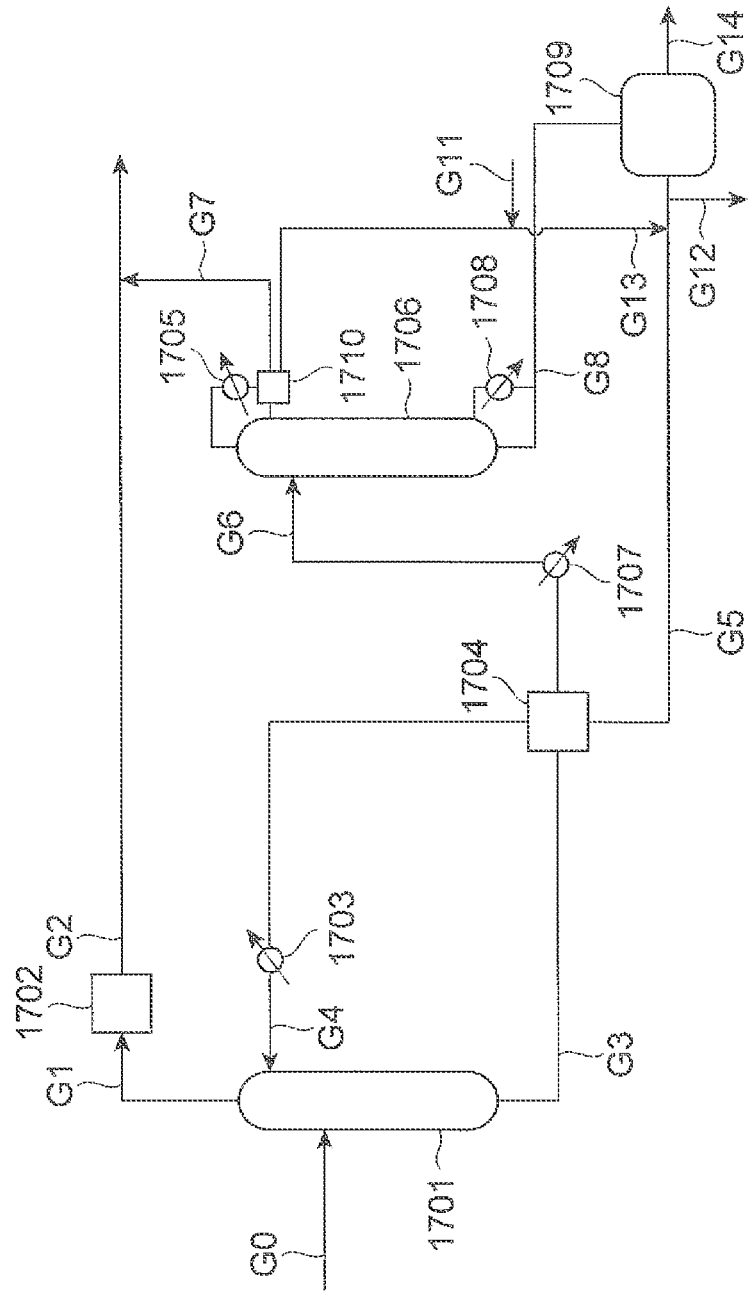
FIG. 17 is a schematic view of an apparatus according to the method for producing an isocyanate of the present embodiment.

The apparatus shown in FIG. 17 was used. An uncondensed gaseous phase component was a gaseous phase component containing ammonia as a main component, and the gaseous phase component was supplied to a gas absorption column 1701 through a line G0. The gas absorption column 1701 was a packed column, and ammonia water (10° C.) was supplied thereto at a rate of approximately 10 kg/Hr through a line G4. A trace amount of ammonia (less than 0.5% with respect to the ammonia recovered from the bottom portion of the gas absorption column 1701) and water were recovered as gaseous phase components from the column top of the gas absorption column 1701 through a line G1, and thereafter, the gaseous phase components were supplied to a pump 1702 for pressure regulation, and were then discharged through a line G2. A solution containing ammonia was recovered from the bottom portion of the gas absorption column 1701 through a line G3, and in the mid-course, it was passed through a heat exchanger 1704, a heater 1707 and a line G6, and was then supplied to a stripping column 1706. The stripping column 1706 was a packed column filled with Heli-Pack. The internal pressure thereof was a slightly compressed pressure (approximately 0.12 MPa), and the temperature of the column bottom portion thereof was set at 110° C. Necessary heat was supplied from a reboiler 1708. After entrained components such as water had been condensed in a condenser 1705, the generated ammonia was discharged and was recovered through a line G7. The ammonia was analyzed by gas chromatography. As a result, it was found that the contents of methane and argon in the ammonia were less than a lower detection limit (0.05 wt %).

Water recovered from the bottom portion of a stripping column 1706 was supplied to a liquid-liquid separator 1709 through a line G8. In the liquid-liquid separator 1709, an organic phase containing 3-methyl-1-propanol was separated from a water phase, and the water phase was then discharged from a line G5. The organic phase was discharged from a line G14, and the recovered 3-methyl-1-butanol was then recycled in the carbamation step.

A portion of absorption water was discharged through a line G12 established in the mid-course of the line G5, and at the same time, the same amount of 1 wt % ammonia water was supplied through a line G13, so that the absorption water was blown down. The concentration of the ammonia water supplied through the line G13 was controlled with solution in a gas-liquid separator 1710 and water supplied through a line G11. The water recovered through the line G12 contained urea.

The absorption water in the line G5 was passed through the heat exchangers 1704 and 1703 and the line G4, and was then supplied to an absorption column 1701.

Example 11

(Carbamation Step)

The same method as that of Example 7 was carried out, with the exceptions that 2.3 kg of urea was used, that 26.0 kg of 4-(α,α-dimethylbenzyl)phenol was used instead of 2-isopropylphenol, and that 1.5 kg of hexamethylenediamine was used, so as to obtain a reaction solution containing 1,6-hexamethylenediurea. Subsequently, the same method as that in the carbamation step of Example 7 was carried out, with the exceptions that 4-(α,α-dimethylbenzyl) phenol was supplied instead of 4-phenylphenol at a rate of approximately 3.0 kg/Hr through a line 96 (FIG. 9), and that a mixed solution of urea and 4-(α,α-dimethylbenzyl)phenol (urea concentration: approximately 10 weight %) was added into a reservoir 905. A reaction solution was recovered in a reservoir 907.

(Precondensation Step)

Subsequently, by using the apparatus shown in FIG. 14, a precondensation step was carried out. A preconcentrator 1401 was a falling-film-type evaporator. The jacket temperature thereof was set at 250° C., and the internal pressure thereof was set at 3 kPa. The reaction solution recovered in the reservoir 907 in the carbamation step was supplied at a rate of approximately 10 kg/Hr to the preconcentrator 1401 through a line D11. The generated gaseous phase component was discharged through a line D13, and it was then condensed together with a gaseous phase component obtained in the after-mentioned pyrolysis step in a distillation column, and the condensate was then recovered in a reservoir 304 shown in FIG. 3. The recovered product was 4-phenylphenol. On the other hand, a liquid phase component in the thin film evaporator 301 was recovered at a rate of approximately 3.5 kg/Hr in a reservoir 303 through a line 32.

(Pyrolysis Step)

Figure 18:
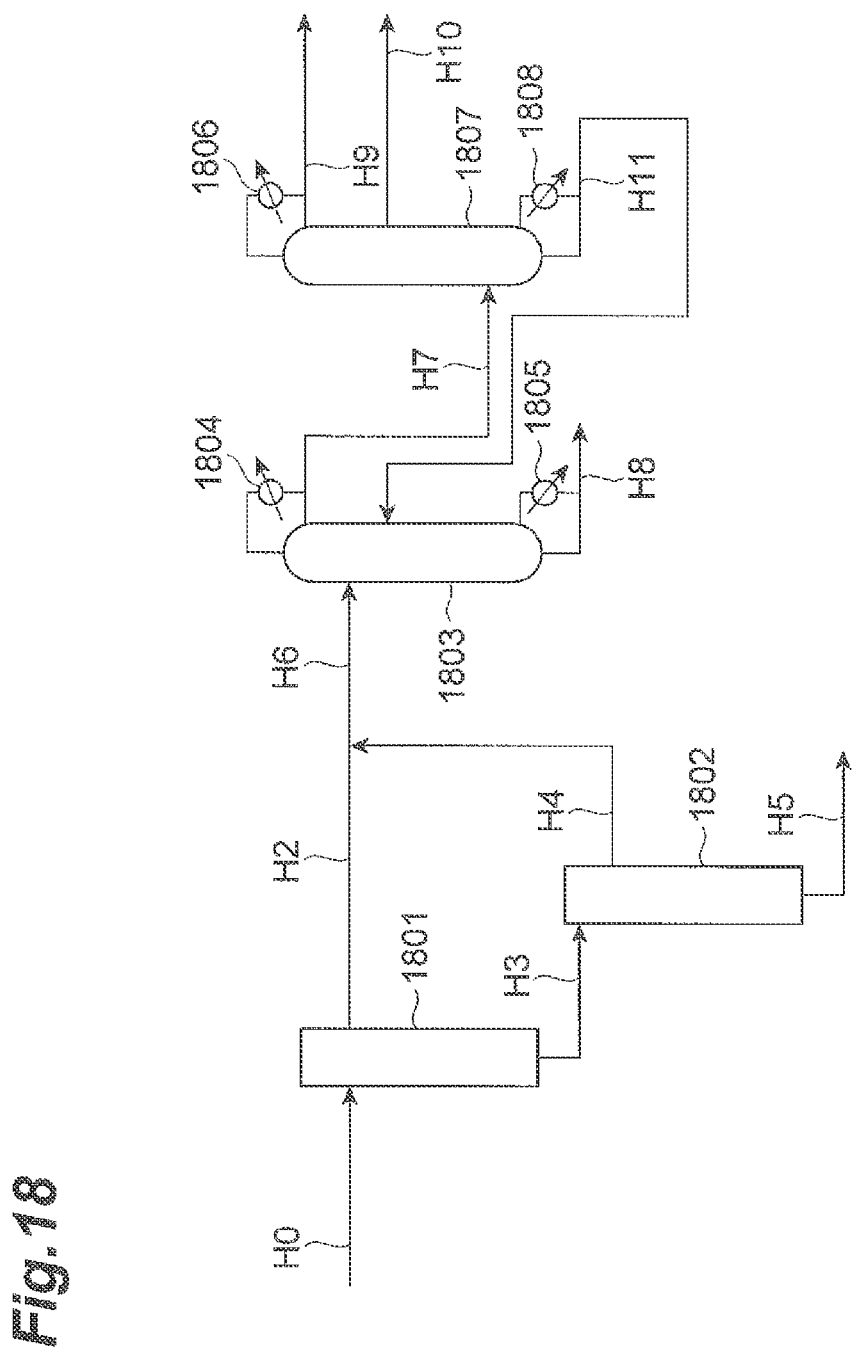
FIG. 18 is a schematic view of an apparatus according to the method for producing an isocyanate of the present embodiment.

By using the apparatus shown in FIG. 18, a pyrolysis step was carried out. Pyrolytic reaction vessels 1801 and 1802 were both falling-film-type evaporators. The internal pressure thereof was set at 1 kPa, and the jacket temperature thereof was set at 250° C. The column top pressure of a separation column 1803 was set at 0.5 kPa, and a total reflux condition of benzyltoluene was created. A reaction solution recovered in a reservoir was supplied to the vessel through a line H0 at a rate of approximately 2.1 kg/Hr, and benzyltoluene was supplied thereto through a line H11 at a rate of approximately 1 kg/Hr. A liquid phase component contained in the pyrolytic reaction vessel 1801 was continuously supplied to the pyrolytic reaction vessel 1802 through a line H3. The liquid phase component in the bottom portion of the pyrolytic reaction vessel 1802 was recovered through a line H5. A gaseous phase component generated in the pyrolytic reaction vessel was discharged from the pyrolytic reaction vessel through lines H2 and H3, and were then supplied to a separation column 1803 through lines H6 and H4. Heat necessary for distillation separation was supplied from a reboiler 1805, and a component containing hexamethylene diisocyanate was recovered from the column top of the separation column 1803, and was then condensed in a condenser 1804. Thereafter, the condensate was supplied to a separation column 1807 through a line H7. The component present at the column bottom of the separation column 1803 was recovered through a line H8. Hexamethylene diisocyanate was subjected to distillation separation in the separation column 1807. Heat necessary for distillation separation was supplied from a reboiler 1808, and hexamethylene diisocyanate was recovered through a line H10 established in the middle stage of the separation column 1807. A gaseous phase component in the column top was condensed in a condenser 1806, and was then recovered through a line H9.

(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising 4-(α,α-dimethylbenzyl)phenol, ammonia and urea as main components. The condenser 904 was a device for carrying out a step of recovering 4-(α,α-dimethylbenzyl)phenol, and urea and/or isocyanic acid, and then separating a gaseous phase component containing ammonia as a main component therefrom, and it was a vertical shell-and-tube condenser. Hot water (approximately 15° C.) was supplied to the shell side, so that the gaseous phase component was condensed. The condensed component was a mixture of 4-(α,α-dimethylbenzyl)phenol and urea. As described above, the mixture was passed through a line 98, and was then supplied to the multistage distillation column 903 again.

(Absorption Step, Step of Separating 4-(α,α-Dimethylbenzyl)Phenol, and Stripping Step)

The same method as that of Example 10 was carried out with the exception that the apparatus shown in FIG. 17 was used. The generated ammonia was discharged through a line G7 and was then recovered. Water recovered from the bottom portion of a stripping column 1706 was passed through a line G8, and was then supplied to a liquid-liquid separator 1709. In the liquid-liquid separator 1709, an organic phase containing 4-(α,α-dimethylbenzyl)phenol was separated from a water phase, and the water phase was then discharged through a line G5. The organic phase was discharged through a line G12, and the recovered 4-(α,α-dimethylbenzyl)phenol was then recycled in the carbamation step.

A portion of absorption water was discharged through a line G12 established in the mid-course of the line G5, and at the same time, the same amount of 1 wt % ammonia water was supplied through a line G11, so that the absorption water was blown down. The water recovered through the line G12 contained urea.

The absorption water in the line G5 was passed through heat exchangers 1704 and 1703, and was then supplied to an absorption column 1701.

Example 12

(Carbamation Step)

By using the apparatus shown in FIG. 2, a carbamation step was carried out. The same method as that in the carbamation step of Example 2 was carried out, in the exceptions that 1.6 kg of 2,4-toluenediamine was used instead of 1-amino-3-aminomethyl-3,5,5-trimethylcyclohexane, and that 1.8 kg of urea and 29.0 kg of 1-butanol were used. A reaction solution was recovered in a reservoir 205.

(Precondensation Step)

By using the apparatus shown in FIG. 3, the same method as that in the precondensation step of Example 2 was carried out.

(Pyrolysis Step)

By using the apparatus shown in FIG. 4, the same method as in the pyrolysis step of Example 2 was carried out with the exception that benzyltoluene was used instead of dibenzyl ether. 2,4-Toluene diisocyanate was recovered through a line 47.

(Recovery of Gaseous Phase Component)

On the other hand, a gaseous phase component recovered from the column top of a multistage distillation column 201 shown in FIG. 2 was supplied to a condenser 203 through a line 23. As a result of the analysis of the gaseous phase component, it was found that the gaseous phase component was a mixture comprising 1-butanol, ammonia and urea as main components. The condenser 203 was a device for carrying out a step of recovering 1-butanol, and urea and/or isocyanic acid, and then separating a gaseous phase component containing ammonia as a main component therefrom, and it was a vertical shell-and-tube condenser. A cooling medium (approximately 0° C.) was supplied to the shell side, so that the gaseous phase component was condensed. The condensed component was a mixture of 1-butanol and urea. As described above, the mixture was passed through a line 24, and was then supplied to the multistage distillation column 201 again.

(Absorption Step and Stripping Step)

By using the apparatus shown in FIG. 5, the same methods as those in the absorption step and the stripping step of Example 2 were carried out. The generated ammonia was recovered through a line 55.

(Separation of 1-Butanol)

Continuously, the apparatus shown in FIG. 5 was used. A liquid present at the column bottom of a stripping column 503 was a mixture comprising 1-butanol, water, and a small amount of ammonia. The mixture was supplied to a distillation column 506 through a line 56, and 1-butanol and water were then subjected to distillation separation. From the column top of the distillation column 506, water (containing a small amount of ammonia) was recovered. The water was passed through lines 57 and 54, and in the mid-course, ammonia water recovered to a gas-liquid separator 511 through a line 59 was added to the water, so that the concentration of ammonia was adjusted. Thereafter, the water was circulated to an absorption column 501.

Example 13

(Carbamation Step)

The same method as that of Example 7 was carried out, with the exceptions that 1.6 kg of urea was used, that 23.0 kg of phenol was used instead of 2-isopropylphenol, and that 1.4 kg of hexamethylenediamine was used. A reaction solution comprising 1,6-hexamethylenediurea was obtained.

The same method as that in the carbamation step of Example 7 was carried out, with the exceptions that the reaction solution was supplied at a rate of approximately 2.0 kg/Hr to a multistage distillation column 903 through a line 95 shown in FIG. 9, that instead of 4-phenylphenol, phenol was supplied thereto at a rate of approximately 1.5 kg/Hr through a line 96, and that a mixed solution of urea and phenol (urea concentration: approximately 15 weight %) was added into a reservoir 905. A reaction solution was recovered at a rate of approximately 2.3 kg/Hr in a reservoir 907.

(Precondensation Step)

Subsequently, by using the apparatus shown in FIG. 14, a precondensation step was carried out. The preconcentrator 1401 was a falling-film-type evaporator. The jacket temperature thereof was set at 250° C., and the internal pressure thereof was set at 3 kPa. The reaction solution recovered in the reservoir 907 in the carbamation step was supplied at a rate of approximately 10 kg/Hr to the preconcentrator 1401 through a line D11. The generated gaseous phase component was discharged through a line D13, and it was then condensed together with a gaseous phase component obtained in the after-mentioned pyrolysis step in a distillation column, and the condensate was then recovered in a reservoir 304 shown in FIG. 3. The recovered product was phenol. On the other hand, a liquid phase component in the thin film evaporator 301 was recovered at a rate of approximately 2.5 kg/Hr in a reservoir 303 through a line 32. As a result, 1,6-hexanediyl-di(phenyl carbamate) was obtained at a yield of 96% with respect to hexamethylenediamine.

(Transesterification Step)

By using the apparatus shown in FIG. 15, the same method as that in the transesterification step of Example 7 was carried out, with the exceptions that 2,4-di($\alpha,\alpha$-dimethylbenzyl)phenol was used instead of 4-nonylphenol, that the column bottom temperature was set at 250° C., and that 2,4-di($\alpha,\alpha$-dimethylbenzyl)phenol was supplied at a rate of approximately 4.2 kg/Hr to the column through a line E5. As a result of the analysis of a solution recovered in a reservoir 1505, it was found that 1,6-hexanediyl-di((2,4-di($\alpha,\alpha$-dimethylbenzyl)phenyl) carbamate) was obtained at a yield of 93% with respect to 1,6-hexanediyl-di(phenyl carbamate).

(Pyrolysis Step)

By using an apparatus shown in FIG. 16, the same method as that in the pyrolysis step of Example 10 was carried out, with the exceptions that the internal pressure of each of the pyrolytic reaction vessels 1601 and 1602 was set at 0.5 kPa, that the jacket temperature thereof was set at 250° C., and that the column top pressure of the separation column 1603 was set at 0.2 kPa. Thereafter, hexamethylene diisocyanate was recovered through a line F10 established at the middle stage of the separation column 1607.

(Recovery of Gaseous Phase Component)

A gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising phenol, ammonia and urea as main components. The condenser 904 was a device for carrying out a step of recovering phenol, and urea and/or isocyanic acid, and then separating a gaseous phase component containing ammonia as a main component therefrom, and it was a vertical shell-and-tube condenser. A cooling medium (approximately 40° C.) was supplied to the shell side, so that the gaseous phase component was condensed. The condensed component was a mixture of phenol and urea.

(Absorption Step and Stripping Step)

By using the apparatus shown in FIG. 5, the same methods as those in the absorption step and the stripping step of Example 2 were carried out with the exception that water (10° C.) was supplied at a rate of approximately 30 kg/Hr to the column through a line 54. The generated ammonia was recovered through a line 55.

(Separation of Phenol)

Continuously, by using the apparatus shown in FIG. 5, the method as that of Example 2 was carried out. Water (containing a small amount of ammonia) was recovered from the column top of a distillation column 506. The water was circulated to an absorption column 501 through lines 57 and 54. Phenol was recovered from the column bottom of the distillation column 506 through a line 58, and it was recycled as a raw material for the carbamation step.

Example 14

(Carbamation Step)

By using the apparatus shown in FIG. 2, a carbamation step was carried out. The same method as that in the carbamation step of Example 2 was carried out, with the exceptions that 1.5 kg of hexamethylenediamine was used instead of 1-amino-3-aminomethyl-3,5,5-trimethylcyclohexane, that 2.9 kg of urea was used, and that 32.0 kg of p-dodecylphenol was used instead of 1-butanol. A reaction solution was recovered in a reservoir 205.

(Precondensation Step)

By using the apparatus shown in FIG. 3, the same method as that in the precondensation step of Example 2 was carried out.

(Pyrolysis Step)

By using the apparatus shown in FIG. 4, the same method as that in the pyrolysis step of Example 2 was carried out with the exception that hexadecane was used instead of dibenzyl ether. Hexamethylene diisocyanate was recovered through a line 47.

(Recovery of Gaseous Phase Component)

On the other hand, a gaseous phase component recovered from the column top of a continuous multistage distillation column 201 shown in FIG. 2 was supplied to a condenser 203 through a line 23. As a result of the analysis of the gaseous phase component, it was found that the gaseous phase component was a mixture comprising p-dodecylphenol, ammonia and urea as main components. The condenser 203 was a device for carrying out a step of recovering p-dodecylphenol, and urea and/or isocyanic acid, and then separating a gaseous phase component containing ammonia as a main component therefrom, and it was a vertical shell-and-tube condenser. Cooling water (approximately 10° C.) was supplied to the shell side, so that the gaseous phase component was condensed. The condensed component was a mixture of p-dodecylphenol and urea. As described above, the mixture was passed through a line 24, and was then supplied to the continuous multistage distillation column 201 again.

(Absorption Step and Stripping Step)

By using the apparatus shown in FIG. 5, the same methods as those in the absorption step and the stripping step of Example 2 were carried out. The generated ammonia was recovered through a line 55.

(Separation of p-Dodecylphenol)

Continuously, the apparatus shown in FIG. 5 was used. A liquid present at the column bottom of a stripping column 503 was a mixture comprising p-dodecylphenol, water, and a small amount of ammonia. The mixture was supplied to a distillation column 506 through a line 56, and p-dodecylphenol and water were then subjected to distillation separation. From the column top of the distillation column 506, water (containing a small amount of ammonia) was recovered. The water was passed through lines 57 and 54, and in the mid-course, ammonia water recovered through a line 59 in a gas-liquid separator 511 was added to the water, so that the concentration of ammonia was adjusted. Thereafter, the water was circulated to an absorption column 501.

Example 15

(Carbamation Step)

By using the apparatus shown in FIG. 2, a carbamation step was carried out. The same method as that in the carbamation step of Example 2 was carried out, with the exceptions that 1.9 kg of hexamethylenediamine was used instead of 1-amino-3-aminomethyl-3,5,5-trimethylcyclohexane, that 3.2 kg of urea was used, and that 53.0 kg of 2,4-di-tert-amylphenol was used instead of 1-butanol. A reaction solution was recovered in a reservoir 205.

(Precondensation Step)

By using the apparatus shown in FIG. 3, the same method as that in the precondensation step of Example 2 was carried out.

(Pyrolysis Step)

By using the apparatus shown in FIG. 4, the same method as that in the pyrolysis step of Example 2 was carried out with the exception that pentadecane was used instead of dibenzyl ether. Hexamethylene diisocyanate was recovered through a line 47.

(Recovery of Gaseous Phase Component)

On the other hand, a gaseous phase component recovered from the column top of a continuous multistage distillation column 201 shown in FIG. 2 was supplied to a condenser 203 through a line 23. As a result of the analysis of the gaseous phase component, it was found that the gaseous phase component was a mixture comprising 2,4-di-tert-amylphenol, ammonia and urea as main components. The condenser 203 was a device for carrying out a step of recovering 2,4-di-tert-amylphenol, and urea and/or isocyanic acid, and then separating a gaseous phase component containing ammonia as a main component therefrom, and it was a vertical shell-and-tube condenser. Cooling water (approximately 25° C.) was supplied to the shell side, so that the gaseous phase component was condensed. The condensed component was a mixture of 2,4-di-tert-amylphenol and urea. As described above, the mixture was passed through a line 24, and was then supplied to the continuous multistage distillation column 201 again.

(Absorption Step and Stripping Step)

By using the apparatus shown in FIG. 5, the same methods as those in the absorption step and the stripping step of Example 2 were carried out. The generated ammonia was recovered through a line 55.

(Separation of 2,4-Di-Tert-Amylphenol)

Continuously, the apparatus shown in FIG. 5 was used. A liquid present at the column bottom of a stripping column 503 was a mixture comprising 2,4-di-tert-amylphenol, water, and a small amount of ammonia. The mixture was supplied to a distillation column 506 through a line 56, and 2,4-di-tert-amylphenol and water were then subjected to distillation separation. From the column top of the distillation column 506, water (containing a small amount of ammonia) was recovered. The water was passed through lines 57 and 54, and in the mid-course, ammonia water recovered through a line 59 in a gas-liquid separator 511 was added to the water, so that the concentration of ammonia was adjusted. Thereafter, the water was circulated to an absorption column 501.

Example 16

(Carbamation Step)

By using the apparatus shown in FIG. 2, a carbamation step was carried out. The same method as that in the carbamation step of Example 2 was carried out, with the exceptions that 1.7 kg of hexamethylenediamine was used instead of 1-amino-3-aminomethyl-3,5,5-trimethylcyclohexane, that 1.8 kg of urea was used, and that 20.0 kg of hydroquinone was used instead of 1-butanol. A reaction solution was recovered in a reservoir 205.

(Precondensation Step)

By using the apparatus shown in FIG. 3, the same method as that in the precondensation step of Example 2 was carried out.

(Pyrolysis Step)

By using the apparatus shown in FIG. 4, the same method as that in the pyrolysis step of Example 2 was carried out with the exception that pentadecane was used instead of dibenzyl ether. Hexamethylene diisocyanate was recovered through a line 47.

(Recovery of Gaseous Phase Component)

On the other hand, a gaseous phase component recovered from the column top of a continuous multistage distillation column 201 shown in FIG. 2 was supplied to a condenser 203 through a line 23. As a result of the analysis of the gaseous phase component, it was found that the gaseous phase component was a mixture comprising hydroquinone, ammonia and urea as main components. The condenser 203 was a device for carrying out a step of recovering hydroquinone, and urea and/or isocyanic acid, and then separating a gaseous phase component containing ammonia as a main component therefrom, and it was a vertical shell-and-tube condenser. Steam (approximately 175° C.) was supplied to the shell side, so that the gaseous phase component was condensed. The condensed component was a mixture of hydroquinone and urea. As described above, the mixture was passed through a line 24, and was then supplied to the continuous multistage distillation column 201 again.
(Absorption Step and Stripping Step)

By using the apparatus shown in FIG. 5, the same methods as those in the absorption step and the stripping step of Example 2 were carried out. The generated ammonia was recovered through a line 55.
(Separation of Hydroquinone)

Continuously, the apparatus shown in FIG. 5 was used. A liquid present at the column bottom of a stripping column 503 was a mixture comprising hydroquinone, water, and a small amount of ammonia. The mixture was supplied to a distillation column 506 through a line 56, and hydroquinone and water were then subjected to distillation separation. From the column top of the distillation column 506, water (containing a small amount of ammonia) was recovered. The water was passed through lines 57 and 54, and in the mid-course, ammonia water recovered through a line 59 in a gas-liquid separator 511 was added to the water, so that the concentration of ammonia was adjusted. Thereafter, the water was circulated to an absorption column 501.

Example 17

(Carbamation Step)

By using the apparatus shown in FIG. 2, a carbamation step was carried out. The same method as that in the carbamation step of Example 2 was carried out, with the exceptions that 1.7 kg of hexamethylenediamine was used instead of 1-amino-3-aminomethyl-3,5,5-trimethylcyclohexane, that 1.8 kg of urea was used, and that 10.0 kg of 2-isopropylphenol and 10.0 kg of 4-phenylphenol were used instead of 1-butanol. A reaction solution was recovered in a reservoir 205.
(Precondensation Step)

By using the apparatus shown in FIG. 3, the same method as that in the precondensation step of Example 2 was carried out.
(Pyrolysis Step)

By using the apparatus shown in FIG. 4, the same method as that in the pyrolysis step of Example 2 was carried out. Hexamethylene diisocyanate was recovered through a line 47.
(Recovery of Gaseous Phase Component)

On the other hand, a gaseous phase component recovered from the column top of a continuous multistage distillation column 201 was supplied to a condenser 203 through a line 23. As a result of the analysis of the gaseous phase component, it was found that the gaseous phase component was a mixture comprising 2-isopropylphenol, ammonia and urea as main components. The condenser 203 was a device for carrying out a step of recovering 2-isopropylphenol, and urea and/or isocyanic acid, and then separating a gaseous phase component containing ammonia as a main component therefrom, and it was a vertical shell-and-tube condenser. Cooling water (approximately 10° C.) was supplied to the shell side, so that the gaseous phase component was condensed. The condensed component was a mixture of 2-isopropylphenol and urea. As described above, the mixture was passed through a line 24, and was then supplied to the continuous multistage distillation column 201 again.
(Absorption Step and Stripping Step)

By using the apparatus shown in FIG. 5, the same methods as those in the absorption step and the stripping step of Example 2 were carried out. The generated ammonia was recovered through a line 55.
(Separation of 2-Isopropylphenol)

Continuously, the apparatus shown in FIG. 5 was used. A liquid present at the column bottom of a stripping column 503 was a mixture comprising 2-isopropylphenol, water, and a small amount of ammonia. The mixture was supplied to a distillation column 506 through a line 56, and 2-isopropylphenol and water were then subjected to distillation separation. From the column top of the distillation column 506, water (containing a small amount of ammonia) was recovered. The water was passed through lines 57 and 54, and in the mid-course, ammonia water recovered through a line 59 in a gas-liquid separator 511 was added to the water, so that the concentration of ammonia was adjusted. Thereafter, the water was circulated to an absorption column 501.

Example 18

(Carbamation Step)

The same method as that of Example 8 was carried out, with the exceptions that 2.1 kg of urea was used, that 45.0 kg of p-heptylphenol was used instead of 2-isopropylphenol, and that 2.1 kg of hexamethylenediamine was used. A reaction solution was recovered in a reservoir 907. An N-substituted carbamate was generated at a yield of approximately 60% with respect to hexamethylenediamine.
(Carbamate Regeneration Step)

The same method as that of Example 8 was carried out with the exception that 4.9 kg of dibutyl carbonate was used instead of urea. A reaction solution was recovered in a reservoir 1103. The yield of an N-substituted carbamate contained in the reaction solution was approximately 90% with respect to hexamethylenediamine.
(Precondensation Step)

The same method as that of Example 8 was carried out.
(Pyrolysis Step)

The same method as that of Example 8 was carried out with the exception that pentadecane was used instead of NeoSK-OIL 1300. Hexamethylene diisocyanate was recovered through a line C9.
(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising p-heptylphenol, ammonia and urea as main components. The condenser 904 was a device for carrying out a step of recovering p-heptylphenol, and urea and/or isocyanic acid, and then separating a gaseous phase component containing ammonia as a main component therefrom, and it was a vertical shell-and-tube condenser. Cooling water (approximately 15° C.) was supplied to the shell side, so that the gaseous phase component was condensed. The condensed component was a mixture of p-heptylphenol and urea.
(Absorption Step, Step of Separating p-Heptylphenol, and Stripping Step)

By using the apparatus shown in FIG. 10, the same method as that of Example 7 was carried out. An organic phase consisting of p-heptylphenol was recovered through a line A4, and it was then recycled as a raw material for the carbamation step. In addition, ammonia was recovered through a line A7. Water recovered from the bottom portion of a stripping column 1004 was passed through a line A8, a heat exchanger 1008 and the like, and was then supplied to an absorption column 1001 through a line A9. A portion of the water was discharged through a line A11, and at the same time, the same amount of water was supplied through a line A10, so that the absorption water was blown down. The water recovered through the line A11 contained urea.

Example 19

(Carbamation Step)

The same method as that of Example 8 was carried out, with the exceptions that 2.7 kg of urea was used, that 38.0 kg of 2-naphthol was used instead of 2-isopropylphenol, and that 1.6 kg of hexamethylenediamine was used. A reaction solution was recovered in a reservoir 907. An N-substituted carbamate was generated at a yield of approximately 66% with respect to hexamethylenediamine.

(Carbamate Regeneration Step)

The same method as that of Example 8 was carried out with the exception that 6.2 kg of phenyl carbamate was used instead of urea. A reaction solution was recovered in a reservoir 1103. The yield of an N-substituted carbamate contained in the reaction solution was approximately 90% with respect to hexamethylenediamine.

(Precondensation Step)

The same method as that of Example 8 was carried out.

(Pyrolysis Step)

The same method as that of Example 8 was carried out with the exception that pentadecane was used instead of NeoSK-OIL 1300. Hexamethylene diisocyanate was recovered through a line C9.

(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising 2-naphthol, ammonia and urea as main components. The condenser 904 was a device for carrying out a step of recovering 2-naphthol, and urea and/or isocyanic acid, and then separating a gaseous phase component containing ammonia as a main component therefrom, and it was a vertical shell-and-tube condenser. Steam (approximately 120° C.) was supplied to the shell side, so that the gaseous phase component was condensed. The condensed component was a mixture of 2-naphthol and urea.

(Absorption Step and Stripping Step)

The same methods as those in the absorption step and the stripping step of Example 2 were carried out. Ammonia was recovered through a line 55.

(Separation of 2-Naphthol)

Continuously, the apparatus shown in FIG. 5 was used. A liquid present at the column bottom of a stripping column 503 was a mixture comprising 2-naphthol, water, and a small amount of ammonia. The mixture was supplied to a distillation column 506 through a line 56, and 2-naphthol and water were then subjected to distillation separation. From the column top of the distillation column 506, water (containing a small amount of ammonia) was recovered. The water was passed through lines 57 and 54, and in the mid-course, ammonia water recovered through a line 59 in a gas-liquid separator 511 was added to the water, so that the concentration of ammonia was adjusted. Thereafter, the water was circulated to an absorption column 501.

Example 20

(Carbamation Step)

The same method as that of Example 8 was carried out, with the exceptions that 1.0 kg of urea was used, that 32.0 kg of 2-phenylphenol was used instead of 2-isopropylphenol, and that 1.0 kg of hexamethylenediamine was used. A reaction solution was recovered in a reservoir 907. An N-substituted carbamate was generated at a yield of approximately 68% with respect to hexamethylenediamine.

(Carbamate Regeneration Step)

The same method as that of Example 8 was carried out with the exception that 0.5 kg of urea was used. A reaction solution was recovered in a reservoir 1103. The yield of an N-substituted carbamate contained in the reaction solution was approximately 90% with respect to hexamethylenediamine.

(Precondensation Step)

The same method as that of Example 8 was carried out.

(Pyrolysis Step)

The same method as that of Example 8 was carried out with the exception that pentadecane was used instead of NeoSK-OIL 1300. Hexamethylene diisocyanate was recovered through a line C9.

(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising 2-phenylphenol, ammonia and urea as main components. The condenser 904 was a device for carrying out a step of recovering 2-phenylphenol, and urea and/or isocyanic acid, and then separating a gaseous phase component containing ammonia as a main component therefrom, and it was a vertical shell-and-tube condenser. Hot water (approximately 60° C.) was supplied to the shell side, so that the gaseous phase component was condensed. The condensed component was a mixture of 2-phenylphenol and urea.

(Absorption Step and Stripping Step)

The same methods as those in the absorption step and the stripping step of Example 2 were carried out. Ammonia was recovered through a line 55.

(Separation of 2-Phenylphenol)

Continuously, the apparatus shown in FIG. 5 was used. A liquid present at the column bottom of a stripping column 503 was a mixture comprising 2-phenylphenol, water, and a small amount of ammonia. The mixture was supplied to a distillation column 506 through a line 56, and 2-phenylphenol and water were then subjected to distillation separation. From the column top of the distillation column 506, water (containing a small amount of ammonia) was recovered. The water was passed through lines 57 and 54, and in the mid-course, ammonia water recovered through a line 59 in a gas-liquid separator 511 was added to the water, so that the concentration of ammonia was adjusted. Thereafter, the water was circulated to an absorption column 501.

Example 21

(Carbamation Step)

The same method as that of Example 8 was carried out, with the exceptions that 1.5 kg of urea was used, that 10.0 kg of 4-ethoxyphenol was used instead of 2-isopropylphenol, and that 1.0 kg of hexamethylenediamine was used. A reaction solution was recovered in a reservoir 907. An N-substituted carbamate was generated at a yield of approximately 77% with respect to hexamethylenediamine.

(Carbamate Regeneration Step)

The same method as that of Example 8 was carried out with the exception that 2.9 kg of diphenyl carbonate was used instead of urea. A reaction solution was recovered in a reservoir 1103. The yield of an N-substituted carbamate contained in the reaction solution was approximately 95% with respect to hexamethylenediamine.

(Precondensation Step)

The same method as that of Example 8 was carried out.

(Pyrolysis Step)

The same method as that of Example 2 was carried out with the exception that the reaction solution obtained in the above described precondensation step was used. Hexamethylene diisocyanate was recovered through a line 47.

(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising 4-ethoxyphenol, ammonia and urea as main components. The condenser 904 was a device for carrying out a step of recovering 4-ethoxyphenol, and urea and/or isocyanic acid, and then separating a gaseous phase component containing ammonia as a main component therefrom, and it was a vertical shell-and-tube condenser. Hot water (approximately 50° C.) was supplied to the shell side, so that the gaseous phase component was condensed. The condensed component was a mixture of 4-ethoxyphenol and urea.

(Absorption Step, Step of Separating 4-Ethoxyphenol, and Stripping Step)

The apparatus shown in FIG. 6 was used, and the same method as that of Example 3 was carried out, with the exceptions that the temperature of water supplied through a line 64 was set at 10° C., and that xylene was used instead of toluene. An organic phase containing 4-ethoxyphenol as a main component was recovered through a line 67, and xylene and 4-ethoxyphenol were then subjected to distillation separation. Thereafter, the two substances were each recycled. A trace amount of ammonia (less than 0.5% with respect to the ammonia recovered from the bottom portion of a gas absorption and/or liquid-liquid separation device 601) and water were recovered as gaseous phase components from the column top of the gas absorption and/or liquid-liquid separation device 601 through a line 61. Ammonia generated in a stripping column 603 was recovered through a line 65. A portion of water recovered from the stripping column 603 was discharged through a line 68, and at the same time, the same amount of water was supplied through a line 69, so that the absorption water was blown down. Thereafter, the absorption water was circulated to the gas absorption and/or liquid-liquid separation device 601 through a line 64. The water recovered through the line 68 contained urea.

Example 22

(Carbamation Step)

The same method as that of Example 8 was carried out, with the exceptions that 1.5 kg of urea was used, that 11.0 kg of hydroquinone was used instead of 2-isopropylphenol, and that 1.2 kg of hexamethylenediamine was used. A reaction solution was recovered in a reservoir 907. An N-substituted carbamate was generated at a yield of approximately 58% with respect to hexamethylenediamine.

(Carbamate Regeneration Step)

The same method as that of Example 8 was carried out with the exception that 1.9 kg of diphenyl carbonate was used instead of urea. A reaction solution was recovered in a reservoir 1103. The yield of an N-substituted carbamate contained in the reaction solution was approximately 92% with respect to hexamethylenediamine.

(Precondensation Step)

The same method as that of Example 8 was carried out.

(Pyrolysis Step)

The same method as that of Example 8 was carried out with the exception that pentadecane was used instead of NeoSK-OIL 1300. Hexamethylene diisocyanate was recovered through a line C9.

(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising hydroquinone, ammonia and urea as main components. The condenser 904 was a device for carrying out a step of recovering hydroquinone, and urea and/or isocyanic acid, and then separating a gaseous phase component containing ammonia as a main component therefrom, and it was a vertical shell-and-tube condenser. Steam (approximately 170° C.) was supplied to the shell side, so that the gaseous phase component was condensed. The condensed component was a mixture of hydroquinone and urea.

(Absorption Step and Stripping Step)

The same methods as those in the absorption step and the stripping step of Example 2 were carried out. Ammonia was recovered through a line 55.

(Separation of Hydroquinone)

Continuously, the apparatus shown in FIG. 5 was used. A liquid present at the column bottom of a stripping column 503 was a mixture comprising hydroquinone, water, and a small amount of ammonia. The mixture was supplied to a distillation column 506 through a line 56, and hydroquinone and water were then subjected to distillation separation. From the column top of the distillation column 506, water (containing a small amount of ammonia) was recovered. The water was passed through lines 57 and 54, and in the mid-course, ammonia water recovered through a line 59 in a gas-liquid separator 511 was added to the water, so that the concentration of ammonia was adjusted. Thereafter, the water was circulated to an absorption column 501.

Example 23

(Carbamation Step)

The same method as that of Example 7 was carried out, with the exceptions that 1.6 kg of urea was used, that 55.0 kg of 2,4-di-tert-amylphenol was used instead of 2-isopropylphenol, and that 1.5 kg of hexamethylenediamine was used. A reaction solution was recovered in a reservoir 907. An N-substituted carbamate was generated at a yield of 89% with respect to hexamethylenediamine.

(Precondensation Step)

The same method as that of Example 8 was carried out.

(Pyrolysis Step)

The same method as that of Example 8 was carried out with the exception that hexadecane was used instead of NeoSK-OIL 1300. Hexamethylene diisocyanate was recovered through a line C9.

(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising 2,4-di-tert-amylphenol, ammonia and urea as main components. The condenser 904 was a device for carrying out a step of recovering 2,4-di-tert-amylphenol, and urea and/or isocyanic acid, and then separating a gaseous phase component containing ammonia as a main component therefrom, and it was a vertical shell-and-tube condenser. Steam (approximately 170° C.) was supplied to the shell side, so that the gaseous phase component was condensed. The condensed component was a mixture of 2,4-di-tert-amylphenol and urea.

(Absorption Step, Step of Separating 2,4-Di-Tert-Amylphenol, and Stripping Step)

By using the apparatus shown in FIG. 10, the same method as that of Example 7 was carried out. An organic phase consisting of 2,4-di-tert-amylphenol was recovered through a line A4, and it was then recycled as a raw material for the carbamation step. In addition, ammonia was recovered through a line A7. Water recovered from the bottom portion of a stripping column 1004 was passed through a line A8, a heat exchanger 1008 and the like, and was then supplied to an absorption column 1001 through a line A9. A portion of the water was discharged through a line A11, and at the same time, the same amount of water was supplied through a line A10, so that the absorption water was blown down. The water recovered through the line A11 contained urea.

Example 24

(Carbamation Step)

The same method as that of Example 7 was carried out, with the exceptions that 2.2 kg of urea was used, that 100 kg of 2,4-di-($\alpha,\alpha$-dimethylbenzyl)phenol was used instead of 2-isopropylphenol, and that 1.8 kg of hexamethylenediamine was used. A reaction solution was recovered in a reservoir 907. An N-substituted carbamate was generated at a yield of approximately 91% with respect to hexamethylenediamine.

(Precondensation Step)

The same method as that of Example 8 was carried out.

(Pyrolysis Step)

The same method as that of Example 8 was carried out with the exception that heptadecane was used instead of NeoSK-OIL 1300. Hexamethylene diisocyanate was recovered through a line C9.

(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising 2,4-di-($\alpha,\alpha$-dimethylbenzyl)phenol, ammonia and urea as main components. The condenser 904 was a device for carrying out a step of recovering 2,4-di-($\alpha,\alpha$-dimethylbenzyl)phenol, and urea and/or isocyanic acid, and then separating a gaseous phase component containing ammonia as a main component therefrom, and it was a vertical shell-and-tube condenser. Hot water (approximately 70° C.) was supplied to the shell side, so that the gaseous phase component was condensed. The condensed component was a mixture of 2,4-di-($\alpha,\alpha$-dimethylbenzyl)phenol and urea.

(Absorption Step, Step of Separating 2,4-di-($\alpha,\alpha$-Dimethylbenzyl)Phenol, and Stripping Step)

The same method as that of Example 10 was carried out with the exception that the apparatus shown in FIG. 17 was used. The generated ammonia was discharged through a line G7 and was then recovered.

Water recovered from the bottom portion of a stripping column 1706 was supplied to a liquid-liquid separator 1709 through a line G8. In the liquid-liquid separator 1709, an organic phase containing 2,4-di-($\alpha,\alpha$-dimethylbenzyl)phenol was separated from a water phase, and the water phase was then discharged from a line G5. The organic phase was discharged from a line G12, and the recovered 2,4-($\alpha,\alpha$-dimethylbenzyl)phenol was then recycled in the carbamation step. A portion of absorption water was discharged through a line G12 established in the mid-course of the line G5, and at the same time, the same amount of 1 wt % ammonia water was supplied through a line G11, so that the absorption water was blown down. The water recovered through the line G12 contained urea. The absorption water in the line G5 was passed through heat exchangers 1704 and 1703, and was then supplied to an absorption column 1701.

Example 25

(Carbamation Step)

The same method as that of Example 7 was carried out, with the exceptions that 1.5 kg of urea was used, that 320 kg of 2-phenylphenol was used instead of 2-isopropylphenol, and that 1.0 kg of hexamethylenediamine was used. A reaction solution was recovered in a reservoir 907. An N-substituted carbamate was generated at a yield of approximately 84% with respect to hexamethylenediamine.

(Precondensation Step)

The same method as that of Example 8 was carried out.

(Pyrolysis step)

The same method as that of Example 8 was carried out with the exception that heptadecane was used instead of NeoSK-OIL 1300. Hexamethylene diisocyanate was recovered through a line C9.

(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising 2-phenylphenol, ammonia and urea as main components. The condenser 904 was a device for carrying out a step of recovering 2-phenylphenol, and urea and/or isocyanic acid, and then separating a gaseous phase component containing ammonia as a main component therefrom, and it was a vertical shell-and-tube condenser. Hot water (approximately 70° C.) was supplied to the shell side, so that the gaseous phase component was condensed. The condensed component was a mixture of 2-phenylphenol and urea.

(Absorption Step, Step of Separating 2-Phenylphenol, and Stripping Step)

The same method as that of Example 10 was carried out with the exception that the apparatus shown in FIG. 17 was used. The generated ammonia was discharged through a line G7 and was then recovered. Water recovered from the bottom portion of a stripping column 1706 was supplied to a liquid-liquid separator 1709 through a line G8. In the liquid-liquid separator 1709, an organic phase containing 2-phenylphenol was separated from a water phase, and the water phase was then discharged from a line G5. The organic phase was discharged from a line G12, and the recovered 2-phenylphenol was then recycled in the carbamation step. A portion of absorption water was discharged through a line G12 established in the mid-course of the line G5, and at the same time, the same amount of 1 wt % ammonia water was supplied through a line G11, so that the absorption water was blown down. The water recovered through the line G12 contained urea. The absorption water in the line G5 was passed through heat exchangers 1704 and 1703, and was then supplied to an absorption column 1701.

Example 26

(Carbamation Step)

By using the apparatus shown in FIG. 9, the same method as that in the carbamation step of Example 7 was carried out, with the exceptions that 4.1 kg of urea was used, that 33.0 kg of 2-phenylethanol was used instead of 2-isopropylphenol, and that 2.1 kg of hexamethylenediamine was used. 1,6-Hexamethylenediurea was obtained at a yield of approximately 90% with respect to hexamethylenediamine.

Subsequently, the same method as that of Example 7 was carried out, with the exceptions that 4-(1,1,3,3-tetramethylbutyl)phenol was used instead of 4-phenylphenol, that a mixed solution of urea and 2-phenylethanol (urea concentration: approximately 5.8 weight %) was added into a reservoir 905, and that instead of 4-phenylphenol, 4-(1,1,3,3-tetramethylbutyl)phenol was supplied at a rate of approximately 2.9 kg/Hr through a line 96 present at the column bottom portion. A reaction solution was discharged from the bottom portion of the multistage distillation column 903, and it was then recovered in a reservoir 907 through a line 99.

(Precondensation Step)

A precondensation step was carried out by the same method as that of Example 7.

(Pyrolysis Step)

The same method as that in the pyrolysis step of Example 7 was carried out with the exception that pentadecane was used instead of dodecane. Hexamethylene diisocyanate was recovered through a line 79.

(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising 2-phenylethanol, ammonia and urea as main components. The condenser 904 was a device for carrying out a step of recovering 2-phenylethanol, and urea and/or isocyanic acid, and then separating a gaseous phase component containing ammonia as a main component therefrom, and it was a vertical shell-and-tube condenser. Hot water (approximately 15° C.) was supplied to the shell side, so that the gaseous phase component was condensed. The condensed component was a mixture of 2-phenylethanol and urea. As described above, the mixture was supplied to the multistage distillation column 903 again through a line 98.

(Absorption Step and Stripping Step)

The same method as that of Example 6 was carried out, and ammonia was recovered through a line 85.

Water recovered from the bottom portion of a stripping column 803 contained 2-phenylethanol and urea. A portion of the water was discharged through a line 87, and at the same time, the same amount of water was supplied through a line 88, so that the absorption water was blown down. Thereafter, the absorption water was circulated to an absorption column 801 through a line 84. The water containing 2-phenylethanol and urea, which had been recovered through the line 87, was subjected to distillation separation, so that 2-phenylethanol containing urea was separated from water. They were recycled as a raw material for carbamation and as absorption water, respectively.

Example 27

(Carbamation Step)

By using the apparatus shown in FIG. 9, the same method as that of in the carbamation step Example 7 was carried out, with the exceptions that 2.4 kg of urea was used, that 19.0 kg of isodecyl alcohol was used instead of 2-isopropylphenol, and that 1.3 kg of hexamethylenediamine was used. 1,6-Hexamethylenediurea was obtained at a yield of approximately 88% with respect to hexamethylenediamine.

Subsequently, the same method as that of Example 7 was carried out, with the exceptions that 2-naphthol was used instead of 4-phenylphenol, that a mixed solution of urea and isodecyl alcohol (urea concentration: approximately 5.6 weight %) was added into a reservoir 905, and that instead of 4-phenylphenol, 2-naphthol was supplied at a rate of approximately 2.1 kg/Hr through a line 96 of the column bottom portion. A reaction solution was discharged from the bottom portion of the multistage distillation column 903, and it was then recovered in a reservoir 907 through a line 99.

(Precondensation Step)

A precondensation step was carried out by the same method as that of Example 7.

(Pyrolysis Step)

The same method as that in the pyrolysis step of Example 7 was carried out with the exception that pentadecane was used instead of dodecane. Hexamethylene diisocyanate was recovered through a line 79.

(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising isodecyl alcohol, ammonia and urea as main components. The condenser 904 was a device for carrying out a step of recovering isodecyl alcohol, and urea and/or isocyanic acid, and then separating a gaseous phase component containing ammonia as a main component therefrom, and it was a vertical shell-and-tube condenser. Hot water (approximately 15° C.) was supplied to the shell side, so that the gaseous phase component was condensed. The condensed component was a mixture of isodecyl alcohol and urea. As described above, the mixture was supplied to the multistage distillation column 903 again through a line 98.

(Absorption Step and Stripping Step)

The same method as that of Example 6 was carried out, and ammonia was recovered through a line 85.

Water recovered from the bottom portion of a stripping column 803 contained isodecyl alcohol and urea. A portion of the water was discharged through a line 87, and at the same time, the same amount of water was supplied through a line 88, so that the absorption water was blown down. Thereafter, the absorption water was circulated to an absorption column 801 through a line 84. The water containing isodecyl alcohol and urea, which had been recovered through the line 87, was subjected to distillation separation, so that isodecyl alcohol containing urea was separated from water. They were recycled as a raw material for carbamation and as absorption water, respectively.

Example 28

(Carbamation Step)

By using the apparatus shown in FIG. 9, the same method as that in the carbamation step of Example 7 was carried out, with the exceptions that 2.4 kg of urea was used, that 19.0 kg of isodecyl alcohol was used instead of 2-isopropylphenol, and that 1.3 kg of hexamethylenediamine was used. 1,6-Hexamethylenediurea was obtained at a yield of approximately 88% with respect to hexamethylenediamine.

Subsequently, the same method as that of Example 7 was carried out, with the exceptions that 2-naphthol was used instead of 4-phenylphenol, that a mixed solution of urea and isodecyl alcohol (urea concentration: approximately 5.6 weight %) was added into a reservoir 905, and that instead of 4-phenylphenol, 2-naphthol was supplied at a rate of approximately 2.1 kg/Hr through a line 96 of the column bottom portion. A reaction solution was discharged from the bottom portion of the multistage distillation column 903, and it was then recovered in a reservoir 907 through a line 99.

(Precondensation Step)

A precondensation step was carried out by the same method as that of Example 7.

(Pyrolysis Step)

The same method as that in the pyrolysis step of Example 7 was carried out with the exception that pentadecane was used instead of dodecane. Hexamethylene diisocyanate was recovered through a line 79.

(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising isodecyl alcohol, ammonia and urea as main components. The condenser 904 was a device for carrying out a step of recovering isodecyl alcohol, and urea and/or isocyanic acid, and then separating a gaseous phase component containing ammonia as a main component therefrom, and it was a vertical shell-and-tube condenser. Hot water (approximately 15° C.) was supplied to the shell side, so that the gaseous phase component was condensed. The condensed component was a mixture of isodecyl alcohol and urea. As described above, the mixture was supplied to the multistage distillation column 903 again through a line 98.

(Absorption Step and Stripping Step)

The same method as that of Example 6 was carried out, and ammonia was recovered through a line 85.

Water recovered from the bottom portion of a stripping column 803 contained isodecyl alcohol and urea. A portion of the water was discharged through a line 87, and at the same time, the same amount of water was supplied through a line 88, so that the absorption water was blown down. Thereafter, the absorption water was circulated to an absorption column 801 through a line 84. The water containing isodecyl alcohol and urea, which had been recovered through the line 87, was subjected to distillation separation, so that isodecyl alcohol containing urea was separated from water. They were recycled as a raw material for carbamation and as absorption water, respectively.

Example 29

(Carbamation Step)

By using the apparatus shown in FIG. 9, a carbamation step was carried out. 3.9 kg of urea was supplied to a stirring tank 901, and the stirring tank 901 was then heated to 150° C. to melt the urea. Thereafter, 1.0 kg of hexamethylenediamine was supplied at a rate of approximately 0.1 kg/Hr to the stirring tank 901 through a line 92. After the total amount of hexamethylenediamine had been supplied, the obtained mixture was stirred for 2 hours. Thereafter, the reaction solution was analyzed. As a result, it was found that 1,6-hexamethylenediurea was generated at a yield of approximately 85% with respect to hexamethylenediamine. The reaction solution was supplied to a multistage distillation column 903 through a line 93 and a line 95. In the mid-course, ammonia was separated from the reaction solution in a gas-liquid separator 902, and was then discharged through a line 94.

The multistage distillation column 903 was a distillation column comprising CASCADE MINI-RINGS (registered trademark) as a filler. Previously, 4-(1,1,3,3-tetramethylbutyl)phenol had been added to the bottom of the distillation column. Thereafter, the column bottom temperature was set at 250° C., and the inside of the column was placed under a total reflux condition. To this column, the reaction solution obtained after gas-liquid separation was added at a rate of approximately 0.5 kg/Hr through a line 95, and 4-(1,1,3,3-tetramethylbutyl)phenol was supplied at a rate of approximately 3.2 kg/Hr through a line 96 present at the column bottom portion. A mixed solution of 2-(1,1,3,3-tetramethylbutyl)phenol and urea obtained in a condenser 904 was supplied to the column through a line 98. The reaction solution was discharged from the bottom portion of the multistage distillation column 903, and was then recovered in a reservoir 907 through a line 99.

(Precondensation Step)

A precondensation step was carried out by the same method as that of Example 7.

(Pyrolysis Step)

The same method as that in the pyrolysis step of Example 7 was carried out with the exception that pentadecane was used instead of dodecane. Hexamethylene diisocyanate was recovered through a line 79.

(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising 4-(1,1,3,3-tetramethylbutyl)phenol, ammonia and urea as main components. The condenser 904 was a device for carrying out a step of recovering 4-(1,1,3,3-tetramethylbutyl)phenol, and urea and/or isocyanic acid, and then separating a gaseous phase component containing ammonia as a main component therefrom, and it was a vertical shell-and-tube condenser. Hot water (approximately 15° C.) was supplied to the shell side, so that the gaseous phase component was condensed. The condensed component was a mixture of 4-(1,1,3,3-tetramethylbutyl) phenol and urea. As described above, the mixture was supplied to the multistage distillation column 903 again through a line 98.
(Absorption Step and Stripping Step)

The same methods as those in the absorption step and the stripping step of Example 2 were carried out. Ammonia was recovered through a line 55.
(Separation of 4-(1,1,3,3-Tetramethylbutyl)Phenol)

Continuously, the apparatus shown in FIG. 5 was used. A liquid present at the column bottom of a stripping column 503 was a mixture comprising 4-(1,1,3,3-tetramethylbutyl) phenol, water and a small amount of ammonia. The mixture was supplied to a distillation column 506 through a line 56, and 4-(1,1,3,3-tetramethylbutyl)phenol and water were subjected to distillation separation. Water (containing a small amount of ammonia) was recovered from the column top of the distillation column 506. The water was passed through lines 57 and 54, and in the mid-course, ammonia water recovered in a gas-liquid separator 511 was added to the water through a line 59, so as to adjust the concentration of ammonia. The mixed solution was circulated to an absorption column 501.

Example 30

(Carbamation Step)

The same method as that in the carbamation step of Example 29 was carried out with the exception that 1.1 kg of hexamethylenediamine and 11 kg of urea were used. 1,6-Hexamethylenediurea was obtained at a yield of approximately 88% with respect to hexamethylenediamine.

Subsequently, the same method as that in the carbamation step of Example 29 was carried out, with the exceptions that 4-ethoxyphenol was used instead of 4-(1,1,3,3-tetramethylbutyl)phenol, that a reaction solution containing 1,6-hexamethylenediurea was added at a rate of approximately 0.3 kg/Hr to the column through a line 95, and that 4-ethoxyphenol was added at a rate of approximately 2.5 kg/Hr to the column through a line 96 present at the column bottom portion. A reaction solution was recovered in a reservoir 907.
(Precondensation Step)

A precondensation step was carried out by the same method as that of Example 7.
(Pyrolysis Step)

The same method as that of Example 2 was carried out with the exception that the reaction solution obtained in the above described precondensation step was used. Hexamethylene diisocyanate was recovered through a line 47. Cyanate was recovered.
(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising 4-ethoxyphenol, ammonia and urea as main components. The condenser 904 was a device for carrying out a step of recovering 4-ethoxyphenol, and urea and/or isocyanic acid, and then separating a gaseous phase component containing ammonia as a main component therefrom, and it was a vertical shell-and-tube condenser. Hot water (approximately 50° C.) was supplied to the shell side, so that the gaseous phase component was condensed. The condensed component was a mixture of 4-ethoxyphenol and urea.
(Absorption Step, Step of Separating 4-Ethoxyphenol, and Stripping Step)

By using the apparatus shown in FIG. 6, the same method as that of Example 3 was carried out, with the exceptions that the temperature of water supplied through a line 64 was set at 10° C., and that xylene was used instead of toluene.

An organic phase containing 4-ethoxyphenol as main components was recovered through a line 67, and xylene was separated from 4-ethoxyphenol according to distillation separation. Thereafter, the two substances were recycled. From the column top of a gas absorption and/or liquid-liquid separation device 601, a trace amount of ammonia (less than 0.5% with respect to the ammonia recovered from the bottom portion of the gas absorption and/or liquid-liquid separation device 601) and water were recovered as gaseous phase components through a line 61.

Ammonia generated in a stripping column 603 was recovered through a line 65. A portion of water, which had been recovered from the bottom portion of the stripping column 603, was discharged through a line 68, and at the same time, the same amount of water was supplied through a line 69, so that the absorption water was blown down. Thereafter, the absorption water was circulated to the gas absorption and/or liquid-liquid separation device 601 through a line 64. The water recovered through the line 68 contained urea.

Example 31

(Carbamation Step)

The same method as that in the carbamation step of Example 29 was carried out with the exception that 1.1 kg of hexamethylenediamine and 9.2 kg of urea were used. 1,6-Hexamethylenediurea was obtained at a yield of approximately 80% with respect to hexamethylenediamine.

Subsequently, the same method as that in the carbamation step of Example 29 was carried out, with the exceptions that 4-(α,α-dimethylbenzyl)phenol was used instead of 4-(1,1,3,3-tetramethylbutyl)phenol, that a reaction solution containing 1,6-hexamethylenediurea was added at a rate of approximately 0.3 kg/Hr to the column through a line 95, and that 4-(α,α-dimethylbenzyl)phenol was added at a rate of approximately 4.2 kg/Hr to the column through a line 96 present at the column bottom portion. A reaction solution was recovered in a reservoir 907.
(Precondensation Step)

A precondensation step was carried out by the same method as that of Example 7.
(Pyrolysis Step)

The same method as that in the pyrolysis step of Example 7 was carried out with the exception that pentadecane was used instead of dodecane. Hexamethylene diisocyanate was recovered through a line 79.
(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising 4-(α,α-dimethylbenzyl)phenol, ammonia and urea as main components. The condenser 904 was a device for carrying out a step of recovering 4-(α,α-dimethylbenzyl)phenol, and urea and/or isocyanic acid, and then separating a gaseous phase component containing ammonia as a main component therefrom, and it was a vertical shell-and-tube condenser. Hot water (approximately 15° C.) was supplied to the shell side, so that the gaseous phase component was condensed. The condensed component was a mixture of 4-(α,α-dimethylbenzyl)phenol and urea. As described above, the mixture was supplied to the multistage distillation column 903 again through a line 98.
(Absorption Step, Step of Separating 4-(α,α-Dimethylbenzyl)Phenol, and Stripping Step)

The same method as that of Example 10 was carried out with the exception that the apparatus shown in FIG. 17 was used. The generated ammonia was discharged through a line G7 and was then recovered.

Water recovered from the bottom portion of a stripping column 1706 was supplied to a liquid-liquid separator 1709 through a line G8. In the liquid-liquid separator 1709, an organic phase containing 4-(α,α-dimethylbenzyl)phenol was separated from a water phase, and the water phase was then discharged from a line G5. The organic phase was discharged from a line G12, and the recovered 4-(α,α-dimethylbenzyl)phenol was then recycled in the carbamation step. A portion of absorption water was discharged through a line G12 established in the mid-course of the line G5, and at the same time, the same amount of 1 wt % ammonia water was supplied through a line G11, so that the absorption water was blown down. The water recovered through the line G12 contained urea. The absorption water in the line G5 was passed through heat exchangers 1704 and 1703, and was then supplied to an absorption column 1701.

Example 32

(Production of N-Unsubstituted Carbamate)

The same method as that for the production of an N-unsubstituted carbamate in Example 9 was carried out, with the exceptions that 3.1 kg of urea was used, and that 35.0 kg of 4-phenylphenol was used instead of phenol. A reaction solution recovered in a reservoir 1304 contained (4-phenylphenyl)carbamate, and the yield of the (4-phenylphenyl) carbamate was approximately 68% with respect to urea.
(Carbamation Step)

The same method as that of Example 7 was carried out, with the exceptions that the reaction solution recovered in the reservoir 1304 in the above described step was used instead of urea and 2-isopropylphenol, and that 1.8 kg of hexamethylenediamine was used. A reaction solution containing 1,6-hexamethylenediurea was obtained.

The same method as that of Example 7 was carried out, with the exceptions that the reaction solution obtained after gas-liquid separation was added at a rate of approximately 1.8 kg/Hr through a line 95, and that 4-phenylphenol was used instead of 4-dodecylphenol. A reaction solution was recovered in a reservoir 907 through a line 99. The reaction solution contained a polymer having a urea bond, as well as an N-substituted carbamate that was a compound of interest in the present step. The yield of the N-substituted carbamate was approximately 70% with respect to hexamethylenediamine.
(Carbamate Regeneration Step)

By using the apparatus shown in FIG. 11, the same method as that in the carbamate regeneration step of Example 8 was carried out, with the exceptions that 6.4 kg of diphenyl carbonate was used instead of urea, that a stirring tank 1101 was heated to 220° C., and that the internal pressure was set at 0.2 MPa. After the reaction had been performed for three hours, a reaction solution was recovered in a reservoir 1103 through a line B3. The yield of an N-substituted carbamate contained in the reaction solution was approximately 97% with respect to hexamethylenediamine.
(Precondensation Step)

By using the apparatus shown in FIG. 3, the same method as that in the precondensation step of Example 8 was carried out.
(Pyrolysis Step)

By using the apparatus shown in FIG. 4, the same method as that of Example 6 was carried out. Hexamethylene diisocyanate was recovered through a line 47.
(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising 4-phenylphenol, ammonia and urea as main components. The condenser 904 was a device for carrying out a step of recovering 4-phenylphenol, and urea and/or isocyanic acid, and then separating a gaseous phase component containing ammonia as a main component therefrom, and it was a vertical shell-and-tube condenser. Hot water (approximately 40° C.) was supplied to the shell side, so that the gaseous phase component was condensed. The condensed component was a mixture of 4-phenylphenol and urea.
(Absorption Step, Step of Separating 4-Phenylphenol, and Stripping Step)

The same method as that of Example 10 was carried out with the exception that the apparatus shown in FIG. 17 was used. The generated ammonia was discharged through a line G7 and was then recovered.

Water recovered from the bottom portion of a stripping column 1706 was supplied to a liquid-liquid separator 1709 through a line G8. In the liquid-liquid separator 1709, an organic phase containing 4-phenylphenol was separated from a water phase, and the water phase was then discharged from a line G5. The organic phase was discharged from a line G12, and the recovered 2-phenylphenol was then recycled in the carbamation step.

A portion of absorption water was discharged through a line G12 established in the mid-course of the line G5, and at the same time, the same amount of 1 wt % ammonia water was supplied through a line G11, so that the absorption water was blown down. The water recovered through the line G12 contained urea.

The absorption water in the line G5 was passed through heat exchangers 1704 and 1703, and was then supplied to an absorption column 1701.

Example 33

(Production of N-Unsubstituted Carbamate)

The same method as that for the production of an N-unsubstituted carbamate in Example 9 was carried out, with the exceptions that 2.4 kg of urea was used, and that 39.0 kg of 4-heptylphenol was used instead of phenol. A reaction solution recovered in a reservoir 1304 contained (4-heptylphenyl)carbamate, and the yield of the (4-heptylphenyl) carbamate was approximately 71% with respect to urea.
(Carbamation Step)

The same method as that of Example 7 was carried out, with the exceptions that the reaction solution recovered in the reservoir 1304 in the above described step was used instead of urea and 2-isopropylphenol, and that 1.2 kg of hexamethylenediamine was used. A reaction solution containing 1,6-hexamethylenediurea was obtained.

The same method as that of Example 7 was carried out, with the exceptions that the reaction solution obtained after gas-liquid separation was added at a rate of approximately 1.0 kg/Hr through a line 95, and that 4-heptylphenol was used instead of 4-phenylphenol. A reaction solution was recovered in a reservoir 907 through a line 99. The reaction solution contained a polymer having a urea bond, as well as an N-substituted carbamate that was a compound of interest in the present step. The yield of the N-substituted carbamate was approximately 78% with respect to hexamethylenediamine.

(Precondensation Step)

By using the apparatus shown in FIG. 3, the same method as that in the precondensation step of Example 8 was carried out.

(Pyrolysis Step)

By using the apparatus shown in FIG. 4, the same method as that of Example 6 was carried out. Hexamethylene diisocyanate was recovered through a line 47. The hexamethylene diisocyanate was obtained at a yield of 71% with respect to hexamethylenediamine.

(Recovery of Gaseous Phase Component)

On the other hand, a gaseous phase component recovered from the column top of a multistage distillation column 903 shown in FIG. 9 was supplied to a condenser 904 through a line 97. As a result of the analysis of the gaseous phase component, it was found that the gaseous phase component was a mixture comprising 4-heptylphenol, ammonia and urea as main components. The condenser 904 was a device for carrying out a step of recovering 4-heptylphenol, and urea and/or isocyanic acid, and then separating a gaseous phase component containing ammonia as a main component therefrom, and it was a vertical shell-and-tube condenser. Hot water (approximately 40° C.) was supplied to the shell side, so that the gaseous phase component was condensed. The condensed component was a mixture of 4-heptylphenol and urea.

(Absorption Step, Step of Separating 4-Heptylphenol, and Stripping Step)

The same method as that of Example 10 was carried out with the exception that the apparatus shown in FIG. 17 was used. The generated ammonia was discharged through a line G7 and was then recovered.

Water recovered from the bottom portion of a stripping column 1706 was supplied to a liquid-liquid separator 1709 through a line G8. In the liquid-liquid separator 1709, an organic phase containing 4-heptylphenol was separated from a water phase, and the water phase was then discharged from a line G5. The organic phase was discharged from a line G12, and the recovered 2-heptylphenol was then recycled in the carbamation step.

A portion of absorption water was discharged through a line G12 established in the mid-course of the line G5, and at the same time, the same amount of 1 wt % ammonia water was supplied through a line G11, so that the absorption water was blown down. The water recovered through the line G12 contained urea.

The absorption water in the line G5 was passed through heat exchangers 1704 and 1703, and was then supplied to an absorption column 1701.

Example 34

(Production of Ammonium Sulfate)

Figure 19:
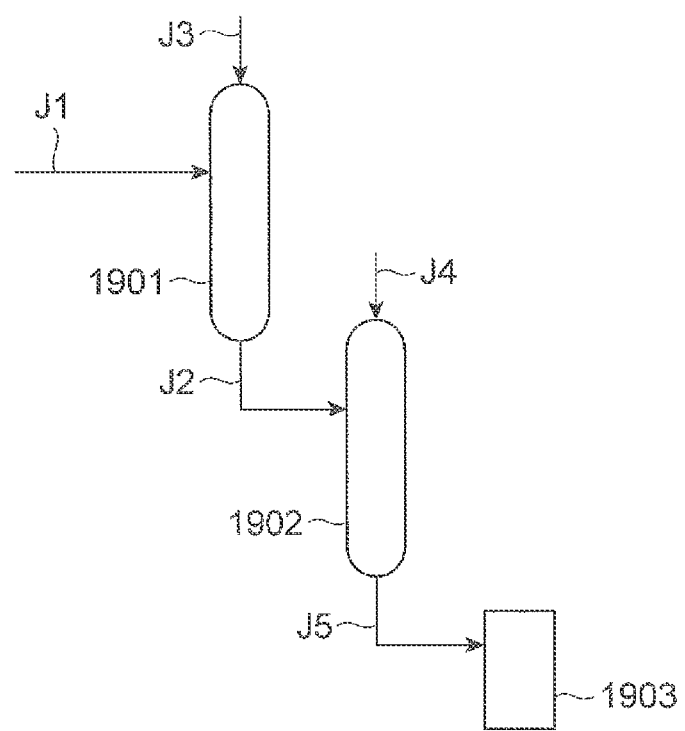
FIG. 19 is a schematic view of an apparatus according to the method for producing an isocyanate of the present embodiment.

The apparatus shown in FIG. 19 was used. Water was supplied at a rate of approximately 7.5 kg/Hr to a plug flow reaction vessel 1901 through a line J3, and the ammonia recovered through a line 55 in Example 2 was supplied thereto through a line J1, so as to generate ammonia water. Subsequently, the ammonia water was supplied to a plug flow reaction vessel 1902 through a line J2, and concentrated sulfuric acid (approximately 70%) was supplied thereto through a line J4, so as to perform a reaction. Thereafter, a reaction solution was recovered in a reservoir 1903 through a line J5. The recovered solution contained ammonium sulfate.

Example 35

(Production of Ammonium Sulfate)

Figure 20:
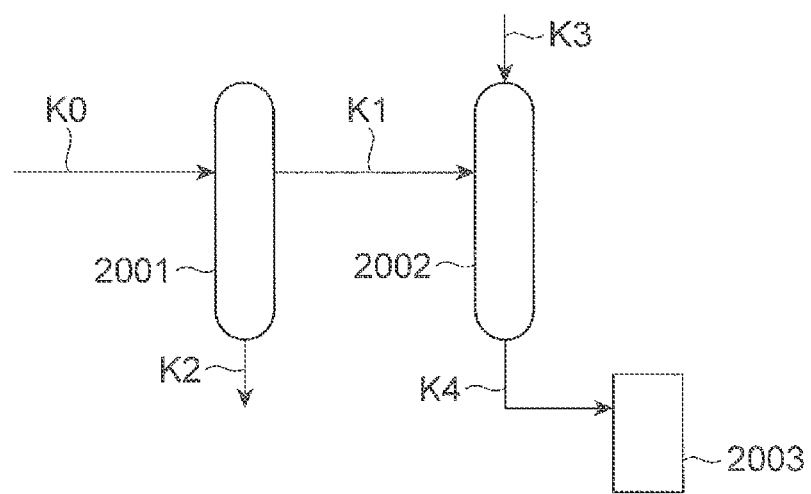
FIG. 20 is a schematic view of an apparatus according to the method for producing an isocyanate of the present embodiment.

The apparatus shown in FIG. 20 was used. A cooling column 2001 was cooled with a cooling medium (approximately 0° C.). To this column, the gaseous phase component, which had been recovered from a condenser 904 in Example 13, was supplied through a line K0. Aggregated phenol adhered to the inside of the cooling column 2001, and thus, the concentration of phenol in the gaseous phase component discharged through a line K1 was a lower detection limit (1 ppm). The operation was terminated, as appropriate, and phenol adhering to the inside of the cooling column 2001 was then washed with water. The washing solution was recovered through a line K2.

The gaseous phase component discharged through the line K1 was supplied to a plug flow reaction vessel 2002, and 30% sulfuric acid was supplied through a line K3, so as to perform a reaction. Thereafter, a reaction solution was recovered in a reservoir 2003 through a line K4. The recovered solution contained ammonium sulfate.

Reference Example 1

(Production of Liquid Ammonia)

Figure 21:
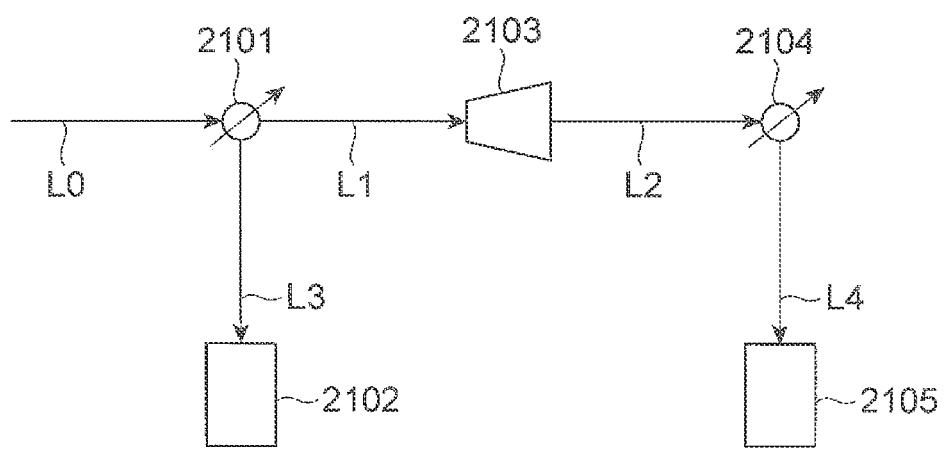
FIG. 21 is a schematic view of an apparatus according to the method for producing an isocyanate of the present embodiment.

The apparatus shown in FIG. 21 was used. The ammonia recovered through a line 65 in Example 3 was supplied through a line L0, and it was then cooled to a temperature of approximately 5° C. in a cooler 2101. Water contained in the ammonia was condensed, and was then recovered in a reservoir 2102 through a line L3. Ammonia discharged from the cooler 2101 through a line L1 was supplied to a compressor 2103, and the pressure was then increased to approximately 0.6 MPa. Subsequently, the ammonia was passed through a line L2, and was then cooled to a temperature of approximately 10° C. in a cooler 2104, so that the ammonia was condensed. The generated liquid ammonia was recovered in a reservoir 2105 through a line L4.

Example 36

(Heat Recovery by Burning of Ammonia)

Figure 22:
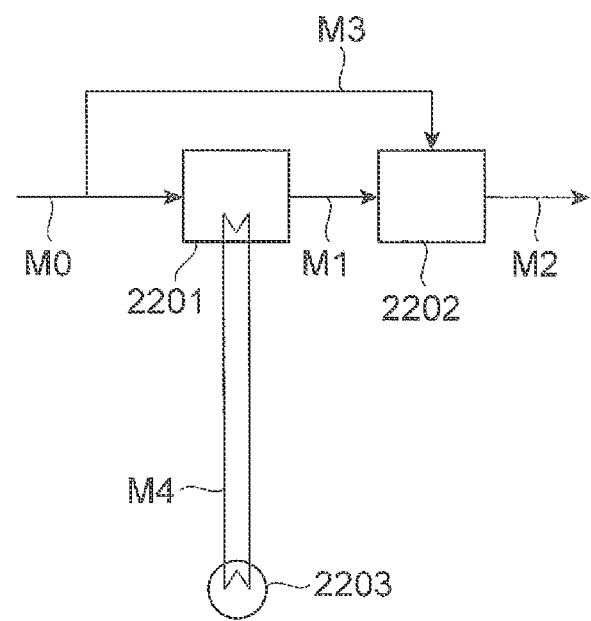
FIG. 22 is a schematic view of an apparatus according to the method for producing an isocyanate of the present embodiment.

The apparatus shown in FIG. 22 was used. The ammonia recovered through a line A7 in Example 8 was supplied to a combustion boiler 2201 through a line M0, and it was then burned. A heating medium in a heating medium line M4 was heated with heat generated as a result of the burning, and the heating medium was then circulated to a heat exchanger 2203. The heat exchanger 2203 was connected with a reboiler 908 shown in FIG. 9, and thus, it was used as a heat source for the carbamation step. Also, it was used as a heat source for a thin film evaporator 1201 shown in FIG. 12. Exhaust gas in the combustion boiler 2201 was supplied to denitration equipment 2202 through a line M1. Ammonia was supplied to the denitration equipment 2202 through a line M3, so that the concentration of nitrogen oxide in the exhaust gas was reduced. Thereafter, the exhaust gas was removed through a line M2.

Example 37

(Heat Recovery by Burning of Ammonia)

The ammonia recovered through a line A7 in Example 8 was supplied to a combustion boiler 2201 through a line M0, and it was then burned. A heating medium in a heating medium line M4 was heated with heat generated as a result of the burning, and the heating medium was then circulated to a heat exchanger 2203. The heat exchanger 2203 was connected with a heating medium going through the jacket of a thin film evaporator 1201 shown in FIG. 12, and it was used as a heat source for the pyrolysis step.

Example 38

(Step of Recovering Organic Hydroxy Compound and Step of Blowing Down Non-Regeneratable High-Boiling Component)

The liquid phase component recovered through a line 73 in Example 7 was supplied to an extruder comprising a degassing function, in which a vent port was established at a position of ⅓ from the discharge port of the extruder in the direction of the screw length, and L/D=45, and the screw diameter was 20 mm. The heater temperature of the extruder was set at 280° C., and the pressure was then reduced to 0.2 kPa. As a result, a gaseous phase component was obtained from the vent port. The gaseous phase component was condensed and was then analyzed. As a result, the gaseous phase component was found to be 4-phenylphenol. The 4-phenylphenol was recycled as a raw material for the carbamation step. The component obtained from the discharge port of the extruder was discarded.

Example 39

(Step of Recovering Organic Hydroxy Compound and Step of Blowing Down Non-Regeneratable High-Boiling Component)

4-Nonylphenol was added at a rate of approximately 0.20 kg/Hr to the liquid phase component recovered through a line F5 in Example 10, and the thus obtained mixture was then supplied to a vertical centrifugal thin film evaporator. The vertical centrifugal thin film evaporator had a mechanism of discharging a concentrated and devolatized liquid by extrusion action, and the temperature thereof was heated to 290° C. by a heating medium jacket, and the internal pressure thereof was reduced to 0.2 kPa. A gaseous phase component was obtained from the gas phase recovery port of the vertical centrifugal thin film evaporator. The gaseous phase component was condensed and was then analyzed. As a result, the gaseous phase component was found to be 4-nonylphenol, and it was recovered at a rate of approximately 0.23 kg/Hr. The 4-nonylphenol was recycled as a raw material for the transesterification step. The component obtained from the discharge port of the vertical centrifugal thin film evaporator was discarded.

Example 40

(Regeneration Step)

Approximately 0.6 kg of urea and approximately 15 kg of 4-heptylphenol were added to approximately 3.0 kg of the liquid phase component recovered through a line 41 in Example 33, and the obtained mixture was then stirred at approximately 80° C. under heating, so as to prepare a homogeneous solution. The solution was analyzed, and as a result, it was found that the concentration of an N-substituted carbamate was 0.52 wt %. The solution was supplied to a continuous multistage distillation column 903 through a line 95 shown in FIG. 9, and the same method as that in the carbamation step of Example 33 was then carried out. Thereafter, a reaction solution was recovered in a reservoir 907. The reaction solution contained 8 wt % of N-substituted carbamate.

(Precondensation Step)

By using the reaction solution obtained in the above described regeneration step, the same method as that in the precondensation step of Example 33 was carried out.

(Separation Step)

By using the reaction solution obtained in the above described precondensation step, the same method as that in the pyrolysis step of Example 11 was carried out. Hexamethylene diisocyanate was recovered through a line H10. The yield of the hexamethylene diisocyanate was 18% with respect to the hexamethylenediamine used in the carbamation step of Example 33.

(Step of Recovering Organic Hydroxy Compound and Step of Blowing Down Non-Regeneratable High-Boiling Component)

A liquid phase component recovered through a line H5 in the above described separation step was supplied to an extruder comprising a degassing function, in which a vent port was established at a position of ⅓ from the discharge port of the extruder in the direction of the screw length, and L/D=45, and the screw diameter was 20 mm. The heater temperature of the extruder was set at 280° C., and the pressure was then reduced to 0.2 kPa. As a result, a gaseous phase component was obtained from the vent port. The gaseous phase component was condensed and was then analyzed. As a result, the gaseous phase component was found to be 4-heptylphenol. The 4-heptylphenol was recycled as a raw material for the carbamation step. The component obtained from the discharge port of the extruder was discarded.

INDUSTRIAL APPLICABILITY

According to the present invention, it becomes unnecessary to treat ammonia as exhaust gas upon the production of isocyanates. Therefore, the present invention is industrially highly useful, and the commercial value thereof is high.

REFERENCE SIGNS LIST

1, 2, 3, 4, 5, 6, 7, 8, 9, 10, 11, 12, 13, 14, 15, 17, 18, 19, 20, 21 . . . line; 101 . . . continuous multistage distillation column; 102 . . . pyrolysis device; 103 . . . condenser; 104 . . . gas absorption column; 105 . . . stripping column; 106 . . . vacuum device; 107 . . . urea production equipment; 109 . . . separation column; 110 . . . purification column; 21, 22, 23, 24, 25 . . . line; 201 . . . continuous multistage distillation column; 203 . . . condenser; 204, 205 . . . reservoir; 31, 32 . . . line; 301 . . . thin film evaporator; 302 . . . condenser; 303, 304 . . . reservoir; 40, 41, 42, 43,

44, 45, 46, 47, 48, 49 ... line; 401 ... pyrolysis device; 404, 407 ... separation column; 402, 405, 408 ... condenser; 403, 406, 409 ... reboiler; 50, 51, 52, 53, 54, 55, 56, 57, 58, 59 ... line; 501 ... gas absorption column; 502 ... pump; 503 ... stripping column; 504, 507 ... condenser; 505, 508 ... reboiler; 506 ... distillation column; 509 ... cooler; 510 ... preheater; 60, 61, 62, 63, 64, 65, 66, 67, 68, 69 ... line; 601 ... gas absorption/liquid-liquid separation device; 602 ... pump; 603 ... stripping column; 604 ... condenser; 605 ... reboiler; 606 ... cooler; 607 ... preheater; 71, 72, 73, 74, 75, 76, 77, 78, 79 ... line; 701 ... pyrolysis device; 702, 705 ... condenser; 703, 706 ... separation column; 704, 707 ... reboiler; 80, 81, 82, 83A, 83B, 84, 85, 86, 87, 88 ... line; 801 ... gas absorption column; 802 ... pump; 803 ... stripping column; 804 ... condenser; 805 ... reboiler; 806 ... heat exchanger; 807 ... cooler; 808 ... preheater; 90, 91, 92, 93, 94, 95, 96, 97, 98, 99 ... line; 901 ... stirring tank; 902 ... gas-liquid separator; 903 ... multistage distillation column; 904 ... condenser; 905, 906, 907 ... reservoir; A0, A1, A2, A3, A4, A5, A6, A7, A8, A9, A10, A11, A12 ... line; 1001 ... gas absorption column; 1002 ... liquid-liquid separator; 1003 ... pump; 1004 ... stripping column; 1005 ... condenser; 1006 ... reboiler; 1007 ... preheater; 1008 ... heat exchanger; 1009 ... cooler; B0, B1, B2, B3 ... line; 1101 ... stirring tank; 1102 ... condenser; 1103 ... reservoir; C1, C2, C3, C4, C5, C6, C7, C8, C9 ... line; 1201 ... thin film evaporator; 1202, 1205 ... condenser; 1203, 1206 ... separation column; 1204, 1207 ... reboiler; 1208 ... reservoir; D0, D1, D2, D3, D4 ... line; 1301 ... stirring tank; 1302 ... condenser; 1303 ... gas-liquid separator; 1304 ... reservoir; D11, D12, D13 ... line; 1401 ... preconcentrator; 1402, 1404 ... reservoir; 1403 ... condenser; E1, E2, E3, E4, E5 ... line; 1501 ... continuous multistage distillation column; 1502 ... reboiler; 1503 ... condenser; 1504, 1505 ... reservoir; F0, F1, F2, F3, F4, F5, F6, F7, F8, F9, F10, F11 ... line; 1601, 1602 ... pyrolytic reaction vessel; 1603, 1607 ... separation column; 1604, 1606 ... condenser; 1605, 1608 ... reboiler; 1609 ... reservoir; G0, G1, G2, G3, G4, G5, G6, G7, G8, G11, G12, G13, G14 ... line; 1701 ... gas absorption column; 1702 ... pump; 1703, 1704 ... heat exchanger; 1705 ... condenser; 1706 ... stripping column; 1707 ... heater; 1708 ... reboiler; 1709 ... liquid-liquid separator; 1710 ... gas-liquid separator; H0, H2, H3, H4, H5, H6, H7, H8, H9, H10, H11 ... line; 1801, 1802 ... pyrolytic reaction vessel; 1803, 1807 ... separation column; 1804, 1806 ... condenser; 1805, 1808 ... reboiler; J1, J2, J3, J4, J5 ... line; 1901, 1902 ... plug flow reaction vessel; 1903 ... reservoir; K0, K1, K2, K3, K4 ... line; 2001 ... cooling column; 2002 ... plug flow reaction vessel; 2003 ... reservoir; L0, L1, L2, L3, L4 ... line; 2101, 2104 ... cooler; 2103 ... compressor; 2102, 2105 ... reservoir; M0, M1, M2, M3 ... line; M4 ... heating medium line; 2201 ... combustion boiler; 2202 ... denitration equipment; 2203 ... heat exchanger.

The invention claimed is:

1. A method of producing an isocyanate, from using an organic primary amine, urea and an organic hydroxy compound as raw materials, comprising:
    a carbamation step of generating an N-substituted carbamate from the organic primary amine, the urea and the organic hydroxy compound according to a carbamation reaction, and then recovering a first gaseous phase component comprising the urea and/or a compound having a carbonyl group derived from the urea, the organic hydroxy compound, and ammonia;
    a condensation step of condensing the first gaseous phase component with a condenser;
    an isocyanate production step of producing an isocyanate by subjecting the N-substituted carbamate to pyrolysis;
    an ammonia absorption step of absorbing a second gaseous phase component recovered as a gaseous phase component from the condenser by absorption water to generate gas-absorbed water, wherein
        the second gaseous phase component comprises ammonia as a main component, urea and/or isocyanic acid, and an organic hydroxy compound, and
        the gas-absorbed water comprises ammonia, urea and/or isocyanic acid, and an organic hydroxy compound;
    an ammonia stripping step of heating the gas-absorbed water to separate the ammonia from the gas-absorbed water;
    an organic hydroxy compound separation step of separating an organic hydroxy compound and a water phase, both contained in a liquid phase component obtained after the separation of the ammonia in the ammonia stripping step; and
    a liquid phase blow-down step of substituting a portion of an aqueous solution obtained in the organic hydroxy compound separation step with water.

2. The method according to claim 1, wherein a liquid phase component obtained after the separation of the ammonia in the ammonia stripping step is used as the absorption water in the ammonia absorption step.

3. The method according to claim 1, wherein a liquid phase component obtained after the separation of the ammonia in the ammonia stripping step comprises an organic hydroxy compound and a water phase, and the organic hydroxy compound is separated from the water phase according to phase separation.

4. The method according to claim 1, wherein ammonia obtained in the ammonia stripping step is further burned to recover heat, and the thus recovered heat is used as a heat source in the carbamation step and/or the isocyanate production step.

5. The method according to claim 1, wherein ammonia obtained in the ammonia stripping step is recovered as liquid ammonia.

6. A method of producing an isocyanate, from using an organic primary amine, urea and an organic hydroxy compound as raw materials, comprising:
    a carbamation step of generating an N-substituted carbamate from the organic primary amine, the urea and the organic hydroxy compound according to a carbamation reaction, and then recovering a first gaseous phase component comprising the urea and/or a compound having a carbonyl group derived from the urea, the organic hydroxy compound, and ammonia;
    a condensation step of condensing the first gaseous phase component with a condenser;
    an isocyanate production step of producing an isocyanate by subjecting the N-substituted carbamate to pyrolysis;
    a regeneration step of allowing a part or the whole of a first residual liquid, from which low-boiling components comprising the isocyanate and the organic hydroxy compound obtained in the isocyanate production step have been separated, to react with urea and an organic hydroxy compound;
    a separation step of subjecting a reaction solution in the regeneration step to a pyrolytic reaction, so as to separate the generated isocyanate from a second residual liquid comprising a non-regeneratable by-product; and a blow-down step of heating the first residual liquid and/or the second residual liquid to recover low-boiling components comprising an organic hydroxy compound, recycling the low-boiling components to at least one of the carbamation step, the isocyanate production step and the regeneration step, and removing high-boiling components comprising non-regeneratable by-products from the system.

7. The method according to claim 6, wherein, in the blow-down step, the first residual liquid and/or the second residual liquid are heated by using at least one device selected from the group consisting of:
   (a) a paddle type dryer comprising a forced transfer device;
   (b) an extruder comprising a degassing function; and
   (c) a vertical thin film evaporator comprising a forced transfer device.

8. The method according to claim 7, wherein, in the blow-down step, the first residual liquid and/or the second residual liquid are heated by using either one device of:
   (a) a paddle type dryer comprising a forced transfer device; and
   (c) a vertical thin film evaporator comprising a forced transfer device.

9. The method according to claim 6, wherein a viscosity of the first residual liquid and/or the second residual liquid is 1000 mPa·s or less.

* * * * *